(12) United States Patent
Maine et al.

(10) Patent No.: US 7,824,908 B2
(45) Date of Patent: Nov. 2, 2010

(54) GENETICALLY ENGINEERED P30 ANTIGEN, IMPROVED ANTIGEN COCKTAIL, AND USES THEREOF

(76) Inventors: Gregory T. Maine, 5743 Constitution Ave., Gurnee, IL (US) 60031; Chandu B. Patel, 1176 Tamarack La., Libertyville, IL (US) 60048; Sanford R. Ginsburg, 928 Carmel Dr., Palatine, IL (US) 60074; Timothy R. Bliese, 475 N. O'Plaine Rd., Gurnee, IL (US) 60031

( * ) Notice: Subject to any disclaimer, the term of this patent is extended or adjusted under 35 U.S.C. 154(b) by 490 days.

(21) Appl. No.: 11/860,383

(22) Filed: Sep. 24, 2007

(65) Prior Publication Data

US 2008/0160606 A1 Jul. 3, 2008

Related U.S. Application Data

(62) Division of application No. 11/316,532, filed on Dec. 21, 2005, now Pat. No. 7,314,924, which is a division of application No. 10/263,153, filed on Oct. 2, 2002, now Pat. No. 7,094,879.

(51) Int. Cl.
*C12N 15/00* (2006.01)
*C07H 21/04* (2006.01)

(52) U.S. Cl. .................. 435/320.1; 536/23.1; 536/23.7

(58) Field of Classification Search ........................ None
See application file for complete search history.

(56) References Cited

U.S. PATENT DOCUMENTS

| | | | |
|---|---|---|---|
| 4,582,788 | A | 4/1986 | Erlich |
| 4,683,194 | A | 7/1987 | Saiki et al. |
| 4,683,202 | A | 7/1987 | Mullis |
| 5,231,020 | A | 7/1993 | Jorgensen |
| 5,643,758 | A | 7/1997 | Guan et al. |
| 5,912,120 | A | 6/1999 | Goldstein et al. |
| 6,183,952 | B1 | 2/2001 | Billing-Medel et al. |
| 6,329,157 | B1 | 12/2001 | Maine et al. |
| 6,372,443 | B1 | 4/2002 | Jacobs et al. |
| 6,395,472 | B1 | 5/2002 | Leary et al. |
| 7,094,879 | B2 | 8/2006 | Maine et al. |

FOREIGN PATENT DOCUMENTS

| | | |
|---|---|---|
| EP | 0050424 B1 | 4/1982 |
| EP | 0084796 B1 | 3/1983 |
| EP | 0201184 B1 | 12/1986 |
| EP | 0237362 B1 | 9/1987 |
| EP | 0237362 B2 | 9/1987 |
| EP | 0258017 B1 | 2/1988 |
| EP | 0751147 B1 | 4/1990 |
| EP | 0431541 A2 | 12/1991 |
| EP | 0201184 B2 | 4/2004 |
| WO | 9602654 A1 | 1/1996 |
| WO | 9961906 A1 | 2/1999 |
| WO | 9966043 A1 | 12/1999 |

OTHER PUBLICATIONS

Stratagene Catalog (1991).*
Hsu, Sheng-Chieh et al., A monoclonal antibody reacts with maltose-binding protein of *Escherichia coli* and related enteric bacteria, vol. 204, No. 2,pp. 16-174, May 1997.
Riggs, Paul, Expression and Purification of Maltose-Binding Protein Fusions, vol. Chapter 16, p. Unit 16.6, May 2001.
Altschul, Stephen et al., Nucleic Acids Research, vol. 25, No. 17,p. 3389-3402, 1997.
Bonhomme, Annie et al, The Journal of Histochemistry & Cytochemistry, vol. 46(12), 1998, pp. 1411-1421.
Burg, J. Lawrence et al., The Journal of Immunology, vol. 141, No. 10, 1988, pp. 3584-3591.
Cesbron-Delauw, M.F. et al., PNAS, vol. 86, 1989, pp. 7537-7541.
Desmonts, Georges et al., Journal of Clinical Microbiology, vol. 11, No. 6, pp. 562-568, 1986.
Gerhold, et al., BioEssays, vol. 18, No. 12, (1996), pp. 973-981.
He, Xiao-Lin, et al., Nature Structural Biology, vol. 9, No. 8, 2002, pp. 606-611.
Higgins, et al., Cabios, (1989) 5L151-153.
Huskinson, Jayne et al., Journal of Clinical Microbiology, vol. 28, No. 12, 1990, pp. 2632-2636.
Jacobs, Leon et al., The Journal of Parasitology, 1956, pp. 308-314.
Johnson, Alan M. et al., Dept. of Micro. and Infectious Diseases, vol. 99, 1991, pp. 127-132.
Kapust, Rachel et al., Protein Science, vol. 8, 1999, pp. 1668-1674.
Kataoka, Kunishhige et al., Biochem. and Biophys. Research Commun., vol. 250, pp. 409-413, 1998.
Kim, Kami et al., Infection and Immunity, vol. 62, No. 1, 1994, pp. 203-209.
Mevelec, Marie-Noelle et al., Mol. and Biochem Parasit., vol. 56, (1992), pp. 227-238.
Mullis, K. et al., Cold Spring Harbor Laboratory, (1986), pp. 263-273.
Nam, Ho-Woo et al., The Korean Journal of Parasitology, vol. 34, No. 2, (1996), pp. 135-141.
Naot, Yehudith et al., The Journal of Infectious Diseases, vol. 142., No. 5, (1980), pp. 757-766.
Needleman, Saul B. et al., J. Mol. Biol. vol. 48, (1970), pp. 443-453.
New England Biolabs, Inc., 1998/99 Catalog, pp. 136-137.
Pearson, William et al, PNAS, vol. 85, (1988), pp. 2444-2448.
Pouletty, Ph. et al, Elsevier Science Publishers, (1984), pp. 289-298.
Prytulla, Stefan et al., FEBS Letters, vol. 399, (1996), pp. 283-289.
Prince, Jeffrey B. et al., Mol. and Bio. Parsit., vol. 34, (1989), pp. 3-13.
Prince, Jeffrey B. et al., Mol. and Bio. Parsit.,vol. 43, (1990), pp. 97-106.

(Continued)

*Primary Examiner*—Robert A Zeman
(74) *Attorney, Agent, or Firm*—Cheryl L. Becker

(57) ABSTRACT

The present invention relates to a genetically engineered P30 antigen and a combination or mixture of antigens (e.g., the genetically engineered P30 antigen and P35) that may be used in the detection of IgM and/or IgG antibodies to *Toxoplasma gondii*. Furthermore, the present invention also relates to methods of using this genetically engineered P30 antigen and combination of antigens, antibodies raised against this genetically engineered P30 antigen and combination of antigens, as well as kits and vaccines containing the genetically engineered P30 antigen and antigens present in the combination.

3 Claims, 84 Drawing Sheets

OTHER PUBLICATIONS

Remington, Jack S., et al., Infectious Diseases of the Fetus & Newborn Infant, 4th Ed. Saunders Company, "Toxoplasmosis", J.S. Remington and J.O. Klein, Eds., pp. 140-267, Saunders, Philadelphia, Pennsylvania (1995).
Robinson, John M. et al., J. Of Clinical Micro.,vol. 31, No. 3, (1993), pp. 629-635.
Russell, Robert B., et al, J. Mol. Biol., vol. 244, (1904), pp. 332-350.
Sabin, Albert B. et al., Science, vol. 108, (1948), pp. 660-663.
Saavedra, Rafael, et al., The Journal of Immunology, vol. 147, No. 6 (1991), pp. 1975-1985.
Sambrook, J., et al., Molecular Cloning, Cold Spring Harbor Laboratory Press, (1989), Cover and table of contents.
Safford, et al., J. Clin. Pathol., Automated Microparticle Enzyme Immunoassays for IgG and IgM Antibodies to Toxoplasma Gondii, vol. 44, (1991), pp. 238-242.
Smith, Advances in Applied Mathematics, vol. 2, (1981), pp. 482-489.
Velge-Roussel, F. et al., Mol. and Biochemical Parasitology, vol. 66, (1994), pp. 31-38.
Walton, Bryce C. et al., American Journal of Tropical Medicine and Hygiene, vol. 15, No. 2, pp. 149-152, 1966.
Wells, Timothy N. C. et al., Journal of Meukocyte Biol., vol. 61, (1997), pp. 545-550.
Withers-Martinez, Chrislaine et al., Protein Engineering, vol. 12, No. 12, (1999), pp. 1113-1120.
Zweig, Mark H. et al., Clin. Chem., vol. 39, No. 4, (1993), pp. 561-577.

* cited by examiner pMBP-c2X-ToxoP30(52-336aa)

1 CCGACACCA TCGAATGGT GCAAAACCT TTCGCGGTA TGGCATGAT
46 AGCGCCCGG AAGAGAGTC AATTCAGGG TGGTGAATG TGAAACCAG
91 TAACGTTAT ACGATGTCG CAGAGTATG CCGGTGTCT CTTATCAGA
136 CCGTTTCCC GCGTGGTGA ACCAGGCCA GCCACGTTT CTGCGAAAA
181 CGCGGGAAA AAGTGGAAG CGGCGATGG CGGAGCTGA ATTACATTC
226 CCAACCGCG TGGCACAAC AACTGGCGG GCAAACAGT CGTTGCTGA
271 TTGGCGTTG CCACCTCCA GTCTGGCCC TGCACGCGC CGTCGCAAA
316 TTGTCGCGG CGATTAAAT CTCGCGCCG ATCAACTGG GTGCCAGCG
361 TGGTGGTGT CGATGGTAG AACGAAGCG GCGTCGAAG CCTGTAAAG
406 CGGCGGTGC ACAATCTTC TCGCGCAAC GCGTCAGTG GGCTGATCA
451 TTAACTATC CGCTGGATG ACCAGGATG CCATTGCTG TGGAAGCTG
496 CCTGCACTA ATGTTCCGG CGTTATTTC TTGATGTCT CTGACCAGA
541 CACCCATCA ACAGTATTA TTTTCTCCC ATGAAGACG GTACGCGAC
586 TGGGCGTGG AGCATCTGG TCGCATTGG GTCACCAGC AAATCGCGC
631 TGTTAGCGG GCCCATTAA GTTCTGTCT CGGCGCGTC TGCGTCTGG
676 CTGGCTGGC ATAAATATC TCACTCGCA ATCAAATTC AGCCGATAG
721 CGGAACGGG AAGGCGACT GGAGTGCCA TGTCCGGTT TTCAACAAA
766 CCATGCAAA TGCTGAATG AGGGCATCG TTCCCACTG CGATGCTGG
811 TTGCCAACG ATCAGATGG CGCTGGGCG CAATGCGCG CCATTACCG
856 AGTCCGGGC TGCGCGTTG GTGCGGATA TCTCGGTAG TGGGATACG
901 ACGATACCG AAGACAGCT CATGTTATA TCCCGCCGT TAACCACCA
946 TCAAACAGG ATTTTCGCC TGCTGGGGC AAACCAGCG TGGACCGCT
991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
Met
1486 TAGGTGTTT TCACGAGCA CTTCACCAA CAAGGACCA TAGCATATG
LysIleGlu GluGlyLys LeuValIle TrpIleAsn GlyAspLys
1531 AAAATCGAA GAAGGTAAA CTGGTAATC TGGATTAAC GGCGATAAA
GlyTyrAsn GlyLeuAla GluValGly LysLysPhe GluLysAsp
1576 GGCTATAAC GGTCTCGCT GAAGTCGGT AAGAAATTC GAGAAAGAT
ThrGlyIle LysValThr ValGluHis ProAspLys LeuGluGlu
1621 ACCGGAATT AAAGTCACC GTTGAGCAT CCGGATAAA CTGGAAGAG
LysPhePro GlnValAla AlaThrGly AspGlyPro AspIleIle
1666 AAATTCCCA CAGGTTGCG GCAACTGGC GATGGCCCT GACATTATC
PheTrpAla HisAspArg PheGlyGly TyrAlaGln SerGlyLeu
1711 TTCTGGGCA CACGACCGC TTTGGTGGC TACGCTCAA TCTGGCCTG
LeuAlaGlu IleThrPro AspLysAla PheGlnAsp LysLeuTyr

FIG.2 pMBP-c2X-ToxoP30(52-336aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.2A pMBP-c2X-ToxoP30(52-336aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACG GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValCysGly
3151 AAGTTGTCT GCGGAAGGA CCCACTACA ATGACCCTC GTGTGCGGG
     LysAspGly ValLysVal ProGlnAsp AsnAsnGln TyrCysSer
3196 AAAGATGGA GTCAAAGTT CCTCAAGAC AACAATCAG TACTGTTCC
     GlyThrThr LeuThrGly CysAsnGlu LysSerPhe LysAspIle
3241 GGGACGACG CTGACTGGT TGCAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyCys ThrGlyGly SerProGlu
3376 GAGTCAAAA AGCGTCATT ATTGGATGC ACAGGGGGA TCGCCTGAG
     LysHisHis CysThrVal LysLeuGlu PheAlaGly AlaAlaGly
3421 AAGCATCAC TGTACCGTG AAACTGGAG TTTGCCGGG GCTGCAGGG
     SerAlaLys SerAlaAla GlyThrAla SerHisVal SerIlePhe
3466 TCAGCAAAA TCGGCTGCG GGAACAGCC AGTCACGTT TCCATTTTT
     AlaMetVal IleGlyLeu IleGlySer IleAlaAla CysValAla
3511 GCCATGGTG ATCGGACTT ATTGGCTCT ATCGCAGCT TGTGTCGCG
3556 TGAAAGCTT GGCACTGGC CGTCGTTTT ACAACGTCG TGACTGGGA
3601 AAACCCTGG CGTTACCCA ACTTAATCG CCTTGCAGC ACATCCCCC
3646 TTTCGCCAG CTGGCGTAA TAGCGAAGA GGCCCGCAC CGATCGCCC
3691 TTCCCAACA GTTGCGCAG CCTGAATGG CGAATGGCA GCTTGGCTG
3736 TTTTGGCGG ATGAGATAA GATTTTCAG CCTGATACA GATTAAATC
3781 AGAACGCAG AAGCGGTCT GATAAAACA GAATTTGCC TGGCGGCAG
3826 TAGCGCGGT GGTCCCACC TGACCCCAT GCCGAACTC AGAAGTGAA
3871 ACGCCGTAG CGCCGATGG TAGTGTGGG GTCTCCCCA TGCGAGAGT
3916 AGGGAACTG CCAGGCATC AAATAAAAC GAAAGGCTC AGTCGAAAG
3961 ACTGGGCCT TCGTTTTA TCTGTTGTT TGTCGGTGA ACGCTCTCC
4006 TGAGTAGGA CAAATCCGC CGGGAGCGG ATTTGAACG TTGCGAAGC
4051 AACGGCCCG GAGGGTGGC GGGCAGGAC GCCCGCCAT AAACTGCCA
4096 GGCATCAAA TTAAGCAGA AGGCCATCC TGACGGATG GCCTTTTTG
```

FIG.2B pMBP-c2X-ToxoP30(52-336aa)

4141 CGTTTCTAC AAACTCTTT TTGTTTATT TTTCTAAAT ACATTCAAA
4186 TATGTATCC GCTCATGAG ACAATAACC CTGATAAAT GCTTCAATA
4231 ATATTGAAA AAGGAAGAG TATGAGTAT TCAACATTT CCGTGTCGC
4276 CCTTATTCC CTTTTTTGC GGCATTTTG CCTTCCTGT TTTTGCTCA
4321 CCCAGAAAC GCTGGTGAA AGTAAAAGA TGCTGAAGA TCAGTTGGG
4366 TGCACGAGT GGGTTACAT CGAACTGGA TCTCAACAG CGGTAAGAT
4411 CCTTGAGAG TTTTCGCCC CGAAGAACG TTCTCCAAT GATGAGCAC
4456 TTTTAAAGT TCTGCTATG TGGCGCGGT ATTATCCCG TGTTGACGC
4501 CGGGCAAGA GCAACTCGG TCGCCGCAT ACACTATTC TCAGAATGA
4546 CTTGGTTGA GTACTCACC AGTCACAGA AAAGCATCT TACGGATGG
4591 CATGACAGT AAGAGAATT ATGCAGTGC TGCCATAAC CATGAGTGA
4636 TAACACTGC GGCCAACTT ACTTCTGAC AACGATCGG AGGACCGAA
4681 GGAGCTAAC CGCTTTTTT GCACAACAT GGGGGATCA TGTAACTCG
4726 CCTTGATCG TTGGGAACC GGAGCTGAA TGAAGCCAT ACCAAACGA
4771 CGAGCGTGA CACCACGAT GCCTGTAGC AATGGCAAC AACGTTGCG
4816 CAAACTATT AACTGGCGA ACTACTTAC TCTAGCTTC CCGGCAACA
4861 ATTAATAGA CTGGATGGA GGCGGATAA AGTTGCAGG ACCACTTCT
4906 GCGCTCGGC CCTTCCGGC TGGCTGGTT TATTGCTGA TAAATCTGG
4951 AGCCGGTGA GCGTGGGTC TCGCGGTAT CATTGCAGC ACTGGGGCC
4996 AGATGGTAA GCCCTCCCG TATCGTAGT TATCTACAC GACGGGGAG
5041 TCAGGCAAC TATGGATGA ACGAAATAG ACAGATCGC TGAGATAGG
5086 TGCCTCACT GATTAAGCA TTGGTAACT GTCAGACCA AGTTTACTC
5131 ATATATACT TTAGATTGA TTTACCCCG GTTGATAAT CAGAAAAGC
5176 CCCAAAAAC AGGAAGATT GTATAAGCA AATATTTAA ATTGTAAAC
5221 GTTAATATT TTGTTAAAA TTCGCGTTA AATTTTTGT TAAATCAGC
5266 TCATTTTTT AACCAATAG GCCGAAATC GGCAAAATC CCTTATAAA
5311 TCAAAAGAA TAGACCGAG ATAGGGTTG AGTGTTGTT CCAGTTTGG
5356 AACAAGAGT CCACTATTA AAGAACGTG GACTCCAAC GTCAAAGGG
5401 CGAAAAACC GTCTATCAG GGCGATGGC CCACTACGT GAACCATCA
5446 CCCAAATCA AGTTTTTTG GGGTCGAGG TGCCGTAAA GCACTAAAT
5491 CGGAACCCT AAAGGGAGC CCCCGATTT AGAGCTTGA CGGGGAAAG
5536 CCGGCGAAC GTGGCGAGA AAGGAAGGG AAGAAAGCG AAAGGAGCG
5581 GGCGCTAGG GCGCTGGCA AGTGTAGCG GTCACGCTG CGCGTAACC
5626 ACCACACCC GCCGCGCTT AATGCGCCG CTACAGGGC GCGTAAAAG
5671 GATCTAGGT GAAGATCCT TTTTGATAA TCTCATGAC CAAAATCCC
5716 TTAACGTGA GTTTTCGTT CCACTGAGC GTCAGACCC CGTAGAAAA
5761 GATCAAAGG ATCTTCTTG AGATCCTTT TTTTCTGCG CGTAATCTG
5806 CTGCTTGCA AACAAAAAA ACCACCGCT ACCAGCGGT GGTTTGTTT
5851 GCCGGATCA AGAGCTACC AACTCTTTT TCCGAAGGT AACTGGCTT
5896 CAGCAGAGC GCAGATACC AAATACTGT CCTTCTAGT GTAGCCGTA
5941 GTTAGGCCA CCACTTCAA GAACTCTGT AGCACCGCC TACATACCT
5986 CGCTCTGCT AATCCTGTT ACCAGTGGC TGCTGCCAG TGGCGATAA
6031 GTCGTGTCT TACCGGGTT GGACTCAAG ACGATAGTT ACCGGATAA
6076 GGCGCAGCG GTCGGGCTG AACGGGGGG TTCGTGCAC ACAGCCCAG
6121 CTTGGAGCG AACGACCTA CACCGAACT GAGATACCT ACAGCGTGA
6166 GCTATGAGA AAGCGCCAC GCTTCCCGA AGGGAGAAA GGCGGACAG

FIG.2C pMBP-c2X-ToxoP30(52-336aa)

```
6211  GTATCCGGT   AAGCGGCAG   GGTCGGAAC   AGGAGAGCG   CACGAGGGA
6256  GCTTCCAGG   GGGAAACGC   CTGGTATCT   TTATAGTCC   TGTCGGGTT
6301  TCGCCACCT   CTGACTTGA   GCTCGATT    TTTGTGATG   CTCGTCAGG
6346  GGGGCGGAG   CCTATGGAA   AAACGCCAG   CAACGCGGC   CTTTTTACG
6391  GTTCCTGGC   CTTTTGCTG   GCCTTTTGC   TCACATGTT   CTTTCCTGC
6436  GTTATCCCC   TGATTCTGT   GGATAACCG   TATTACCGC   CTTTGAGTG
6481  AGCTGATAC   CGCTCGCCG   CAGCCGAAC   GACCGAGCG   CAGCGAGTC
6526  AGTGAGCGA   GGAAGCGGA   AGAGCGCCT   GATGCGGTA   TTTTCTCCT
6571  TACGCATCT   GTGCGGTAT   TTCACACCG   CATATATGG   TGCACTCTC
6616  AGTACAATC   TGCTCTGAT   GCCGCATAG   TTAAGCCAG   TATACACTC
6661  CGCTATCGC   TACGTGACT   GGGTCATGG   CTGCGCCCC   GACACCCGC
6706  CAACACCCG   CTGACGCGC   CCTGACGGG   CTTGTCTGC   TCCCGGCAT
6751  CCGCTTACA   GACAAGCTG   TGACCGTCT   CCGGGAGCT   GCATGTGTC
6796  AGAGGTTTT   CACCGTCAT   CACCGAAAC   GCGCGAGGC   AGCTGCGGT
6841  AAAGCTCAT   CAGCGTGGT   CGTGCAGCG   ATTCACAGA   TGTCTGCCT
6886  GTTCATCCG   CGTCCAGCT   CGTTGAGTT   TCTCCAGAA   GCGTTAATG
6931  TCTGGCTTC   TGATAAAGC   GGGCCATGT   TAAGGGCGG   TTTTTTCCT
6976  GTTTGGTCA   CTGATGCCT   CCGTGTAAG   GGGGATTTC   TGTTCATGG
7021  GGGTAATGA   TACCGATGA   AACGAGAGA   GGATGCTCA   CGATACGGG
7066  TTACTGATG   ATGAACATG   CCCGGTTAC   TGGAACGTT   GTGAGGGTA
7111  AACAACTGG   CGGTATGGA   TGCGGCGGG   ACCAGAGAA   AAATCACTC
7156  AGGGTCAAT   GCCAGCGCT   TCGTTAATA   CAGATGTAG   GTGTTCCAC
7201  AGGGTAGCC   AGCAGCATC   CTGCGATGC   AGATCCGGA   ACATAATGG
7246  TGCAGGGCG   CTGACTTCC   GCGTTTCCA   GACTTTACG   AAACACGGA
7291  AACCGAAGA   CCATTCATG   TTGTTGCTC   AGGTCGCAG   ACGTTTTGC
7336  AGCAGCAGT   CGCTTCACG   TTCGCTCGC   GTATCGGTG   ATTCATTCT
7381  GCTAACCAG   TAAGGCAAC   CCCGCCAGC   CTAGCCGGG   TCCTCAACG
7426  ACAGGAGCA   CGATCATGC   GCACCCGTG   GCCAGGACC   CAACGCTGC
7471  CCGAAATT
```

FIG.2D

ToxoP30(52-336aa)

```
      LeuValAla AsnGlnVal ValThrCys ProAspLys LysSerThr
  1   CTTGTTGCC AATCAAGTT GTCACCTGC CCAGATAAA AAATCGACA
      AlaAlaVal IleLeuThr ProThrGlu AsnHisPhe ThrLeuLys
 46   GCCGCGGTC ATTCTCACA CCGACGGAG AACCACTTC ACTCTCAAG
      CysProLys ThrAlaLeu ThrGluPro ProThrLeu AlaTyrSer
 91   TGCCCTAAA ACAGCGCTC ACAGAGCCT CCCACTCTT GCGTACTCA
      ProAsnArg GlnIleCys ProAlaGly ThrThrSer SerCysThr
136   CCCAACAGG CAAATCTGC CCAGCGGGT ACTACAAGT AGCTGTACA
      SerLysAla ValThrLeu SerSerLeu IleProGlu AlaGluAsp
181   TCAAAGGCT GTAACATTG AGCTCCTTG ATTCCTGAA GCAGAAGAT
      SerTrpTrp ThrGlyAsp SerAlaSer LeuAspThr AlaGlyIle
226   AGCTGGTGG ACGGGGAT TCTGCTAGT CTCGACACG GCAGGCATC
      LysLeuThr ValProIle GluLysPhe ProValThr ThrGlnThr
271   AAACTCACG GTTCCAATC GAGAAGTTC CCCGTGACA ACGCAGACG
      PheValVal GlyCysIle LysGlyAsp AspAlaGln SerCysMet
316   TTTGTGGTC GGTTGCATC AAGGGAGAC GACGCACAG AGTTGTATG
      ValThrVal ThrValGln AlaArgAla SerSerVal ValAsnAsn
361   GTCACAGTG ACAGTACAA GCCAGAGCC TCATCGGTC GTCAATAAT
      ValAlaArg CysSerTyr GlyAlaAsp SerThrLeu GlyProVal
406   GTCGCAAGG TGCTCCTAC GGTGCAGAC AGCACTCTT GGTCCTGTC
      LysLeuSer AlaGluGly ProThrThr MetThrLeu ValCysGly
451   AAGTTGTCT GCGGAAGGA CCCACTACA ATGACCCTC GTGTGCGGG
      LysAspGly ValLysVal ProGlnAsp AsnAsnGln TyrCysSer
496   AAAGATGGA GTCAAAGTT CCTCAAGAC AACAATCAG TACTGTTCC
      GlyThrThr LeuThrGly CysAsnGlu LysSerPhe LysAspIle
541   GGGACGACG CTGACTGGT TGCAACGAG AAATCGTTC AAAGATATT
      LeuProLys LeuThrGlu AsnProTrp GlnGlyAsn AlaSerSer
586   TTGCCAAAA TTAACTGAG AACCCGTGG CAGGGTAAC GCTTCGAGT
      AspLysGly AlaThrLeu ThrIleLys LysGluAla PheProAla
631   GATAAGGGT GCCACGCTA ACGATCAAG AAGGAAGCA TTTCCAGCC
      GluSerLys SerValIle IleGlyCys ThrGlyGly SerProGlu
676   GAGTCAAAA AGCGTCATT ATTGGATGC ACAGGGGGA TCGCCTGAG
      LysHisHis CysThrVal LysLeuGlu PheAlaGly AlaAlaGly
721   AAGCATCAC TGTACCGTG AAACTGGAG TTTGCCGGG GCTGCAGGG
      SerAlaLys SerAlaAla GlyThrAla SerHisVal SerIlePhe
766   TCAGCAAAA TCGGCTGCG GGAACAGCC AGTCACGTT TCCATTTTT
      AlaMetVal IleGlyLeu IleGlySer IleAlaAla CysValAla
811   GCCATGGTG ATCGGACTT ATTGGCTCT ATCGCAGCT TGTGTCGCG
```

FIG.3 pMBP-p2X-ToxoP30(52-336aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                 Met
1486 TAGGTGTTT TCACGAGCA CTTCACCAA CAAGGACCA TAGCATATG
     LysIleLys ThrGlyAla ArgIleLeu AlaLeuSer AlaLeuThr
1531 AAAATAAAA ACAGGTGCA CGCATCCTC GCATTATCC GCATTAACG
     ThrMetMet PheSerAla SerAlaLeu AlaLysIle GluGluGly
1576 ACGATGATG TTTTCCGCC TCGGCTCTC GCCAAAATC GAAGAAGGT
     LysLeuVal IleTrpIle AsnGlyAsp LysGlyTyr AsnGlyLeu
1621 AAACTGGTA ATCTGGATT AACGGCGAT AAAGGCTAT AACGGTCTC
     AlaGluVal GlyLysLys PheGluLys AspThrGly IleLysVal
1666 GCTGAAGTC GGTAAGAAA TTCGAGAAA GATACCGGA ATTAAAGTC
     ThrValGlu HisProAsp LysLeuGlu GluLysPhe ProGlnVal
1711 ACCGTTGAG CATCCGGAT AAACTGGAA GAGAAATTC CCACAGGTT
     AlaAlaThr GlyAspGly ProAspIle IlePheTrp AlaHisAsp
```

FIG.5 pMBP-p2X-ToxoP30(52-336aa)

```
1756 GCGGCAACT GGCGATGGC CCTGACATT ATCTTCTGG GCACACGAC
     ArgPheGly GlyTyrAla GlnSerGly LeuLeuAla GluIleThr
1801 CGCTTTGGT GGCTACGCT CAATCTGGC CTGTTGGCT GAAATCACC
     ProAspLys AlaPheGln AspLysLeu TyrProPhe ThrTrpAsp
1846 CCGGACAAA GCGTTCCAG GACAAGCTG TATCCGTTT ACCTGGGAT
     AlaValArg TyrAsnGly LysLeuIle AlaTyrPro IleAlaVal
1891 GCCGTACGT TACAACGGC AAGCTGATT GCTTACCCG ATCGCTGTT
     GluAlaLeu SerLeuIle TyrAsnLys AspLeuLeu ProAsnPro
1936 GAAGCGTTA TCGCTGATT TATAACAAA GATCTGCTG CCGAACCCG
     ProLysThr TrpGluGlu IleProAla LeuAspLys GluLeuLys
1981 CCAAAAACC TGGGAAGAG ATCCCGGCG CTGGATAAA GAACTGAAA
     AlaLysGly LysSerAla LeuMetPhe AsnLeuGln GluProTyr
2026 GCGAAAGGT AAGAGCGCG CTGATGTTC AACCTGCAA GAACCGTAC
     PheThrTrp ProLeuIle AlaAlaAsp GlyGlyTyr AlaPheLys
2071 TTCACCTGG CCGCTGATT GCTGCTGAC GGGGGTTAT GCGTTCAAG
     TyrGluAsn GlyLysTyr AspIleLys AspValGly ValAspAsn
2116 TATGAAAAC GGCAAGTAC GACATTAAA GACGTGGGC GTGGATAAC
     AlaGlyAla LysAlaGly LeuThrPhe LeuValAsp LeuIleLys
2161 GCTGGCGCG AAAGCGGGT CTGACCTTC CTGGTTGAC CTGATTAAA
     AsnLysHis MetAsnAla AspThrAsp TyrSerIle AlaGluAla
2206 AACAAACAC ATGAATGCA GACACCGAT TACTCCATC GCAGAAGCT
     AlaPheAsn LysGlyGlu ThrAlaMet ThrIleAsn GlyProTrp
2251 GCCTTTAAT AAAGGCGAA ACAGCGATG ACCATCAAC GGCCCGTGG
     AlaTrpSer AsnIleAsp ThrSerLys ValAsnTyr GlyValThr
2296 GCATGGTCC AACATCGAC ACCAGCAAA GTGAATTAT GGTGTAACG
     ValLeuPro ThrPheLys GlyGlnPro SerLysPro PheValGly
2341 GTACTGCCG ACCTTCAAG GGTCAACCA TCCAAACCG TTCGTTGGC
     ValLeuSer AlaGlyIle AsnAlaAla SerProAsn LysGluLeu
2386 GTGCTGAGC GCAGGTATT AACGCCGCC AGTCCGAAC AAAGAGCTG
     AlaLysGlu PheLeuGlu AsnTyrLeu LeuThrAsp GluGlyLeu
2431 GCAAAAGAG TTCCTCGAA AACTATCTG CTGACTGAT GAAGGTCTG
     GluAlaVal AsnLysAsp LysProLeu GlyAlaVal AlaLeuLys
2476 GAAGCGGTT AATAAAGAC AAACCGCTG GGTGCCGTA GCGCTGAAG
     SerTyrGlu GluGluLeu AlaLysAsp ProArgIle AlaAlaThr
2521 TCTTACGAG GAAGAGTTG GCGAAAGAT CCACGTATT GCCGCCACT
     MetGluAsn AlaGlnLys GlyGluIle MetProAsn IleProGln
2566 ATGGAAAAC GCCCAGAAA GGTGAAATC ATGCCGAAC ATCCCGCAG
     MetSerAla PheTrpTyr AlaValArg ThrAlaVal IleAsnAla
2611 ATGTCCGCT TTCTGGTAT GCCGTGCGT ACTGCGGTG ATCAACGCC
     AlaSerGly ArgGlnThr ValAspGlu AlaLeuLys AspAlaGln
2656 GCCAGCGGT CGTCAGACT GTCGATGAA GCCCTGAAA GACGCGCAG
     ThrAsnSer SerSerAsn AsnAsnAsn AsnAsnAsn AsnAsnAsn
2701 ACTAATTCG AGCTCGAAC AACAACAAC AATAACAAT AACAACAAC
     LeuGlyIle GluGlyArg IleSerGlu PheLeuVal AlaAsnGln
2746 CTCGGGATC GAGGGAAGG ATTTCAGAA TTCCTTGTT GCCAATCAA
     ValValThr CysProAsp LysLysSer ThrAlaAla ValIleLeu
```

FIG.5A pMBP-p2X-ToxoP30(52-336aa)

```
2791 GTTGTCACC TGCCCAGAT AAAAAATCG ACAGCCGCG GTCATTCTC
     ThrProThr GluAsnHis PheThrLeu LysCysPro LysThrAla
2836 ACACCGACG GAGAACCAC TTCACTCTC AAGTGCCCT AAAACAGCG
     LeuThrGlu ProProThr LeuAlaTyr SerProAsn ArgGlnIle
2881 CTCACAGAG CCTCCCACT CTTGCGTAC TCACCCAAC AGGCAAATC
     CysProAla GlyThrThr SerSerCys ThrSerLys AlaValThr
2926 TGCCCAGCG GGTACTACA AGTAGCTGT ACATCAAAG GCTGTAACA
     LeuSerSer LeuIlePro GluAlaGlu AspSerTrp TrpThrGly
2971 TTGAGCTCC TTGATTCCT GAAGCAGAA GATAGCTGG TGGACGGGG
     AspSerAla SerLeuAsp ThrAlaGly IleLysLeu ThrValPro
3016 GATTCTGCT AGTCTCGAC ACGGCAGGC ATCAAACTC ACAGTTCCA
     IleGluLys PheProVal ThrThrGln ThrPheVal ValGlyCys
3061 ATCGAGAAG TTCCCCGTG ACAACGCAG ACGTTTGTG GTCGGTTGC
     IleLysGly AspAspAla GlnSerCys MetValThr ValThrVal
3106 ATCAAGGGA GACGACGCA CAGAGTTGT ATGGTCACA GTGACAGTA
     GlnAlaArg AlaSerSer ValValAsn AsnValAla ArgCysSer
3151 CAAGCCAGA GCCTCATCG GTCGTCAAT AATGTCGCA AGGTGCTCC
     TyrGlyAla AspSerThr LeuGlyPro ValLysLeu SerAlaGlu
3196 TACGGTGCA GACAGCACT CTTGGTCCT GTCAAGTTG TCTGCGGAA
     GlyProThr ThrMetThr LeuValCys GlyLysAsp GlyValLys
3241 GGACCCACT ACAATGACC CTCGTGTGC GGGAAAGAT GGAGTCAAA
     ValProGln AspAsnAsn GlnTyrCys SerGlyThr ThrLeuThr
3286 GTTCCTCAA GACAACAAT CAGTACTGT TCCGGGACG ACGCTGACT
     GlyCysAsn GluLysSer PheLysAsp IleLeuPro LysLeuThr
3331 GGTTGCAAC GAGAAATCG TTCAAAGAT ATTTTGCCA AAATTAACT
     GluAsnPro TrpGlnGly AsnAlaSer SerAspLys GlyAlaThr
3376 GAGAACCCG TGGCAGGGT AACGCTTCG AGTGATAAG GGTGCCACG
     LeuThrIle LysLysGlu AlaPhePro AlaGluSer LysSerVal
3421 CTAACGATC AAGAAGGAA GCATTTCCA GCCGAGTCA AAAAGCGTC
     IleIleGly CysThrGly GlySerPro GluLysHis HisCysThr
3466 ATTATTGGA TGCACAGGG GGATCGCCT GAGAAGCAT CACTGTACC
     ValLysLeu GluPheAla GlyAlaAla GlySerAla LysSerAla
3511 GTGAAACTG GAGTTTGCC GGGGCTGCA GGGTCAGCA AAATCGGCT
     AlaGlyThr AlaSerHis ValSerIle PheAlaMet ValIleGly
3556 GCGGGAACA GCCAGTCAC GTTTCCATT TTTGCCATG GTGATCGGA
     LeuIleGly SerIleAla AlaCysVal Ala
3601 CTTATTGGC TCTATCGCA GCTTGTGTC GCGTGAAAG CTTGGCACT
3646 GGCCGTCGT TTTACAACG TCGTGACTG GGAAAACCC TGGCGTTAC
3691 CCAACTTAA TCGCCTTGC AGCACATCC CCCTTTCGC CAGCTGGCG
3736 TAATAGCGA AGAGGCCCG CACCGATCG CCCTTCCCA ACAGTTGCG
3781 CAGCCTGAA TGGCGAATG GCAGCTTGG CTGTTTTGG CGGATGAGA
3826 TAAGATTTT CAGCCTGAT ACAGATTAA ATCAGAACG CAGAAGCGG
3871 TCTGATAAA ACAGAATTT GCCTGGCGG CAGTAGCGC GGTGGTCCC
3916 ACCTGACCC CATGCCGAA CTCAGAAGT GAAACGCCG TAGCGCCGA
3961 TGGTAGTGT GGGGTCTCC CCATGCGAG AGTAGGGAA CTGCCAGGC
4006 ATCAAATAA AACGAAAGG CTCAGTCGA AAGACTGGG CCTTTCGTT
```

FIG.5B pMBP-p2X-ToxoP30(52-336aa)

```
4051 TTATCTGTT GTTTGTCGG TGAACGCTC TCCTGAGTA GGACAAATC
4096 CGCCGGGAG CGGATTTGA ACGTTGCGA AGCAACGGC CCGGAGGGT
4141 GGCGGGCAG GACGCCCGC CATAAACTG CCAGGCATC AAATTAAGC
4186 AGAAGGCCA TCCTGACGG ATGGCCTTT TTGCGTTTC TACAAACTC
4231 TTTTTGTTT ATTTTTCTA AATACATTC AAATATGTA TCCGCTCAT
4276 GAGACAATA ACCCTGATA AATGCTTCA ATAATATTG AAAAAGGAA
4321 GAGTATGAG TATTCAACA TTTCCGTGT CGCCCTTAT TCCCTTTTT
4366 TGCGGCATT TTGCCTTCC TGTTTTTGC TCACCCAGA AACGCTGGT
4411 GAAAGTAAA AGATGCTGA AGATCAGTT GGGTGCACG AGTGGGTTA
4456 CATCGAACT GGATCTCAA CAGCGGTAA GATCCTTGA GAGTTTTCG
4501 CCCCGAAGA ACGTTCTCC AATGATGAG CACTTTTAA AGTTCTGCT
4546 ATGTGGCGC GGTATTATC CCGTGTTGA CGCCGGGCA AGAGCAACT
4591 CGGTCGCCG CATACACTA TTCTCAGAA TGACTTGGT TGAGTACTC
4636 ACCAGTCAC AGAAAAGCA TCTTACGGA TGGCATGAC AGTAAGAGA
4681 ATTATGCAG TGCTGCCAT AACCATGAG TGATAACAC TGCGGCCAA
4726 CTTACTTCT GACAACGAT CGGAGGACC GAAGGAGCT AACCGCTTT
4771 TTTGCACAA CATGGGGGA TCATGTAAC TCGCCTTGA TCGTTGGGA
4816 ACCGGAGCT GAATGAAGC CATACCAAA CGACGAGCG TGACACCAC
4861 GATGCCTGT AGCAATGGC AACAACGTT GCGCAAACT ATTAACTGG
4906 CGAACTACT TACTCTAGC TTCCCGGCA ACAATTAAT AGACTGGAT
4951 GGAGGCGGA TAAAGTTGC AGGACCACT TCTGCGCTC GGCCCTTCC
4996 GGCTGGCTG GTTTATTGC TGATAAATC TGGAGCCGG TGAGCGTGG
5041 GTCTCGCGG TATCATTGC AGCACTGGG GCCAGATGG TAAGCCCTC
5086 CCGTATCGT AGTTATCTA CACGACGGG GAGTCAGGC AACTATGGA
5131 TGAACGAAA TAGACAGAT CGCTGAGAT AGGTGCCTC ACTGATTAA
5176 GCATTGGTA ACTGTCAGA CCAAGTTTA CTCATATAT ACTTTAGAT
5221 TGATTTACC CCGGTTGAT AATCAGAAA AGCCCCAAA AACAGGAAG
5266 ATTGTATAA GCAAATATT TAAATTGTA AACGTTAAT ATTTTGTTA
5311 AAATTCGCG TTAAATTTT TGTTAAATC AGCTCATTT TTTAACCAA
5356 TAGGCCGAA ATCGGCAAA ATCCCTTAT AAATCAAAA GAATAGACC
5401 GAGATAGGG TTGAGTGTT GTTCCAGTT TGGAACAAG AGTCCACTA
5446 TTAAAGAAC GTGGACTCC AACGTCAAA GGGCGAAAA ACCGTCTAT
5491 CAGGGCGAT GGCCCACTA CGTGAACCA TCACCCAAA TCAAGTTTT
5536 TTGGGGTCG AGGTGCCGT AAAGCACTA AATCGGAAC CCTAAAGGG
5581 AGCCCCCGA TTTAGAGCT TGACGGGGA AAGCCGGCG AACGTGGCG
5626 AGAAAGGAA GGGAAGAAA GCGAAAGGA GCGGGCGCT AGGGCGCTG
5671 GCAAGTGTA GCGGTCACG CTGCGCGTA ACCACCACA CCCGCCGCG
5716 CTTAATGCG CCGCTACAG GGCGCGTAA AAGGATCTA GGTGAAGAT
5761 CCTTTTTGA TAATCTCAT GACCAAAAT CCCTTAACG TGAGTTTTC
5806 GTTCCACTG AGCGTCAGA CCCCGTAGA AAAGATCAA AGGATCTTC
5851 TTGAGATCC TTTTTTTCT GCGCGTAAT CTGCTGCTT GCAAACAAA
5896 AAAACCACC GCTACCAGC GGTGGTTTG TTTGCCGGA TCAAGAGCT
5941 ACCAACTCT TTTTCCGAA GGTAACTGG CTTCAGCAG AGCGCAGAT
5986 ACCAAATAC TGTCCTTCT AGTGTAGCC GTAGTTAGG CCACCACTT
6031 CAAGAACTC TGTAGCACC GCCTACATA CCTCGCTCT GCTAATCCT
6076 GTTACCAGT GGCTGCTGC CAGTGGCGA TAAGTCGTG TCTTACCGG
```

FIG.5C pMBP-p2X-ToxoP30(52-336aa)

```
6121  GTTGGACTC AAGACGATA GTTACCGGA TAAGGCGCA GCGGTCGGG
6166  CTGAACGGG GGGTTCGTG CACACAGCC CAGCTTGGA GCGAACGAC
6211  CTACACCGA ACTGAGATA CCTACAGCG TGAGCTATG AGAAAGCGC
6256  CACGCTTCC CGAAGGGAG AAAGGCGGA CAGGTATCC GGTAAGCGG
6301  CAGGGTCGG AACAGGAGA GCGCACGAG GGAGCTTCC AGGGGGAAA
6346  CGCCTGGTA TCTTTATAG TCCTGTCGG GTTTCGCCA CCTCTGACT
6391  TGAGCGTCG ATTTTTGTG ATGCTCGTC AGGGGGGCG GAGCCTATG
6436  GAAAAACGC CAGCAACGC GGCCTTTTT ACGGTTCCT GGCCTTTTG
6481  CTGGCCTTT TGCTCACAT GTTCTTTCC TGCGTTATC CCCTGATTC
6526  TGTGGATAA CCGTATTAC CGCCTTTGA GTGAGCTGA TACCGCTCG
6571  CCGCAGCCG AACGACCGA GCGCAGCGA GTCAGTGAG CGAGGAAGC
6616  GGAAGAGCG CCTGATGCG GTATTTCT CCTTACGCA TCTGTGCGG
6661  TATTTCACA CCGCATATA TGGTGCACT CTCAGTACA ATCTGCTCT
6706  GATGCCGCA TAGTTAAGC CAGTATACA CTCCGCTAT CGCTACGTG
6751  ACTGGGTCA TGGCTGCGC CCCGACACC CGCCAACAC CCGCTGACG
6796  CGCCCTGAC GGGCTTGTC TGCTCCCGG CATCCGCTT ACAGACAAG
6841  CTGTGACCG TCTCCGGGA GCTGCATGT GTCAGAGGT TTTCACCGT
6886  CATCACCGA AACGCGCGA GGCAGCTGC GGTAAAGCT CATCAGCGT
6931  GGTCGTGCA GCGATTCAC AGATGTCTG CCTGTTCAT CCGCGTCCA
6976  GCTCGTTGA GTTTCTCCA GAAGCGTTA ATGTCTGGC TTCTGATAA
7021  AGCGGGCCA TGTTAAGGG CGGTTTTTT CCTGTTTGG TCACTGATG
7066  CCTCCGTGT AAGGGGGAT TTCTGTTCA TGGGGGTAA TGATACCGA
7111  TGAAACGAG AGAGGATGC TCACGATAC GGGTTACTG ATGATGAAC
7156  ATGCCCGGT TACTGGAAC GTTGTGAGG GTAAACAAC TGGCGGTAT
7201  GGATGCGGC GGGACCAGA GAAAAATCA CTCAGGGTC AATGCCAGC
7246  GCTTCGTTA ATACAGATG TAGGTGTTC CACAGGGTA GCCAGCAGC
7291  ATCCTGCGA TGCAGATCC GGAACATAA TGGTGCAGG GCGCTGACT
7336  TCCGCGTTT CCAGACTTT ACGAAACAC GGAAACCGA AGACCATTC
7381  ATGTTGTTG CTCAGGTCG CAGACGTTT TGCAGCAGC AGTCGCTTC
7426  ACGTTCGCT CGCGTATCG GTGATTCAT TCTGCTAAC CAGTAAGGC
7471  AACCCCGCC AGCCTAGCC GGGTCCTCA ACGACAGGA GCACGATCA
7516  TGCGCACCC GTGGCCAGG ACCCAACGC pMBP-c2X-ToxoP30del1C(52-324aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                                Met
1486 TAGGTGTTT TCACGAGCA CTTCACCAA CAAGGACCA TAGCATATG
      LysIleGlu GluGlyLys LeuValIle TrpIleAsn GlyAspLys
1531 AAAATCGAA GAAGGTAAA CTGGTAATC TGGATTAAC GGCGATAAA
      GlyTyrAsn GlyLeuAla GluValGly LysLysPhe GluLysAsp
1576 GGCTATAAC GGTCTCGCT GAAGTCGGT AAGAAATTC GAGAAAGAT
      ThrGlyIle LysValThr ValGluHis ProAspLys LeuGluGlu
1621 ACCGGAATT AAAGTCACC GTTGAGCAT CCGGATAAA CTGGAAGAG
      LysPhePro GlnValAla AlaThrGly AspGlyPro AspIleIle
1666 AAATTCCCA CAGGTTGCG GCAACTGGC GATGGCCCT GACATTATC
      PheTrpAla HisAspArg PheGlyGly TyrAlaGln SerGlyLeu
1711 TTCTGGGCA CACGACCGC TTTGGTGGC TACGCTCAA TCTGGCCTG
      LeuAlaGlu IleThrPro AspLysAla PheGlnAsp LysLeuTyr
```

FIG.8 pMBP-c2X-ToxoP30dellC(52-324aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAGGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.8A pMBP-c2X-ToxoP30del1C(52-324aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValCysGly
3151 AAGTTGTCT GCGGAAGGA CCCACTACA ATGACCCTC GTGTGCGGG
     LysAspGly ValLysVal ProGlnAsp AsnAsnGln TyrCysSer
3196 AAAGATGGA GTCAAAGTT CCTCAAGAC AACAATCAG TACTGTTCC
     GlyThrThr LeuThrGly CysAsnGlu LysSerPhe LysAspIle
3241 GGGACGACG CTGACTGGT TGCAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyCys ThrGlyGly SerProGlu
3376 GAGTCAAAA AGCGTCATT ATTGGATGC ACAGGGGGA TCGCCTGAG
     LysHisHis CysThrVal LysLeuGlu PheAlaGly AlaAlaGly
3421 AAGCATCAC TGTACCGTG AAACTGGAG TTTGCCGGG GCTGCAGGG
     SerAlaLys SerAlaAla GlyThrAla SerHisVal SerIlePhe
3466 TCAGCAAAA TCGGCTGCG GGAACAGCC AGTCACGTT TCCATTTTT
     AlaMetVal
3511 GCCATGGTG TGAAAGCTT GGCACTGGC CGTCGTTTT ACAACGTCG
3556 TGACTGGGA AAACCCTGG CGTTACCCA ACTTAATCG CCTTGCAGC
3601 ACATCCCCC TTTCGCCAG CTGGCGTAA TAGCGAAGA GGCCCGCAC
3646 CGATCGCCC TTCCCAACA GTTGCGCAG CCTGAATGG CGAATGGCA
3691 GCTTGGCTG TTTTGGCGG ATGAGATAA GATTTTCAG CCTGATACA
3736 GATTAAATC AGAACGCAG AAGCGGTCT GATAAAACA GAATTTGCC
3781 TGGCGGCAG TAGCGCGGT GGTCCCACC TGACCCCAT GCCGAACTC
3826 AGAAGTGAA ACGCCGTAG CGCCGATGG TAGTGTGGG GTCTCCCCA
3871 TGCGAGAGT AGGGAACTG CCAGGCATC AAATAAAAC GAAAGGCTC
3916 AGTCGAAAG ACTGGGCCT TCGTTTTA TCTGTTGTT TGTCGGTGA
3961 ACGCTCTCC TGAGTAGGA CAAATCCGC CGGGAGCGG ATTTGAACG
4006 TTGCGAAGC AACGGCCCG GAGGGTGGC GGGCAGGAC GCCCGCCAT
4051 AAACTGCCA GGCATCAAA TTAAGCAGA AGGCCATCC TGACGGATG
4096 GCCTTTTTG CGTTTCTAC AAACTCTTT TGTTTATT TTTCTAAAT
```

FIG.8B pMBP-c2X-ToxoP30dellC(52-324aa)

```
4141  ACATTCAAA TATGTATCC GCTCATGAG ACAATAACC CTGATAAAT
4186  GCTTCAATA ATATTGAAA AAGGAAGAG TATGAGTAT TCAACATTT
4231  CCGTGTCGC CCTTATTCC CTTTTTTGC GGCATTTTG CCTTCCTGT
4276  TTTTGCTCA CCCAGAAAC GCTGGTGAA AGTAAAAGA TGCTGAAGA
4321  TCAGTTGGG TGCACGAGT GGGTTACAT CGAACTGGA TCTCAACAG
4366  CGGTAAGAT CCTTGAGAG TTTTCGCCC CGAAGAACG TTCTCCAAT
4411  GATGAGCAC TTTTAAAGT TCTGCTATG TGGCGCGGT ATTATCCCG
4456  TGTTGACGC CGGGCAAGA GCAACTCGG TCGCCGCAT ACACTATTC
4501  TCAGAATGA CTTGGTTGA GTACTCACC AGTCACAGA AAAGCATCT
4546  TACGGATGG CATGACAGT AAGAGAATT ATGCAGTGC TGCCATAAC
4591  CATGAGTGA TAACACTGC GGCCAACTT ACTTCTGAC AACGATCGG
4636  AGGACCGAA GGAGCTAAC CGCTTTTTT GCACAACAT GGGGGATCA
4681  TGTAACTCG CCTTGATCG TTGGGAACC GGAGCTGAA TGAAGCCAT
4726  ACCAAACGA CGAGCGTGA CACCACGAT GCCTGTAGC AATGGCAAC
4771  AACGTTGCG CAAACTATT AACTGGCGA ACTACTTAC TCTAGCTTC
4816  CCGGCAACA ATTAATAGA CTGGATGGA GGCGGATAA AGTTGCAGG
4861  ACCACTTCT GCGCTCGGC CCTTCCGGC TGGCTGGTT TATTGCTGA
4906  TAAATCTGG AGCCGGTGA GCGTGGGTC TCGCGGTAT CATTGCAGC
4951  ACTGGGGCC AGATGGTAA GCCCTCCCG TATCGTAGT TATCTACAC
4996  GACGGGGAG TCAGGCAAC TATGGATGA ACGAAATAG ACAGATCGC
5041  TGAGATAGG TGCCTCACT GATTAAGCA TTGGTAACT GTCAGACCA
5086  AGTTTACTC ATATATACT TTAGATTGA TTTACCCCG GTTGATAAT
5131  CAGAAAAGC CCCAAAAAC AGGAAGATT GTATAAGCA AATATTTAA
5176  ATTGTAAAC GTTAATATT TTGTTAAAA TTCGCGTTA AATTTTTGT
5221  TAAATCAGC TCATTTTTT AACCAATAG GCCGAAATC GGCAAAATC
5266  CCTTATAAA TCAAAAGAA TAGACCGAG ATAGGGTTG AGTGTTGTT
5311  CCAGTTTGG AACAAGAGT CCACTATTA AAGAACGTG GACTCCAAC
5356  GTCAAAGGG CGAAAAACC GTCTATCAG GGCGATGGC CCACTACGT
5401  GAACCATCA CCCAAATCA GTTTTTTG GGTCGAGG TGCCGTAAA
5446  GCACTAAAT CGGAACCCT AAAGGGAGC CCCCGATTT AGAGCTTGA
5491  CGGGGAAAG CCGGCGAAC GTGGCGAGA AAGGAAGGG AAGAAAGCG
5536  AAAGGAGCG GGCGCTAGG GCGCTGGCA AGTGTAGCG GTCACGCTG
5581  CGCGTAACC ACCACACCC GCCGCGCTT AATGCGCCG CTACAGGGC
5626  GCGTAAAAG GATCTAGGT GAAGATCCT TTTTGATAA TCTCATGAC
5671  CAAAATCCC TTAACGTGA GTTTTCGTT CCACTGAGC GTCAGACCC
5716  CGTAGAAAA GATCAAAGG ATCTTCTTG AGATCCTTT TTTTCTGCG
5761  CGTAATCTG CTGCTTGCA AACAAAAAA ACCACCGCT ACCAGCGGT
5806  GGTTTGTTT GCCGGATCA AGAGCTACC AACTCTTTT TCCGAAGGT
5851  AACTGGCTT CAGCAGAGC GCAGATACC AAATACTGT CCTTCTAGT
5896  GTAGCCGTA GTTAGGCCA CCACTTCAA GAACTCTGT AGCACCGCC
5941  TACATACCT CGCTCTGCT AATCCTGTT ACCAGTGGC TGCTGCCAG
5986  TGGCGATAA GTCGTGTCT TACCGGGTT GGACTCAAG ACGATAGTT
6031  ACCGGATAA GGCGCAGCG GTCGGGCTG AACGGGGGG TTCGTGCAC
6076  ACAGCCCAG CTTGGAGCG AACGACCTA CACCGAACT GAGATACCT
6121  ACAGCGTGA GCTATGAGA AAGCGCCAC GCTTCCCGA AGGGAGAAA
6166  GGCGGACAG GTATCCGGT AAGCGGCAG GGTCGGAAC AGGAGAGCG
```

FIG.8C pMBP-c2X-ToxoP30dellC(52-324aa)

```
6211 CACGAGGGA GCTTCCAGG GGGAAACGC CTGGTATCT TTATAGTCC
6256 TGTCGGGTT TCGCCACCT CTGACTTGA GCGTCGATT TTTGTGATG
6301 CTCGTCAGG GGGGCGGAG CCTATGGAA AAACGCCAG CAACGCGGC
6346 CTTTTTACG GTTCCTGGC CTTTTGCTG GCCTTTTGC TCACATGTT
6391 CTTTCCTGC GTTATCCCC TGATTCTGT GGATAACCG TATTACCGC
6436 CTTTGAGTG AGCTGATAC CGCTCGCCG CAGCCGAAC GACCGAGCG
6481 CAGCGAGTC AGTGAGCGA GGAAGCGGA AGAGCGCCT GATGCGGTA
6526 TTTTCTCCT TACGCATCT GTGCGGTAT TCACACCG CATATATGG
6571 TGCACTCTC AGTACAATC TGCTCTGAT GCCGCATAG TTAAGCCAG
6616 TATACACTC CGCTATCGC TACGTGACT GGGTCATGG CTGCGCCCC
6661 GACACCCGC CAACACCCG CTGACGCGC CCTGACGGG CTTGTCTGC
6706 TCCCGGCAT CCGCTTACA GACAAGCTG TGACCGTCT CCGGGAGCT
6751 GCATGTGTC AGAGGTTTT CACCGTCAT CACCGAAAC GCGCGAGGC
6796 AGCTGCGGT AAAGCTCAT CAGCGTGGT CGTGCAGCG ATTCACAGA
6841 TGTCTGCCT GTTCATCCG CGTCCAGCT CGTTGAGTT TCTCCAGAA
6886 GCGTTAATG TCTGGCTTC TGATAAAGC GGGCCATGT TAAGGGCGG
6931 TTTTTTCCT GTTTGGTCA CTGATGCCT CCGTGTAAG GGGGATTTC
6976 TGTTCATGG GGGTAATGA TACCGATGA AACGAGAGA GGATGCTCA
7021 CGATACGGG TTACTGATG ATGAACATG CCCGGTTAC TGGAACGTT
7066 GTGAGGGTA AACAACTGG CGGTATGGA TGCGGCGGG ACCAGAGAA
7111 AAATCACTC AGGGTCAAT GCCAGCGCT TCGTTAATA CAGATGTAG
7156 GTGTTCCAC AGGGTAGCC AGCAGCATC CTGCGATGC AGATCCGGA
7201 ACATAATGG TGCAGGGCG CTGACTTCC GCGTTTCCA GACTTTACG
7246 AAACACGGA AACCGAAGA CCATTCATG TTGTTGCTC AGGTCGCAG
7291 ACGTTTGC AGCAGCAGT CGCTTCACG TTCGCTCGC GTATCGGTG
7336 ATTCATTCT GCTAACCAG TAAGGCAAC CCGCCAGC CTAGCCGGG
7381 TCCTCAACG ACAGGAGCA CGATCATGC GCACCCGTG GCCAGGACC
7426 CAACGCTGC CCGAAATT
```

FIG.8D

ToxoP30del1C(52-324aa)

```
        LeuValAla  AsnGlnVal  ValThrCys  ProAspLys  LysSerThr
  1     CTTGTTGCC  AATCAAGTT  GTCACCTGC  CCAGATAAA  AAATCGACA
        AlaAlaVal  IleLeuThr  ProThrGlu  AsnHisPhe  ThrLeuLys
 46     GCCGCGGTC  ATTCTCACA  CCGACGGAG  AACCACTTC  ACTCTCAAG
        CysProLys  ThrAlaLeu  ThrGluPro  ProThrLeu  AlaTyrSer
 91     TGCCCTAAA  ACAGCGCTC  ACAGAGCCT  CCCACTCTT  GCGTACTCA
        ProAsnArg  GlnIleCys  ProAlaGly  ThrThrSer  SerCysThr
136     CCCAACAGG  CAAATCTGC  CCAGCGGGT  ACTACAAGT  AGCTGTACA
        SerLysAla  ValThrLeu  SerSerLeu  IleProGlu  AlaGluAsp
181     TCAAAGGCT  GTAACATTG  AGCTCCTTG  ATTCCTGAA  GCAGAAGAT
        SerTrpTrp  ThrGlyAsp  SerAlaSer  LeuAspThr  AlaGlyIle
226     AGCTGGTGG  ACGGGGGAT  TCTGCTAGT  CTCGACACG  GCAGGCATC
        LysLeuThr  ValProIle  GluLysPhe  ProValThr  ThrGlnThr
271     AAACTCACA  GTTCCAATC  GAGAAGTTC  CCCGTGACA  ACGCAGACG
        PheValVal  GlyCysIle  LysGlyAsp  AspAlaGln  SerCysMet
316     TTTGTGGTC  GGTTGCATC  AAGGGAGAC  GACGCACAG  AGTTGTATG
        ValThrVal  ThrValGln  AlaArgAla  SerSerVal  ValAsnAsn
361     GTCACAGTG  ACAGTACAA  GCCAGAGCC  TCATCGGTC  GTCAATAAT
        ValAlaArg  CysSerTyr  GlyAlaAsp  SerThrLeu  GlyProVal
406     GTCGCAAGG  TGCTCCTAC  GGTGCAGAC  AGCACTCTT  GGTCCTGTC
        LysLeuSer  AlaGluGly  ProThrThr  MetThrLeu  ValCysGly
451     AAGTTGTCT  GCGGAAGGA  CCCACTACA  ATGACCCTC  GTGTGCGGG
        LysAspGly  ValLysVal  ProGlnAsp  AsnAsnGln  TyrCysSer
496     AAAGATGGA  GTCAAAGTT  CCTCAAGAC  AACAATCAG  TACTGTTCC
        GlyThrThr  LeuThrGly  CysAsnGlu  LysSerPhe  LysAspIle
541     GGGACGACG  CTGACTGGT  TGCAACGAG  AAATCGTTC  AAAGATATT
        LeuProLys  LeuThrGlu  AsnProTrp  GlnGlyAsn  AlaSerSer
586     TTGCCAAAA  TTAACTGAG  AACCCGTGG  CAGGGTAAC  GCTTCGAGT
        AspLysGly  AlaThrLeu  ThrIleLys  LysGluAla  PheProAla
631     GATAAGGGT  GCCACGCTA  ACGATCAAG  AAGGAAGCA  TTTCCAGCC
        GluSerLys  SerValIle  IleGlyCys  ThrGlyGly  SerProGlu
676     GAGTCAAAA  AGCGTCATT  ATTGGATGC  ACAGGGGGA  TCGCCTGAG
        LysHisHis  CysThrVal  LysLeuGlu  PheAlaGly  AlaAlaGly
721     AAGCATCAC  TGTACCGTG  AAACTGGAG  TTTGCCGGG  GCTGCAGGG
        SerAlaLys  SerAlaAla  GlyThrAla  SerHisVal  SerIlePhe
766     TCAGCAAAA  TCGGCTGCG  GGAACAGCC  AGTCACGTT  TCCATTTTT
        AlaMetVal
811     GCCATGGTG
```

FIG.9 pMBP-c2X-ToxoP30del2(52-311aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                   Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG. 11 pMBP-c2X-ToxoP30del2(52-311aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.11A pMBP-c2X-ToxoP30del2(52-311aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValCysGly
3151 AAGTTGTCT GCGGAAGGA CCCACTACA ATGACCCTC GTGTGCGGG
     LysAspGly ValLysVal ProGlnAsp AsnAsnGln TyrCysSer
3196 AAAGATGGA GTCAAAGTT CCTCAAGAC AACAATCAG TACTGTTCC
     GlyThrThr LeuThrGly CysAsnGlu LysSerPhe LysAspIle
3241 GGGACGACG CTGACTGGT TGCAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyCys ThrGlyGly SerProGlu
3376 GAGTCAAAA AGCGTCATT ATTGGATGC ACAGGGGGA TCGCCTGAG
     LysHisHis CysThrVal LysLeuGlu PheAlaGly AlaAlaGly
3421 AAGCATCAC TGTACCGTG AAACTGGAG TTTGCCGGG GCTGCAGGG
     SerAlaLys SerAla
3466 TCAGCAAAA TCGGCTTGA AAGCTTGGC ACTGGCCGT CGTTTTACA
3511 ACGTCGTGA CTGGGAAAA CCCTGGCGT TACCCAACT TAATCGCCT
3556 TGCAGCACA TCCCCCTTT CGCCAGCTG GCGTAATAG CGAAGAGGC
3601 CCGCACCGA TCGCCCTTC CAACAGTT GCGCAGCCT GAATGGCGA
3646 ATGGCAGCT TGGCTGTTT TGGCGGATG AGATAAGAT TTTCAGCCT
3691 GATACAGAT TAAATCAGA ACGCAGAAG CGGTCTGAT AAAACAGAA
3736 TTTGCCTGG CGGCAGTAG CGCGGTGGT CCCACCTGA CCCCATGCC
3781 GAACTCAGA AGTGAAACG CCGTAGCGC CGATGGTAG TGTGGGGTC
3826 TCCCCATGC GAGAGTAGG GAACTGCCA GGCATCAAA TAAAACGAA
3871 AGGCTCAGT CGAAAGACT GGGCCTTTC GTTTTATCT GTTGTTTGT
3916 CGGTGAACG CTCTCCTGA GTAGGACAA ATCCGCCGG GAGCGGATT
3961 TGAACGTTG CGAAGCAAC GGCCCGGAG GGTGGCGGG CAGGACGCC
4006 CGCCATAAA CTGCCAGGC ATCAAATTA AGCAGAAGG CCATCCTGA
4051 CGGATGGCC TTTTGCGT TTCTACAAA CTCTTTTTG TTTATTTTT
4096 CTAAATACA TTCAAATAT GTATCCGCT CATGAGACA ATAACCCTG
4141 ATAAATGCT TCAATAATA TTGAAAAAG GAAGAGTAT GAGTATTCA
```

FIG. 11B pMBP-c2X-ToxoP30del2(52-311aa)

```
4186  ACATTTCCG TGTCGCCCT TATTCCCTT TTTTGCGGC ATTTTGCCT
4231  TCCTGTTTT TGCTCACCC AGAAACGCT GGTGAAAGT AAAAGATGC
4276  TGAAGATCA GTTGGGTGC ACGAGTGGG TTACATCGA ACTGGATCT
4321  CAACAGCGG TAAGATCCT TGAGAGTTT CGCCCCGA AGAACGTTC
4366  TCCAATGAT GAGCACTTT TAAAGTTCT GCTATGTGG CGCGGTATT
4411  ATCCCGTGT TGACGCCGG GCAAGAGCA ACTCGGTCG CCGCATACA
4456  CTATTCTCA GAATGACTT GGTTGAGTA CTCACCAGT CACAGAAAA
4501  GCATCTTAC GGATGGCAT GACAGTAAG AGAATTATG CAGTGCTGC
4546  CATAACCAT GAGTGATAA CACTGCGGC CAACTTACT TCTGACAAC
4591  GATCGGAGG ACCGAAGGA GCTAACCGC TTTTTTGCA CAACATGGG
4636  GGATCATGT AACTCGCCT TGATCGTTG GGAACCGGA GCTGAATGA
4681  AGCCATACC AAACGACGA GCGTGACAC CACGATGCC TGTAGCAAT
4726  GGCAACAAC GTTGCGCAA ACTATTAAC TGGCGAACT ACTTACTCT
4771  AGCTTCCCG GCAACAATT AATAGACTG GATGGAGGC GGATAAAGT
4816  TGCAGGACC ACTTCTGCG CTCGGCCCT TCCGGCTGG CTGGTTTAT
4861  TGCTGATAA ATCTGGAGC CGGTGAGCG TGGGTCTCG CGGTATCAT
4906  TGCAGCACT GGGGCCAGA TGGTAAGCC CTCCCGTAT CGTAGTTAT
4951  CTACACGAC GGGGAGTCA GGCAACTAT GGATGAACG AAATAGACA
4996  GATCGCTGA GATAGGTGC CTCACTGAT TAAGCATTG GTAACTGTC
5041  AGACCAAGT TTACTCATA TATACTTTA GATTGATTT ACCCCGGTT
5086  GATAATCAG AAAAGCCCC AAAAACAGG AAGATTGTA TAAGCAAAT
5131  ATTTAAATT GTAAACGTT AATATTTTG TTAAAATTC GCGTTAAAT
5176  TTTTGTTAA ATCAGCTCA TTTTTTAAC CAATAGGCC GAAATCGGC
5221  AAAATCCCT TATAAATCA AAAGAATAG ACCGAGATA GGGTTGAGT
5266  GTTGTTCCA GTTTGGAAC AAGAGTCCA CTATTAAAG AACGTGGAC
5311  TCCAACGTC AAAGGGCGA AAAACCGTC TATCAGGGC GATGGCCCA
5356  CTACGTGAA CCATCACCC AAATCAAGT TTTTTGGGG TCGAGGTGC
5401  CGTAAAGCA CTAAATCGG AACCCTAAA GGGAGCCCC CGATTTAGA
5446  GCTTGACGG GGAAAGCCG GCGAACGTG GCGAGAAAG GAAGGGAAG
5491  AAAGCGAAA GGAGCGGGC GCTAGGGCG CTGGCAAGT GTAGCGGTC
5536  ACGCTGCGC GTAACCACC ACACCCGCC GCGCTTAAT GCGCCGCTA
5581  CAGGGCGCG TAAAAGGAT CTAGGTGAA GATCCTTTT TGATAATCT
5626  CATGACCAA AATCCCTTA ACGTGAGTT TTCGTTCCA CTGAGCGTC
5671  AGACCCCGT AGAAAAGAT CAAAGGATC TTCTTGAGA TCCTTTTTT
5716  TCTGCGCGT AATCTGCTG CTTGCAAAC AAAAAAACC ACCGCTACC
5761  AGCGGTGGT TTGTTTGCC GGATCAAGA GCTACCAAC TCTTTTTCC
5806  GAAGGTAAC TGGCTTCAG CAGAGCGCA GATACCAAA TACTGTCCT
5851  TCTAGTGTA GCCGTAGTT AGGCCACCA CTTCAAGAA CTCTGTAGC
5896  ACCGCCTAC ATACCTCGC TCTGCTAAT CCTGTTACC AGTGGCTGC
5941  TGCCAGTGG CGATAAGTC GTGTCTTAC CGGGTTGGA CTCAAGACG
5986  ATAGTTACC GGATAAGGC GCAGCGGTC GGGCTGAAC GGGGGGTTC
6031  GTGCACACA GCCCAGCTT GGAGCGAAC GACCTACAC CGAACTGAG
6076  ATACCTACA GCGTGAGCT ATGAGAAAG CGCCACGCT TCCCGAAGG
6121  GAGAAAGGC GGACAGGTA TCCGGTAAG CGGCAGGGT CGGAACAGG
6166  AGAGCGCAC GAGGGAGCT TCCAGGGGG AAACGCCTG GTATCTTTA
6211  TAGTCCTGT CGGGTTTCG CCACCTCTG ACTTGAGCG TCGATTTTT
```

FIG.11C pMBP-c2X-ToxoP30del2(52-311aa)

```
6256  GTGATGCTC GTCAGGGGG GCGGAGCCT ATGGAAAAA CGCCAGCAA
6301  CGCGGCCTT TTTACGGTT CCTGGCCTT TTGCTGGCC TTTTGCTCA
6346  CATGTTCTT TCCTGCGTT ATCCCCTGA TTCTGTGGA TAACCGTAT
6391  TACCGCCTT TGAGTGAGC TGATACCGC TCGCCGCAG CCGAACGAC
6436  CGAGCGCAG CGAGTCAGT GAGCGAGGA AGCGGAAGA GCGCCTGAT
6481  GCGGTATTT TCTCCTTAC GCATCTGTG CGGTATTTC ACACCGCAT
6526  ATATGGTGC ACTCTCAGT ACAATCTGC TCTGATGCC GCATAGTTA
6571  AGCCAGTAT ACACTCCGC TATCGCTAC GTGACTGGG TCATGGCTG
6616  CGCCCCGAC ACCCGCCAA CACCCGCTG ACGCGCCCT GACGGGCTT
6661  GTCTGCTCC CGGCATCCG CTTACAGAC AAGCTGTGA CCGTCTCCG
6706  GGAGCTGCA TGTGTCAGA GGTTTTCAC CGTCATCAC CGAAACGCG
6751  CGAGGCAGC TGCGGTAAA GCTCATCAG CGTGGTCGT GCAGCGATT
6796  CACAGATGT CTGCCTGTT CATCCGCGT CCAGCTCGT TGAGTTTCT
6841  CCAGAAGCG TTAATGTCT GGCTTCTGA TAAAGCGGG CCATGTTAA
6886  GGGCGGTTT TTTCCTGTT TGGTCACTG ATGCCTCCG TGTAAGGGG
6931  GATTTCTGT TCATGGGGG TAATGATAC CGATGAAAC GAGAGAGGA
6976  TGCTCACGA TACGGGTTA CTGATGATG AACATGCCC GGTTACTGG
7021  AACGTTGTG AGGGTAAAC AACTGGCGG TATGGATGC GGCGGGACC
7066  AGAGAAAAA TCACTCAGG GTCAATGCC AGCGCTTCG TTAATACAG
7111  ATGTAGGTG TTCCACAGG GTAGCCAGC AGCATCCTG CGATGCAGA
7156  TCCGGAACA TAATGGTGC AGGGCGCTG ACTTCCGCG TTTCCAGAC
7201  TTTACGAAA CACGGAAAC CGAAGACCA TTCATGTTG TTGCTCAGG
7246  TCGCAGACG TTTTGCAGC AGCAGTCGC TTCACGTTC GCTCGCGTA
7291  TCGGTGATT CATTCTGCT AACCAGTAA GGCAACCCC GCCAGCCTA
7336  GCCGGGTCC TCAACGACA GGAGCACGA TCATGCGCA CCCGTGGCC
7381  AGGACCCAA CGCTGCCCG AAATT
```

FIG.11D

ToxoP30del2(52-311aa)

```
          LeuValAla  AsnGlnVal  ValThrCys  ProAspLys  LysSerThr
  1       CTTGTTGCC  AATCAAGTT  GTCACCTGC  CCAGATAAA  AAATCGACA
          AlaAlaVal  IleLeuThr  ProThrGlu  AsnHisPhe  ThrLeuLys
 46       GCCGCGGTC  ATTCTCACA  CCGACGGAG  AACCACTTC  ACTCTCAAG
          CysProLys  ThrAlaLeu  ThrGluPro  ProThrLeu  AlaTyrSer
 91       TGCCCTAAA  ACAGCGCTC  ACAGAGCCT  CCCACTCTT  GCGTACTCA
          ProAsnArg  GlnIleCys  ProAlaGly  ThrThrSer  SerCysThr
136       CCCAACAGG  CAAATCGC   CCAGCGGGT  ACTACAAGT  AGCTGTACA
          SerLysAla  ValThrLeu  SerSerLeu  IleProGlu  AlaGluAsp
181       TCAAAGGCT  GTAACATTG  AGCTCCTTG  ATTCCTGAA  GCAGAAGAT
          SerTrpTrp  ThrGlyAsp  SerAlaSer  LeuAspThr  AlaGlyIle
226       AGCTGGTGG  ACGGGGGAT  TCTGCTAGT  CTCGACACG  GCAGGCATC
          LysLeuThr  ValProIle  GluLysPhe  ProValThr  ThrGlnThr
271       AAACTCACA  GTTCCAATC  GAGAAGTTC  CCCGTGACA  ACGCAGACG
          PheValVal  GlyCysIle  LysGlyAsp  AspAlaGln  SerCysMet
316       TTTGTGGTC  GGTTGCATC  AAGGGAGAC  GACGCACAG  AGTTGTATG
          ValThrVal  ThrValGln  AlaArgAla  SerSerVal  ValAsnAsn
361       GTCACAGTG  ACAGTACAA  GCCAGAGCC  TCATCGGTC  GTCAATAAT
          ValAlaArg  CysSerTyr  GlyAlaAsp  SerThrLeu  GlyProVal
406       GTCGCAAGG  TGCTCCTAC  GGTGCAGAC  AGCACTCTT  GGTCCTGTC
          LysLeuSer  AlaGluGly  ProThrThr  MetThrLeu  ValCysGly
451       AAGTTGTCT  GCGGAAGGA  CCCACTACA  ATGACCCTC  GTGTGCGGG
          LysAspGly  ValLysVal  ProGlnAsp  AsnAsnGln  TyrCysSer
496       AAAGATGGA  GTCAAAGTT  CCTCAAGAC  AACAATCAG  TACTGTTCC
          GlyThrThr  LeuThrGly  CysAsnGlu  LysSerPhe  LysAspIle
541       GGGACGACG  CTGACTGGT  TGCAACGAG  AAATCGTTC  AAAGATATT
          LeuProLys  LeuThrGlu  AsnProTrp  GlnGlyAsn  AlaSerSer
586       TTGCCAAAA  TTAACTGAG  AACCCGTGG  CAGGGTAAC  GCTTCGAGT
          AspLysGly  AlaThrLeu  ThrIleLys  LysGluAla  PheProAla
631       GATAAGGGT  GCCACGCTA  ACGATCAAG  AAGGAAGCA  TTTCCAGCC
          GluSerLys  SerValIle  IleGlyCys  ThrGlyGly  SerProGlu
676       GAGTCAAAA  AGCGTCATT  ATTGGATGC  ACAGGGGGA  TCGCCTGAG
          LysHisHis  CysThrVal  LysLeuGlu  PheAlaGly  AlaAlaGly
721       AAGCATCAC  TGTACCGTG  AAACTGGAG  TTTGCCGGG  GCTGCAGGG
          SerAlaLys  SerAla
766       TCAGCAAAA  TCGGCT
```

FIG.12 pMBP-c2X-ToxoP30del3C(52-300aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                  Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG.15 pMBP-c2X-ToxoP30del3C(52-300aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.15A pMBP-c2X-ToxoP30del3C(52-300aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValCysGly
3151 AAGTTGTCT GCGGAAGGA CCCACTACA ATGACCCTC GTGTGCGGG
     LysAspGly ValLysVal ProGlnAsp AsnAsnGln TyrCysSer
3196 AAAGATGGA GTCAAAGTT CCTCAAGAC AACAATCAG TACTGTTCC
     GlyThrThr LeuThrGly CysAsnGlu LysSerPhe LysAspIle
3241 GGGACGACG CTGACTGGT TGCAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyCys ThrGlyGly SerProGlu
3376 GAGTCAAAA AGCGTCATT ATTGGATGC ACAGGGGGA TCGCCTGAG
     LysHisHis CysThrVal LysLeuGlu
3421 AAGCATCAC TGTACCGTG AAACTGGAG TGAAAGCTT GGCACTGGC
3466 CGTCGTTTT ACAACGTCG TGACTGGGA AAACCCTGG CGTTACCCA
3511 ACTTAATCG CCTTGCAGC ACATCCCCC TTTCGCCAG CTGGCGTAA
3556 TAGCGAAGA GGCCCGCAC CGATCGCCC TTCCCAACA GTTGCGCAG
3601 CCTGAATGG CGAATGGCA GCTTGGCTG TTTTGGCGG ATGAGATAA
3646 GATTTTCAG CCTGATACA GATTAAATC AGAACGCAG AAGCGGTCT
3691 GATAAAACA GAATTTGCC TGGCGGCAG TAGCGCGGT GGTCCCACC
3736 TGACCCCAT GCCGAACTC AGAAGTGAA ACGCCGTAG CGCCGATGG
3781 TAGTGTGGG GTCTCCCCA TGCGAGAGT AGGGAACTG CCAGGCATC
3826 AAATAAAAC GAAAGGCTC AGTCGAAAG ACTGGGCCT TTCGTTTTA
3871 TCTGTTGTT TGTCGGTGA ACGCTCTCC TGAGTAGGA CAAATCCGC
3916 CGGGAGCGG ATTTGAACG TTGCGAAGC AACGGCCCG GAGGGTGGC
3961 GGGCAGGAC GCCCGCCAT AAACTGCCA GGCATCAAA TTAAGCAGA
4006 AGGCCATCC TGACGGATG GCCTTTTTG CGTTTCTAC AAACTCTTT
4051 TTGTTTATT TTTCTAAAT ACATTCAAA TATGTATCC GCTCATGAG
4096 ACAATAACC CTGATAAAT GCTTCAATA ATATTGAAA AGGAAGAG
4141 TATGAGTAT TCAACATTT CCGTGTCGC CCTTATTCC CTTTTTTGC
4186 GGCATTTTG CCTTCCTGT TTTTGCTCA CCCAGAAAC GCTGGTGAA
```

FIG.15B pMBP-c2X-ToxoP30del3C(52-300aa)

```
4231 AGTAAAAGA TGCTGAAGA TCAGTTGGG TGCACGAGT GGGTTACAT
4276 CGAACTGGA TCTCAACAG CGGTAAGAT CCTTGAGAG TTTTCGCCC
4321 CGAAGAACG TTCTCCAAT GATGAGCAC TTTTAAAGT TCTGCTATG
4366 TGGCGCGGT ATTATCCCG TGTTGACGC CGGGCAAGA GCAACTCGG
4411 TCGCCGCAT ACACTATTC TCAGAATGA CTTGGTTGA GTACTCACC
4456 AGTCACAGA AAAGCATCT TACGGATGG CATGACAGT AAGAGAATT
4501 ATGCAGTGC TGCCATAAC CATGAGTGA TAACACTGC GGCCAACTT
4546 ACTTCTGAC AACGATCGG AGGACCGAA GGAGCTAAC CGCTTTTTT
4591 GCACAACAT GGGGGATCA TGTAACTCG CCTTGATCG TTGGGAACC
4636 GGAGCTGAA TGAAGCCAT ACCAAACGA CGAGCGTGA CACCACGAT
4681 GCCTGTAGC AATGGCAAC AACGTTGCG CAAACTATT AACTGGCGA
4726 ACTACTTAC TCTAGCTTC CCGGCAACA ATTAATAGA CTGGATGGA
4771 GGCGGATAA AGTTGCAGG ACCACTTCT GCGCTCGGC CCTTCCGGC
4816 TGGCTGGTT TATTGCTGA TAAATCTGG AGCCGGTGA GCGTGGGTC
4861 TCGCGGTAT CATTGCAGC ACTGGGGCC AGATGGTAA GCCCTCCCG
4906 TATCGTAGT TATCTACAC GACGGGGAG TCAGGCAAC TATGGATGA
4951 ACGAAATAG ACAGATCGC TGAGATAGG TGCCTCACT GATTAAGCA
4996 TTGGTAACT GTCAGACCA AGTTTACTC ATATATACT TTAGATTGA
5041 TTTACCCCG GTTGATAAT CAGAAAAGC CCCAAAAAC AGGAAGATT
5086 GTATAAGCA AATATTTAA ATTGTAAAC GTTAATATT TTGTTAAAA
5131 TTCGCGTTA AATTTTTGT TAAATCAGC TCATTTTTT AACCAATAG
5176 GCCGAAATC GGCAAAATC CCTTATAAA TCAAAAGAA TAGACCGAG
5221 ATAGGGTTG AGTGTTGTT CCAGTTTGG AACAAGAGT CCACTATTA
5266 AAGAACGTG GACTCCAAC GTCAAAGGG CGAAAAACC GTCTATCAG
5311 GGCGATGGC CCACTACGT GAACCATCA CCCAAATCA AGTTTTTTG
5356 GGGTCGAGG TGCCGTAAA GCACTAAAT CGGAACCCT AAAGGGAGC
5401 CCCCGATTT AGAGCTTGA CGGGGAAAG CCGGCGAAC GTGGCGAGA
5446 AAGGAAGGG AAGAAAGCG AAAGGAGCG GGCGCTAGG GCGCTGGCA
5491 AGTGTAGCG GTCACGCTG CGCGTAACC ACCACACCC GCCGCGCTT
5536 AATGCGCCG CTACAGGGC GCGTAAAAG GATCTAGGT GAAGATCCT
5581 TTTTGATAA TCTCATGAC CAAAATCCC TTAACGTGA GTTTTCGTT
5626 CCACTGAGC GTCAGACCC CGTAGAAAA GATCAAAGG ATCTTCTTG
5671 AGATCCTTT TTTTCTGCG CGTAATCTG CTGCTTGCA AACAAAAAA
5716 ACCACCGCT ACCAGCGGT GGTTTGTTT GCCGGATCA AGAGCTACC
5761 AACTCTTTT TCCGAAGGT AACTGGCTT CAGCAGAGC GCAGATACC
5806 AAATACTGT CCTTCTAGT GTAGCCGTA GTTAGGCCA CCACTTCAA
5851 GAACTCTGT AGCACCGCC TACATACCT CGCTCTGCT AATCCTGTT
5896 ACCAGTGGC TGCTGCCAG TGGCGATAA GTCGTGTCT TACCGGGTT
5941 GGACTCAAG ACGATAGTT ACCGGATAA GGCGCAGCG GTCGGGCTG
5986 AACGGGGGG TTCGTGCAC ACAGCCCAG CTTGGAGCG AACGACCTA
6031 CACCGAACT GAGATACCT ACAGCGTGA GCTATGAGA AAGCGCCAC
6076 GCTTCCCGA AGGGAGAAA GGCGGACAG GTATCCGGT AAGCGGCAG
6121 GGTCGGAAC AGGAGAGCG CACGAGGGA GCTTCCAGG GGGAAACGC
6166 CTGGTATCT TTATAGTCC TGTCGGGTT TCGCCACCT CTGACTTGA
6211 GCGTCGATT TTTGTGATG CTCGTCAGG GGGGCGGAG CCTATGGAA
6256 AAACGCCAG CAACGCGGC CTTTTTACG GTTCCTGGC CTTTTGCTG
```

FIG. 15C pMBP-c2X-ToxoP30del3C(52-300aa)

```
6301  GCCTTTTGC TCACATGTT CTTTCCTGC GTTATCCCC TGATTCTGT
6346  GGATAACCG TATTACCGC CTTTGAGTG AGCTGATAC CGCTCGCCG
6391  CAGCCGAAC GACCGAGCG CAGCGAGTC AGTGAGCGA GGAAGCGGA
6436  AGAGCGCCT GATGCGGTA TTTTCTCCT TACGCATCT GTGCGGTAT
6481  TTCACACCG CATATATGG TGCACTCTC AGTACAATC TGCTCTGAT
6526  GCCGCATAG TTAAGCCAG TATACACTC CGCTATCGC TACGTGACT
6571  GGGTCATGG CTGCGCCCC GACACCCGC CAACACCCG CTGACGCGC
6616  CCTGACGGG CTTGTCTGC TCCCGGCAT CCGCTTACA GACAAGCTG
6661  TGACCGTCT CCGGGAGCT GCATGTGTC AGAGGTTTT CACCGTCAT
6706  CACCGAAAC GCGCGAGGC AGCTGCGGT AAAGCTCAT CAGCGTGGT
6751  CGTGCAGCG ATTCACAGA TGTCTGCCT GTTCATCCG CGTCCAGCT
6796  CGTTGAGTT CTCCAGAA GCGTTAATG TCTGGCTTC TGATAAAGC
6841  GGGCCATGT TAAGGGCGG TTTTTTCCT GTTTGGTCA CTGATGCCT
6886  CCGTGTAAG GGGGATTTC TGTTCATGG GGTAATGA TACCGATGA
6931  AACGAGAGA GGATGCTCA CGATACGGG TTACTGATG ATGAACATG
6976  CCCGGTTAC TGGAACGTT GTGAGGGTA ACAACTGG CGGTATGGA
7021  TGCGGCGGG ACCAGAGAA AAATCACTC AGGGTCAAT GCCAGCGCT
7066  TCGTTAATA CAGATGTAG GTGTTCCAC AGGGTAGCC AGCAGCATC
7111  CTGCGATGC AGATCCGGA ACATAATGG TGCAGGGCG CTGACTTCC
7156  GCGTTTCCA GACTTTACG AAACACGGA AACCGAAGA CCATTCATG
7201  TTGTTGCTC AGGTCGCAG ACGTTTGC AGCAGCAGT CGCTTCACG
7246  TTCGCTCGC GTATCGGTG ATTCATTCT GCTAACCAG TAAGGCAAC
7291  CCCGCCAGC CTAGCCGGG TCCTCAACG ACAGGAGCA CGATCATGC
7336  GCACCCGTG GCCAGGACC CAACGCTGC CCGAAATT
```

FIG.15D

ToxoP30del3C(52-300aa)

```
        LeuValAla AsnGlnVal ValThrCys ProAspLys LysSerThr
  1     CTTGTTGCC AATCAAGTT GTCACCTGC CCAGATAAA AAATCGACA
        AlaAlaVal IleLeuThr ProThrGlu AsnHisPhe ThrLeuLys
 46     GCCGCGGTC ATTCTCACA CCGACGGAG AACCACTTC ACTCTCAAG
        CysProLys ThrAlaLeu ThrGluPro ProThrLeu AlaTyrSer
 91     TGCCCTAAA ACAGCGCTC ACAGAGCCT CCCACTCTT GCGTACTCA
        ProAsnArg GlnIleCys ProAlaGly ThrThrSer SerCysThr
136     CCCAACAGG CAAATCTGC CCAGCGGGT ACTACAAGT AGCTGTACA
        SerLysAla ValThrLeu SerSerLeu IleProGlu AlaGluAsp
181     TCAAAGGCT GTAACATTG AGCTCCTTG ATTCCTGAA GCAGAAGAT
        SerTrpTrp ThrGlyAsp SerAlaSer LeuAspThr AlaGlyIle
226     AGCTGGTGG ACGGGGGAT TCTGCTAGT CTCGACACG GCAGGCATC
        LysLeuThr ValProIle GluLysPhe ProValThr ThrGlnThr
271     AAACTCACA GTTCCAATC GAGAAGTTC CCCGTGACA ACGCAGACG
        PheValVal GlyCysIle LysGlyAsp AspAlaGln SerCysMet
316     TTTGTGGTC GGTTGCATC AAGGGAGAC GACGCACAG AGTTGTATG
        ValThrVal ThrValGln AlaArgAla SerSerVal ValAsnAsn
361     GTCACAGTG ACAGTACAA GCCAGAGCC TCATCGGTC GTCAATAAT
        ValAlaArg CysSerTyr GlyAlaAsp SerThrLeu GlyProVal
406     GTCGCAAGG TGCTCCTAC GGTGCAGAC AGCACTCTT GGTCCTGTC
        LysLeuSer AlaGluGly ProThrThr MetThrLeu ValCysGly
451     AAGTTGTCT GCGGAAGGA CCCACTACA ATGACCCTC GTGTGCGGG
        LysAspGly ValLysVal ProGlnAsp AsnAsnGln TyrCysSer
496     AAAGATGGA GTCAAAGTT CCTCAAGAC AACAATCAG TACTGTTCC
        GlyThrThr LeuThrGly CysAsnGlu LysSerPhe LysAspIle
541     GGGACGACG CTGACTGGT TGCAACGAG AAATCGTTC AAAGATATT
        LeuProLys LeuThrGlu AsnProTrp GlnGlyAsn AlaSerSer
586     TTGCCAAAA TTAACTGAG AACCCGTGG CAGGGTAAC GCTTCGAGT
        AspLysGly AlaThrLeu ThrIleLys LysGluAla PheProAla
631     GATAAGGGT GCCACGCTA ACGATCAAG AAGGAAGCA TTTCCAGCC
        GluSerLys SerValIle IleGlyCys ThrGlyGly SerProGlu
676     GAGTCAAAA AGCGTCATT ATTGGATGC ACAGGGGGA TCGCCTGAG
        L pMBP-c2X-ToxoP30del4C(52-294aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                 Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG.19 pMBP-c2X-ToxoP30del4C(52-294aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG AAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.19A pMBP-c2X-ToxoP30del4C(52-294aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValCysGly
3151 AAGTTGTCT GCGGAAGGA CCCACTACA ATGACCCTC GTGTGCGGG
     LysAspGly ValLysVal ProGlnAsp AsnAsnGln TyrCysSer
3196 AAAGATGGA GTCAAAGTT CCTCAAGAC AACAATCAG TACTGTTCC
     GlyThrThr LeuThrGly CysAsnGlu LysSerPhe LysAspIle
3241 GGGACGACG CTGACTGGT TGCAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyCys ThrGlyGly SerProGlu
3376 GAGTCAAAA AGCGTCATT ATTGGATGC ACAGGGGGA TCGCCTGAG
     LysHisHis
3421 AAGCATCAC TGAAAGCTT GGCACTGGC CGTCGTTTT ACAACGTCG
3466 TGACTGGGA AAACCCTGG CGTTACCCA ACTTAATCG CCTTGCAGC
3511 ACATCCCCC TTTCGCCAG CTGGCGTAA TAGCGAAGA GGCCCGCAC
3556 CGATCGCCC TTCCCAACA GTTGCGCAG CCTGAATGG CGAATGGCA
3601 GCTTGGCTG TTTTGGCGG ATGAGATAA GATTTTCAG CCTGATACA
3646 GATTAAATC AGAACGCAG AAGCGGTCT GATAAAACA GAATTTGCC
3691 TGGCGGCAG TAGCGCGGT GGTCCCACC TGACCCCAT GCCGAACTC
3736 AGAAGTGAA ACGCCGTAG CGCCGATGG TAGTGTGGG GTCTCCCCA
3781 TGCGAGAGT AGGGAACTG CCAGGCATC AAATAAAAC GAAAGGCTC
3826 AGTCGAAAG ACTGGGCCT TTCGTTTTA TCTGTTGTT TGTCGGTGA
3871 ACGCTCTCC TGAGTAGGA CAAATCCGC CGGGAGCGG ATTTGAACG
3916 TTGCGAAGC AACGGCCCG GAGGGTGGC GGGCAGGAC GCCCGCCAT
3961 AAACTGCCA GGCATCAAA TTAAGCAGA AGGCCATCC TGACGGATG
4006 GCCTTTTTG CGTTTCTAC AAACTCTTT TTGTTTATT TTTCTAAAT
4051 ACATTCAAA TATGTATCC GCTCATGAG ACAATAACC CTGATAAAT
4096 GCTTCAATA ATATTGAAA AAGGAAGAG TATGAGTAT TCAACATTT
4141 CCGTGTCGC CCTTATTCC CTTTTTTGC GGCATTTTG CCTTCCTGT
4186 TTTTGCTCA CCCAGAAAC GCTGGTGAA AGTAAAAGA TGCTGAAGA
```

FIG.19B pMBP-c2X-ToxoP30del4C(52-294aa)

```
4231  TCAGTTGGG  TGCACGAGT  GGGTTACAT  CGAACTGGA  TCTCAACAG
4276  CGGTAAGAT  CCTTGAGAG  TTTTCGCCC  CGAAGAACG  TTCTCCAAT
4321  GATGAGCAC  TTTTAAAGT  TCTGCTATG  TGGCGCGGT  ATTATCCCG
4366  TGTTGACGC  CGGGCAAGA  GCAACTCGG  TCGCCGCAT  ACACTATTC
4411  TCAGAATGA  CTTGGTTGA  GTACTCACC  AGTCACAGA  AAAGCATCT
4456  TACGGATGG  CATGACAGT  AAGAGAATT  ATGCAGTGC  TGCCATAAC
4501  CATGAGTGA  TAACACTGC  GGCCAACTT  ACTTCTGAC  AACGATCGG
4546  AGGACCGAA  GGAGCTAAC  CGCTTTTTT  GCACAACAT  GGGGGATCA
4591  TGTAACTCG  CCTTGATCG  TTGGGAACC  GGAGCTGAA  TGAAGCCAT
4636  ACCAAACGA  CGAGCGTGA  CACCACGAT  GCCTGTAGC  AATGGCAAC
4681  AACGTTGCG  CAAACTATT  AACTGGCGA  ACTACTTAC  TCTAGCTTC
4726  CCGGCAACA  ATTAATAGA  CTGGATGGA  GGCGGATAA  AGTTGCAGG
4771  ACCACTTCT  GCGCTCGGC  CCTTCCGGC  TGGCTGGTT  TATTGCTGA
4816  TAAATCTGG  AGCCGGTGA  GCGTGGGTC  TCGCGGTAT  CATTGCAGC
4861  ACTGGGGCC  AGATGGTAA  GCCCTCCCG  TATCGTAGT  TATCTACAC
4906  GACGGGGAG  TCAGGCAAC  TATGGATGA  ACGAAATAG  ACAGATCGC
4951  TGAGATAGG  TGCCTCACT  GATTAAGCA  TTGGTAACT  GTCAGACCA
4996  AGTTTACTC  ATATATACT  TTAGATTGA  TTTACCCCG  GTTGATAAT
5041  CAGAAAAGC  CCCAAAAAC  AGGAAGATT  GTATAAGCA  AATATTTAA
5086  ATTGTAAAC  GTTAATATT  TTGTTAAAA  TTCGCGTTA  AATTTTTGT
5131  TAAATCAGC  TCATTTTTT  AACCAATAG  GCCGAAATC  GGCAAAATC
5176  CCTTATAAA  TCAAAAGAA  TAGACCGAG  ATAGGGTTG  AGTGTTGTT
5221  CCAGTTTGG  AACAAGAGT  CCACTATTA  AAGAACGTG  GACTCCAAC
5266  GTCAAAGGG  CGAAAAACC  GTCTATCAG  GGCGATGGC  CCACTACGT
5311  GAACCATCA  CCCAAATCA  AGTTTTTTG  GGGTCGAGG  TGCCGTAAA
5356  GCACTAAAT  CGGAACCCT  AAAGGGAGC  CCCCGATTT  AGAGCTTGA
5401  CGGGGAAAG  CCGGCGAAC  GTGGCGAGA  AAGGAAGGG  AAGAAAGCG
5446  AAAGGAGCG  GGCGCTAGG  GCGCTGGCA  AGTGTAGCG  GTCACGCTG
5491  CGCGTAACC  ACCACACCC  GCCGCGCTT  AATGCGCCG  CTACAGGGC
5536  GCGTAAAAG  GATCTAGGT  GAAGATCCT  TTTTGATAA  TCTCATGAC
5581  CAAAATCCC  TTAACGTGA  GTTTTCGTT  CCACTGAGC  GTCAGACCC
5626  CGTAGAAAA  GATCAAAGG  ATCTTCTTG  AGATCCTTT  TTTTCTGCG
5671  CGTAATCTG  CTGCTTGCA  AACAAAAAA  ACCACCGCT  ACCAGCGGT
5716  GGTTTGTTT  GCCGGATCA  AGAGCTACC  AACTCTTTT  TCCGAAGGT
5761  AACTGGCTT  CAGCAGAGC  GCAGATACC  AAATACTGT  CCTTCTAGT
5806  GTAGCCGTA  GTTAGGCCA  CCACTTCAA  GAACTCTGT  AGCACCGCC
5851  TACATACCT  CGCTCTGCT  AATCCTGTT  ACCAGTGGC  TGCTGCCAG
5896  TGGCGATAA  GTCGTGTCT  TACCGGGTT  GGACTCAAG  ACGATAGTT
5941  ACCGGATAA  GGCGCAGCG  GTCGGGCTG  AACGGGGGG  TTCGTGCAC
5986  ACAGCCCAG  CTTGGAGCG  AACGACCTA  CACCGAACT  GAGATACCT
6031  ACAGCGTGA  GCTATGAGA  AAGCGCCAC  GCTTCCCGA  AGGGAG pMBP-c2X-ToxoP30del4C(52-294aa)

```
6301  CTTTCCTGC GTTATCCCC TGATTCTGT GGATAACCG TATTACCGC
6346  CTTTGAGTG AGCTGATAC CGCTCGCCG CAGCCGAAC GACCGAGCG
6391  CAGCGAGTC AGTGAGCGA GGAAGCGGA AGAGCGCCT GATGCGGTA
6436  TTTTCTCCT TACGCATCT GTGCGGTAT TCACACCG CATATATGG
6481  TGCACTCTC AGTACAATC TGCTCTGAT GCCGCATAG TTAAGCCAG
6526  TATACACTC CGCTATCGC TACGTGACT GGGTCATGG CTGCGCCCC
6571  GACACCCGC CAACACCCG CTGACGCGC CCTGACGGG CTTGTCTGC
6616  TCCCGGCAT CCGCTTACA GACAAGCTG TGACCGTCT CCGGGAGCT
6661  GCATGTGTC AGAGGTTTT CACCGTCAT CACCGAAAC GCGCGAGGC
6706  AGCTGCGGT AAAGCTCAT CAGCGTGGT CGTGCAGCG ATTACAGA
6751  TGTCTGCCT GTTCATCCG CGTCCAGCT CGTTGAGTT CTCCAGAA
6796  GCGTTAATG TCTGGCTTC TGATAAAGC GGGCCATGT TAAGGGCGG
6841  TTTTTTCCT GTTTGGTCA CTGATGCCT CCGTGTAAG GGGGATTTC
6886  TGTTCATGG GGGTAATGA TACCGATGA AACGAGAGA GGATGCTCA
6931  CGATACGGG TTACTGATG ATGAACATG CCCGGTTAC TGGAACGTT
6976  GTGAGGGTA AACAACTGG CGGTATGGA TGCGGCGGG ACCAGAGAA
7021  AAATCACTC AGGGTCAAT GCCAGCGCT TCGTTAATA CAGATGTAG
7066  GTGTTCCAC AGGGTAGCC AGCAGCATC CTGCGATGC AGATCCGGA
7111  ACATAATGG TGCAGGGCG CTGACTTCC GCGTTTCCA GACTTTACG
7156  AAACACGGA AACCGAAGA CCATTCATG TTGTTGCTC AGGTCGCAG
7201  ACGTTTTGC AGCAGCAGT CGCTTCACG TTCGCTCGC GTATCGGTG
7246  ATTCATTCT GCTAACCAG TAAGGCAAC CCCGCCAGC CTAGCCGGG
7291  TCCTCAACG ACAGGAGCA CGATCATGC GCACCCGTG GCCAGGACC
7336  CAACGCTGC CCGAAATT
```

FIG.19D

ToxoP30del4C(52-294aa)

```
        LeuValAla AsnGlnVal ValThrCys ProAspLys LysSerThr
  1     CTTGTTGCC AATCAAGTT GTCACCTGC CCAGATAAA AAATCGACA
        AlaAlaVal IleLeuThr ProThrGlu AsnHisPhe ThrLeuLys
 46     GCCGCGGTC ATTCTCACA CCGACGGAG AACCACTTC ACTCTCAAG
        CysProLys ThrAlaLeu ThrGluPro ProThrLeu AlaTyrSer
 91     TGCCCTAAA ACAGCGCTC ACAGAGCCT CCCACTCTT GCGTACTCA
        ProAsnArg GlnIleCys ProAlaGly ThrThrSer SerCysThr
136     CCCAACAGG CAAATCTGC CCAGCGGGT ACTACAAGT AGCTGTACA
        SerLysAla ValThrLeu SerSerLeu IleProGlu AlaGluAsp
181     TCAAAGGCT GTAACATTG AGCTCCTTG ATTCCTGAA GCAGAAGAT
        SerTrpTrp ThrGlyAsp SerAlaSer LeuAspThr AlaGlyIle
226     AGCTGGTGG ACGGGGGAT TCTGCTAGT CTCGACACG GCAGGCATC
        LysLeuThr ValProIle GluLysPhe ProValThr ThrGlnThr
271     AAACTCACA GTTCCAATC GAGAAGTTC CCCGTGACA ACGCAGACG
        PheValVal GlyCysIle LysGlyAsp AspAlaGln SerCysMet
316     TTTGTGGTC GGTTGCATC AAGGGAGAC GACGCACAG AGTTGTATG
        ValThrVal ThrValGln AlaArgAla SerSerVal ValAsnAsn
361     GTCACAGTG ACAGTACAA GCCAGAGCC TCATCGGTC GTCAATAAT
        ValAlaArg CysSerTyr GlyAlaAsp SerThrLeu GlyProVal
406     GTCGCAAGG TGCTCCTAC GGTGCAGAC AGCACTCTT GGTCCTGTC
        LysLeuSer AlaGluGly ProThrThr MetThrLeu ValCysGly
451     AAGTTGTCT GCGGAAGGA CCCACTACA ATGACCCTC GTGTGCGGG
        LysAspGly ValLysVal ProGlnAsp AsnAsnGln TyrCysSer
496     AAAGATGGA GTCAAAGTT CCTCAAGAC AACAATCAG TACTGTTCC
        GlyThrThr LeuThrGly CysAsnGlu LysSerPhe LysAspIle
541     GGGACGACG CTGACTGGT TGCAACGAG AAATCGTTC AAAGATATT
        LeuProLys LeuThrGlu AsnProTrp GlnGlyAsn AlaSerSer
586     TTGCCAAAA TTAACTGAG AACCCGTGG CAGGGTAAC GCTTCGAGT
        AspLysGly AlaThrLeu ThrIleLys LysGluAla PheProAla
631     GATAAGGGT GCCACGCTA ACGATCAAG AAGGAAGCA TTTCCAGCC
        GluSerLys SerValIle IleGlyCys ThrGlyGly SerProGlu
676     GAGTCAAAA AGCGTCATT ATTGGATGC ACAGGGGGA TCGCCTGAG
        LysHisHis
721     AAGCATCAC
```

FIG.20 pMBP-c2X-ToxoP30del4del8(83-294aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                   Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG.22 pMBP-c2X-ToxoP30del4del8(83-294aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     ProLysThr AlaLeuThr GluProPro ThrLeuAla TyrSerPro
2701 CCTAAAACA GCGCTCACA GAGCCTCCC ACTCTTGCG TACTCACCC
     AsnArgGln IleCysPro AlaGlyThr ThrSerSer CysThrSer
2746 AACAGGCAA ATCTGCCCA GCGGGTACT ACAAGTAGC TGTACATCA
     LysAlaVal ThrLeuSer SerLeuIle ProGluAla GluAspSer
```

FIG.22A pMBP-c2X-ToxoP30del4del8(83-294aa)

```
2791 AAGGCTGTA ACATTGAGC TCCTTGATT CCTGAAGCA GAAGATAGC
     TrpTrpThr GlyAspSer AlaSerLeu AspThrAla GlyIleLys
2836 TGGTGGACG GGGGATTCT GCTAGTCTC GACACGGCA GGCATCAAA
     LeuThrVal ProIleGlu LysPhePro ValThrThr GlnThrPhe
2881 CTCACAGTT CCAATCGAG AAGTTCCCC GTGACAACG CAGACGTTT
     ValValGly CysIleLys GlyAspAsp AlaGlnSer CysMetVal
2926 GTGGTCGGT TGCATCAAG GGAGACGAC GCACAGAGT TGTATGGTC
     ThrValThr ValGlnAla ArgAlaSer SerValVal AsnAsnVal
2971 ACAGTGACA GTACAAGCC AGAGCCTCA TCGGTCGTC AATAATGTC
     AlaArgCys SerTyrGly AlaAspSer ThrLeuGly ProValLys
3016 GCAAGGTGC TCCTACGGT GCAGACAGC ACTCTTGGT CCTGTCAAG
     LeuSerAla GluGlyPro ThrThrMet ThrLeuVal CysGlyLys
3061 TTGTCTGCG GAAGGACCC ACTACAATG ACCCTCGTG TGCGGGAAA
     AspGlyVal LysValPro GlnAspAsn AsnGlnTyr CysSerGly
3106 GATGGAGTC AAAGTTCCT CAAGACAAC AATCAGTAC TGTTCCGGG
     ThrThrLeu ThrGlyCys AsnGluLys SerPheLys AspIleLeu
3151 ACGACGCTG ACTGGTTGC AACGAGAAA TCGTTCAAA GATATTTTG
     ProLysLeu ThrGluAsn ProTrpGln GlyAsnAla SerSerAsp
3196 CCAAAATTA ACTGAGAAC CCGTGGCAG GGTAACGCT TCGAGTGAT
     LysGlyAla ThrLeuThr IleLysLys GluAlaPhe ProAlaGlu
3241 AAGGGTGCC ACGCTAACG ATCAAGAAG GAAGCATTT CCAGCCGAG
     SerLysSer ValIleIle GlyCysThr GlyGlySer ProGluLys
3286 TCAAAAAGC GTCATTATT GGATGCACA GGGGGATCG CCTGAGAAG
     HisHis
3331 CATCACTGA AAGCTTGGC ACTGGCCGT CGTTTTACA ACGTCGTGA
3376 CTGGGAAAA CCCTGGCGT TACCCAACT TAATCGCCT TGCAGCACA
3421 TCCCCCTTT CGCCAGCTG GCGTAATAG CGAAGAGGC CCGCACCGA
3466 TCGCCCTTC CCAACAGTT GCGCAGCCT GAATGGCGA ATGGCAGCT
3511 TGGCTGTTT TGGCGGATG AGATAAGAT TTTCAGCCT GATACAGAT
3556 TAAATCAGA ACGCAGAAG CGGTCTGAT AAAACAGAA TTTGCCTGG
3601 CGGCAGTAG CGCGGTGGT CCCACCTGA CCCCATGCC GAACTCAGA
3646 AGTGAAACG CCGTAGCGC CGATGGTAG TGTGGGGTC TCCCCATGC
3691 GAGAGTAGG GAACTGCCA GGCATCAAA TAAAACGAA AGGCTCAGT
3736 CGAAAGACT GGGCCTTTC GTTTTATCT GTTGTTTGT CGGTGAACG
3781 CTCTCCTGA GTAGGACAA ATCCGCCGG GAGCGGATT TGAACGTTG
3826 CGAAGCAAC GGCCCGGAG GGTGGCGGG CAGGACGCC CGCCATAAA
3871 CTGCCAGGC ATCAAATTA AGCAGAAGG CCATCCTGA CGGATGGCC
3916 TTTTTGCGT TTCTACAAA CTCTTTTTG TTTATTTTT CTAAATACA
3961 TTCAAATAT GTATCCGCT CATGAGACA ATAACCCTG ATAAATGCT
4006 TCAATAATA TTGAAAAAG GAAGAGTAT GAGTATTCA ACATTTCCG
4051 TGTCGCCCT TATTCCCTT TTTTGCGGC ATTTTGCCT TCCTGTTTT
4096 TGCTCACCC AGAAACGCT GGTGAAAGT AAAAGATGC TGAAGATCA
4141 GTTGGGTGC ACGAGTGGG TTACATCGA ACTGGATCT CAACAGCGG
4186 TAAGATCCT TGAGAGTTT TCGCCCCGA AGAACGTTC TCCAATGAT
4231 GAGCACTTT TAAAGTTCT GCTATGTGG CGCGGTATT ATCCCGTGT
4276 TGACGCCGG GCAAGAGCA ACTCGGTCG CCGCATACA CTATTCTCA
```

FIG.22B pMBP-c2X-ToxoP30del4del8(83-294aa)

```
4321 GAATGACTT GGTTGAGTA CTCACCAGT CACAGAAAA GCATCTTAC
4366 GGATGGCAT GACAGTAAG AGAATTATG CAGTGCTGC CATAACCAT
4411 GAGTGATAA CACTGCGGC CAACTTACT TCTGACAAC GATCGGAGG
4456 ACCGAAGGA GCTAACCGC TTTTTTGCA CAACATGGG GGATCATGT
4501 AACTCGCCT TGATCGTTG GGAACCGGA GCTGAATGA AGCCATACC
4546 AAACGACGA GCGTGACAC CACGATGCC TGTAGCAAT GGCAACAAC
4591 GTTGCGCAA ACTATTAAC TGGCGAACT ACTTACTCT AGCTTCCCG
4636 GCAACAATT AATAGACTG GATGGAGGC GGATAAAGT TGCAGGACC
4681 ACTTCTGCG CTCGGCCCT TCCGGCTGG CTGGTTTAT TGCTGATAA
4726 ATCTGGAGC CGGTGAGCG TGGGTCTCG CGGTATCAT TGCAGCACT
4771 GGGGCCAGA TGGTAAGCC CTCCCGTAT CGTAGTTAT CTACACGAC
4816 GGGGAGTCA GGCAACTAT GGATGAACG AAATAGACA GATCGCTGA
4861 GATAGGTGC CTCACTGAT TAAGCATTG GTAACTGTC AGACCAAGT
4906 TTACTCATA TATACTTTA GATTGATTT ACCCCGGTT GATAATCAG
4951 AAAAGCCCC AAAAACAGG AAGATTGTA TAAGCAAAT ATTTAAATT
4996 GTAAACGTT AATATTTTG TTAAAATTC GCGTTAAAT TTTTGTTAA
5041 ATCAGCTCA TTTTTTAAC CAATAGGCC GAAATCGGC AAAATCCCT
5086 TATAAATCA AAAGAATAG ACCGAGATA GGGTTGAGT GTTGTTCCA
5131 GTTTGGAAC AAGAGTCCA CTATTAAAG AACGTGGAC TCCAACGTC
5176 AAAGGGCGA AAAACCGTC TATCAGGGC GATGGCCCA CTACGTGAA
5221 CCATCACCC AAATCAAGT TTTTTGGGG TCGAGGTGC CGTAAAGCA
5266 CTAAATCGG AACCCTAAA GGGAGCCCC CGATTTAGA GCTTGACGG
5311 GGAAAGCCG GCGAACGTG GCGAGAAAG GAAGGGAAG AAAGCGAAA
5356 GGAGCGGGC GCTAGGGCG CTGGCAAGT GTAGCGGTC ACGCTGCGC
5401 GTAACCACC ACACCCGCC GCGCTTAAT GCGCCGCTA CAGGGCGCG
5446 TAAAAGGAT CTAGGTGAA GATCCTTTT TGATAATCT CATGACCAA
5491 AATCCCTTA ACGTGAGTT TTCGTTCCA CTGAGCGTC AGACCCCGT
5536 AGAAAAGAT CAAAGGATC TTCTTGAGA TCCTTTTTT TCTGCGCGT
5581 AATCTGCTG CTTGCAAAC AAAAAAACC ACCGCTACC AGCGGTGGT
5626 TTGTTTGCC GGATCAAGA GCTACCAAC TCTTTTTCC GAAGGTAAC
5671 TGGCTTCAG CAGAGCGCA GATACCAAA TACTGTCCT TCTAGTGTA
5716 GCCGTAGTT AGGCCACCA CTTCAAGAA CTCTGTAGC ACCGCCTAC
5761 ATACCTCGC TCTGCTAAT CCTGTTACC AGTGGCTGC TGCCAGTGG
5806 CGATAAGTC GTGTCTTAC CGGGTTGGA CTCAAGACG ATAGTTACC
5851 GGATAAGGC GCAGCGGTC GGGCTGAAC GGGGGGTTC GTGCACACA
5896 GCCCAGCTT GGAGCGAAC GACCTACAC CGAACTGAG ATACCTACA
5941 GCGTGAGCT ATGAGAAAG CGCCACGCT TCCCGAAGG GAGAAAGGC
5986 GGACAGGTA TCCGGTAAG CGGCAGGGT CGGAACAGG AGAGCGCAC
6031 GAGGGAGCT TCCAGGGGG AAACGCCTG GTATCTTTA TAGTCCTGT
6076 CGGGTTTCG CCACCTCTG ACTTGAGCG TCGATTTTT GTGATGCTC
6121 GTCAGGGGG GCGGAGCCT ATGGAAAAA CGCCAGCAA CGCGGCCTT
6166 TTTACGGTT CCTGGCCTT TTGCTGGCC TTTTGCTCA CATGTTCTT
6211 TCCTGCGTT ATCCCCTGA TTCTGTGGA TAACCGTAT TACCGCCTT
6256 TGAGTGAGC TGATACCGC TCGCCGCAG CCGAACGAC CGAGCGCAG
6301 CGAGTCAGT GAGCGAGGA AGCGGAAGA GCGCCTGAT GCGGTATTT
6346 TCTCCTTAC GCATCTGTG CGGTATTTC ACACCGCAT ATATGGTGC
```

FIG.22C pMBP-c2X-ToxoP30del4del8(83-294aa)

```
6391  ACTCTCAGT ACAATCTGC TCTGATGCC GCATAGTTA AGCCAGTAT
6436  ACACTCCGC TATCGCTAC GTGACTGGG TCATGGCTG CGCCCCGAC
6481  ACCCGCCAA CACCCGCTG ACGCGCCCT GACGGGCTT GTCTGCTCC
6526  CGGCATCCG CTTACAGAC AAGCTGTGA CCGTCTCCG GGAGCTGCA
6571  TGTGTCAGA GGTTTTCAC CGTCATCAC CGAAACGCG CGAGGCAGC
6616  TGCGGTAAA GCTCATCAG CGTGGTCGT GCAGCGATT CACAGATGT
6661  CTGCCTGTT CATCCGCGT CCAGCTCGT TGAGTTTCT CCAGAAGCG
6706  TTAATGTCT GGCTTCTGA TAAAGCGGG CCATGTTAA GGGCGGTTT
6751  TTTCCTGTT TGGTCACTG ATGCCTCCG TGTAAGGGG GATTTCTGT
6796  TCATGGGGG TAATGATAC CGATGAAAC GAGAGAGGA TGCTCACGA
6841  TACGGGTTA CTGATGATG AACATGCCC GGTTACTGG AACGTTGTG
6886  AGGGTAAAC AACTGGCGG TATGGATGC GGCGGGACC AGAGAAAAA
6931  TCACTCAGG GTCAATGCC AGCGCTTCG TTAATACAG ATGTAGGTG
6976  TTCCACAGG GTAGCCAGC AGCATCCTG CGATGCAGA TCCGGAACA
7021  TAATGGTGC AGGGCGCTG ACTTCCGCG TTTCCAGAC TTTACGAAA
7066  CACGGAAAC CGAAGACCA TTCATGTTG TTGCTCAGG TCGCAGACG
7111  TTTTGCAGC AGCAGTCGC TTCACGTTC GCTCGCGTA TCGGTGATT
7156  CATTCTGCT AACCAGTAA GGCAACCCC GCCAGCCTA GCCGGGTCC
7201  TCAACGACA GGAGCACGA TCATGCGCA CCCGTGGCC AGGACCCAA
7246  CGCTGCCCG AAATT
```

FIG.22D

ToxoP30del4del8(83-294aa)

```
        ProLysThr AlaLeuThr GluProPro ThrLeuAla TyrSerPro
  1     CCTAAAACA GCGCTCACA GAGCCTCCC ACTCTTGCG TACTCACCC
        AsnArgGln IleCysPro AlaGlyThr ThrSerSer CysThrSer
 46     AACAGGCAA ATCTGCCCA GCGGGTACT ACAAGTAGC TGTACATCA
        LysAlaVal ThrLeuSer SerLeuIle ProGluAla GluAspSer
 91     AAGGCTGTA ACATTGAGC TCCTTGATT CCTGAAGCA GAAGATAGC
        TrpTrpThr GlyAspSer AlaSerLeu AspThrAla GlyIleLys
136     TGGTGGACG GGGGATTCT GCTAGTCTC GACACGGCA GGCATCAAA
        LeuThrVal ProIleGlu LysPhePro ValThrThr GlnThrPhe
181     CTCACAGTT CCAATCGAG AAGTTCCCC GTGACAACG CAGACGTTT
        ValValGly CysIleLys GlyAspAsp AlaGlnSer CysMetVal
226     GTGGTCGGT TGCATCAAG GGAGACGAC GCACAGAGT TGTATGGTC
        ThrValThr ValGlnAla ArgAlaSer SerValVal AsnAsnVal
271     ACAGTGACA GTACAAGCC AGAGCCTCA TCGGTCGTC AATAATGTC
        AlaArgCys SerTyrGly AlaAspSer ThrLeuGly ProValLys
316     GCAAGGTGC TCCTACGGT GCAGACAGC ACTCTTGGT CCTGTCAAG
        LeuSerAla GluGlyPro ThrThrMet ThrLeuVal CysGlyLys
361     TTGTCTGCG GAAGGACCC ACTACAATG ACCCTCGTG TGCGGGAAA
        AspGlyVal LysValPro GlnAspAsn AsnGlnTyr CysSerGly
406     GATGGAGTC AAAGTTCCT CAAGACAAC AATCAGTAC TGTTCCGGG
        ThrThrLeu ThrGlyCys AsnGluLys SerPheLys AspIleLeu
451     ACGACGCTG ACTGGTTGC AACGAGAAA TCGTTCAAA GATATTTTG
        ProLysLeu ThrGluAsn ProTrpGln GlyAsnAla SerSerAsp
496     CCAAAATTA ACTGAGAAC CCGTGGCAG GGTAACGCT TCGAGTGAT
        LysGlyAla ThrLeuThr IleLysLys GluAlaPhe ProAlaGlu
541     AAGGGTGCC ACGCTAACG ATCAAGAAG GAAGCATTT CCAGCCGAG
        SerLysSer ValIleIle GlyCysThr GlyGlySer ProGluLys
586     TCAAAAAGC GTCATTATT GGATGCACA GGGGATCG CCTGAGAAG
        HisHis
631     CATCAC
```

FIG. 23 pMBP-c2X-ToxoP30del10(52-284aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                    Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG. 25 pMBP-c2X-ToxoP30del10(52-284aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.25A pMBP-c2X-ToxoP30del10(52-284aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGlyGly ProThrThr MetThrLeu ValCysGly
3151 AAGTTGTCT GCGGGAGGA CCCACTACA ATGACCCTC GTGTGCGGG
     LysAspGly ValLysVal ProGlnAsp AsnAsnGln TyrCysSer
3196 AAAGATGGA GTCAAAGTT CCTCAAGAC AACAATCAG TACTGTTCC
     GlyThrThr LeuThrGly CysAsnGlu LysSerPhe LysAspIle
3241 GGGACGACG CTGACTGGT TGCAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGly
3376 GAGTCAAAA AGCGTCATT ATTGGATGA AAGCTTGGC ACTGGCCGT
3421 CGTTTTACA ACGTCGTGA CTGGGAAAA CCCTGGCGT TACCCAACT
3466 TAATCGCCT TGCAGCACA TCCCCCTTT CGCCAGCTG GCGTAATAG
3511 CGAAGAGGC CCGCACCGA TCGCCCTTC CCAACAGTT GCGCAGCCT
3556 GAATGGCGA ATGGCAGCT GGCTGTTTT GGCGGATG AGATAAGAT
3601 TTTCAGCCT GATACAGAT TAAATCAGA ACGCAGAAG CGGTCTGAT
3646 AAAACAGAA TTTGCCTGG CGGCAGTAG CGCGGTGGT CCCACCTGA
3691 CCCCATGCC GAACTCAGA AGTGAAACG CCGTAGCGC CGATGGTAG
3736 TGTGGGGTC TCCCCATGC GAGAGTAGG GAACTGCCA GGCATCAAA
3781 TAAAACGAA AGGCTCAGT CGAAAGACT GGGCCTTTC GTTTTATCT
3826 GTTGTTTGT CGGTGAACG CTCTCCTGA GTAGGACAA ATCCGCCGG
3871 GAGCGGATT TGAACGTTG CGAAGCAAC GGCCCGGAG GGTGGCGGG
3916 CAGGACGCC CGCCATAAA CTGCCAGGC ATCAAATTA AGCAGAAGG
3961 CCATCCTGA CGGATGGCC TTTTGCGT TTCTACAAA CTCTTTTTG
4006 TTTATTTTT CTAAATACA TTCAAATAT GTATCCGCT CATGAGACA
4051 ATAACCCTG ATAAATGCT TCAATAATA TTGAAAAAG GAAGAGTAT
4096 GAGTATTCA ACATTTCCG TGTCGCCCT TATTCCCTT TTTTGCGGC
4141 ATTTTGCCT TCCTGTTTT TGCTCACCC AGAAACGCT GGTGAAAGT
4186 AAAAGATGC TGAAGATCA GTTGGGTGC ACGAGTGGG TTACATCGA
4231 ACTGGATCT CAACAGCGG TAAGATCCT TGAGAGTTT TCGCCCCGA
```

FIG.25B pMBP-c2X-ToxoP30del10(52-284aa)

```
4276 AGAACGTTC TCCAATGAT GAGCACTTT TAAAGTTCT GCTATGTGG
4321 CGCGGTATT ATCCCGTGT TGACGCCGG GCAAGAGCA ACTCGGTCG
4366 CCGCATACA CTATTCTCA GAATGACTT GGTTGAGTA CTCACCAGT
4411 CACAGAAAA GCATCTTAC GGATGGCAT GACAGTAAG AGAATTATG
4456 CAGTGCTGC CATAACCAT GAGTGATAA CACTGCGGC CAACTTACT
4501 TCTGACAAC GATCGGAGG ACCGAAGGA GCTAACCGC TTTTTTGCA
4546 CAACATGGG GGATCATGT AACTCGCCT TGATCGTTG GGAACCGGA
4591 GCTGAATGA AGCCATACC AAACGACGA GCGTGACAC CACGATGCC
4636 TGTAGCAAT GGCAACAAC GTTGCGCAA ACTATTAAC TGGCGAACT
4681 ACTTACTCT AGCTTCCCG GCAACAATT AATAGACTG GATGGAGGC
4726 GGATAAAGT TGCAGGACC ACTTCTGCG CTCGGCCCT TCCGGCTGG
4771 CTGGTTTAT TGCTGATAA ATCTGGAGC CGGTGAGCG TGGGTCTCG
4816 CGGTATCAT TGCAGCACT GGGGCCAGA TGGTAAGCC CTCCCGTAT
4861 CGTAGTTAT CTACACGAC GGGGAGTCA GGCAACTAT GGATGAACG
4906 AAATAGACA GATCGCTGA GATAGGTGC CTCACTGAT TAAGCATTG
4951 GTAACTGTC AGACCAAGT TTACTCATA TATACTTTA GATTGATTT
4996 ACCCCGGTT GATAATCAG AAAAGCCCC AAAAACAGG AAGATTGTA
5041 TAAGCAAAT ATTTAAATT GTAAACGTT AATATTTTG TTAAAATTC
5086 GCGTTAAAT TTTTGTTAA ATCAGCTCA TTTTTTAAC CAATAGGCC
5131 GAAATCGGC AAAATCCCT TATAAATCA AAAGAATAG ACCGAGATA
5176 GGGTTGAGT GTTGTTCCA GTTTGGAAC AAGAGTCCA CTATTAAAG
5221 AACGTGGAC TCCAACGTC AAAGGGCGA AAAACCGTC TATCAGGGC
5266 GATGGCCCA CTACGTGAA CCATCACCC AAATCAAGT TTTTTGGGG
5311 TCGAGGTGC CGTAAAGCA CTAAATCGG AACCCTAAA GGGAGCCCC
5356 CGATTTAGA GCTTGACGG GGAAAGCCG GCGAACGTG GCGAGAAAG
5401 GAAGGGAAG AAAGCGAAA GGAGCGGGC GCTAGGGCG CTGGCAAGT
5446 GTAGCGGTC ACGCTGCGC GTAACCACC ACACCCGCC GCGCTTAAT
5491 GCGCCGCTA CAGGGCGCG TAAAAGGAT CTAGGTGAA GATCCTTTT
5536 TGATAATCT CATGACCAA AATCCCTTA ACGTGAGTT TCGTTCCA
5581 CTGAGCGTC AGACCCCGT AGAAAAGAT CAAAGGATC TTCTTGAGA
5626 TCCTTTTTT TCTGCGCGT AATCTGCTG CTTGCAAAC AAAAAAACC
5671 ACCGCTACC AGCGGTGGT TTGTTTGCC GGATCAAGA GCTACCAAC
5716 TCTTTTTCC GAAGGTAAC TGGCTTCAG CAGAGCGCA GATACCAAA
5761 TACTGTCCT TCTAGTGTA GCCGTAGTT AGGCCACCA CTTCAAGAA
5806 CTCTGTAGC ACCGCCTAC ATACCTCGC TCTGCTAAT CCTGTTACC
5851 AGTGGCTGC TGCCAGTGG CGATAAGTC GTGTCTTAC CGGGTTGGA
5896 CTCAAGACG ATAGTTACC GGATAAGGC GCAGCGGTC GGGCTGAAC
5941 GGGGGGTTC GTGCACACA GCCCAGCTT GGAGCGAAC GACCTACAC
5986 CGAACTGAG ATACCTACA GCGTGAGCT ATGAGAAAG CGCCACGCT
6031 TCCCGAAGG GAGAAAGGC GGACAGGTA TCCGGTAAG CGGCAGGGT
6076 CGGAACAGG AGAGCGCAC GAGGGAGCT TCCAGGGGG AAACGCCTG
6121 GTATCTTTA TAGTCCTGT CGGGTTTCG CCACCTCTG ACTTGAGCG
6166 TCGATTTTT GTGATGCTC GTCAGGGGG GCGGAGCCT ATGGAAAAA
6211 CGCCAGCAA CGCGGCCTT TTTACGGTT CCTGGCCTT TTGCTGGCC
6256 TTTTGCTCA CATGTTCTT TCCTGCGTT ATCCCCTGA TTCTGTGGA
6301 TAACCGTAT TACCGCCTT TGAGTGAGC TGATACCGC TCGCCGCAG
```

FIG.25C pMBP-c2X-ToxoP30del10(52-284aa)

```
6346 CCGAACGAC CGAGCGCAG CGAGTCAGT GAGCGAGGA AGCGGAAGA
6391 GCGCCTGAT GCGGTATTT TCTCCTTAC GCATCTGTG CGGTATTTC
6436 ACACCGCAT ATATGGTGC ACTCTCAGT ACAATCTGC TCTGATGCC
6481 GCATAGTTA AGCCAGTAT ACACTCCGC TATCGCTAC GTGACTGGG
6526 TCATGGCTG CGCCCCGAC ACCCGCCAA CACCCGCTG ACGCGCCCT
6571 GACGGGCTT GTCTGCTCC CGGCATCCG CTTACAGAC AAGCTGTGA
6616 CCGTCTCCG GGAGCTGCA TGTGTCAGA GGTTTTCAC CGTCATCAC
6661 CGAAACGCG CGAGGCAGC TGCGGTAAA GCTCATCAG CGTGGTCGT
6706 GCAGCGATT CACAGATGT CTGCCTGTT CATCCGCGT CCAGCTCGT
6751 TGAGTTTCT CCAGAAGCG TTAATGTCT GGCTTCTGA TAAAGCGGG
6796 CCATGTTAA GGGCGGTTT TTTCCTGTT TGGTCACTG ATGCCTCCG
6841 TGTAAGGGG GATTTCTGT TCATGGGGG TAATGATAC CGATGAAAC
6886 GAGAGAGGA TGCTCACGA TACGGGTTA CTGATGATG AACATGCCC
6931 GGTTACTGG AACGTTGTG AGGGTAAAC AACTGGCGG TATGGATGC
6976 GGCGGGACC AGAGAAAAA TCACTCAGG GTCAATGCC AGCGCTTCG
7021 TTAATACAG ATGTAGGTG TTCCACAGG GTAGCCAGC AGCATCCTG
7066 CGATGCAGA TCCGGAACA TAATGGTGC AGGGCGCTG ACTTCCGCG
7111 TTTCCAGAC TTTACGAAA CACGGAAAC CGAAGACCA TTCATGTTG
7156 TTGCTCAGG TCGCAGACG TTTTGCAGC AGCAGTCGC TTCACGTTC
7201 GCTCGCGTA TCGGTGATT CATTCTGCT AACCAGTAA GGCAACCCC
7246 GCCAGCCTA GCCGGGTCC TCAACGACA GGAGCACGA TCATGCGCA
7291 CCCGTGGCC AGGACCCAA CGCTGCCCG AAATT
```

FIG.25D

ToxoP30del10(52-284aa)

```
        LeuValAla  AsnGlnVal  ValThrCys  ProAspLys  LysSerThr
  1     CTTGTTGCC  AATCAAGTT  GTCACCTGC  CCAGATAAA  AAATCGACA
        AlaAlaVal  IleLeuThr  ProThrGlu  AsnHisPhe  ThrLeuLys
 46     GCCGCGGTC  ATTCTCACA  CCGACGGAG  AACCACTTC  ACTCTCAAG
        CysProLys  ThrAlaLeu  ThrGluPro  ProThrLeu  AlaTyrSer
 91     TGCCCTAAA  ACAGCGCTC  ACAGAGCCT  CCCACTCTT  GCGTACTCA
        ProAsnArg  GlnIleCys  ProAlaGly  ThrThrSer  SerCysThr
136     CCCAACAGG  CAAATCTGC  CCAGCGGGT  ACTACAAGT  AGCTGTACA
        SerLysAla  ValThrLeu  SerSerLeu  IleProGlu  AlaGluAsp
181     TCAAAGGCT  GTAACATTG  AGCTCCTTG  ATTCCTGAA  GCAGAAGAT
        SerTrpTrp  ThrGlyAsp  SerAlaSer  LeuAspThr  AlaGlyIle
226     AGCTGGTGG  ACGGGGGAT  TCTGCTAGT  CTCGACACG  GCAGGCATC
        LysLeuThr  ValProIle  GluLysPhe  ProValThr  ThrGlnThr
271     AAACTCACA  GTTCCAATC  GAGAAGTTC  CCCGTGACA  ACGCAGACG
        PheValVal  GlyCysIle  LysGlyAsp  AspAlaGln  SerCysMet
316     TTTGTGGTC  GGTTGCATC  AAGGGAGAC  GACGCACAG  AGTTGTATG
        ValThrVal  ThrValGln  AlaArgAla  SerSerVal  ValAsnAsn
361     GTCACAGTG  ACAGTACAA  GCCAGAGCC  TCATCGGTC  GTCAATAAT
        ValAlaArg  CysSerTyr  GlyAlaAsp  SerThrLeu  GlyProVal
406     GTCGCAAGG  TGCTCCTAC  GGTGCAGAC  AGCACTCTT  GGTCCTGTC
        LysLeuSer  AlaGlyGly  ProThrThr  MetThrLeu  ValCysGly
451     AAGTTGTCT  GCGGGAGGA  CCCACTACA  ATGACCCTC  GTGTGCGGG
        LysAspGly  ValLysVal  ProGlnAsp  AsnAsnGln  TyrCysSer
496     AAAGATGGA  GTCAAAGTT  CCTCAAGAC  AACAATCAG  TACTGTTCC
        GlyThrThr  LeuThrGly  CysAsnGlu  LysSerPhe  LysAspIle
541     GGGACGACG  CTGACTGGT  TGCAACGAG  AAATCGTTC  AAAGATATT
        LeuProLys  LeuThrGlu  AsnProTrp  GlnGlyAsn  AlaSerSer
586     TTGCCAAAA  TTAACTGAG  AACCCGTGG  CAGGGTAAC  GCTTCGAGT
        AspLysGly  AlaThrLeu  ThrIleLys  LysGluAla  PheProAla
631     GATAAGGGT  GCCACGCTA  ACGATCAAG  AAGGAAGCA  TTTCCAGCC
        GluSerLys  SerValIle  IleGly
676     GAGTCAAAA  AGCGTCATT  ATTGGA
```

FIG.26 pMBP-c2X-ToxoP30del11(52-214aa)

```
   1  CCGACACCA TCGAATGGT GCAAAACCT TTCGCGGTA TGGCATGAT
  46  AGCGCCCGG AAGAGAGTC AATTCAGGG TGGTGAATG TGAAACCAG
  91  TAACGTTAT ACGATGTCG CAGAGTATG CCGGTGTCT CTTATCAGA
 136  CCGTTTCCC GCGTGGTGA ACCAGGCCA GCCACGTTT CTGCGAAAA
 181  CGCGGGAAA AAGTGGAAG CGGCGATGG CGGAGCTGA ATTACATTC
 226  CCAACCGCG TGGCACAAC AACTGGCGG GCAAACAGT CGTTGCTGA
 271  TTGGCGTTG CCACCTCCA GTCTGGCCC TGCACGCGC CGTCGCAAA
 316  TTGTCGCGG CGATTAAAT CTCGCGCCG ATCAACTGG GTGCCAGCG
 361  TGGTGGTGT CGATGGTAG AACGAAGCG GCGTCGAAG CCTGTAAAG
 406  CGGCGGTGC ACAATCTTC TCGCGCAAC GCGTCAGTG GGCTGATCA
 451  TTAACTATC CGCTGGATG ACCAGGATG CCATTGCTG TGGAAGCTG
 496  CCTGCACTA ATGTTCCGG CGTTATTTC TTGATGTCT CTGACCAGA
 541  CACCCATCA ACAGTATTA TTTTCTCCC ATGAAGACG GTACGCGAC
 586  TGGGCGTGG AGCATCTGG TCGCATTGG GTCACCAGC AAATCGCGC
 631  TGTTAGCGG GCCCATTAA GTTCTGTCT CGGCGCGTC TGCGTCTGG
 676  CTGGCTGGC ATAAATATC TCACTCGCA ATCAAATTC AGCCGATAG
 721  CGGAACGGG AAGGCGACT GGAGTGCCA TGTCCGGTT TTCAACAAA
 766  CCATGCAAA TGCTGAATG AGGGCATCG TTCCCACTG CGATGCTGG
 811  TTGCCAACG ATCAGATGG CGCTGGGCG CAATGCGCG CCATTACCG
 856  AGTCCGGGC TGCGCGTTG GTGCGGATA TCTCGGTAG TGGGATACG
 901  ACGATACCG AAGACAGCT CATGTTATA TCCCGCCGT TAACCACCA
 946  TCAAACAGG ATTTTCGCC TGCTGGGGC AAACCAGCG TGGACCGCT
 991  TGCTGCAAC TCTCTCAGG GCCAGGCGG TGAAGGGCA ATCAGCTGT
1036  TGCCCGTCT CACTGGTGA AAAGAAAAA CCACCCTGG CGCCCAATA
1081  CGCAAACCG CCTCTCCCC GCGCGTTGG CCGATTCAT TAATGCAGC
1126  TGGCACGAC AGGTTTCCC GACTGGAAA GCGGGCAGT GAGCGCAAC
1171  GCAATTAAT GTAAGTTAG CTCACTCAT TAGGCACAA TTCTCATGT
1216  TTGACAGCT TATCATCGA CTGCACGGT GCACCAATG CTTCTGGCG
1261  TCAGGCAGC CATCGGAAG CTGTGGTAT GGCTGTGCA GGTCGTAAA
1306  TCACTGCAT AATTCGTGT CGCTCAAGG CGCACTCCC GTTCTGGAT
1351  AATGTTTTT TGCGCCGAC ATCATAACG GTTCTGGCA AATATTCTG
1396  AAATGAGCT GTTGACAAT TAATCATCG GCTCGTATA ATGTGTGGA
1441  ATTGTGAGC GGATAACAA TTTCACACA GGAAACAGC CAGTCCGTT
                                                    Met
1486  TAGGTGTTT TCACGAGCA CTTCACCAA CAAGGACCA TAGCATATG
      LysIleGlu GluGlyLys LeuValIle TrpIleAsn GlyAspLys
1531  AAAATCGAA GAAGGTAAA CTGGTAATC TGGATTAAC GGCGATAAA
      GlyTyrAsn GlyLeuAla GluValGly LysLysPhe GluLysAsp
1576  GGCTATAAC GGTCTCGCT GAAGTCGGT AAGAAATTC GAGAAAGAT
      ThrGlyIle LysValThr ValGluHis ProAspLys LeuGluGlu
1621  ACCGGAATT AAAGTCACC GTTGAGCAT CCGGATAAA CTGGAAGAG
      LysPhePro GlnValAla AlaThrGly AspGlyPro AspIleIle
1666  AAATTCCCA CAGGTTGCG GCAACTGGC GATGGCCCT GACATTATC
      PheTrpAla HisAspArg PheGlyGly TyrAlaGln SerGlyLeu
1711  TTCTGGGCA CACGACCGC TTTGGTGGC TACGCTCAA TCTGGCCTG
      LeuAlaGlu IleThrPro AspLysAla PheGlnAsp LysLeuTyr
```

FIG.28 pMBP-c2X-ToxoP30del11(52-214aa)

```
1756  TTGGCTGAA ATCACCCCG GACAAAGCG TTCCAGGAC AAGCTGTAT
      ProPheThr TrpAspAla ValArgTyr AsnGlyLys LeuIleAla
1801  CCGTTTACC TGGGATGCC GTACGTTAC AACGGCAAG CTGATTGCT
      TyrProIle AlaValGlu AlaLeuSer LeuIleTyr AsnLysAsp
1846  TACCCGATC GCTGTTGAA GCGTTATCG CTGATTTAT AACAAAGAT
      LeuLeuPro AsnProPro LysThrTrp GluGluIle ProAlaLeu
1891  CTGCTGCCG AACCCGCCA AAACCTGG GAAGAGATC CCGGCGCTG
      AspLysGlu LeuLysAla LysGlyLys SerAlaLeu MetPheAsn
1936  GATAAAGAA CTGAAAGCG AAAGGTAAG AGCGCGCTG ATGTTCAAC
      LeuGlnGlu ProTyrPhe ThrTrpPro LeuIleAla AlaAspGly
1981  CTGCAAGAA CCGTACTTC ACCTGGCCG CTGATTGCT GCTGACGGG
      GlyTyrAla PheLysTyr GluAsnGly LysTyrAsp IleLysAsp
2026  GGTTATGCG TTCAAGTAT GAAAACGGC AAGTACGAC ATTAAAGAC
      ValGlyVal AspAsnAla GlyAlaLys AlaGlyLeu ThrPheLeu
2071  GTGGGCGTG GATAACGCT GGCGCGAAA GCGGGTCTG ACCTTCCTG
      ValAspLeu IleLysAsn LysHisMet AsnAlaAsp ThrAspTyr
2116  GTTGACCTG ATTAAAAAC AAACACATG AATGCAGAC ACCGATTAC
      SerIleAla GluAlaAla PheAsnLys GlyGluThr AlaMetThr
2161  TCCATCGCA GAAGCTGCC TTTAATAAA GGCGAAACA GCGATGACC
      IleAsnGly ProTrpAla TrpSerAsn IleAspThr SerLysVal
2206  ATCAACGGC CCGTGGGCA TGGTCCAAC ATCGACACC AGCAAAGTG
      AsnTyrGly ValThrVal LeuProThr PheLysGly GlnProSer
2251  AATTATGGT GTAACGGTA CTGCCGACC TTCAAGGGT CAACCATCC
      LysProPhe ValGlyVal LeuSerAla GlyIleAsn AlaAlaSer
2296  AAACCGTTC GTTGGCGTG CTGAGCGCA GGTATTAAC GCCGCCAGT
      ProAsnLys GluLeuAla LysGluPhe LeuGluAsn TyrLeuLeu
2341  CCGAACAAA GAGCTGGCA AAAGAGTTC CTCGAAAAC TATCTGCTG
      ThrAspGlu GlyLeuGlu AlaValAsn LysAspLys ProLeuGly
2386  ACTGATGAA GGTCTGGAA GCGGTTAAT AAAGACAAA CCGCTGGGT
      AlaValAla LeuLysSer TyrGluGlu GluLeuAla LysAspPro
2431  GCCGTAGCG CTGAAGTCT TACGAGGAA GAGTTGGCG AAAGATCCA
      ArgIleAla AlaThrMet GluAsnAla GlnLysGly GluIleMet
2476  CGTATTGCC GCCACTATG GAAAACGCC CAGAAAGGT GAAATCATG
      ProAsnIle ProGlnMet SerAlaPhe TrpTyrAla ValArgThr
2521  CCGAACATC CCGCAGATG TCCGCTTTC TGGTATGCC GTGCGTACT
      AlaValIle AsnAlaAla SerGlyArg GlnThrVal AspGluAla
2566  GCGGTGATC AACGCCGCC AGCGGTCGT CAGACTGTC GATGAAGCC
      LeuLysAsp AlaGlnThr AsnSerSer SerAsnAsn AsnAsnAsn
2611  CTGAAAGAC GCGCAGACT AATTCGAGC TCGAACAAC AACAACAAT
      AsnAsnAsn AsnAsnLeu GlyIleGlu GlyArgIle SerGluPhe
2656  AACAATAAC AACAACCTC GGGATCGAG GGAAGGATT TCAGAATTC
      LeuValAla AsnGlnVal ValThrCys ProAspLys LysSerThr
2701  CTTGTTGCC AATCAAGTT GTCACCTGC CCAGATAAA AAATCGACA
      AlaAlaVal IleLeuThr ProThrGlu AsnHisPhe ThrLeuLys
2746  GCCGCGGTC ATTCTCACA CCGACGGAG AACCACTTC ACTCTCAAG
      CysProLys ThrAlaLeu ThrGluPro ProThrLeu AlaTyrSer
```

FIG.28A pMBP-c2X-ToxoP30del11(52-214aa)

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACAGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu Val
3151 AAGTTGTCT GCGGAAGGA CCCACTACA ATGACCCTC GTGTGAAAG
3196 CTTGGCACT GGCCGTCGT TTTACAACG TCGTGACTG GGAAAACCC
3241 TGGCGTTAC CCAACTTAA TCGCCTTGC AGCACATCC CCCTTTCGC
3286 CAGCTGGCG TAATAGCGA AGAGGCCCG CACCGATCG CCCTTCCCA
3331 ACAGTTGCG CAGCCTGAA TGGCGAATG GCAGCTTGG CTGTTTTGG
3376 CGGATGAGA TAAGATTTT CAGCCTGAT ACAGATTAA ATCAGAACG
3421 CAGAAGCGG TCTGATAAA ACAGAATTT GCCTGGCGG CAGTAGCGC
3466 GGTGGTCCC ACCTGACCC CATGCCGAA CTCAGAAGT GAAACGCCG
3511 TAGCGCCGA TGGTAGTGT GGGGTCTCC CCATGCGAG AGTAGGGAA
3556 CTGCCAGGC ATCAAATAA AACGAAAGG CTCAGTCGA AAGACTGGG
3601 CCTTTCGTT TTATCTGTT GTTTGTCGG TGAACGCTC TCCTGAGTA
3646 GGACAAATC CGCCGGGAG CGGATTTGA ACGTTGCGA AGCAACGGC
3691 CCGGAGGGT GGCGGGCAG GACGCCCGC CATAAACTG CCAGGCATC
3736 AAATTAAGC AGAAGGCCA TCCTGACGG ATGGCCTTT TTGCGTTTC
3781 TACAAACTC TTTTTGTTT ATTTTTCTA AATACATTC AAATATGTA
3826 TCCGCTCAT GAGACAATA ACCCTGATA AATGCTTCA ATAATATTG
3871 AAAAAGGAA GAGTATGAG TATTCAACA TTTCCGTGT CGCCCTTAT
3916 TCCCTTTTT TGCGGCATT TTGCCTTCC TGTTTTTGC TCACCCAGA
3961 AACGCTGGT GAAAGTAAA AGATGCTGA AGATCAGTT GGGTGCACG
4006 AGTGGGTTA CATCGAACT GGATCTCAA CAGCGGTAA GATCCTTGA
4051 GAGTTTTCG CCCCGAAGA ACGTTCTCC AATGATGAG CACTTTTAA
4096 AGTTCTGCT ATGTGGCGC GGTATTATC CCGTGTTGA CGCCGGGCA
4141 AGAGCAACT CGGTCGCCG CATACACTA TTCTCAGAA TGACTTGGT
4186 TGAGTACTC ACCAGTCAC AGAAAAGCA TCTTACGGA TGGCATGAC
4231 AGTAAGAGA ATTATGCAG TGCTGCCAT AACCATGAG TGATAACAC
4276 TGCGGCCAA CTTACTTCT GACAACGAT CGGAGGACC GAAGGAGCT
4321 AACCGCTTT TTGCACAA CATGGGGGA TCATGTAAC TCGCCTTGA
4366 TCGTTGGGA ACCGGAGCT GAATGAAGC CATACCAAA CGACGAGCG
4411 TGACACCAC GATGCCTGT AGCAATGGC AACAACGTT GCGCAAACT
4456 ATTAACTGG CGAACTACT TACTCTAGC TTCCCGGCA ACAATTAAT
```

FIG.28B pMBP-c2X-ToxoP30del11(52-214aa)

```
4501  AGACTGGAT GGAGGCGGA TAAAGTTGC AGGACCACT TCTGCGCTC
4546  GGCCCTTCC GGCTGGCTG GTTTATTGC TGATAAATC TGGAGCCGG
4591  TGAGCGTGG GTCTCGCGG TATCATTGC AGCACTGGG GCCAGATGG
4636  TAAGCCCTC CCGTATCGT AGTTATCTA CACGACGGG GAGTCAGGC
4681  AACTATGGA TGAACGAAA TAGACAGAT CGCTGAGAT AGGTGCCTC
4726  ACTGATTAA GCATTGGTA ACTGTCAGA CCAAGTTTA CTCATATAT
4771  ACTTTAGAT TGATTTACC CCGGTTGAT AATCAGAAA AGCCCCAAA
4816  AACAGGAAG ATTGTATAA GCAAATATT TAAATTGTA AACGTTAAT
4861  ATTTTGTTA AAATTCGCG TTAAATTTT TGTTAAATC AGCTCATTT
4906  TTTAACCAA TAGGCCGAA ATCGGCAAA ATCCCTTAT AAATCAAAA
4951  GAATAGACC GAGATAGGG TTGAGTGTT GTTCCAGTT TGGAACAAG
4996  AGTCCACTA TTAAAGAAC GTGGACTCC AACGTCAAA GGGCGAAAA
5041  ACCGTCTAT CAGGGCGAT GGCCCACTA CGTGAACCA TCACCCAAA
5086  TCAAGTTTT TTGGGGTCG AGGTGCCGT AAAGCACTA AATCGGAAC
5131  CCTAAAGGG AGCCCCCGA TTTAGAGCT TGACGGGGA AAGCCGGCG
5176  AACGTGGCG AGAAAGGAA GGGAAGAAA GCGAAAGGA GCGGGCGCT
5221  AGGGCGCTG GCAAGTGTA GCGGTCACG CTGCGCGTA ACCACCACA
5266  CCCGCCGCG CTTAATGCG CCGCTACAG GGCGCGTAA AAGGATCTA
5311  GGTGAAGAT CCTTTTTGA TAATCTCAT GACCAAAAT CCCTTAACG
5356  TGAGTTTTC GTTCCACTG AGCGTCAGA CCCCGTAGA AAAGATCAA
5401  AGGATCTTC TTGAGATCC TTTTTTTCT GCGCGTAAT CTGCTGCTT
5446  GCAAACAAA AAAACCACC GCTACCAGC GGTGGTTTG TTTGCCGGA
5491  TCAAGAGCT ACCAACTCT TTTTCCGAA GGTAACTGG CTTCAGCAG
5536  AGCGCAGAT ACCAAATAC TGTCCTTCT AGTGTAGCC GTAGTTAGG
5581  CCACCACTT CAAGAACTC TGTAGCACC GCCTACATA CCTCGCTCT
5626  GCTAATCCT GTTACCAGT GGCTGCTGC CAGTGGCGA TAAGTCGTG
5671  TCTTACCGG GTTGGACTC AAGACGATA GTTACCGGA TAAGGCGCA
5716  GCGGTCGGG CTGAACGGG GGGTTCGTG CACACAGCC CAGCTTGGA
5761  GCGAACGAC CTACACCGA ACTGAGATA CCTACAGCG TGAGCTATG
5806  AGAAAGCGC CACGCTTCC CGAAGGGAG AAAGGCGGA CAGGTATCC
5851  GGTAAGCGG CAGGGTCGG AACAGGAGA GCGCACGAG GGAGCTTCC
5896  AGGGGGAAA CGCCTGGTA TCTTTATAG TCCTGTCGG GTTTCGCCA
5941  CCTCTGACT TGAGCGTCG ATTTTGTG ATGCTCGTC AGGGGGGCG
5986  GAGCCTATG GAAAAACGC CAGCAACGC GGCCTTTTT ACGGTTCCT
6031  GGCCTTTTG CTGGCCTTT TGCTCACAT GTTCTTTCC TGCGTTATC
6076  CCCTGATTC TGTGGATAA CCGTATTAC CGCCTTTGA GTGAGCTGA
6121  TACCGCTCG CCGCAGCCG AACGACCGA GCGCAGCGA GTCAGTGAG
6166  CGAGGAAGC GGAAGAGCG CCTGATGCG GTATTTTCT CCTTACGCA
6211  TCTGTGCGG TATTTCACA CCGCATATA TGGTGCACT CTCAGTACA
6256  ATCTGCTCT GATGCCGCA TAGTTAAGC CAGTATACA CTCCGCTAT
6301  CGCTACGTG ACTGGGTCA TGGCTGCGC CCCGACACC CGCCAACAC
6346  CCGCTGACG CGCCCTGAC GGGCTTGTC TGCTCCCGG CATCCGCTT
6391  ACAGACAAG CTGTGACCG TCTCCGGGA GCTGCATGT GTCAGAGGT
6436  TTTCACCGT CATCACCGA AACGCGCGA GGCAGCTGC GGTAAAGCT
6481  CATCAGCGT GGTCGTGCA GCGATTCAC AGATGTCTG CCTGTTCAT
6526  CCGCGTCCA GCTCGTTGA GTTTCTCCA GAAGCGTTA ATGTCTGGC
```

FIG. 28C pMBP-c2X-ToxoP30del11(52-214aa)

```
6571 TTCTGATAA AGCGGGCCA TGTTAAGGG CGGTTTTTT CCTGTTTGG
6616 TCACTGATG CCTCCGTGT AAGGGGGAT TTCTGTTCA TGGGGGTAA
6661 TGATACCGA TGAAACGAG AGAGGATGC TCACGATAC GGGTTACTG
6706 ATGATGAAC ATGCCCGGT TACTGGAAC GTTGTGAGG GTAAACAAC
6751 TGGCGGTAT GGATGCGGC GGGACCAGA GAAAAATCA CTCAGGGTC
6796 AATGCCAGC GCTTCGTTA ATACAGATG TAGGTGTTC CACAGGGTA
6841 GCCAGCAGC ATCCTGCGA TGCAGATCC GGAACATAA TGGTGCAGG
6886 GCGCTGACT TCCGCGTTT CCAGACTTT ACGAAACAC GGAAACCGA
6931 AGACCATTC ATGTTGTTG CTCAGGTCG CAGACGTTT TGCAGCAGC
6976 AGTCGCTTC ACGTTCGCT CGCGTATCG GTGATTCAT TCTGCTAAC
7021 CAGTAAGGC AACCCCGCC AGCCTAGCC GGGTCCTCA ACGACAGGA
7066 GCACGATCA TGCGCACCC GTGGCCAGG ACCCAACGC TGCCCGAAA
7111 TT
```

FIG.28D

ToxoP30del11(52-214aa)

```
        LeuValAla AsnGlnVal ValThrCys ProAspLys LysSerThr
  1     CTTGTTGCC AATCAAGTT GTCACCTGC CCAGATAAA AAATCGACA
        AlaAlaVal IleLeuThr ProThrGlu AsnHisPhe ThrLeuLys
 46     GCCGCGGTC ATTCTCACA CCGACGGAG AACCACTTC ACTCTCAAG
        CysProLys ThrAlaLeu ThrGluPro ProThrLeu AlaTyrSer
 91     TGCCCTAAA ACAGCGCTC ACAGAGCCT CCCACTCTT GCGTACTCA
        ProAsnArg GlnIleCys ProAlaGly ThrThrSer SerCysThr
136     CCCAACAGG CAAATCTGC CCAGCGGGT ACTACAAGT AGCTGTACA
        SerLysAla ValThrLeu SerSerLeu IleProGlu AlaGluAsp
181     TCAAAGGCT GTAACATTG AGCTCCTTG ATTCCTGAA GCAGAAGAT
        SerTrpTrp ThrGlyAsp SerAlaSer LeuAspThr AlaGlyIle
226     AGCTGGTGG ACGGGGGAT TCTGCTAGT CTCGACACG GCAGGCATC
        LysLeuThr ValProIle GluLysPhe ProValThr ThrGlnThr
271     AAACTCACA GTTCCAATC GAGAAGTTC CCCGTGACA ACGCAGACG
        PheValVal GlyCysIle LysGlyAsp AspAlaGln SerCysMet
316     TTTGTGGTC GGTTGCATC AAGGGAGAC GACGCACAG AGTTGTATG
        ValThrVal ThrValGln AlaArgAla SerSerVal ValAsnAsn
361     GTCACAGTG ACAGTACAA GCCAGAGCC TCATCGGTC GTCAATAAT
        ValAlaArg CysSerTyr GlyAlaAsp SerThrLeu GlyProVal
406     GTCGCAAGG TGCTCCTAC GGTGCAGAC AGCACTCTT GGTCCTGTC
        LysLeuSer AlaGluGly ProThrThr MetThrLeu Val
451     AAGTTGTCT GCGGAAGGA CCCACTACA ATGACCCTC GTG
```

FIG.29 pMBP-c2X-ToxoP30MIX1

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                  Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG.31 pMBP-c2X-ToxoP30MIX1

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIG.31A pMBP-c2X-ToxoP30MIX1

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACGGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValAlaGly
3151 AAGTTGTCT GCGGAAGGA CCCACTACA ATGACCCTC GTGGCTGGG
     LysAspGly ValLysVal ProGlnAsn AsnAsnGln TyrAlaSer
3196 AAAGATGGA GTCAAAGTT CCTCAAGAC AATAATCAG TACGCTTCC
     GlyThrThr LeuThrGly AlaAsnGlu LysSerPhe LysAspIle
3241 GGGACGACG CTGACTGGT GCTAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyAla ThrGlyGly SerProGlu
3376 GAGTCAAAA AGCGTCATT ATTGGAGCT ACAGGGGGA TCGCCTGAG
     LysHisHis AlaThrVal LysLeuGlu
3421 AAGCATCAC GCTACCGTG AAACTGGAG TGAAAGCTT GGCACTGGC
3466 CGTCGTTTT ACAACGTCG TGACTGGGA AAACCCTGG CGTTACCCA
3511 ACTTAATCG CCTTGCAGC ACATCCCCC TTTCGCCAG CTGGCGTAA
3556 TAGCGAAGA GGCCCGCAC CGATCGCCC TTCCCAACA GTTGCGCAG
3601 CCTGAATGG CGAATGGCA GCTTGGCTG TTTGGCGG ATGAGATAA
3646 GATTTTCAG CCTGATACA GATTAAATC AGAACGCAG AAGCGGTCT
3691 GATAAAACA GAATTTGCC TGGCGGCAG TAGCGCGGT GGTCCCACC
3736 TGACCCCAT GCCGAACTC AGAAGTGAA ACGCCGTAG CGCCGATGG
3781 TAGTGTGGG GTCTCCCCA TGCGAGAGT AGGGAACTG CCAGGCATC
3826 AAATAAAAC GAAAGGCTC AGTCGAAAG ACTGGGCCT TTCGTTTTA
3871 TCTGTTGTT TGTCGGTGA ACGCTCTCC TGAGTAGGA CAAATCCGC
3916 CGGGAGCGG ATTTGAACG TTGCGAAGC AACGGCCCG GAGGGTGGC
3961 GGGCAGGAC GCCCGCCAT AAACTGCCA GGCATCAAA TTAAGCAGA
4006 AGGCCATCC TGACGGATG GCCTTTTTG CGTTTCTAC AAACTCTTT
4051 TTGTTTATT TTTCTAAAT ACATTCAAA TATGTATCC GCTCATGAG
4096 ACAATAACC CTGATAAAT GCTTCAATA ATATTGAAA AAGGAAGAG
4141 TATGAGTAT TCAACATTT CCGTGTCGC CCTTATTCC CTTTTTTGC
4186 GGCATTTTG CCTTCCTGT TTTGCTCA CCCAGAAAC GCTGGTGAA
```

FIG.31B pMBP-c2X-ToxoP30MIX1

```
4231 AGTAAAAGA TGCTGAAGA TCAGTTGGG TGCACGAGT GGGTTACAT
4276 CGAACTGGA TCTCAACAG CGGTAAGAT CCTTGAGAG TTTTCGCCC
4321 CGAAGAACG TTCTCCAAT GATGAGCAC TTTTAAAGT TCTGCTATG
4366 TGGCGCGGT ATTATCCCG TGTTGACGC CGGGCAAGA GCAACTCGG
4411 TCGCCGCAT ACACTATTC TCAGAATGA CTTGGTTGA GTACTCACC
4456 AGTCACAGA AAAGCATCT TACGGATGG CATGACAGT AAGAGAATT
4501 ATGCAGTGC TGCCATAAC CATGAGTGA TAACACTGC GGCCAACTT
4546 ACTTCTGAC AACGATCGG AGGACCGAA GGAGCTAAC CGCTTTTTT
4591 GCACAACAT GGGGGATCA TGTAACTCG CCTTGATCG TTGGGAACC
4636 GGAGCTAAA TGAAGCCAT ACCAAACGA CGAGCGTGA CACCACGAT
4681 GCCTGTAGC AATGGCAAC AACGTTGCG CAAACTATT AACTGGCGA
4726 ACTACTTAC TCTAGCTTC CCGGCAACA ATTAATAGA CTGGATGGA
4771 GGCGGATAA AGTTGCAGG ACCACTTCT GCGCTCGGC CCTTCCGGC
4816 TGGCTGGTT TATTGCTGA TAAATCTGG AGCCGGTGA GCGTGGGTC
4861 TCGCGGTAT CATTGCAGC ACTGGGGCC AGATGGTAA GCCCTCCCG
4906 TATCGTAGT TATCTACAC GACGGGGAG TCAGGCAAC TATGGATGA
4951 ACGAAATAG ACAGATCGC TGAGATAGG TGCCTCACT GATTAAGCA
4996 TTGGTAACT GTCAGACCA AGTTTACTC ATATATACT TTAGATTGA
5041 TTTACCCCG GTTGATAAT CAGAAAAGC CCCAAAAAC AGGAAGATT
5086 GTATAAGCA AATATTTAA ATTGTAAAC GTTAATATT TTGTTAAAA
5131 TTCGCGTTA AATTTTTGT TAAATCAGC TCATTTTTT AACCAATAG
5176 GCCGAAATC GGCAAAATC CCTTATAAA TCAAAAGAA TAGACCGAG
5221 ATAGGGTTG AGTGTTGTT CCAGTTTGG AACAAGAGT CCACTATTA
5266 AAGAACGTG GACTCCAAC GTCAAAGGG CGAAAAACC GTCTATCAG
5311 GGCGATGGC CCACTACGT GAACCATCA CCCAAATCA AGTTTTTTG
5356 GGGTCGAGG TGCCGTAAA GCACTAAAT CGGAACCCT AAAGGGAGC
5401 CCCCGATTT AGAGCTTGA CGGGGAAAG CCGGCGAAC GTGGCGAGA
5446 AAGGAAGGG AAGAAAGCG AAAGGAGCG GGCGCTAGG GCGCTGGCA
5491 AGTGTAGCG GTCACGCTG CGCGTAACC ACCACACCC GCCGCGCTT
5536 AATGCGCCG CTACAGGGC GCGTAAAAG GATCTAGGT GAAGATCCT
5581 TTTTGATAA TCTCATGAC CAAAATCCC TTAACGTGA GTTTTCGTT
5626 CCACTGAGC GTCAGACCC CGTAGAAAA GATCAAAGG ATCTTCTTG
5671 AGATCCTTT TTTTCTGCG CGTAATCTG CTGCTTGCA AACAAAAAA
5716 ACCACCGCT ACCAGCGGT GGTTTGTTT GCCGGATCA AGAGCTACC
5761 AACTCTTTT TCCGAAGGT AACTGGCTT CAGCAGAGC GCAGATACC
5806 AAATACTGT CCTTCTAGT GTAGCCGTA GTTAGGCCA CCACTTCAA
5851 GAACTCTGT AGCACCGCC TACATACCT CGCTCTGCT AATCCTGTT
5896 ACCAGTGGC TGCTGCCAG TGGCGATAA GTCGTGTCT TACCGGGTT
5941 GGACTCAAG ACGATAGTT ACCGGATAA GGCGCAGCG GTCGGGCTG
5986 AACGGGGGG TTCGTGCAC ACAGCCCAG CTTGGAGCG AACGACCTA
6031 CACCGAACT GAGATACCT ACAGCGTGA GCTATGAGA AAGCGCCAC
6076 GCTTCCCGA AGGGAGAAA GGCGGACAG GTATCCGGT AAGCGGCAG
6121 GGTCGGAAC AGGAGAGCG CACGAGGGA GCTTCCAGG GGGAAACGC
6166 CTGGTATCT TTATAGTCC TGTCGGGTT TCGCCACCT CTGACTTGA
6211 GCGTCGATT TTTGTGATG CTCGTCAGG GGGCGGAG CCTATGGAA
6256 AAACGCCAG CAACGCGGC CTTTTTACG GTTCCTGGC CTTTTGCTG
```

FIG.31C pMBP-c2X-ToxoP30MIX1

```
6301  GCCTTTTGC TCACATGTT CTTTCCTGC GTTATCCCC TGATTCTGT
6346  GGATAACCG TATTACCGC CTTTGAGTG AGCTGATAC CGCTCGCCG
6391  CAGCCGAAC GACCGAGCG CAGCGAGTC AGTGAGCGA GGAAGCGGA
6436  AGAGCGCCT GATGCGGTA TTTTCTCCT TACGCATCT GTGCGGTAT
6481  TTCACACCG CATATATGG TGCACTCTC AGTACAATC TGCTCTGAT
6526  GCCGCATAG TTAAGCCAG TATACACTC CGCTATCGC TACGTGACT
6571  GGGTCATGG CTGCGCCCC GACACCCGC CAACACCCG CTGACGCGC
6616  CCTGACGGG CTTGTCTGC TCCCGGCAT CCGCTTACA GACAAGCTG
6661  TGACCGTCT CCGGGAGCT GCATGTGTC AGAGGTTTT CACCGTCAT
6706  CACCGAAAC GCGCGAGGC AGCTGCGGT AAAGCTCAT CAGCGTGGT
6751  CGTGCAGCG ATTCACAGA TGTCTGCCT GTTCATCCG CGTCCAGCT
6796  CGTTGAGTT TCTCCAGAA GCGTTAATG TCTGGCTTC TGATAAAGC
6841  GGGCCATGT TAAGGGCGG TTTTTTCCT GTTTGGTCA CTGATGCCT
6886  CCGTGTAAG GGGGATTTC TGTTCATGG GGGTAATGA TACCGATGA
6931  AACGAGAGA GGATGCTCA CGATACGGG TTACTGATG ATGAACATG
6976  CCCGGTTAC TGGAACGTT GTGAGGGTA AACAACTGG CGGTATGGA
7021  TGCGGCGGG ACCAGAGAA AAATCACTC AGGGTCAAT GCCAGCGCT
7066  TCGTTAATA CAGATGTAG GTGTTCCAC AGGGTAGCC AGCAGCATC
7111  CTGCGATGC AGATCCGGA ACATAATGG TGCAGGGCG CTGACTTCC
7156  GCGTTTCCA GACTTTACG AAACACGGA AACCGAAGA CCATTCATG
7201  TTGTTGCTC AGGTCGCAG ACGTTTGC AGCAGCAGT CGCTTCACG
7246  TTCGCTCGC GTATCGGTG ATTCATTCT GCTAACCAG TAAGGCAAC
7291  CCCGCCAGC CTAGCCGGG TCCTCAACG ACAGGAGCA CGATCATGC
7335  GCACCCGTG GCCAGGACC CAACGCTGC CCGAAATT
```

FIG. 31D

ToxoP30MIX1

```
        LeuValAla  AsnGlnVal  ValThrCys  ProAspLys  LysSerThr
  1     CTTGTTGCC  AATCAAGTT  GTCACCTGC  CCAGATAAA  AAATCGACA
        AlaAlaVal  IleLeuThr  ProThrGlu  AsnHisPhe  ThrLeuLys
 46     GCCGCGGTC  ATTCTCACA  CCGACGGAG  AACCACTTC  ACTCTCAAG
        CysProLys  ThrAlaLeu  ThrGluPro  ProThrLeu  AlaTyrSer
 91     TGCCCTAAA  ACAGCGCTC  ACAGAGCCT  CCCACTCTT  GCGTACTCA
        ProAsnArg  GlnIleCys  ProAlaGly  ThrThrSer  SerCysThr
136     CCCAACAGG  CAAATCTGC  CCAGCGGGT  ACTACAAGT  AGCTGTACA
        SerLysAla  ValThrLeu  SerSerLeu  IleProGlu  AlaGluAsp
181     TCAAAGGCT  GTAACATTG  AGCTCCTTG  ATTCCTGAA  GCAGAAGAT
        SerTrpTrp  ThrGlyAsp  SerAlaSer  LeuAspThr  AlaGlyIle
226     AGCTGGTGG  ACGGGGGAT  TCTGCTAGT  CTCGACACG  GCAGGCATC
        LysLeuThr  ValProIle  GluLysPhe  ProValThr  ThrGlnThr
271     AAACTCACA  GTTCCAATC  GAGAAGTTC  CCCGTGACA  ACGCAGACG
        PheValVal  GlyCysIle  LysGlyAsp  AspAlaGln  SerCysMet
316     TTTGTGGTC  GGTTGCATC  AAGGGAGAC  GACGCACAG  AGTTGTATG
        ValThrVal  ThrValGln  AlaArgAla  SerSerVal  ValAsnAsn
361     GTCACGGTG  ACAGTACAA  GCCAGAGCC  TCATCGGTC  GTCAATAAT
        ValAlaArg  CysSerTyr  GlyAlaAsp  SerThrLeu  GlyProVal
406     GTCGCAAGG  TGCTCCTAC  GGTGCAGAC  AGCACTCTT  GGTCCTGTC
        LysLeuSer  AlaGluGly  ProThrThr  MetThrLeu  ValAlaGly
451     AAGTTGTCT  GCGGAAGGA  CCCACTACA  ATGACCCTC  GTGGCTGGG
        LysAspGly  ValLysVal  ProGlnAsp  AsnAsnGln  TyrAlaSer
496     AAAGATGGA  GTCAAAGTT  CCTCAAGAC  AATAATCAG  TACGCTTCC
        GlyThrThr  LeuThrGly  AlaAsnGlu  LysSerPhe  LysAspIle
541     GGGACGACG  CTGACTGGT  GCTAACGAG  AAATCGTTC  AAAGATATT
        LeuProLys  LeuThrGlu  AsnProTrp  GlnGlyAsn  AlaSerSer
586     TTGCCAAAA  TTAACTGAG  AACCCGTGG  CAGGGTAAC  GCTTCGAGT
        AspLysGly  AlaThrLeu  ThrIleLys  LysGluAla  PheProAla
631     GATAAGGGT  GCCACGCTA  ACGATCAAG  AAGGAAGCA  TTTCCAGCC
        GluSerLys  SerValIle  IleGlyAla  ThrGlyGly  SerProGlu
676     GAGTCAAAA  AGCGTCATT  ATTGGAGCT  ACAGGGGGA  TCGCCTGAG
        LysHisHis  AlaThrVal  LysLeuGlu
721     AAGCATCAC  GCTACCGTG  AAACTGGAG
```

FIG.32 pMBP-c2X-ToxoP30MIX3

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                   Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIG.33 pMBP-c2X-ToxoP30MIX3

```
1756  TTGGCTGAA ATCACCCCG GACAAAGCG TTCCAGGAC AAGCTGTAT
      ProPheThr TrpAspAla ValArgTyr AsnGlyLys LeuIleAla
1801  CCGTTTACC TGGGATGCC GTACGTTAC AACGGCAAG CTGATTGCT
      TyrProIle AlaValGlu AlaLeuSer LeuIleTyr AsnLysAsp
1846  TACCCGATC GCTGTTGAA GCGTTATCG CTGATTTAT AACAAAGAT
      LeuLeuPro AsnProPro LysThrTrp GluGluIle ProAlaLeu
1891  CTGCTGCCG AACCCGCCA AAAACCTGG GAAGAGATC CCGGCGCTG
      AspLysGlu LeuLysAla LysGlyLys SerAlaLeu MetPheAsn
1936  GATAAAGAA CTGAAAGCG AAAGGTAAG AGCGCGCTG ATGTTCAAC
      LeuGlnGlu ProTyrPhe ThrTrpPro LeuIleAla AlaAspGly
1981  CTGCAAGAA CCGTACTTC ACCTGGCCG CTGATTGCT GCTGACGGG
      GlyTyrAla PheLysTyr GluAsnGly LysTyrAsp IleLysAsp
2026  GGTTATGCG TTCAAGTAT GAAAACGGC AAGTACGAC ATTAAAGAC
      ValGlyVal AspAsnAla GlyAlaLys AlaGlyLeu ThrPheLeu
2071  GTGGGCGTG GATAACGCT GGCGCGAAA GCGGGTCTG ACCTTCCTG
      ValAspLeu IleLysAsn LysHisMet AsnAlaAsp ThrAspTyr
2116  GTTGACCTG ATTAAAAAC AAACACATG AATGCAGAC ACCGATTAC
      SerIleAla GluAlaAla PheAsnLys GlyGluThr AlaMetThr
2161  TCCATCGCA GAAGCTGCC TTTAATAAA GGCGAAACA GCGATGACC
      IleAsnGly ProTrpAla TrpSerAsn IleAspThr SerLysVal
2206  ATCAACGGC CCGTGGGCA TGGTCCAAC ATCGACACC AGCAAAGTG
      AsnTyrGly ValThrVal LeuProThr PheLysGly GlnProSer
2251  AATTATGGT GTAACGGTA CTGCCGACC TTCAAGGGT CAACCATCC
      LysProPhe ValGlyVal LeuSerAla GlyIleAsn AlaAlaSer
2296  AAACCGTTC GTTGGCGTG CTGAGCGCA GGTATTAAC GCCGCCAGT
      ProAsnLys GluLeuAla LysGluPhe LeuGluAsn TyrLeuLeu
2341  CCGAACAAA GAGCTGGCA AAAGAGTTC CTCGAAAAC TATCTGCTG
      ThrAspGlu GlyLeuGlu AlaValAsn LysAspLys ProLeuGly
2386  ACTGATGAA GGTCTGGAA GCGGTTAAT AAAGACAAA CCGCTGGGT
      AlaValAla LeuLysSer TyrGluGlu GluLeuAla LysAspPro
2431  GCCGTAGCG CTGAAGTCT TACGAGGAA GAGTTGGCG AAAGATCCA
      ArgIleAla AlaThrMet GluAsnAla GlnLysGly GluIleMet
2476  CGTATTGCC GCCACTATG GAAAACGCC CAGAAAGGT GAAATCATG
      ProAsnIle ProGlnMet SerAlaPhe TrpTyrAla ValArgThr
2521  CCGAACATC CCGCAGATG TCCGCTTTC TGGTATGCC GTGCGTACT
      AlaValIle AsnAlaAla SerGlyArg GlnThrVal AspGluAla
2566  GCGGTGATC AACGCCGCC AGCGGTCGT CAGACTGTC GATGAAGCC
      LeuLysAsp AlaGlnThr AsnSerSer SerAsnAsn AsnAsnAsn
2611  CTGAAAGAC GCGCAGACT AATTCGAGC TCGAACAAC AACAACAAT
      AsnAsnAsn AsnAsnLeu GlyIleGlu GlyArgIle SerGluPhe
2656  AACAATAAC AACAACCTC GGGATCGAG GGAAGGATT TCAGAATTC
      LeuValAla AsnGlnVal ValThrCys ProAspLys LysSerThr
2701  CTTGTTGCC AATCAAGTT GTCACCTGC CCAGATAAA AAATCGACA
      AlaAlaVal IleLeuThr ProThrGlu AsnHisPhe ThrLeuLys
2746  GCCGCGGTC ATTCTCACA CCGACGGAG AACCACTTC ACTCTCAAG
      CysProLys ThrAlaLeu ThrGluPro ProThrLeu AlaTyrSer
```

FIG.33A pMBP-c2X-ToxoP30MIX3

```
2791  TGCCCTAAA  ACAGCGCTC  ACAGAGCCT  CCCACTCTT  GCGTACTCA
      ProAsnArg  GlnIleCys  ProAlaGly  ThrThrSer  SerCysThr
2836  CCCAACAGG  CAAATCTGC  CCAGCGGGT  ACTACAAGT  AGCTGTACA
      SerLysAla  ValThrLeu  SerSerLeu  IleProGlu  AlaGluAsp
2881  TCAAAGGCT  GTAACATTG  AGCTCCTTG  ATTCCTGAA  GCAGAAGAT
      SerTrpTrp  ThrGlyAsp  SerAlaSer  LeuAspThr  AlaGlyIle
2926  AGCTGGTGG  ACGGGGGAT  TCTGCTAGT  CTCGACACG  GCAGGCATC
      LysLeuThr  ValProIle  GluLysPhe  ProValThr  ThrGlnThr
2971  AAACTCACA  GTTCCAATC  GAGAAGTTC  CCCGTGACA  ACGCAGACG
      PheValVal  GlyCysIle  LysGlyAsp  AspAlaGln  SerCysMet
3016  TTTGTGGTC  GGTTGCATC  AAGGGAGAC  GACGCACAG  AGTTGTATG
      ValThrVal  ThrValGln  AlaArgAla  SerSerVal  ValAsnAsn
3061  GTCACGGTG  ACAGTACAA  GCCAGAGCC  TCATCGGTC  GTCAATAAT
      ValAlaArg  AlaSerTyr  GlyAlaAsp  SerThrLeu  GlyProVal
3106  GTCGCAAGG  GCTTCCTAC  GGTGCAGAC  AGCACTCTT  GGTCCTGTC
      LysLeuSer  AlaGluGly  ProThrThr  MetThrLeu  ValAlaGly
3151  AAGTTGTCT  GCGGAAGGA  CCCACTACA  ATGACCCTC  GTGGCTGGG
      LysAspGly  ValLysVal  ProGlnAsp  AsnAsnGln  TyrAlaSer
3196  AAAGATGGA  GTCAAAGTT  CCTCAAGAC  AACAATCAG  TACGCTTCC
      GlyThrThr  LeuThrGly  AlaAsnGlu  LysSerPhe  LysAspIle
3241  GGGACGACG  CTGACTGGT  GCTAACGAG  AAATCGTTC  AAAGATATT
      LeuProLys  LeuThrGlu  AsnProTrp  GlnGlyAsn  AlaSerSer
3286  TTGCCAAAA  TTAACTGAG  AACCCGTGG  CAGGGTAAC  GCTTCGAGT
      AspLysGly  AlaThrLeu  ThrIleLys  LysGluAla  PheProAla
3331  GATAAGGGT  GCCACGCTA  ACGATCAAG  AAGGAAGCA  TTTCCAGCC
      GluSerLys  SerValIle  IleGlyAla  ThrGlyGly  SerProGlu
3376  GAGTCAAAA  AGCGTCATT  ATTGGAGCT  ACAGGGGGA  TCGCCTGAG
      LysHisHis  AlaThrVal  LysLeuGlu
3421  AAGCATCAC  GCTACCGTG  AAACTGGAG  TGAAAGCTT  GGCACTGGC
3466  CGTCGTTTT  ACAACGTCG  TGACTGGGA  AAACCCTGG  CGTTACCCA
3511  ACTTAATCG  CCTTGCAGC  ACATCCCCC  TTTCGCCAG  CTGGCGTAA
3556  TAGCGAAGA  GGCCCGCAC  CGATCGCCC  TTCCCAACA  GTTGCGCAG
3601  CCTGAATGG  CGAATGGCA  GCTTGGCTG  TTTTGGCGG  ATGAGATAA
3646  GATTTTCAG  CCTGATACA  GATTAAATC  AGAACGCAG  AAGCGGTCT
3691  GATAAAACA  GAATTTGCC  TGGCGGCAG  TAGCGCGGT  GGTCCCACC
3736  TGACCCCAT  GCCGAACTC  AGAAGTGAA  ACGCCGTAG  CGCCGATGG
3781  TAGTGTGGG  GTCTCCCCA  TGCGAGAGT  AGGGAACTG  CCAGGCATC
3826  AAATAAAAC  GAAAGGCTC  AGTCGAAAG  ACTGGGCCT  TTCGTTTTA
3871  TCTGTTGTT  TGTCGGTGA  ACGCTCTCC  TGAGTAGGA  CAAATCCGC
3916  CGGGAGCGG  ATTTGAACG  TTGCGAAGC  AACGGCCCG  GAGGGTGGC
3961  GGGCAGGAC  GCCCGCCAT  AAACTGCCA  GGCATCAAA  TTAAGCAGA
4006  AGGCCATCC  TGACGGATG  GCCTTTTTG  CGTTTCTAC  AAACTCTTT
4051  TTGTTTATT  TTTCTAAAT  ACATTCAAA  TATGTATCC  GCTCATGAG
4096  ACAATAACC  CTGATAAAT  GCTTCAATA  ATATTGAAA  AAGGAAGAG
4141  TATGAGTAT  TCAACATTT  CCGTGTCGC  CCTATTCCC  TTTTTTGC
4186  GGCATTTTG  CCTTCCTGT  TTTTGCTCA  CCCAGAAAC  GCTGGTGAA
```

FIG.33B pMBP-c2X-ToxoP30MIX3

```
4231 AGTAAAAGA TGCTGAAGA TCAGTTGGG TGCACGAGT GGGTTACAT
4276 CGAACTGGA TCTCAACAG CGGTAAGAT CCTTGAGAG TTTTCGCCC
4321 CGAAGAACG TTCTCCAAT GATGAGCAC TTTTAAAGT TCTGCTATG
4366 TGGCGCGGT ATTATCCCG TGTTGACGC CGGGCAAGA GCAACTCGG
4411 TCGCCGCAT ACACTATTC TCAGAATGA CTTGGTTGA GTACTCACC
4456 AGTCACAGA AAAGCATCT TACGGATGG CATGACAGT AAGAGAATT
4501 ATGCAGTGC TGCCATAAC CATGAGTGA TAACACTGC GGCCAACTT
4546 ACTTCTGAC AACGATCGG AGGACCGAA GGAGCTAAC CGCTTTTTT
4591 GCACAACAT GGGGGATCA TGTAACTCG CCTTGATCG TTGGGAACC
4636 GGAGCTGAA TGAAGCCAT ACCAAACGA CGAGCGTGA CACCACGAT
4681 GCCTGTAGC AATGGCAAC AACGTTGCG CAAACTATT AACTGGCGA
4726 ACTACTTAC TCTAGCTTC CCGGCAACA ATTAATAGA CTGGATGGA
4771 GGCGGATAA AGTTGCAGG ACCACTTCT GCGCTCGGC CCTTCCGGC
4816 TGGCTGGTT TATTGCTGA TAAATCTGG AGCCGGTGA GCGTGGGTC
4861 TCGCGGTAT CATTGCAGC ACTGGGGCC AGATGGTAA GCCCTCCCG
4906 TATCGTAGT TATCTACAC GACGGGGAG TCAGGCAAC TATGGATGA
4951 ACGAAATAG ACAGATCGC TGAGATAGG TGCCTCACT GATTAAGCA
4996 TTGGTAACT GTCAGACCA AGTTTACTC ATATATACT TTAGATTGA
5041 TTTACCCCG GTTGATAAT CAGAAAAGC CCCAAAAAC AGGAAGATT
5086 GTATAAGCA AATATTTAA ATTGTAAAC GTTAATATT TTGTTAAAA
5131 TTCGCGTTA AATTTTTGT TAAATCAGC TCATTTTTT AACCAATAG
5176 GCCGAAATC GGCAAAATC CCTTATAAA TCAAAAGAA TAGACCGAG
5221 ATAGGGTTG AGTGTTGTT CCAGTTTGG AACAAGAGT CCACTATTA
5266 AAGAACGTG GACTCCAAC GTCAAGGG CGAAAAACC GTCTATCAG
5311 GGCGATGGC CCACTACGT GAACCATCA CCCAAATCA AGTTTTTTG
5356 GGGTCGAGG TGCCGTAAA GCACTAAAT CGGAACCCT AAAGGGAGC
5401 CCCCGATTT AGAGCTTGA CGGGGAAAG CCGGCGAAC GTGGCGAGA
5446 AAGGAAGGG AAGAAAGCG AAAGGAGCG GCGCTAGG GCGCTGGCA
5491 AGTGTAGCG GTCACGCTG CGCGTAACC ACCACACCC GCCGCGCTT
5536 AATGCGCCG CTACAGGGC GCGTAAAAG GATCTAGGT GAAGATCCT
5581 TTTTGATAA TCTCATGAC CAAAATCCC TTAACGTGA GTTTTCGTT
5626 CCACTGAGC GTCAGACCC CGTAGAAAA GATCAAAGG ATCTTCTTG
5671 AGATCCTTT TTTTCTGCG CGTAATCTG CTGCTTGCA AACAAAAAA
5716 ACCACCGCT ACCAGCGGT GGTTTGTTT GCCGGATCA AGAGCTACC
5761 AACTCTTTT TCCGAAGGT AACTGGCTT CAGCAGAGC GCAGATACC
5806 AAATACTGT CCTTCTAGT GTAGCCGTA GTTAGGCCA CCACTTCAA
5851 GAACTCTGT AGCACCGCC TACATACCT CGCTCTGCT AATCCTGTT
5896 ACCAGTGGC TGCTGCCAG TGGCGATAA GTCGTGTCT TACCGGGTT
5941 GGACTCAAG ACGATAGTT ACCGGATAA GGCGCAGCG GTCGGGCTG
5986 AACGGGGGG TTCGTGCAC ACAGCCCAG CTTGGAGCG AACGACCTA
6031 CACCGAACT GAGATACCT ACAGCGTGA GCTATGAGA AAGCGCCAC
6076 GCTTCCCGA AGGGAGAAA GGCGGACAG GTATCCGGT AAGCGGCAG
6121 GGTCGGAAC AGGAGAGCG CACGAGGGA GCTTCCAGG GGGAAACGC
6166 CTGGTATCT TTATAGTCC TGTCGGGTT TCGCCACCT CTGACTTGA
6211 GCGTCGATT TTTGTGATG CTCGTCAGG GGGCGGAG CCTATGGAA
6256 AAACGCCAG CAACGCGGC CTTTTTACG GTTCCTGGC CTTTTGCTG
```

FIG.33C pMBP-c2X-ToxoP30MIX3

```
6301  GCCTTTTGC TCACATGTT CTTTCCTGC GTTATCCCC TGATTCTGT
6346  GGATAACCG TATTACCGC CTTTGAGTG AGCTGATAC CGCTCGCCG
6391  CAGCCGAAC GACCGAGCG CAGCGAGTC AGTGAGCGA GGAAGCGGA
6436  AGAGCGCCT GATGCGGTA TTTTCTCCT TACGCATCT GTGCGGTAT
6481  TTCACACCG CATATATGG TGCACTCTC AGTACAATC TGCTCTGAT
6526  GCCGCATAG TTAAGCCAG TATACACTC CGCTATCGC TACGTGACT
6571  GGGTCATGG CTGCGCCCC GACACCCGC CAACACCCG CTGACGCGC
6616  CCTGACGGG CTTGTCTGC TCCCGGCAT CCGCTTACA GACAAGCTG
6661  TGACCGTCT CCGGGAGCT GCATGTGTC AGAGGTTTT CACCGTCAT
6706  CACCGAAAC GCGCGAGGC AGCTGCGGT AAAGCTCAT CAGCGTGGT
6751  CGTGCAGCG ATTCACAGA TGTCTGCCT GTTCATCCG CGTCCAGCT
6796  CGTTGAGTT TCTCCAGAA GCGTTAATG TCTGGCTTC TGATAAAGC
6841  GGGCCATGT TAAGGGCGG TTTTTTCCT GTTTGGTCA CTGATGCCT
6886  CCGTGTAAG GGGGATTTC TGTTCATGG GGGTAATGA TACCGATGA
6931  AACGAGAGA GGATGCTCA CGATACGGG TTACTGATG ATGAACATG
6976  CCCGGTTAC TGGAACGTT GTGAGGGTA AACAACTGG CGGTATGGA
7021  TGCGGCGGG ACCAGAGAA AAATCACTC AGGGTCAAT GCCAGCGCT
7066  TCGTTAATA CAGATGTAG GTGTTCCAC AGGGTAGCC AGCAGCATC
7111  CTGCGATGC AGATCCGGA ACATAATGG TGCAGGGCG CTGACTTCC
7156  GCGTTTCCA GACTTTACG AAACACGGA AACCGAAGA CCATTCATG
7201  TTGTTGCTC AGGTCGCAG ACGTTTTGC AGCAGCAGT CGCTTCACG
7246  TTCGCTCGC GTATCGGTG ATTCATTCT GCTAACCAG TAAGGCAAC
7291  CCCGCCAGC CTAGCCGGG TCCTCAACG ACAGGAGCA CGATCATGC
7336  GCACCCGTG GCCAGGACC CAACGCTGC CCGAAATT
```

FIG.33D

ToxoP30MIX3

```
         LeuValAla  AsnGlnVal  ValThrCys  ProAspLys  LysSerThr
    1    CTTGTTGCC  AATCAAGTT  GTCACCTGC  CCAGATAAA  AAATCGACA
         AlaAlaVal  IleLeuThr  ProThrGlu  AsnHisPhe  ThrLeuLys
   46    GCCGCGGTC  ATTCTCACA  CCGACGGAG  AACCACTTC  ACTCTCAAG
         CysProLys  ThrAlaLeu  ThrGluPro  ProThrLeu  AlaTyrSer
   91    TGCCCTAAA  ACAGCGCTC  ACAGAGCCT  CCCACTCTT  GCGTACTCA
         ProAsnArg  GlnIleCys  ProAlaGly  ThrThrSer  SerCysThr
  136    CCCAACAGG  CAAATCTGC  CCAGCGGGT  ACTACAAGT  AGCTGTACA
         SerLysAla  ValThrLeu  SerSerLeu  IleProGlu  AlaGluAsp
  181    TCAAAGGCT  GTAACATTG  AGCTCCTTG  ATTCCTGAA  GCAGAAGAT
         SerTrpTrp  ThrGlyAsp  SerAlaSer  LeuAspThr  AlaGlyIle
  226    AGCTGGTGG  ACGGGGGAT  TCTGCTAGT  CTCGACACG  GCAGGCATC
         LysLeuThr  ValProIle  GluLysPhe  ProValThr  ThrGlnThr
  271    AAACTCACA  GTTCCAATC  GAGAAGTTC  CCCGTGACA  ACGCAGACG
         PheValVal  GlyCysIle  LysGlyAsp  AspAlaGln  SerCysMet
  316    TTTGTGGTC  GGTTGCATC  AAGGGAGAC  GACGCACAG  AGTTGTATG
         ValThrVal  ThrValGln  AlaArgAla  SerSerVal  ValAsnAsn
  361    GTCACGGTG  ACAGTACAA  GCCAGAGCC  TCATCGGTC  GTCAATAAT
         ValAlaArg  AlaSerTyr  GlyAlaAsp  SerThrLeu  GlyProVal
  406    GTCGCAAGG  GCTTCCTAC  GGTGCAGAC  AGCACTCTT  GGTCCTGTC
         LysLeuSer  AlaGluGly  ProThrThr  MetThrLeu  ValAlaGly
  451    AAGTTGTCT  GCGGAAGGA  CCCACTACA  ATGACCCTC  GTGGCTGGG
         LysAspGly  ValLysVal  ProGlnAsp  AsnAsnGln  TyrAlaSer
  496    AAAGATGGA  GTCAAAGTT  CCTCAAGAC  AACAATCAG  TACGCTTCC
         GlyThrThr  LeuThrGly  AlaAsnGlu  LysSerPhe  LysAspIle
  541    GGGACGACG  CTGACTGGT  GCTAACGAG  AAATCGTTC  AAAGATATT
         LeuProLys  LeuThrGlu  AsnProTrp  GlnGlyAsn  AlaSerSer
  586    TTGCCAAAA  TTAACTGAG  AACCCGTGG  CAGGGTAAC  GCTTCGAGT
         AspLysGly  AlaThrLeu  ThrIleLys  LysGluAla  PheProAla
  631    GATAAGGGT  GCCACGCTA  ACGATCAAG  AAGGAAGCA  TTTCCAGCC
         GluSerLys  SerValIle  IleGlyAla  ThrGlyGly  SerProGlu
  676    GAGTCAAAA  AGCGTCATT  ATTGGAGCT  ACAGGGGGA  TCGCCTGAG
         LysHisHis  AlaThrVal  LysLeuGlu
  721    AAGCATCAC  GCTACCGTG  AAACTGGAG
```

FIG.34 pMBP-c2X-ToxoP30MIX5

```
   1  CCGACACCA TCGAATGGT GCAAAACCT TTCGCGGTA TGGCATGAT
  46  AGCGCCCGG AAGAGAGTC AATTCAGGG TGGTGAATG TGAAACCAG
  91  TAACGTTAT ACGATGTCG CAGAGTATG CCGGTGTCT CTTATCAGA
 136  CCGTTTCCC GCGTGGTGA ACCAGGCCA GCCACGTTT CTGCGAAAA
 181  CGCGGGAAA AAGTGGAAG CGGCGATGG CGGAGCTGA ATTACATTC
 226  CCAACCGCG TGGCACAAC AACTGGCGG GCAAACAGT CGTTGCTGA
 271  TTGGCGTTG CCACCTCCA GTCTGGCCC TGCACGCGC CGTCGCAAA
 316  TTGTCGCGG CGATTAAAT CTCGCGCCG ATCAACTGG GTGCCAGCG
 361  TGGTGGTGT CGATGGTAG AACGAAGCG GCGTCGAAG CCTGTAAAG
 406  CGGCGGTGC ACAATCTTC TCGCGCAAC GCGTCAGTG GGCTGATCA
 451  TTAACTATC CGCTGGATG ACCAGGATG CCATTGCTG TGGAAGCTG
 496  CCTGCACTA ATGTTCCGG CGTTATTTC TTGATGTCT CTGACCAGA
 541  CACCCATCA ACAGTATTA TTTTCTCCC ATGAAGACG GTACGCGAC
 586  TGGGCGTGG AGCATCTGG TCGCATTGG GTCACCAGC AAATCGCGC
 631  TGTTAGCGG GCCCATTAA GTTCTGTCT CGGCGCGTC TGCGTCTGG
 676  CTGGCTGGC ATAAATATC TCACTCGCA ATCAAATTC AGCCGATAG
 721  CGGAACGGG AAGGCGACT GGAGTGCCA TGTCCGGTT TTCAACAAA
 766  CCATGCAAA TGCTGAATG AGGGCATCG TTCCCACTG CGATGCTGG
 811  TTGCCAACG ATCAGATGG CGCTGGGCG CAATGCGCG CCATTACCG
 856  AGTCCGGGC TGCGCGTTG GTGCGGATA TCTCGGTAG TGGGATACG
 901  ACGATACCG AAGACAGCT CATGTTATA TCCCGCCGT TAACCACCA
 946  TCAAACAGG ATTTTCGCC TGCTGGGGC AAACCAGCG TGGACCGCT
 991  TGCTGCAAC TCTCTCAGG GCCAGGCGG TGAAGGGCA ATCAGCTGT
1036  TGCCCGTCT CACTGGTGA AAAGAAAAA CCACCCTGG CGCCCAATA
1081  CGCAAACCG CCTCTCCCC GCGCGTTGG CCGATTCAT TAATGCAGC
1126  TGGCACGAC AGGTTTCCC GACTGGAAA GCGGGCAGT GAGCGCAAC
1171  GCAATTAAT GTAAGTTAG CTCACTCAT TAGGCACAA TTCTCATGT
1216  TTGACAGCT TATCATCGA CTGCACGGT GCACCAATG CTTCTGGCG
1261  TCAGGCAGC CATCGGAAG CTGTGGTAT GGCTGTGCA GGTCGTAAA
1306  TCACTGCAT AATTCGTGT CGCTCAAGG CGCACTCCC GTTCTGGAT
1351  AATGTTTTT TGCGCCGAC ATCATAACG GTTCTGGCA AATATTCTG
1396  AAATGAGCT GTTGACAAT TAATCATCG GCTCGTATA ATGTGTGGA
1441  ATTGTGAGC GGATAACAA TTTCACACA GGAAACAGC CAGTCCGTT
                                                   Met
1486  TAGGTGTTT TCACGAGCA CTTCACCAA CAAGGACCA TAGCATATG
      LysIleGlu GluGlyLys LeuValIle TrpIleAsn GlyAspLys
1531  AAAATCGAA GAAGGTAAA CTGGTAATC TGGATTAAC GGCGATAAA
      GlyTyrAsn GlyLeuAla GluValGly LysLysPhe GluLysAsp
1576  GGCTATAAC GGTCTCGCT GAAGTCGGT AAGAAATTC GAGAAAGAT
      ThrGlyIle LysValThr ValGluHis ProAspLys LeuGluGlu
1621  ACCGGAATT AAAGTCACC GTTGAGCAT CCGGATAAA CTGGAAGAG
      LysPhePro GlnValAla AlaThrGly AspGlyPro AspIleIle
1666  AAATTCCCA CAGGTTGCG GCAACTGGC GATGGCCCT GACATTATC
      PheTrpAla HisAspArg PheGlyGly TyrAlaGln SerGlyLeu
1711  TTCTGGGCA CACGACCGC TTTGGTGGC TACGCTCAA TCTGGCCTG
      LeuAlaGlu IleThrPro AspLysAla PheGlnAsp LysLeuTyr
```

FIG.35 pMBP-c2X-ToxoP30MIX5

```
1756  TTGGCTGAA ATCACCCCG GACAAAGCG TTCCAGGAC AAGCTGTAT
      ProPheThr TrpAspAla ValArgTyr AsnGlyLys LeuIleAla
1801  CCGTTTACC TGGGATGCC GTACGTTAC AACGGCAAG CTGATTGCT
      TyrProIle AlaValGlu AlaLeuSer LeuIleTyr AsnLysAsp
1846  TACCCGATC GCTGTTGAA GCGTTATCG CTGATTTAT AACAAAGAT
      LeuLeuPro AsnProPro LysThrTrp GluGluIle ProAlaLeu
1891  CTGCTGCCG AACCCGCCA AAAACCTGG GAAGAGATC CCGGCGCTG
      AspLysGlu LeuLysAla LysGlyLys SerAlaLeu MetPheAsn
1936  GATAAAGAA CTGAAAGCG AAAGGTAAG AGCGCGCTG ATGTTCAAC
      LeuGlnGlu ProTyrPhe ThrTrpPro LeuIleAla AlaAspGly
1981  CTGCAAGAA CCGTACTTC ACCTGGCCG CTGATTGCT GCTGACGGG
      GlyTyrAla PheLysTyr GluAsnGly LysTyrAsp IleLysAsp
2026  GGTTATGCG TTCAAGTAT GAAAACGGC AAGTACGAC ATTAAGAC
      ValGlyVal AspAsnAla GlyAlaLys AlaGlyLeu ThrPheLeu
2071  GTGGGCGTG GATAACGCT GGCGCGAAA GCGGGTCTG ACCTTCCTG
      ValAspLeu IleLysAsn LysHisMet AsnAlaAsp ThrAspTyr
2116  GTTGACCTG ATTAAAAAC AAACACATG AATGCAGAC ACCGATTAC
      SerIleAla GluAlaAla PheAsnLys GlyGluThr AlaMetThr
2161  TCCATCGCA GAAGCTGCC TTTAATAAA GGCGAAACA GCGATGACC
      IleAsnGly ProTrpAla TrpSerAsn IleAspThr SerLysVal
2206  ATCAACGGC CCGTGGGCA TGGTCCAAC ATCGACACC AGCAAAGTG
      AsnTyrGly ValThrVal LeuProThr PheLysGly GlnProSer
2251  AATTATGGT GTAACGGTA CTGCCGACC TTCAAGGGT CAACCATCC
      LysProPhe ValGlyVal LeuSerAla GlyIleAsn AlaAlaSer
2296  AAACCGTTC GTTGGCGTG CTGAGCGCA GGTATTAAC GCCGCCAGT
      ProAsnLys GluLeuAla LysGluPhe LeuGluAsn TyrLeuLeu
2341  CCGAACAAA GAGCTGGCA AAAGAGTTC CTCGAAAAC TATCTGCTG
      ThrAspGlu GlyLeuGlu AlaValAsn LysAspLys ProLeuGly
2386  ACTGATGAA GGTCTGGAA GCGGTTAAT AAAGACAAA CCGCTGGGT
      AlaValAla LeuLysSer TyrGluGlu GluLeuAla LysAspPro
2431  GCCGTAGCG CTGAAGTCT TACGAGGAA GAGTTGGCG AAAGATCCA
      ArgIleAla AlaThrMet GluAsnAla GlnLysGly GluIleMet
2476  CGTATTGCC GCCACTATG GAAAACGCC CAGAAAGGT GAAATCATG
      ProAsnIle ProGlnMet SerAlaPhe TrpTyrAla ValArgThr
2521  CCGAACATC CCGCAGATG TCCGCTTTC TGGTATGCC GTGCGTACT
      AlaValIle AsnAlaAla SerGlyArg GlnThrVal AspGluAla
2566  GCGGTGATC AACGCCGCC AGCGGTCGT CAGACTGTC GATGAAGCC
      LeuLysAsp AlaGlnThr AsnSerSer SerAsnAsn AsnAsnAsn
2611  CTGAAAGAC GCGCAGACT AATTCGAGC TCGAACAAC AACAACAAT
      AsnAsnAsn AsnAsnLeu GlyIleGlu GlyArgIle SerGluPhe
2656  AACAATAAC AACAACCTC GGGATCGAG GGAAGGATT TCAGAATTC
      LeuValAla AsnGlnVal ValThrCys ProAspLys LysSerThr
2701  CTTGTTGCC AATCAAGTT GTCACCTGC CCAGATAAA AAATCGACA
      AlaAlaVal IleLeuThr ProThrGlu AsnHisPhe ThrLeuLys
2746  GCCGCGGTC ATTCTCACA CCGACGGAG AACCACTTC ACTCTCAAG
      AlaProLys ThrAlaLeu ThrGluPro ProThrLeu AlaTyrSer
```

FIG.35A pMBP-c2X-ToxoP30MIX5

```
2791 GCTCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACGGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValAlaGly
3151 AAGTTGTCT GCGGAAGGA CCCACTACA ATGACCCTC GTGGCTGGG
     LysAspGly ValLysVal ProGlnAsp AsnAsnGln TyrAlaSer
3196 AAAGATGGA GTCAAAGTT CCTCAAGAC AACAATCAG TACGCTTCC
     GlyThrThr LeuThrGly AlaAsnGlu LysSerPhe LysAspIle
3241 GGGACGACG CTGACTGGT GCTAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyAla ThrGlyGly SerProGlu
3376 GAGTCAAAA AGCGTCATT ATTGGAGCT ACAGGGGGA TCGCCTGAG
     LysHisHis AlaThrVal LysLeuGlu
3421 AAGCATCAC GCTACCGTG AAACTGGAG TGAAAGCTT GGCACTGGC
3466 CGTCGTTTT ACAACGTCG TGACTGGGA AAACCCTGG CGTTACCCA
3511 ACTTAATCG CCTTGCAGC ACATCCCCC TTTCGCCAG CTGGCGTAA
3556 TAGCGAAGA GGCCCGCAC CGATCGCCC TTCCCAACA GTTGCGCAG
3601 CCTGAATGG CGAATGGCA GCTTGGCTG TTTTGGCGG ATGAGATAA
3646 GATTTTCAG CCTGATACA GATTAAATC AGAACGCAG AAGCGGTCT
3691 GATAAAACA GAATTTGCC TGGCGGCAG TAGCGCGGT GGTCCCACC
3736 TGACCCCAT GCCGAACTC AGAAGTGAA ACGCCGTAG CGCCGATGG
3781 TAGTGTGGG GTCTCCCCA TGCGAGAGT AGGGAACTG CCAGGCATC
3826 AAATAAAAC GAAAGGCTC AGTCGAAAG ACTGGGCCT TTCGTTTTA
3871 TCTGTTGTT TGTCGGTGA ACGCTCTCC TGAGTAGGA CAAATCCGC
3916 CGGGAGCGG ATTTGAACG TTGCGAAGC AACGGCCCG GAGGGTGGC
3961 GGGCAGGAC GCCCGCCAT AAACTGCCA GGCATCAAA TTAAGCAGA
4006 AGGCCATCC TGACGGATG GCCTTTTTG CGTTTCTAC AAACTCTTT
4051 TTGTTTATT TTTCTAAAT ACATTCAAA TATGTATCC GCTCATGAG
4096 ACAATAACC CTGATAAAT GCTTCAATA ATATTGAAA AAGGAAGAG
4141 TATGAGTAT TCAACATTT CCGTGTCGC CCTATTCC CTTTTTTGC
4186 GGCATTTTG CCTTCCTGT TTTTGCTCA CCCAGAAAC GCTGGTGAA
```

FIG.35B pMBP-c2X-ToxoP30MIX5

```
4231 AGTAAAAGA TGCTGAAGA TCAGTTGGG TGCACGAGT GGGTTACAT
4276 CGAACTGGA TCTCAACAG CGGTAAGAT CCTTGAGAG TTTTCGCCC
4321 CGAAGAACG TTCTCCAAT GATGAGCAC TTTTAAAGT TCTGCTATG
4366 TGGCGCGGT ATTATCCCG TGTTGACGC CGGGCAAGA GCAACTCGG
4411 TCGCCGCAT ACACTATTC TCAGAATGA CTTGGTTGA GTACTCACC
4456 AGTCACAGA AAAGCATCT TACGGATGG CATGACAGT AAGAGAATT
4501 ATGCAGTGC TGCCATAAC CATGAGTGA TAACACTGC GGCCAACTT
4546 ACTTCTGAC AACGATCGG AGGACCGAA GGAGCTAAC CGCTTTTTT
4591 GCACAACAT GGGGGATCA TGTAACTCG CCTTGATCG TTGGGAACC
4636 GGAGCTGAA TGAAGCCAT ACCAAACGA CGAGCGTGA CACCACGAT
4681 GCCTGTAGC AATGGCAAC AACGTTGCG CAAACTATT AACTGGCGA
4726 ACTACTTAC TCTAGCTTC CCGGCAACA ATTAATAGA CTGGATGGA
4771 GGCGGATAA AGTTGCAGG ACCACTTCT GCGCTCGGC CCTTCCGGC
4816 TGGCTGGTT TATTGCTGA TAAATCTGG AGCCGGTGA GCGTGGGTC
4861 TCGCGGTAT CATTGCAGC ACTGGGGCC AGATGGTAA GCCCTCCCG
4906 TATCGTAGT TATCTACAC GACGGGGAG TCAGGCAAC TATGGATGA
4951 ACGAAATAG ACAGATCGC TGAGATAGG TGCCTCACT GATTAAGCA
4996 TTGGTAACT GTCAGACCA AGTTTACTC ATATATACT TTAGATTGA
5041 TTTACCCCG GTTGATAAT CAGAAAAGC CCCAAAAAC AGGAAGATT
5086 GTATAAGCA AATATTTAA ATTGTAAAC GTTAATATT TTGTTAAAA
5131 TTCGCGTTA AATTTTTGT TAAATCAGC TCATTTTTT AACCAATAG
5176 GCCGAAATC GGCAAAATC CCTTATAAA TCAAAAGAA TAGACCGAG
5221 ATAGGGTTG AGTGTTGTT CCAGTTTGG AACAAGAGT CCACTATTA
5266 AAGAACGTG GACTCCAAC GTCAAAGGG CGAAAAACC GTCTATCAG
5311 GGCGATGGC CCACTACGT GAACCATCA CCCAAATCA AGTTTTTTG
5356 GGGTCGAGG TGCCGTAAA GCACTAAAT CGGAACCCT AAAGGGAGC
5401 CCCCGATTT AGAGCTTGA CGGGGAAAG CCGGCGAAC GTGGCGAGA
5446 AAGGAAGGG AAGAAAGCG AAAGGAGCG GGCGCTAGG GCGCTGGCA
5491 AGTGTAGCG GTCACGCTG CGCGTAACC ACCACACCC GCCGCGCTT
5536 AATGCGCCG CTACAGGGC GCGTAAAAG GATCTAGGT GAAGATCCT
5581 TTTTGATAA TCTCATGAC CAAAATCCC TTAACGTGA GTTTTCGTT
5626 CCACTGAGC GTCAGACCC CGTAGAAAA GATCAAAGG ATCTTCTTG
5671 AGATCCTTT TTTTCTGCG CGTAATCTG CTGCTTGCA AACAAAAAA
5716 ACCACCGCT ACCAGCGGT GGTTTGTTT GCCGGATCA AGAGCTACC
5761 AACTCTTTT TCCGAAGGT AACTGGCTT CAGCAGAGC GCAGATACC
5806 AAATACTGT CCTTCTAGT GTAGCCGTA GTTAGGCCA CCACTTCAA
5851 GAACTCTGT AGCACCGCC TACATACCT CGCTCTGCT AATCCTGTT
5896 ACCAGTGGC TGCTGCCAG TGGCGATAA GTCGTGTCT TACCGGGTT
5941 GGACTCAAG ACGATAGTT ACCGGATAA GGCGCAGCG TCGGGCTG
5986 AACGGGGGG TTCGTGCAC ACAGCCCAG CTTGGAGCG AACGACCTA
6031 CACCGAACT GAGATACCT ACAGCGTGA GCTATGAGA AAGCGCCAC
6076 GCTTCCCGA AGGGAGAAA GGCGGACAG GTATCCGGT AAGCGGCAG
6121 GGTCGGAAC AGGAGAGCG CACGAGGGA GCTTCCAGG GGGAAACGC
6166 CTGGTATCT TTATAGTCC TGTCGGGTT TCGCCACCT CTGACTTGA
6211 GCGTCGATT TTTGTGATG CTCGTCAGG GGGCGGAG CCTATGGAA
6256 AAACGCCAG CAACGCGGC CTTTTTACG GTTCCTGGC CTTTTGCTG
```

FIG.35C pMBP-c2X-ToxoP30MIX5

```
6301  GCCTTTTGC TCACATGTT CTTTCCTGC GTTATCCCC TGATTCTGT
6346  GGATAACCG TATTACCGC CTTTGAGTG AGCTGATAC CGCTCGCCG
6391  CAGCCGAAC GACCGAGCG CAGCGAGTC AGTGAGCGA GGAAGCGGA
6436  AGAGCGCCT GATGCGGTA TTTTCTCCT TACGCATCT GTGCGGTAT
6481  TTCACACCG CATATATGG TGCACTCTC AGTACAATC TGCTCTGAT
6526  GCCGCATAG TTAAGCCAG TATACACTC CGCTATCGC TACGTGACT
6571  GGGTCATGG CTGCGCCCC GACACCCGC CAACACCCG CTGACGCGC
6616  CCTGACGGG CTTGTCTGC TCCCGGCAT CCGCTTACA GACAAGCTG
6661  TGACCGTCT CCGGGAGCT GCATGTGTC AGAGGTTTT CACCGTCAT
6706  CACCGAAAC GCGCGAGGC AGCTGCGGT AAAGCTCAT CAGCGTGGT
6751  CGTGCAGCG ATTCACAGA TGTCTGCCT GTTCATCCG CGTCCAGCT
6796  CGTTGAGTT CTCCAGAA GCGTTAATG TCTGGCTTC TGATAAAGC
6841  GGGCCATGT TAAGGGCGG TTTTTTCCT GTTTGGTCA CTGATGCCT
6886  CCGTGTAAG GGGGATTTC TGTTCATGG GGGTAATGA TACCGATGA
6931  AACGAGAGA GGATGCTCA CGATACGGG TTACTGATG ATGAACATG
6976  CCCGGTTAC TGGAACGTT GTGAGGGTA AACAACTGG CGGTATGGA
7021  TGCGGCGGG ACCAGAGAA AAATCACTC AGGGTCAAT GCCAGCGCT
7066  TCGTTAATA CAGATGTAG GTGTTCCAC AGGGTAGCC AGCAGCATC
7111  CTGCGATGC AGATCCGGA ACATAATGG TGCAGGGCG CTGACTTCC
7156  GCGTTTCCA GACTTTACG AAACACGGA AACCGAAGA CCATTCATG
7201  TTGTTGCTC AGGTCGCAG ACGTTTGC AGCAGCAGT CGCTTCACG
7246  TTCGCTCGC GTATCGGTG ATTCATTCT GCTAACCAG TAAGGCAAC
7291  CCCGCCAGC CTAGCCGGG TCCTCAACG ACAGGAGCA CGATCATGC
7336  GCACCCGTG GCCAGGACC CAACGCTGC CCGAAATT
```

FIG.35D

ToxoP30MIX5

```
        LeuValAla AsnGlnVal ValThrCys ProAspLys LysSerThr
  1     CTTGTTGCC AATCAAGTT GTCACCTGC CCAGATAAA AAATCGACA
        AlaAlaVal IleLeuThr ProThrGlu AsnHisPhe ThrLeuLys
 46     GCCGCGGTC ATTCTCACA CCGACGGAG AACCACTTC ACTCTCAAG
        AlaProLys ThrAlaLeu ThrGluPro ProThrLeu AlaTyrSer
 91     GCTCCTAAA ACAGCGCTC ACAGAGCCT CCCACTCTT GCGTACTCA
        ProAsnArg GlnIleCys ProAlaGly ThrThrSer SerCysThr
136     CCCAACAGG CAAATCTGC CCAGCGGGT ACTACAAGT AGCTGTACA
        SerLysAla ValThrLeu SerSerLeu IleProGlu AlaGluAsp
181     TCAAAGGCT GTAACATTG AGCTCCTTG ATTCCTGAA GCAGAAGAT
        SerTrpTrp ThrGlyAsp SerAlaSer LeuAspThr AlaGlyIle
226     AGCTGGTGG ACGGGGGAT TCTGCTAGT CTCGACACG GCAGGCATC
        LysLeuThr ValProIle GluLysPhe ProValThr ThrGlnThr
271     AAACTCACA GTTCCAATC GAGAAGTTC CCCGTGACA ACGCAGACG
        PheValVal GlyCysIle LysGlyAsp AspAlaGln SerCysMet
316     TTTGTGGTC GGTTGCATC AAGGGAGAC GACGCACAG AGTTGTATG
        ValThrVal ThrValGln AlaArgAla SerSerVal ValAsnAsn
361     GTCACGGTG ACAGTACAA GCCAGAGCC TCATCGGTC GTCAATAAT
        ValAlaArg CysSerTyr GlyAlaAsp SerThrLeu GlyProVal
406     GTCGCAAGG TGCTCCTAC GGTGCAGAC AGCACTCTT GGTCCTGTC
        LysLeuSer AlaGluGly ProThrThr MetThrLeu ValAlaGly
451     AAGTTGTCT GCGGAAGGA CCCACTACA ATGACCCTC GTGGCTGGG
        LysAspGly ValLysVal ProGlnAsp AsnAsnGln TyrAlaSer
496     AAAGATGGA GTCAAAGTT CCTCAAGAC AACAATCAG TACGCTTCC
        GlyThrThr LeuThrGly AlaAsnGlu LysSerPhe LysAspIle
541     GGGACGACG CTGACTGGT GCTAACGAG AAATCGTTC AAAGATATT
        LeuProLys LeuThrGlu AsnProTrp GlnGlyAsn AlaSerSer
586     TTGCCAAAA TTAACTGAG AACCCGTGG CAGGGTAAC GCTTCGAGT
        AspLysGly AlaThrLeu ThrIleLys LysGluAla PheProAla
631     GATAAGGGT GCCACGCTA ACGATCAAG AAGGAAGCA TTTCCAGCC
        GluSerLys SerValIle IleGlyAla ThrGlyGly SerProGlu
676     GAGTCAAAA AGCGTCATT ATTGGAGCT ACAGGGGGA TCGCCTGAG
        LysHisHis AlaThrVal LysLeuGlu
721     AAGCATCAC GCTACCGTG AAACTGGAG
```

FIG.36

GENETICALLY ENGINEERED P30 ANTIGEN, IMPROVED ANTIGEN COCKTAIL, AND USES THEREOF

The present application is a divisional of allowed U.S. patent application Ser. No. 11/316,532, filed on Dec. 21, 2005, now U.S. Pat. No. 7,314,924 to which priority is claimed, which is, in turn, a divisional of Ser. No. 10/263,153, filed Oct. 2, 2002, now U.S. Pat. No. 7,094,879, issued on Aug. 22, 2006, to which priority is also claimed, both hereby being incorporated in their entirety by reference.

BACKGROUND OF THE INVENTION

1. Technical Field

The present invention relates to a genetically engineered P30 antigen as well as a combination or mixture of antigens which may be used in the detection of IgM and/or IgG antibodies to *Toxoplasma gondii*. Furthermore, the present invention also relates to methods of using this genetically engineered P30 antigen and combination of antigens, antibodies raised against this genetically engineered P30 antigen and combination of antigens, as well as kits and vaccines containing the genetically engineered P30 antigen and antigens present in the combination.

2. Background Information

*Toxoplasma gondii* is an obligate intracellular parasite which is classified among the Coccidia. This parasite has relatively broad host range infecting both mammals and birds. The organism is ubiquitous in nature and exists in three forms: tachyzoite, cyst, and oocyst (Remington, J. S., McLeod, R., Desmonds, G., Infectious Diseases of the Fetus and Newborn Infant (J. S. Remington and J. O. Klein, Eds.), pp. 140-267, Saunders, Philadelphia (1995)). Tachyzoites, found during acute infection, are the invasive form capable of invading all nucleated mammalian cells. After the acute stage of infection, tissue cysts called bradyzoites are formed within host cells and persist within the host organism for the life of the host. Cysts are important in transmission of infection, especially in humans, as the ingestion of raw or undercooked meat can result in the ingestion of bradyzoites which can infect the individual resulting in an acute infection. Oocysts represent a stage of sexual reproduction which occurs only in the intestinal lining of the cat family from which they are excreted in the feces.

A *T. gondii* infection acquired through contaminated meat or cat feces in a healthy adult is often asymptomatic. In pregnant women and immunosuppressed patients, the clinical outcome can be very serious. An acute infection with *T. gondii* acquired during pregnancy, especially during the first trimester, can result in intrauterine transmission to the unborn fetus resulting in severe fetal and neonatal complications, including mental retardation and fetal death. Recrudescence of a previous *T. gondii* infection or an acute infection in an immunosuppressed individual can be pathogenic. Toxoplasmic encephalitis is a major cause of morbidity and mortality in AIDS patients. *Toxoplasma* infection has also been shown to be a significant cause of chorioretinitis in children and adults.

Diagnosis of infection with *T. gondii* may be established by the isolation of *T. gondii* from blood or body fluids, demonstration of the presence of the organism in the placenta or tissues of the fetus, demonstration of the presence of antigen by detection of specific nucleic acid sequences (e.g., DNA probes), or detection of *T. gondii* specific immunoglobulins synthesized by the host in response to infection using serologic tests.

The detection of *T. gondii* specific antibodies and determination of antibody titer are important tools used in the diagnosis of toxoplasmosis. The most widely used serologic tests for the diagnosis of toxoplasmosis are the Sabin-Feldman dye test (Sabin, A. B. and Feldman, H. A. (1948) Science 108, 660-663), the indirect hemagglutination (IHA) test (Jacobs, L. and Lunde, M. (1957) J. Parasitol. 43, 308-314), the IFA test (Walton, B. C. et al. (1966) Am. J. Trop. Med. Hyg. 15, 149-152), the agglutination test (Fondation Mérieux, Sérologie de l'Infection Toxoplasmique en Particulier á Son Début: Méthodes et Interprétation des Résultants, Lyon, 182 pp. (1975)) and the ELISA (Naot, Y. and Remington, J. S. (1980) J. Infect. Dis. 142, 757-766). The ELISA test is one the easiest tests to perform, and many automated serologic tests for the detection of *Toxoplasma* specific IgM and IgG are commercially available.

The current tests for the detection of IgM and IgG antibodies in infected individuals can vary widely in their ability to detect serum antibody. Hence, there is significant inter-assay variation seen among the commercially available kits. The differences observed between the different commercial kits are caused primarily by the preparation of the antigen used for the serologic test. Most kits use either whole or sonicated tachyzoites grown in tissue culture or in mice which contain a high proportion of extra-parasitic material, for example, mammalian cells, tissue culture components, etc. Due to the lack of a purified, standardized antigen or standard method for preparing the tachyzoite antigen, it is not surprising that inter-assay variability exists resulting in different assays having different performance characteristics in terms of assay sensitivity and specificity.

Given the limitations of serologic tests employing the tachyzoite antigen, as described above, as well as the persistent problems regarding determination of onset of infection, purified recombinant antigens obtained by molecular biology are an attractive alternative in that they can be purified and standardized. In the literature, a number of Toxo genes have been cloned and expressed in a suitable host to produce immunoreactive, recombinant Toxo antigens. For example, the Toxo P22 (SAG2), P24 (GRA1), P25, P28 (GRA2), P29 (GRA7), P30 (SAG1), P35, P41 (GRA4), P54 (ROP2), P66 (ROP1), and the Toxo P68 antigens have been described (Prince et al. (1990) Mol. Biochem. Parasitol 43, 97-106; Cesbron-Delauw et al. (1989) Proc. Nat. Acad. Sci. 86, 7537-7541; Johnson et al. (1991) Gene 99, 127-132; Prince et al. (1989) Mol. Biochem. Parasitol. 34, 3-13; Bonhomme et al. (1998) J. Histochem. Cytochem. 46, 1411-1421; Burg et al. (1988) J. Immunol. 141, 3584-3591; Knapp et al. (1989) EPA 431541A2; Mevelec et al. (1992) Mol. Biochem. Parasitol. 56, 227-238; Saavedra et al. (1991) J. Immunol. 147, 1975-1982); EPA 751 147).

It is plausible that no single Toxo antigen can replace the tachyzoite in an initial screening immunoassay for the detection of Toxo-specific immunoglobulins. This may be due to several reasons. First, the antibodies produced during infection vary with the stage of infection, i.e., the antibodies produced by an infected individual vary over time reacting with different epitopes. Secondly, the epitopes present in a recombinant antigen may be different or less reactive than native antigen prepared from the tachyzoite depending on the host used for expression and the purification scheme employed. Thirdly, different recombinant antigens may be needed to detect the different classes of immunoglobulins produced in response to an infection, e.g., IgM, IgG, IgA and IgE.

In order to overcome the limitations of the tachyzoite antigen in terms of assay specificity and sensitivity, a search was done for Toxo antigens which could be used in combination in order to configure new assays for the detection of Toxo-specific immunoglobulins. Maine et al. (in U.S. Pat. No. 6,329,157 B1) disclose recombinant Toxo antigen cocktails for the detection of Toxo-specific IgG and IgM. It was determined that the above mentioned Toxo antigen cocktails could be improved and enhanced by expression of Toxo P30 in *E. coli* as a soluble protein with genetically engineered modifications. This genetically engineered P30 antigen and improved antigen cocktail will be described in further detail below.

SUMMARY OF THE INVENTION

The present invention includes a genetically engineered *Toxoplasma gondii* P30 antigen as well as a composition comprising both *Toxoplasma gondii* genetically engineered P30 antigen and P35 antigen. This genetically engineered antigen and composition may be used as diagnostic reagents, and the genetically engineered antigen and the antigens within this composition may be produced either recombinantly or synthetically.

In particular, the present invention includes an isolated nucleotide sequence or fragment thereof comprising or complementary to a nucleotide sequence having at least 70% nucleotide sequence identity to a nucleotide sequence selected from the group consisting of SEQ ID NO:22, SEQ ID NO:27 and SEQ ID NO:63. The present invention also includes an isolated nucleotide sequence or fragment thereof encoding a polypeptide, wherein the polypeptide has at least 70% amino acid sequence identity to an amino acid sequence selected from the group consisting of SEQ ID NO:23, SEQ ID NO:28 and SEQ ID NO:64. The present invention also includes a purified polypeptide encoded by any of the nucleotide sequences presented above.

Additionally, the present invention includes a purified polypeptide or fragment thereof having at least 70% amino acid sequence identity to an amino acid sequence selected from the group consisting of SEQ ID NO:23, SEQ ID NO:28 and SEQ ID NO:64. Also, the present invention includes a purified polypeptide or fragment thereof comprising an amino acid sequence having 1-6 additional amino acids at the C-terminus of SEQ ID NO:28. The invention also includes a purified polypeptide or fragment thereof comprising an amino acid sequence as in SEQ ID NO:23 in which any one or more of the five C-terminal amino acids have been changed from cysteine to alanine. Further, the present invention also includes a polyclonal or monoclonal antibody directed against these purified polypeptides.

The present invention also includes a composition comprising a polypeptide, wherein the polypeptide comprises an amino acid sequence selected from the group consisting of SEQ ID NO:23, SEQ ID NO:28 and SEQ ID NO:64. This composition may be used as a diagnostic reagent, and the polypeptide of the composition may be produced by recombinant or synthetic means.

Additionally, the present invention includes a method for detecting the presence of IgM antibodies to *Toxoplasma gondii* in a test sample comprising the steps of: a) contacting the test sample suspected of containing the IgM antibodies with a composition comprising a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64; and b) detecting the presence of polypeptide/IgM antibody complexes, wherein presence of the complexes indicates presence of the IgM antibodies in the test sample.

Furthermore, the present invention also includes a method for detecting the presence of IgM antibodies to *Toxoplasma gondii* in a test sample comprising the steps of: a) contacting the test sample suspected of containing the IgM antibodies with a composition comprising a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64, for a time and under conditions sufficient for the formation of IgM antibody/antigen complexes; b) adding a conjugate to the resulting IgM antibody/antigen complexes for a time and under conditions sufficient to allow said conjugate to bind to the bound antibody, wherein the conjugate comprises an antibody attached to a signal-generating compound capable of generating a detectable signal; and c) detecting presence of IgM antibodies which may be present in the test sample by detecting presence of a signal generated by the signal-generating compound.

Moreover, the present invention encompasses a method for detecting the presence of IgG antibodies to *Toxoplasma gondii* in a test sample comprising the steps of: a) contacting the test sample suspected of containing the IgG antibodies with a composition comprising: 1) a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64 and 2) P35; and b) detecting presence of antigen/IgG antibody complexes, presence of the complexes indicating presence of said IgG antibodies in the test sample.

The invention also encompasses a method for detecting the presence of IgG antibodies to *Toxoplasma gondii* in a test sample comprising the steps of: a) contacting the test sample suspected of containing the IgG antibodies with a composition comprising: 1) a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64 and 2) P35, for a time and under conditions sufficient for formation of IgG antibody/antigen complexes; b) adding a conjugate to resulting IgG antibody/antigen complexes for a time and under conditions sufficient to allow the conjugate to bind to bound antibody, wherein the conjugate comprises an antibody attached to a signal-generating compound capable of generating a detectable signal; and c) detecting IgG antibodies which may be present in the test sample by detecting presence of a signal generated by said signal-generating compound.

Furthermore, the present invention includes a method for detecting the presence of IgM antibodies to *Toxoplasma gondii* in a test sample comprising the steps of: a) contacting the test sample suspected of containing the IgM antibodies with anti-antibody specific for the IgM antibodies for a time and under conditions sufficient to allow for formation of anti-antibody/IgM antibody complexes; b) adding a conjugate to resulting anti-antibody/IgM antibody complexes for a time and under conditions sufficient to allow the conjugate to bind to bound antibody, wherein the conjugate comprises a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, attached to a signal generating compound capable of generating a detectable signal; and c) detecting IgM antibodies which may be present in the test sample by detecting presence of a signal generated by the signal-generating compound.

Further, the present invention includes a method for detecting the presence of IgG antibodies to *Toxoplasma gondii* in a test sample comprising the steps of: a) contacting the test sample suspected of containing the IgG antibodies with anti-antibody specific for the IgG antibodies for a time and under conditions sufficient to allow for formation of anti-antibody/IgG antibody complexes; b) adding a conjugate to resulting anti-antibody/IgG antibody complexes for a time and under conditions sufficient to allow the conjugate to bind to bound antibody, wherein the conjugate comprises: 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, and 2) P35, each attached to a signal-generating compound capable of generating a detectable signal; and c) detecting IgG antibodies which may be present in the test sample by detecting the presence of a signal generated by each of the signal-generating compounds.

The present invention also encompasses a vaccine comprising: a) at least one polypeptide selected from the group consisting of: 1) a polypeptide, wherein the polypeptide comprises amino acid sequence having at least 70% amino acid sequence identity to an amino acid sequence selected from the group consisting of SEQ ID NO:23, SEQ ID NO:28 and SEQ ID NO:64 and 2) P35, and b) a pharmaceutically acceptable adjuvant.

Also, the invention includes a kit for determining the presence of IgM antibodies to *Toxoplasma gondii* in a test sample comprising a composition comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64; and a conjugate comprising an antibody attached to a signal-generating compound capable of generating a detectable signal.

Also, the present invention includes a kit for determining the presence of IgG antibodies to *Toxoplasma gondii* in a test sample comprising: a composition comprising 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64 and 2) P35; and a conjugate comprising an antibody attached to a signal-generating compound capable of generating a detectable signal.

Additionally, the present invention encompasses a kit for determining the presence of IgM antibodies to *Toxoplasma gondii* in a test sample comprising:

a) an anti-antibody specific for IgM antibody; and b) a composition comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64.

Furthermore, the present invention includes a kit for determining the presence of IgM antibodies to *Toxoplasma gondii* in a test sample comprising:

a) an anti-antibody specific for IgM antibody;

b) a conjugate comprising: 1) a composition comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, attached to 2) a signal-generating compound capable of generating a detectable signal.

Also, the invention includes a kit for determining the presence of IgG antibodies to *Toxoplasma gondii* in a test sample comprising:

a) an anti-antibody specific for IgG antibody; and b) a composition comprising: 1) a polypeptide, wherein said polypeptide comprises an amino acid sequence having at least 70% amino acid sequence identity to an amino acid sequence selected from the group consisting of SEQ ID NO:23, SEQ ID NO:28 and SEQ ID NO:64 and 2) P35.

Another kit of the present invention includes a kit for determining the presence of IgG antibodies to *Toxoplasma gondii* in a test sample comprising:

a) an anti-antibody specific for IgG antibody;

b) a conjugate comprising: 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, and 2) P35, each attached to a signal-generating compound capable of generating a detectable signal.

Further, the present invention includes a method for detecting the presence of IgM antibodies to *Toxoplasma gondii* in a test sample comprising the steps of: (a) contacting said test sample suspected of containing IgM antibodies with anti-antibody specific for the IgM antibodies for a time and under conditions sufficient to allow for formation of anti-antibody IgM complexes; (b) adding antigen to resulting anti-antibody/IgM complexes for a time and under conditions sufficient to allow the antigen to bind to bound IgM antibody, the antigen comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64; and (c) adding a conjugate to resulting anti-antibody/IgM/antigen complexes, the conjugate comprising a composition comprising monoclonal or polyclonal antibody attached to a signal-generating compound capable of generating a detectable signal; and (d) detecting IgM antibodies which may be present in the test sample by detecting a signal generated by the signal-generating compound.

Additionally, the invention includes a method for detecting the presence of IgG antibodies to *Toxoplasma gondii* in a test sample comprising the steps of: (a) contacting the test sample suspected of containing IgG antibodies with anti-antibody specific for the IgG antibodies for a time and under conditions sufficient to allow for formation of anti-antibody IgG complexes; (b) adding antigen to resulting anti-antibody/IgG complexes for a time and under conditions sufficient to allow the antigen to bind to bound IgG antibody, the antigen comprising a mixture of 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, and 2) P35; (c) adding a conjugate to resulting anti-antibody/IgG/antigen complexes, the conjugate comprising a composition comprising a monoclonal or polyclonal antibody attached to a signal-generating compound capable of generating a detectable signal; and (d) detecting IgG antibodies which may be present in the test sample by detecting a signal generated by the signal-generating compound.

The present invention also includes a method for detecting the presence of IgM and IgG antibodies to *Toxoplasma gondii* in a test sample comprising the steps of: a) contacting the test sample suspected of containing said IgM and IgG antibodies with a composition comprising 1) a polypeptide, wherein said polypeptide comprises an amino acid sequence having at least 70% amino acid sequence identity to an amino acid sequence selected from the group consisting of SEQ ID NO:23, SEQ ID NO:28 and SEQ ID NO:64, and 2) P35, for a time and under conditions sufficient for the formation of IgM and IgG antibody/antigen complexes; b) adding a conjugate to the resulting IgM antibody/antigen complexes and IgG antibody/antigen complexes for a time and under conditions sufficient to allow the conjugate to bind to the bound IgM and IgG antibody, wherein the conjugate comprises an antibody attached to a signal-generating compound capable of generating a detectable signal; and c) detecting the presence of IgM and IgG antibodies which may be present in said test sample by detecting a signal generated by the signal-generating compound.

The invention also encompasses a method for detecting the presence of IgM and IgG antibodies to *Toxoplasma gondii* in a test sample comprising the steps of: a) contacting the test sample suspected of containing the IgM and IgG antibodies with anti-antibody specific for the IgM antibodies and the IgG antibodies for a time and under conditions sufficient to allow for formation of anti-antibody/IgM antibody complexes and anti-antibody/IgG antibody complexes; b) adding a conjugate to resulting anti-antibody/IgM antibody complexes and resulting anti-antibody/IgG antibody complexes for a time and under conditions sufficient to allow the conjugate to bind to bound antibody, wherein the conjugate comprises a composition comprising: 1) a polypeptide, wherein the polypeptide comprises an amino acid sequence having at least 70% amino acid sequence identity to an amino acid sequence-selected from the group consisting of SEQ ID NO:23, SEQ ID NO:28 and SEQ ID NO:64, and 2) P35, each attached to a signal-generating compound capable of generating a detectable signal; and c) detecting IgM and IgG antibodies which may be present in the test sample by detecting a signal generated by the signal-generating compound.

Moreover, the present invention also encompasses a method for detecting the presence of IgM and IgG antibodies to *Toxoplasma gondii* in a test sample comprising the steps of: (a) contacting the test sample suspected of containing IgM and IgG antibodies with anti-antibody specific for the IgM antibodies and with anti-antibody specific for the IgG antibodies for a time and under conditions sufficient to allow for formation of anti-antibody/IgM complexes and anti-antibody/IgG complexes; (b) adding antigen to resulting anti-antibody/IgM complexes and resulting anti-antibody/IgG complexes for a time and under conditions sufficient to allow said antigen to bind to bound IgM and IgG antibody, the antigen comprising a mixture of: 1) a polypeptide, wherein said polypeptide comprises an amino acid sequence selected from the group consisting of SEQ ID NO:23, SEQ ID NO:28 and SEQ ID NO:64 and 2) P35; and (c) adding a conjugate to resulting anti-antibody/IgM/antigen complexes and anti-antibody/IgG/antigen complexes, the conjugate comprising a composition comprising monoclonal or polyclonal antibody attached to a signal-generating compound capable of generating a detectable signal; and (d) detecting IgM and IgG antibodies which may be present in the test sample by detecting a signal generated by the signal-generating compound.

The present invention also includes a method of producing monoclonal antibodies comprising the steps of injecting a non-human mammal with a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64; fusing spleen cells of the non-human mammal with myeloma cells in order to generate hybridomas; and culturing the hybridomas for a time and under conditions sufficient for the hybridomas to produce the monoclonal antibodies.

Moreover, the present invention encompasses the plasmid pMBP-c2X-ToxoP30del3C(52-300aa), the plasmid pMBP-c2X-ToxoP30del4C(52-294aa), as well as the plasmid pMBP-c2X-ToxoP30MIX1.

The invention also includes an isolated nucleotide sequence comprising or complementary to the nucleotide sequence of SEQ ID NO:20 as well as a purified polypeptide comprising the amino acid sequence of SEQ ID NO:21.

Furthermore, the present invention includes an isolated nucleotide sequence comprising or complementary to the nucleotide sequence of SEQ ID NO:25 as well as a purified polypeptide comprising the amino acid sequence of SEQ ID NO:26.

Additionally, the invention includes an isolated nucleotide sequence comprising or complementary to the nucleotide sequence of SEQ ID NO:61 as well as a purified polypeptide comprising the amino acid sequence of SEQ ID NO:62.

The present invention also includes portions or fragments of ToxoP30del3C(52-300aa), ToxoP30del4C(52-294aa), or ToxoP30MIX1, which have the same antigenic properties as the region of ToxoP30del3C(52-300aa) which consists of amino acids 1-249, as the region of ToxoP30del4C(52-294aa) which consists of amino acids 1-243, and the region of ToxoP30MIX1 which consists of amino acids 1-249, respectively.

All U.S. patents and publications referred to herein are hereby incorporated in their entirety by reference.

BRIEF DESCRIPTION OF THE DRAWINGS

FIG. 2 represents the DNA sequence [SEQ ID NO:3] of nucleotides 1-7478 encoding the amino acid sequence [SEQ ID NO:4] of the MBP-ToxoP30(52-336aa) fusion protein of plasmid pMBP-c2X-ToxoP30(52-336aa).

FIG. 3 represents the DNA sequence [SEQ ID NO:5] of nucleotides 1-855 of the ToxoP30(52-336aa) gene and the corresponding encoded amino acid sequence [SEQ ID NO:6] of the ToxoP30(52-336aa) protein.

FIG. 5 represents the DNA sequence [SEQ ID NO:7] of nucleotides 1-7553 and the corresponding encoded amino acid sequence [SEQ ID NO:8] of the MBP-ToxoP30(52-336aa) fusion protein of plasmid pMBP-p2X-ToxoP30(52-336aa).

FIG. 8 represents the DNA sequence [SEQ ID NO:10] of nucleotides 1-7442 and the corresponding encoded amino acid sequence [SEQ ID NO:11] of the MBP-ToxoP30del1C (52-324aa) fusion protein of plasmid pMBP-c2X-ToxoP30del1C(52-324aa).

FIG. 9 represents the DNA sequence [SEQ ID NO:12] of nucleotides 1-819 of the ToxoP30del1C(52-324) gene and the corresponding encoded amino acid sequence [SEQ ID NO:13] of the ToxoP30del1C(52-324aa) protein.

FIG. 11 represents the DNA sequence [SEQ ID NO:15] of nucleotides 1-7403 and the corresponding encoded amino acid sequence [SEQ ID NO:16] of the MBP-ToxoP30del2 (52-311aa) fusion protein of plasmid pMBP-c2X-ToxoP30del2(52-311aa).

FIG. 12 represents the DNA sequence [SEQ ID NO:17] of nucleotides 1-780 of the ToxoP30del2(52-311aa) gene and the corresponding encoded amino acid sequence [SEQ ID NO:18] of the ToxoP30del2(52-311aa) protein.

FIG. 15 represents the DNA sequence [SEQ ID NO:20] of nucleotides 1-7370 and the corresponding encoded amino acid sequence [SEQ ID NO:21] of the MBP-ToxoP30del3C (52-300aa) fusion protein of plasmid pMBP-c2X-ToxoP30del3C(52-300aa).

FIG. 16 represents the DNA sequence [SEQ ID NO:22] of nucleotides 1-747 of the ToxoP30del3(52-300aa) and the corresponding encoded amino acid sequence [SEQ ID NO:23] of the ToxoP30del3C(52-300aa) protein.

FIG. 19 represents the DNA sequence [SEQ ID NO:25] of nucleotides 1-7352 and the corresponding encoded amino acid sequence [SEQ ID NO:26] of the MBP-ToxoP30del4C (52-294aa) fusion protein of plasmid pMBP-c2X-ToxoP30del4C(52-294aa).

FIG. 20 represents the DNA sequence [SEQ ID NO:27] of nucleotides 1-729 of the ToxoP30del4C(52-294aa) gene and the corresponding encoded amino acid sequence [SEQ ID NO:28] of the ToxoP30del4C(52-294aa) protein.

FIG. 22 represents the DNA sequence [SEQ ID NO:30] of nucleotides 1-7259 and the corresponding encoded amino acid sequence [SEQ ID NO:31] of the MBP-ToxoP30del4del8(83-294aa) fusion protein of plasmid pMBP-c2X-ToxoP30del4del8(83-294aa).

FIG. 23 represents the DNA sequence [SEQ ID NO:32] of nucleotides 1-636 of the ToxoP30del4del8(83-294aa) gene and the corresponding amino acid sequence [SEQ ID NO:33] of the ToxoP30del4del8(83-294aa) protein.

FIG. 25 represents the DNA sequence [SEQ ID NO:35] of nucleotides 1-7322 and the corresponding encoded amino acid sequence [SEQ ID NO:36] of the MBP-ToxoP30del10 (52-284aa) fusion protein of plasmid pMBP-c2X-ToxoP30del10(52-284aa).

FIG. 26 represents the DNA sequence [SEQ ID NO:37] of nucleotides 1-699 of the ToxoP30del10(52-284aa) gene and the corresponding encoded amino acid sequence [SEQ ID NO:38] of the ToxoP30del10(52-284aa) protein.

FIG. 28 represents the DNA sequence [SEQ ID NO:40] of nucleotides 1-7112 and the corresponding encoded amino acid sequence [SEQ ID NO:41] of the MBP-ToxoP30del11 (52-214aa) fusion protein of plasmid pMBP-c2X-ToxoP30del11(52-214aa).

FIG. 29 represents the DNA sequence [SEQ ID NO:42] of nucleotides 1-489 of the ToxoP30del11(52-214aa) gene and the corresponding encoded amino acid sequence [SEQ ID NO:43] of the ToxoP30del11(52-214aa) protein.

FIG. 31 represents the DNA sequence [SEQ ID NO:61] of nucleotides 1-7370 and the corresponding encoded amino acid sequence [SEQ ID NO:62] of the MBP-ToxoP30MIX1 fusion protein of plasmid pMBP-c2X-ToxoP30MIX1.

FIG. 32 represents the DNA sequence [SEQ ID NO:63] of nucleotides 1-747 of the ToxoP30MIX1 gene and the corresponding encoded amino acid sequence [SEQ ID NO:64] of the ToxoP30MIX1 protein.

FIG. 33 represents the DNA sequence [SEQ ID NO:66] of nucleotides 1-7370 and the corresponding encoded amino acid sequence [SEQ ID NO:67] of the MBP-ToxoP30MIX3 fusion protein of plasmid pMBP-c2X-ToxoP30MIX3.

FIG. 34 represents the DNA sequence [SEQ ID NO:68] of nucleotides 1-747 of the ToxoP30MIX3 gene and the corresponding amino acid sequence [SEQ ID NO:69] of the ToxoP30MIX3 protein.

FIG. 35 represents the DNA sequence [SEQ ID NO:71] of nucleotides 1-7370 and the corresponding encoded amino acid sequence [SEQ ID NO:72] of the MBP-ToxoP30MIX5 fusion protein of plasmid pMBP-c2X-ToxoP30MIX5.

FIG. 36 represents the DNA sequence [SEQ ID NO:73] of nucleotides 1-747 of the ToxoP30MIX5 gene and the corresponding encoded amino acid sequence [SEQ ID NO:74] of the ToxoP30MIX5 protein.

DETAILED DESCRIPTION OF THE INVENTION

Figure 1:
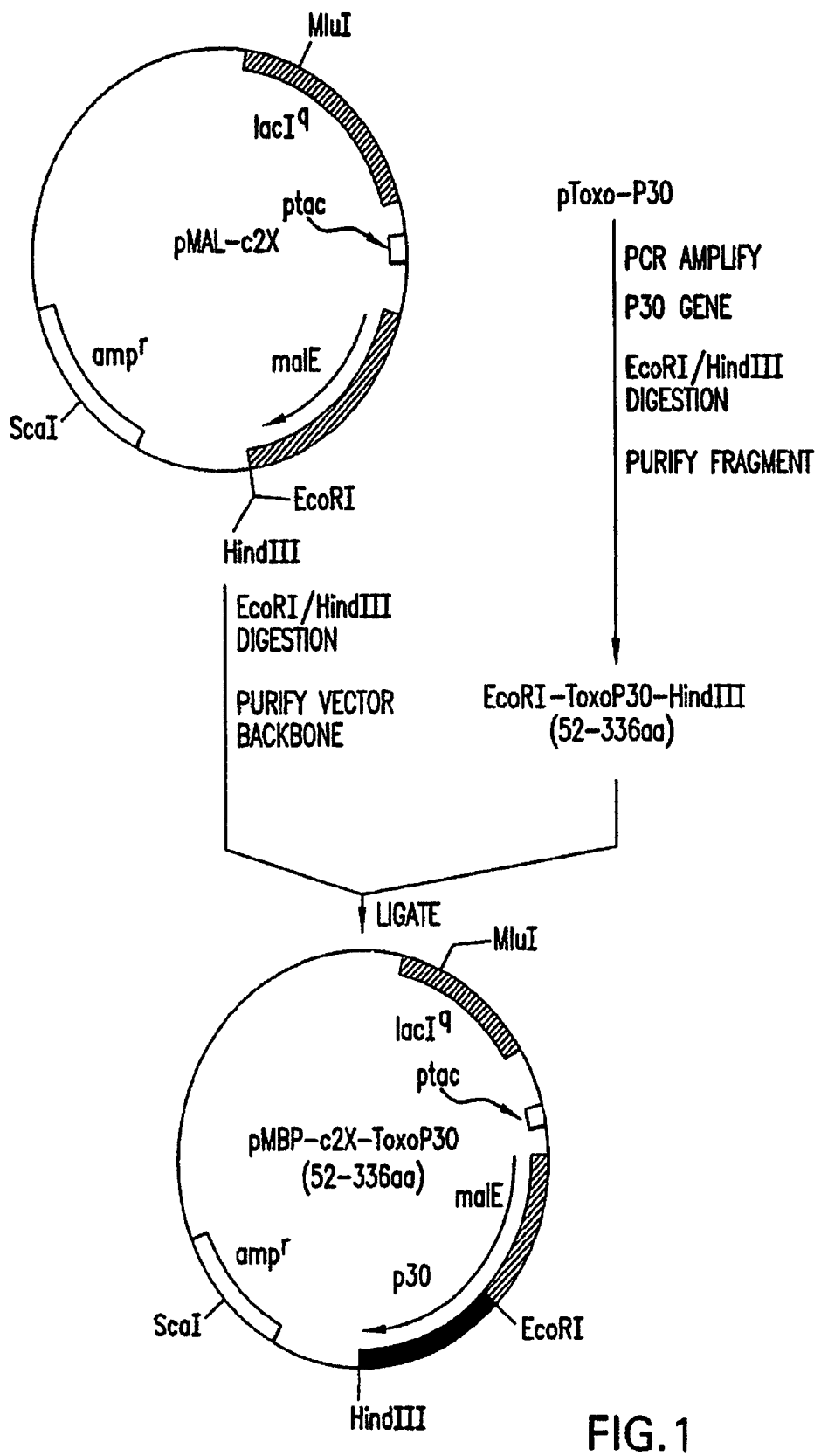
FIG. 1 is a schematic of the construction of plasmid pMBP-c2X-ToxoP30(52-336aa). (The amino acid range in parentheses, noted here and throughout the application, refers to the amino acid sequence (e.g., present in the plasmid, protein, etc.) which has been derived from the native P30 antigen.)

The difficulties of known assays for the detection of IgG and IgM antibodies to *T. gondii* have been described, in detail, above. Thus, there was a need to discover immunoassays that could accurately detect the presence of such antibodies in positive serum or plasma, thereby eliminating the problem of false negative or false positive tests. The present invention provides such needed immunoassays and, in particular, an antigen and combinations of antigens which accurately detect the presence of IgG and/or IgM antibodies in human sera.

In particular, the present invention includes genetically engineered versions of the P30 antigen referred to herein as "ToxoP30del3C(52-300aa)" and "ToxoP30del4C(52-294aa)", which contain small and precise deletions at the C-terminus of each protein that maximize the anti-Toxo IgG and IgM immunoreactivity of the P30 antigen in an immunoassay. The present invention also includes a genetically engineered version of the P30 antigen referred to herein as "ToxoP30MIX1", which contains the same deletion at the C-terminus as ToxoP30del3C(52-300aa) as well as five C-terminal cysteine residues changed to alanine. The invention also includes a polypeptide comprising the amino acid sequence of ToxoP30del3C(52-300aa) in which any one or more of the last five cysteines at the C-terminus have been changed to alanine.

The nucleotide sequence of the gene encoding the ToxoP30del3C antigen is shown in FIG. 16 and is represented by SEQ ID NO:22. The amino acid sequence of this antigen is also shown in FIG. 16 and is represented by SEQ ID NO:23. The nucleotide sequence of the gene encoding the ToxoP30del4C antigen is shown in FIG. 20 and is represented by SEQ ID NO:27. The amino acid sequence of this antigen is also shown in FIG. 20 and is represented by SEQ ID NO: 28. The nucleotide sequence of the gene encoding the ToxoP30MIX1 antigen is shown in FIG. 32 and is represented by SEQ ID NO:63. The amino acid sequence of this antigen is also shown in FIG. 32 and is represented by SEQ ID NO:64.

It should be noted that the present invention also encompasses nucleotide sequences comprising or complementary to a nucleotide sequence having at least about 70% nucleotide sequence identity, preferably at least about 80% nucleotide sequence identity, and more preferably at least about 90% nucleotide sequence identity to the nucleotide sequence of SEQ ID NO:22, SEQ ID NO:27 or SEQ ID NO:63. (All integers within the ranges noted above (i.e., between 70 and 100) are also considered to fall within the scope of the present invention.) The sequence having the above-described percent identity or complementary sequences may be derived from species or sources other than from which the isolated, original sequences were derived.

Also, it should be noted that the present invention encompasses a polypeptide sequence comprising an amino acid sequence having at least about 70% amino acid sequence identity, preferably at least about 80% amino acid sequence identity, and more preferably at least about 90% amino acid sequence identity to the amino acid sequence of SEQ ID NO:23, SEQ ID NO:28 or SEQ ID NO:64. (All integers within the ranges noted above (i.e, between 70 and 100) are also considered to fall within the scope of the present invention.)

For purposes of the present invention, "complementarity" is defined as the degree of relatedness between two DNA segments. It is determined by measuring the ability of the sense strand of one DNA segment to hybridize with the anti-sense strand of the other DNA segment, under appropriate conditions, to form a double helix. In the double helix, wherever adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of two DNA segments.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup (Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleotide sequence which is hybridizable, under moderately stringent conditions, to a nucleic acid having a nucleotide sequence comprising or complementary to the nucleotide sequences described above. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferably at least about 25 nucleotides identical or complementary to a region of the specified nucleotide sequence. (See U.S. Pat. No. 6,183,952 B1.) In contrast, a "fragment" of a specified polypeptide refers to an amino acid sequence which comprises at least about 5 amino acids, more preferably at least about 10 amino acids, and even more preferably at least 15 amino acids derived from the specified polypeptide.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. A fragment or subfragment that is functionally equivalent to the original polypeptide sequence from which it is derived refers to a sequence which has the same properties (e.g., binding, antigenic, etc.) as the original polypeptide.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be but are not limited to intracellular localization signals.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al, *Cold Spring Harbor Symp. Quant. Biol.* 51:263-273 (1986); Erlich et al., European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

Furthermore, the present invention also includes a polyclonal or monoclonal antibody raised against ToxoP30del3C, ToxoP30del4C, or ToxoP30MIX1. Such an antibody may be used, for example, in an immunoassay, a vaccine, a kit, or for research purposes.

As noted above, the present invention also encompasses a composition or mixture comprising the following two antigens: genetically engineered P30 and P35. This combination or mixture of antigens may be utilized for the detection of IgG in IgG-positive sera or plasma (i.e., as a diagnostic reagent). Furthermore, the antigens may be produced either recombinantly or synthetically. Additionally, the present invention also includes a composition comprising antibodies raised against these antigens.

Further, as noted above, present invention also includes the genetically engineered P30 antigen. This antigen may be used for the detection of IgM in IgM-positive sera or plasma (i.e., as a diagnostic reagent), and the antigen may be produced either recombinantly or synthetically. Furthermore, the present invention also includes antibodies raised against this antigen.

If, in fact, one wishes to measure both the titer of IgM and IgG in a serum or plasma sample, then a composition or mixture of antigens such as genetically engineered P30 and P35 may be utilized in an immunoassay. Such a combination of antigens is also included within the scope of the present invention.

The present invention also includes methods of detecting IgM and/or IgG using the combinations of antigens described above. More specifically, there are two basic types of assays, competitive and non-competitive (e.g., immunometric and sandwich). In both assays, antibody or antigen reagents are covalently or non-covalently attached to the solid phase. Linking agents for covalent attachment are known and may be part of the solid phase or derivatized to it prior to coating. Examples of solid phases used in immunoassays are porous and non-porous materials, latex particles, magnetic particles, microparticles, beads, membranes, microtiter wells and plastic tubes. The choice of solid phase material and method of labeling the antigen or antibody reagent are determined based upon desired assay format performance characteristics. For some immunoassays, no label is required. For example, if the antigen is on a detectable particle such as a red blood cell, reactivity can be established based upon agglutination. Alternatively, an antigen-antibody reaction may result in a visible change (e.g., radial immunodiffusion). In most cases, one of the antibody or antigen reagents used in an immunoassay is attached to a signal generating compound or "label". This signal generating compound or "label" is in itself detectable or may be reacted with one or more additional compounds to generate a detectable product (see also U.S. Pat. No. 6,395,472 B1). Examples of such signal generating compounds include chromogens, radioisotopes (e.g., 125I, 131I, 32P, 3H, 35S, and 14C), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

There are two general formats commonly used to monitor specific antibody titer and type in humans: (1) antigen is presented on a solid phase, as described above, the human biological fluid containing the specific antibodies is allowed to react with the antigen, and then antibody bound to antigen is detected with an anti-human antibody coupled to a signal generating compound and (2) an anti-human antibody is bound to the solid phase, the human biological fluid containing specific antibodies is allowed to react with the bound antibody, and then antigen attached to a signal generating compound is added to detect specific antibody present in the fluid sample. In both formats, the anti-human antibody reagent may recognize all antibody classes, or alternatively, be specific for a particular class or subclass of antibody, depending upon the intended purpose of the assay. These assays formats as well as other known formats are intended to be within the scope of the present invention and are well known to those of ordinary skill in the art.

In particular, two illustrative examples of an immunometric antibody-capture based immunoassay are the IMx Toxo IgM and Toxo IgG antibody assays manufactured by Abbott Laboratories (Abbott Park, Ill.). Both assays are automated Microparticle Enzyme Immunoassays (MEIA) which measure antibodies to Toxoplasma gondii (T. gondii) in human serum or plasma (Safford et al. (1991) J. Clin. Pathol. 44:238-242). One assay qualitatively measures IgM antibodies, indicative of recent exposure or acute infection, and the other assay quantitatively measures IgG, indicative of chronic or past infection. These assays use microparticles coated with T. gondii antigens as the solid phase. In particular, specimen is added to the coated microparticles to allow antibodies specific for T. gondii to bind. Subsequently, an alkaline phosphatase conjugated anti-human IgM (or anti-human IgG) is added that specifically binds to IgM (or IgG) class antibodies complexed to the T. gondii antigens. Following addition of a suitable substrate (e.g., 4-methyumbelliferyl phosphate), the rate of enzyme-catalyzed turnover is monitored based upon fluorescence.

The mixture of genetically engineered P30 and P35 may be used in the IgG Abbott immunoassay, and the genetically engineered P30 antigen alone may be utilized in the IgM Abbott immunoassay. Additionally, a mixture of genetically engineered P30 and P35 may be utilized in either assay, if desired. Furthermore, it must be noted that other non-Abbott assays or platforms may also be utilized, with each antigen or combination of antigens for purposes of the present invention.

Thus, the present invention includes a method of detecting IgM antibodies in a test sample comprising the steps of: (a) contacting the test sample suspected of containing the IgM antibodies with genetically engineered P30; (b) detecting the presence of IgM antibodies present in the test sample. More specifically, the present invention includes a method of detecting IgM antibodies in a test sample comprising the steps of: (a) contacting the test sample suspected of containing the IgM antibodies with genetically engineered P30 for a time and under conditions sufficient to allow the formation of IgM antibody/antigen complexes; (b) adding a conjugate to the resulting IgM antibody/antigen complexes for a time and under conditions sufficient to allow the conjugate to bind to the bound antibody, the conjugate comprising an antibody (directed against the IgM) attached to a signal generating compound capable of generating a detectable signal; (c) detecting the presence of the IgM antibody which may be present in the test sample by detecting the signal generated by the signal generating compound. A control or calibrator may also be used which binds to this antigen. Furthermore, the method may also comprise the use of P35 in addition to genetically engineered P30.

Additionally, the present invention further includes a method for detecting the presence of IgM which may be present in a test sample. This method comprises the steps of: (a) contacting the test sample suspected of containing IgM antibodies with anti-antibody specific for the IgM, for a time and under conditions sufficient to allow for formation of anti-antibody/IgM complexes and (b) detecting the presence of IgM which may be present in the test sample. (Such anti-antibodies are commercially available and may be created, for example, by immunizing a mammal with purified mu-chain of the antibody.)

More specifically, this method may comprise the steps of: (a) contacting the test sample suspected of containing the IgM antibodies with anti-antibody specific for the IgM, under time and conditions sufficient to allow the formation of anti-antibody/IgM complexes; (b) adding a conjugate to the resulting anti-antibody/IgM complexes for a time and under conditions sufficient to allow the conjugate to bind to the bound antibody, the conjugate comprising genetically engineered P30 attached to a signal generating compound capable of generating a detectable signal; and (c) detecting the presence of the IgM antibodies which may be present in the test sample by detecting the signal generated by the signal generating compound. A control or calibrator may be used which comprises antibody to the anti-antibody. Furthermore, the conjugate may also comprise P35, if desired.

In each of the above assays, IgG may be detected by substituting the genetically engineered P30 with a genetically engineered P30 and P35 mixture. Also, anti-antibody specific for IgG will be used. Additionally, if one wishes to detect both IgM and IgG antibodies, genetically engineered P30 and P35 may be utilized in the immunoassay.

The present invention also encompasses a third method for detecting the presence of IgM in a test sample. This method comprises the steps of: (a) contacting the test sample suspected of containing IgM antibodies with anti-antibody specific for the IgM, under time and conditions sufficient to allow the formation of anti-antibody IgM complexes; (b) adding antigen to the resulting anti-antibody/IgM complexes for a time and under conditions sufficient to allow the antigen to bind to the bound IgM antibody, the antigen comprising the genetically engineered P30; and (c) adding a conjugate to the resulting anti-antibody/IgM/antigen complexes, the conjugate comprising a composition comprising monoclonal or polyclonal antibody attached to a signal generating compound capable of detecting a detectable signal, the monoclonal or polyclonal antibody being directed against the antigen; and (d) detecting the presence of the IgM antibodies which may be present in the test sample by detecting the signal generated by the signal generating compound. Again, a control or calibrator may be used which comprises antibody to the anti-antibody. The antigen mixture may further comprise P35, if desired.

In this method, IgG may be detected by substituting the genetically engineered P30 antigen with a genetically engineered P30 and P35 mixture, and utilizing anti-antibody specific for IgG. However, if one wishes to detect both IgM and IgG antibodies, genetically engineered P30 and P35 may be utilized in the immunoassay.

It should also be noted that all of the above methods may be used to detect IgA antibodies (with an alpha-specific conjugate) and/or IgE antibodies (with an epsilon-specific conjugate) should such detection be desired.

Additionally, the present invention also includes a vaccine comprising a mixture of genetically engineered P30 and P35 antigens and a pharmaceutically acceptable adjuvant. Such a vaccine may be administered if one desires to raise IgG antibodies in a mammal. The present invention also includes a vaccine comprising the genetically engineered P30 antigen and a pharmaceutically acceptable adjuvant (e.g., Freund's adjuvant or Phosphate Buffered Saline). Such a vaccine may be administered if one desires to raise IgM antibodies in a mammal. Additionally, the present invention also includes a vaccine comprising a mixture of genetically engineered P30 and P35 antigens as well as a pharmaceutically acceptable adjuvant. This vaccine should be administered if one desires to raise both IgM and IgG antibodies in a mammal.

Kits are also included within the scope of the present invention. More specifically, the present invention includes kits for determining the presence of IgG and/or IgM. In particular, a kit for determining the presence of IgM in a test sample comprises a) genetically engineered P30; and b) a conjugate comprising an antibody (directed against IgM) attached to a signal-generating compound capable of generating a detectable signal. The kit may also contain a control or calibrator which comprises a reagent which binds to genetically engineered P30.

Again, if one desires to detect IgG, rather than IgM, the kit will comprise a mixture of genetically engineered P30 and P35, rather than genetically engineered P30, as well as an antibody directed against IgG. If one wishes to detect both IgM and IgG, the kit will comprise genetically engineered P30 and P35.

The present invention also includes another type of kit for detecting IgM and/or IgG in a test sample. If utilized for detecting the presence of IgM, the kit may comprise a) an anti-antibody specific for IgM, and b) genetically engineered P30. A control or calibrator comprising a reagent which binds to genetically engineered P30 may also be included. More specifically, the kit may comprise a) an anti-antibody specific for IgM, and b) a conjugate comprising genetically engineered P30, the conjugate being attached to a signal-generating compound capable of generating a detectable signal. Again, the kit may also comprise a control or calibrator comprising a reagent which binds to genetically engineered P30.

Additionally, if one desires to detect IgG, rather than IgM, the kit will comprise a mixture of genetically engineered P30 and P35, rather than genetically engineered P30 alone, as well as anti-antibody specific for IgG. If one wishes to detect both IgM and IgG, the kit may comprise genetically engineered P30 and P35.

The present invention may be illustrated by the use of the following non-limiting examples:

EXAMPLE 1

General Methodology

Materials and Sources

Restriction enzymes, T4 DNA ligase, and the pMAL™ Protein Fusion and Purification System were purchased from New England Biolabs, Inc. (Beverly, Mass.).

DNA and protein molecular weight standards, plasmid mini-prep kit, ethidium bromide, and pre-cast polyacrylamide gels, were purchased from BioRad Laboratories (Richmond, Calif.).

Maltose was purchased from Sigma Chemical Co. (St. Louis, Mo.).

QIAquick™ 4 PCR Purification Kit and QIAquick™ Gel Extraction Kit were purchased from Qiagen, Inc. (Valencia, Calif.).

Synthetic oligonucleotides were purchased from Sigma Genosys (The Woodlands, Tex.).

EPICURIAN Coli™ XL-1 BLUE (recA1 endA1 gyrA96 thi-1 hsdR17 supE44 relA1 lac [F' proAB lacI$^q$ ZDM15 Tn10 (Tet$^r$)]) supercompetent *E. coli* cells were obtained from Stratagene Cloning Systems, Inc. (La Jolla, Calif.).

A GeneAmp™ reagent kit and AmpliTaq™ DNA Polymerase were purchased from Perkin-Elmer Cetus (Norwalk, Conn.).

SeaKem GTG agarose was purchased from BioWhittaker Molecular Applications (Rockland, Me.).

Bacto-Tryptone, Bacto-Yeast Extract, Bacto-Agar ampicillin, buffers, isopropyl-β-D-thiogalactoside (IPTG), bovine serum albumin (BSA), Sephacryl S-300, fetal calf serum (Toxo antibody free), sucrose, sodium azide, urea, EDTA, Triton X-100, 1-ethyl-3-(3-dimethylaminopropyl) carbodiimide (EDAC), 2-(N-morpholino)ethanesulfonic acid (MES), inorganic salts, sodium dodecyl sulfate (SDS), Tween 20, glycerol, 4-methylumbelliferyl phosphate (MUP), tris-(hydroxymethyl)-aminomethane (Tris), AxSYM Toxo IgG and IgM assay reagents, calibrators, and controls, sulfate-derivatized microparticles, non-fat dry milk, Nipasept, A56620, Brij-35, mouse serum, mannitol, AxSYM instrument, reagents, and commodities were purchased from Abbott Manufacturing, Inc. (Abbott Park, Ill.).

Media, Buffers and General Reagents

"Superbroth II" contained 11.25 g/L tryptone, 22.5 g/L yeast extract, 11.4 g/L potassium phosphate dibasic, 1.7 g/L potassium phosphate monobasic, 10 ml/L glycerol, adjusted pH to 7.2 with sodium hydroxide.

General Methods

All enzyme digestions of DNA were performed according to suppliers' instructions. At least 5 units of enzyme were used per microgram of DNA, and sufficient incubation time was allowed for complete digestion of DNA. Supplier protocols were followed for the various kits used in the manipulation of DNA and transformation of DNA into *E. coli*, for polymerase chain reaction (PCR), and for purification of maltose binding protein (MBP) and MBP fusion proteins. Standard procedures were used for preparation of *E. coli* lysates containing CMP-KDO synthetase (CKS) (U.S. Pat. No. 6,329,157 B1), restriction analysis of DNA on agarose gels, purification of DNA fragments from agarose gels, and ligation of DNA fragments with T4 DNA ligase. (Maniatis et al., *Molecular Cloning: A Laboratory Manual*, 2$^{nd}$ ed. (Cold Spring Harbor Laboratory Press, New York, 1989)). DNA sequence analysis was performed by Lark Technologies, Inc. (Houston, Tex.).

EXAMPLE 2

Construction of pMBP-ToxoP30 Expression Vectors

In order to improve the immunoreactivity of the Toxo antigen cocktails described in U.S. Pat. No. 6,329,157 B1 in an immunoassay, a suitable heterologous protein expression system was pursued that would permit the production of soluble Toxo P30 in *E. coli*. The *E. coli* maltose binding protein (MBP) fusion and purification system described in U.S. Pat. No. 5,643,758 has been found to be useful for the production and purification of soluble fusion proteins in *E. coli*. (In particular, the vectors described therein have sequences coding for the recognition site of a specific protease (e.g., Factor Xa, enterokinase or Genenase™) such that the protein of interest may be cleaved from MBP.) Fusion of proteins to MBP enhances their solubility in *E. coli* (Kapust and Waugh (1999) Protein Science 8, 1668-1674). Several different constructs were made taking into consideration the observation that native Toxo P30 is post-translationally cleaved prior to insertion into the tachyzoite membrane (Burg et al. (1988) J. Immunol. 141:3584-3591). The exact cleavage sites for Toxo P30 are unknown.

Plasmid pToxo-P30 described in U.S. Pat. No. 6,329,157 B1 was used as template DNA for a series of PCR reactions to generate DNA fragments containing different portions of the Toxo P30 gene. The pToxo-P30 plasmid DNA was prepared using standard methods. The pMAL-c2X (cytoplasmic expression vector) and pMAL-p2X (periplasmic expression vector) plasmids were purchased from New England Biolabs, Beverly Mass. and were digested with the restriction enzymes EcoRI and HindIII in preparation for subcloning the Toxo P30 gene fragments.

Step A: Construction of pMBP-c2X-ToxoP30(52-336aa)

The plasmid pMBP-c2X-ToxoP30(52-336aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 1). Plasmid pMAL-c2X was digested with EcoRI/HindIII and the vector backbone was purified with a Qiaquick PCR purification kit. A sense primer, starting at nucleotide 464 of the P30 gene containing an EcoRI site and an antisense primer containing a HindIII site, starting at nucleotide 1318 of the P30 gene (Burg et al. (1988) J. Immunol. 141:3584-3591) were synthesized as shown below:

```
Sense Primer
                                       [SEQ ID NO: 1]
5'-GGCGAATTCCTTGTTGCCAATCAAGTTGTCACC-3'

(EcoRI site is underlined)
```

```
Antisense Primer
                                       [SEQ ID NO: 2]
5'-CGCTGAAGCTTTCACGCGACACAAGCTGCGA-3'

(HindIII site is underlined)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 855 base pair DNA fragment containing Toxo P30 was purified with a Qiaquick PCR purification kit. The purified 855 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30 (52-336aa) contained the Toxo P30 gene cloned at the EcoRI/HindIII sites of pMAL-c2X. The complete DNA sequence [SEQ ID NO:3] of plasmid pMBP-c2X-ToxoP30(52-336aa) is shown in FIG. 2 and the corresponding amino acid sequence [SEQ ID NO:4] of the MBP-ToxoP30(52-336aa) fusion protein is also shown in FIG. 2, wherein amino acid residues 392-676 of SEQ ID NO:4 correspond to amino acids 52-336 of the P30 antigen of *Toxoplasma gondii*. The DNA sequence [SEQ ID NO:5] of ToxoP30(52-336aa) is shown in FIG. 3, and the corresponding amino acid sequence [SEQ ID NO:6] of the ToxoP30(52-336aa) protein is also shown in FIG. 3, wherein amino acid residues 1-285 of SEQ ID NO:6 correspond to amino acids 52-336 of the P30 antigen of *Toxoplasma gondii*.

Step B: Construction of pMBP-p2X-ToxoP30(52-336aa)

Figure 4:
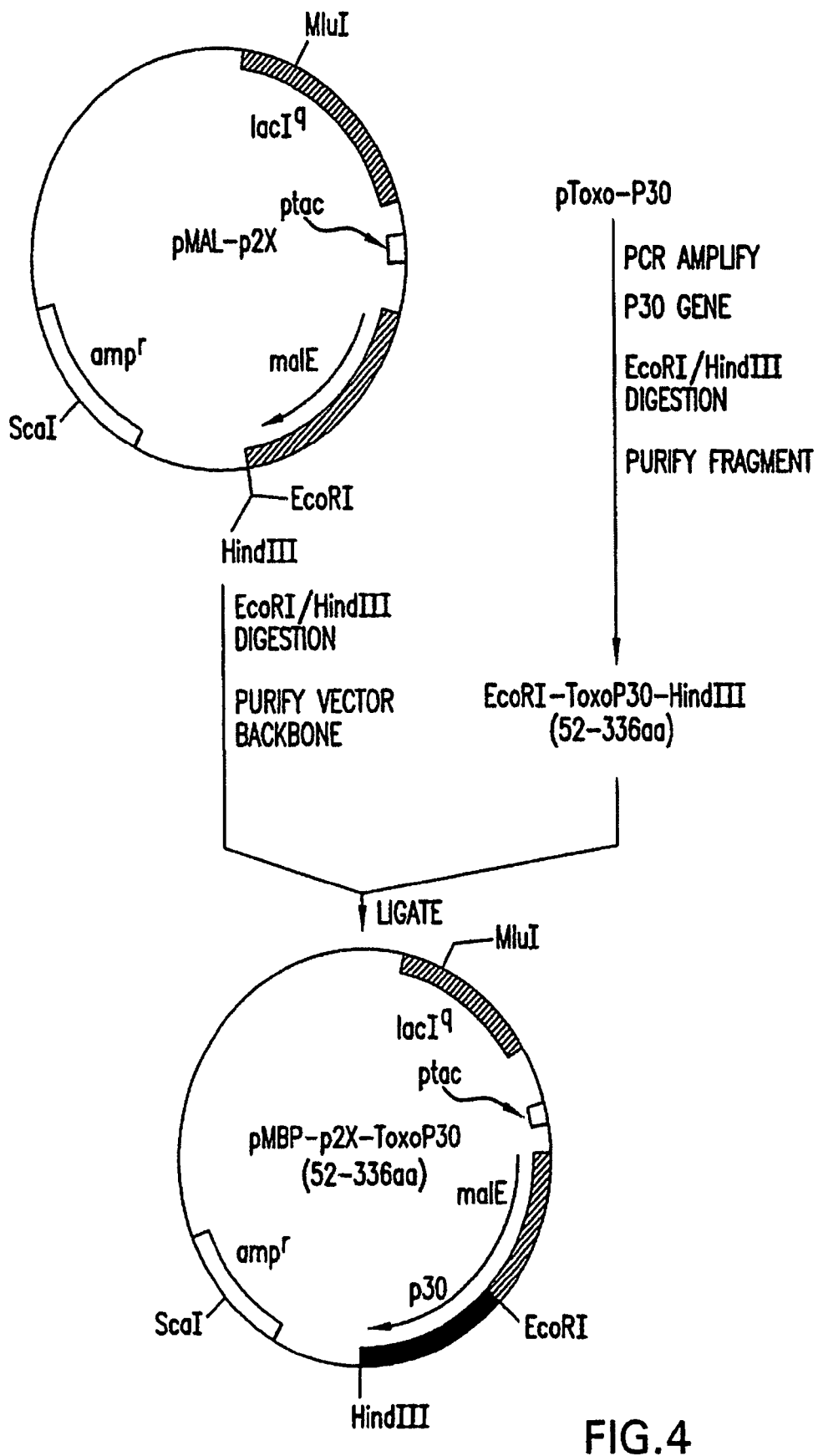
FIG. 4 is a schematic of the construction of plasmid pMBP-p2X-ToxoP30(52-336aa).

The plasmid pMBP-p2X-ToxoP30(52-336aa) was constructed by cloning a DNA fragment containing Toxo P30, obtained by PCR amplification of Toxo P30 DNA contained in plasmid pToxo-P30, into the EcoRI/HindIII sites of pMAL-p2X (FIG. 4). Plasmid pMAL-p2X was digested with EcoRI/HindIII, and the vector backbone was purified with a Qiaquick PCR purification kit. A sense primer, starting at nucleotide 464 of the P30 gene containing an EcoRI site, and an antisense primer containing a HindIII site, starting at nucleotide 1318 of the P30 gene (Burg et al. (1988) J. Immunol. 141:3584-3591) were synthesized as shown below:

```
Sense Primer
                                       [SEQ ID NO: 1]
5'-GGCGAATTCCTTGTTGCCAATCAAGTTGTCACC-3'

(EcoRI site is underlined)

Antisense Primer
                                       [SEQ ID NO: 2]
5'-CGCTGAAGCTTTCACGCGACACAAGCTGCGA-3'

(HindIII site is underlined)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 855 base pair DNA fragment containing Toxo P30 was purified with a Qiaquick PCR purification kit. The purified 855 base pair fragment was ligated to pMAL-p2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-p2X-ToxoP30 (52-336aa) contained the Toxo P30 gene cloned at the EcoRI/HindIII sites of pMAL-p2X. The complete DNA sequence [SEQ ID NO:7] of plasmid pMBP-p2X-ToxoP30(52-336aa) is shown in FIG. 5, and the corresponding amino acid sequence [SEQ ID NO:8] of the MBP-ToxoP30P(52-336aa) fusion protein is shown in FIG. 5, wherein amino acid residues 417-701 of SEQ ID NO:8 correspond to amino acids 52-336 of the P30 antigen of *Toxoplasma gondii*.

Step C: Construction of pMBP-c2X-ToxoP30del1C(52-324aa)

Figure 6:
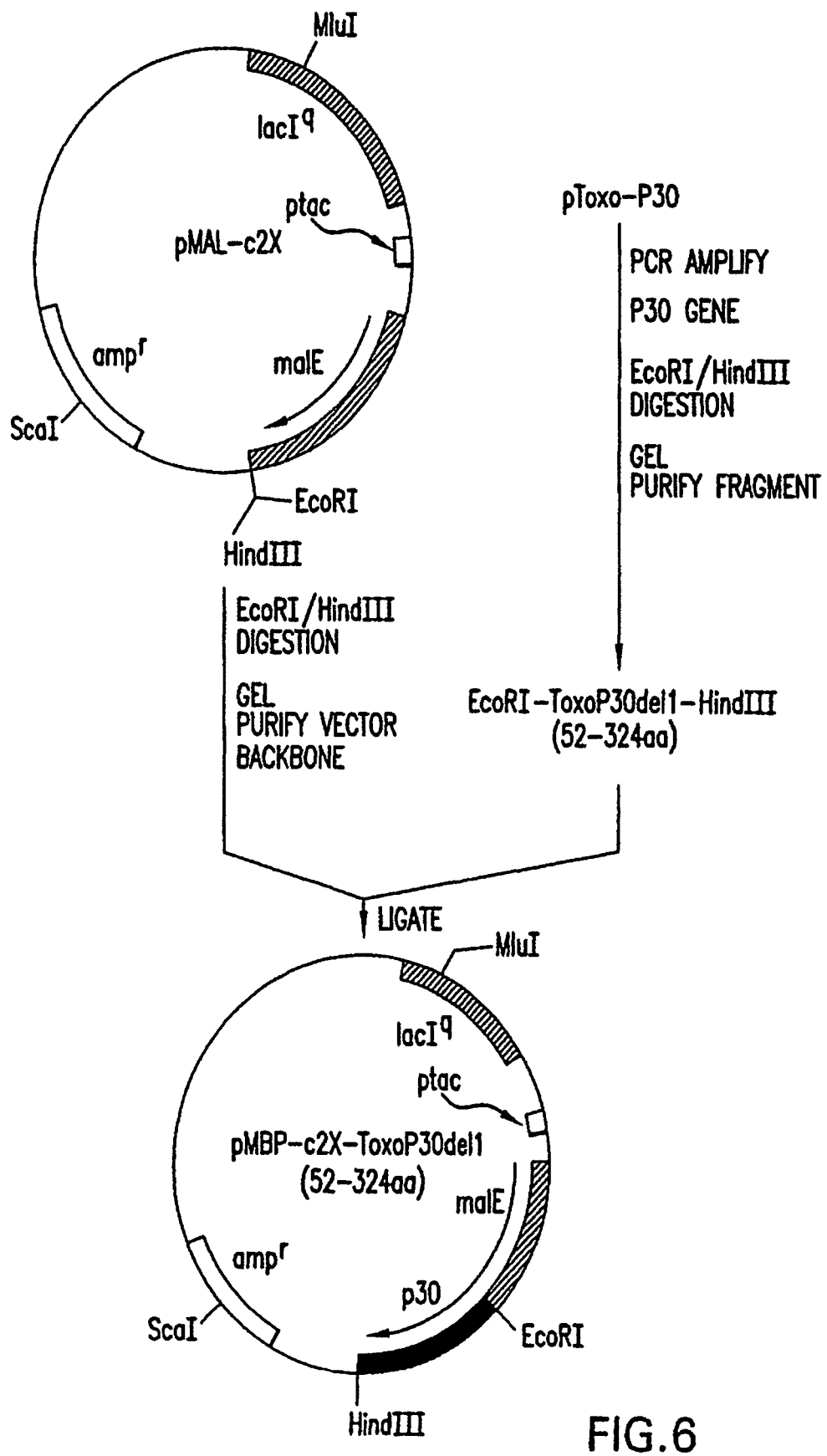
FIG. 6 is a schematic of the construction of plasmid pMBP-c2X-ToxoP30del1C(52-324aa).

The plasmid pMBP-c2X-ToxoP30del1(52-324aa), an intermediate in the construction of plasmid pMBP-c2X-ToxoP30del1C, was constructed by cloning a DNA fragment containing Toxo P30, obtained by PCR amplification of Toxo P30 DNA contained in plasmid pToxo-P30, into the EcoRI/HindIII sites of pMAL-c2X (FIG. 6). Plasmid pMAL-c2X was digested with EcoRI/HindIII and the vector backbone was purified on an agarose gel. A sense primer, starting at nucleotide 464 of the P30 gene containing an EcoRI site and an antisense primer containing a HindIII site, starting at nucleotide 1282 of the P30 gene (Burg et al. (1988) J. Immunol. 141:3584-3591) were synthesized as shown below:

```
Sense Primer
                                   [SEQ ID NO: 1]
5'-GGCGAATTCCTTGTTGCCAATCAAGTTGTCACC-3'

(EcoRI site is underlined)

Antisense Primer
                                   [SEQ ID NO: 9]
5'-CAGGTCAAGCTTTCACACCATGGCAAAAATGGAAACGTG-3'

(HindIII site is underlined.)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 819 base pair DNA fragment containing Toxo P30del1 was purified on an agarose gel. The purified 819 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del1(52-324aa) contained the Toxo P30del1 gene cloned at the EcoRI/HindIII sites of pMAL-c2X.

Figure 7:
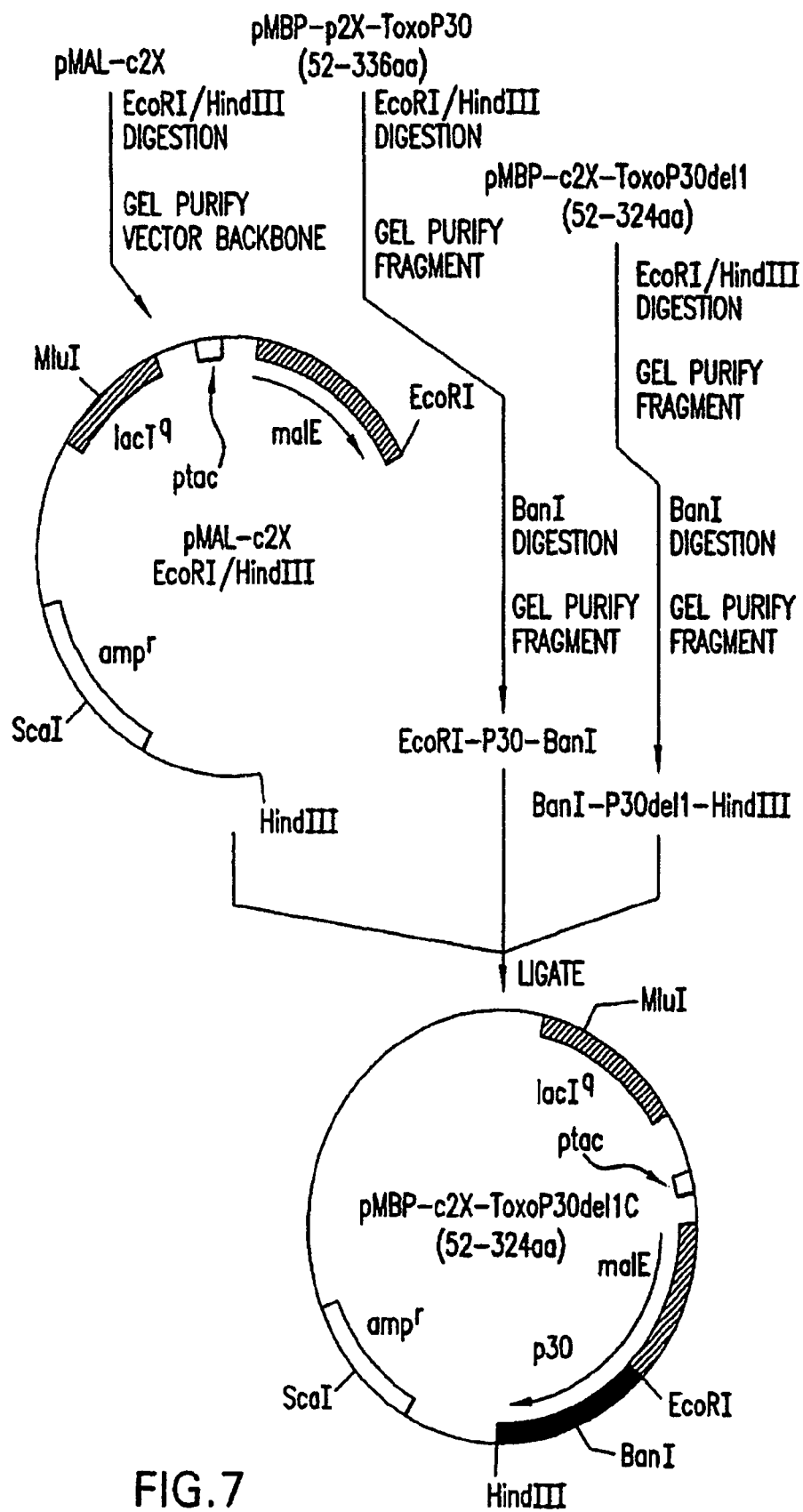
FIG. 7 is a schematic of the construction of plasmid pMBP-c2X-ToxoP30del1C(52-324aa).

Analysis of the DNA sequence of plasmid pMBP-c2X-ToxoP30del1(52-324aa) and analysis of the corresponding amino acid sequence revealed base changes in the P30 gene resulting in two amino acid changes from the published sequence (Burg et al. (1988) J. Immunol. 141:3584-3591). These mutations were located downstream of the synthetic EcoRI site (nucleotide 464) and upstream of a BanI site (nucleotide 1100) following the numbering convention of Burg et al., cited above. The mutations in plasmid pMBP-c2X-ToxoP30del1(52-324aa) were corrected as follows: Plasmid pMBP-c2X-ToxoP30del1C(52-324aa) was constructed by cloning an EcoRI/BanI fragment from plasmid pMBP-p2X-ToxoP30(52-336aa), containing the 5' corrected portion of the Toxo P30 gene, and a BanI/HindIII fragment from plasmid pMBP-c2X-ToxoP30del1(52-324aa), containing the 3' portion of the Toxo P30del1 gene, into the EcoRI/HindIII sites of pMAL-c2X (FIG. 7). Plasmid pMAL-c2X was digested with EcoRI/HindIII, and the vector backbone was purified on an agarose gel. Plasmid DNAs pMBP-p2X-ToxoP30(52-336aa) and pMBP-c2X-ToxoP30del1(52-324aa) were prepared by general methods. Plasmids pMBP-p2X-ToxoP30(52-336aa) and pMBP-c2X-ToxoP30del1(52-324aa) were digested with EcoRI/HindIII and the 855 and 819 base pair fragments, containing the Toxo P30 gene, were purified on an agarose gel. The 855 base pair EcoRI/HindIII fragment was digested with BanI and the 637 base pair EcoRI/BanI fragment, containing the 5' corrected portion of the Toxo P30 gene, was purified on an agarose gel. The 819 base pair EcoRI/HindIII fragment was digested with BanI and the 182 base pair BanI/HindIII fragment, containing the 3' portion of the Toxo P30del1 gene, was purified on an agarose gel. The purified 637 and 182 base pair fragments were ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del1C (52-324aa) contained the Toxo P30del1C gene cloned at the EcoRI/HindIII sites of pMAL-c2X. The complete DNA sequence [SEQ ID NO:10] of plasmid pMBP-c2X-ToxoP30del1C(52-324aa) is shown in FIG. 8 and the corresponding amino acid sequence [SEQ ID NO:11] of the MBP-ToxoP30del1C(52-324aa) fusion protein is also shown in FIG. 8, wherein amino acid residues 392-664 of SEQ ID NO:11 correspond to amino acids 52-324 of the P30 antigen of *Toxoplasma gondii*. The DNA sequence [SEQ ID NO:12] of ToxoP30del1C(52-324aa) is shown in FIG. 9 and the corresponding amino acid sequence [SEQ ID NO:13] of the ToxoP30del1C(52-324aa) protein is also shown in FIG. 9, wherein amino acid residues 1-273 of SEQ ID NO:13 correspond to amino acids 52-324 of the P30 antigen of *Toxoplasma gondii*.

Step D: Construction of pMBP-c2X-ToxoP30del2(52-311aa)

Figure 10:
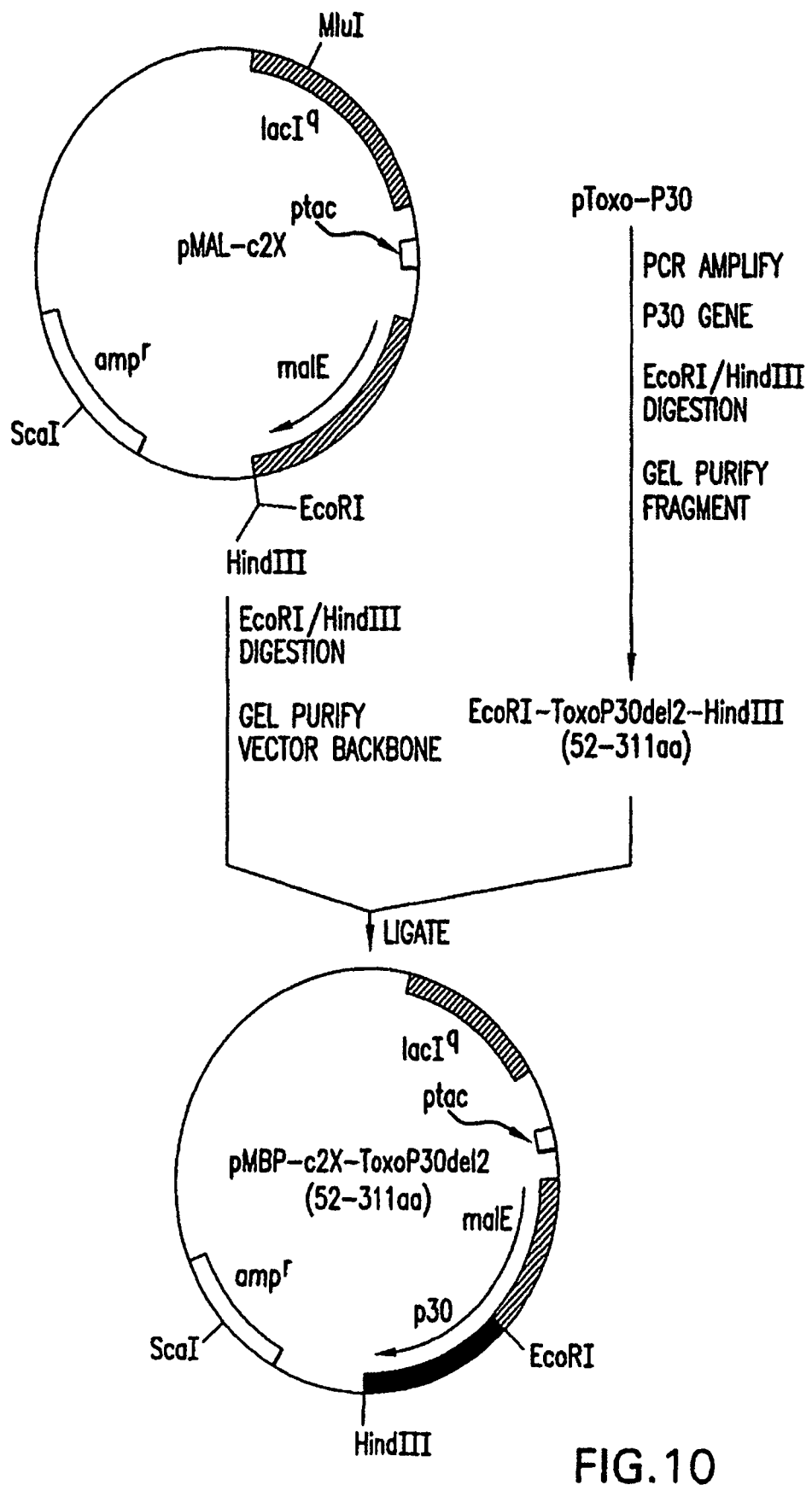
FIG. 10 is a schematic of the construction of plasmid pMBP-c2X-ToxoP30del2(52-311aa).
Figure 13:
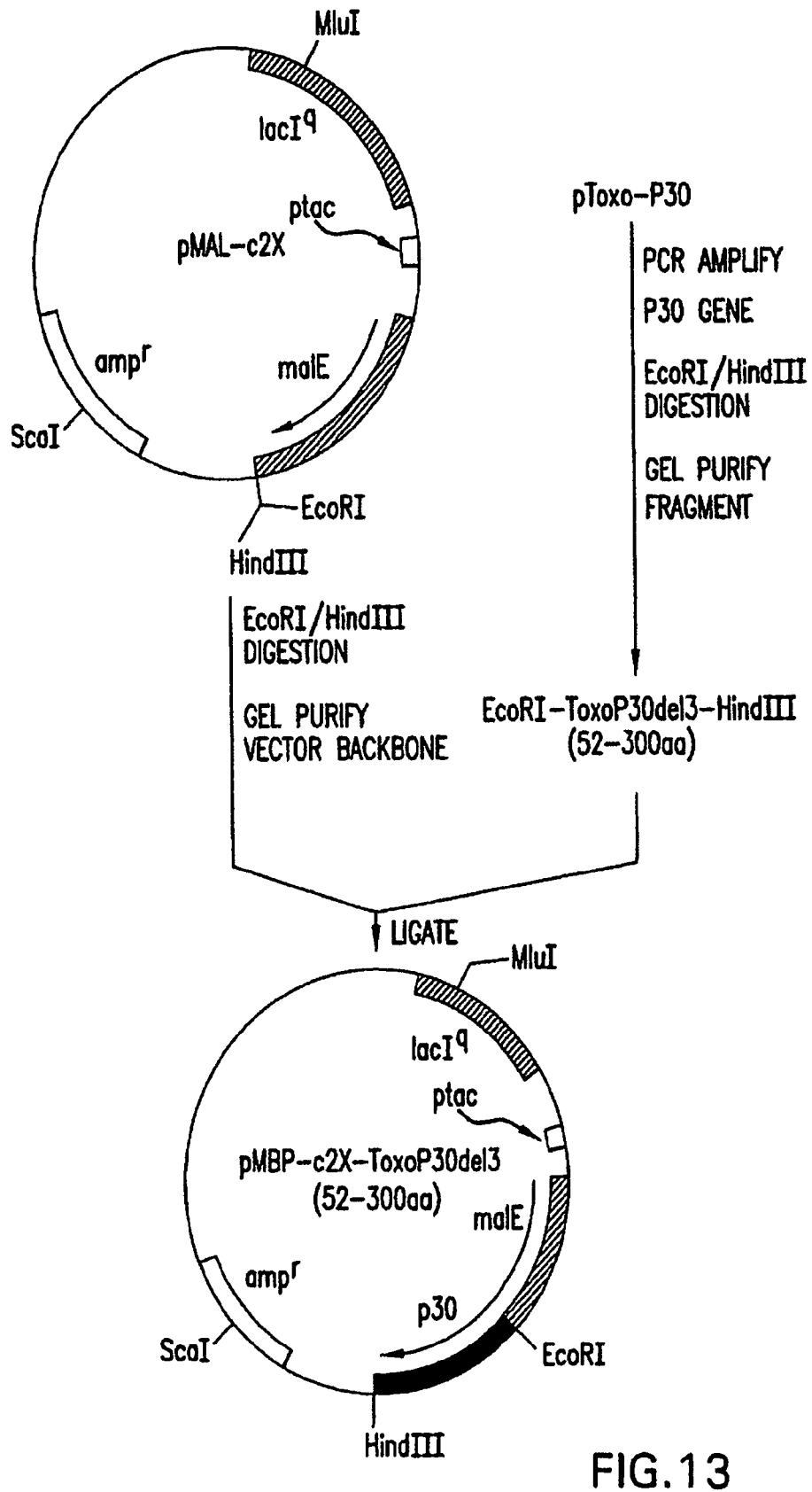
FIG. 13 is a schematic of the construction of plasmid pMBP-c2X-ToxoP30del3(52-300aa).
Figure 14:
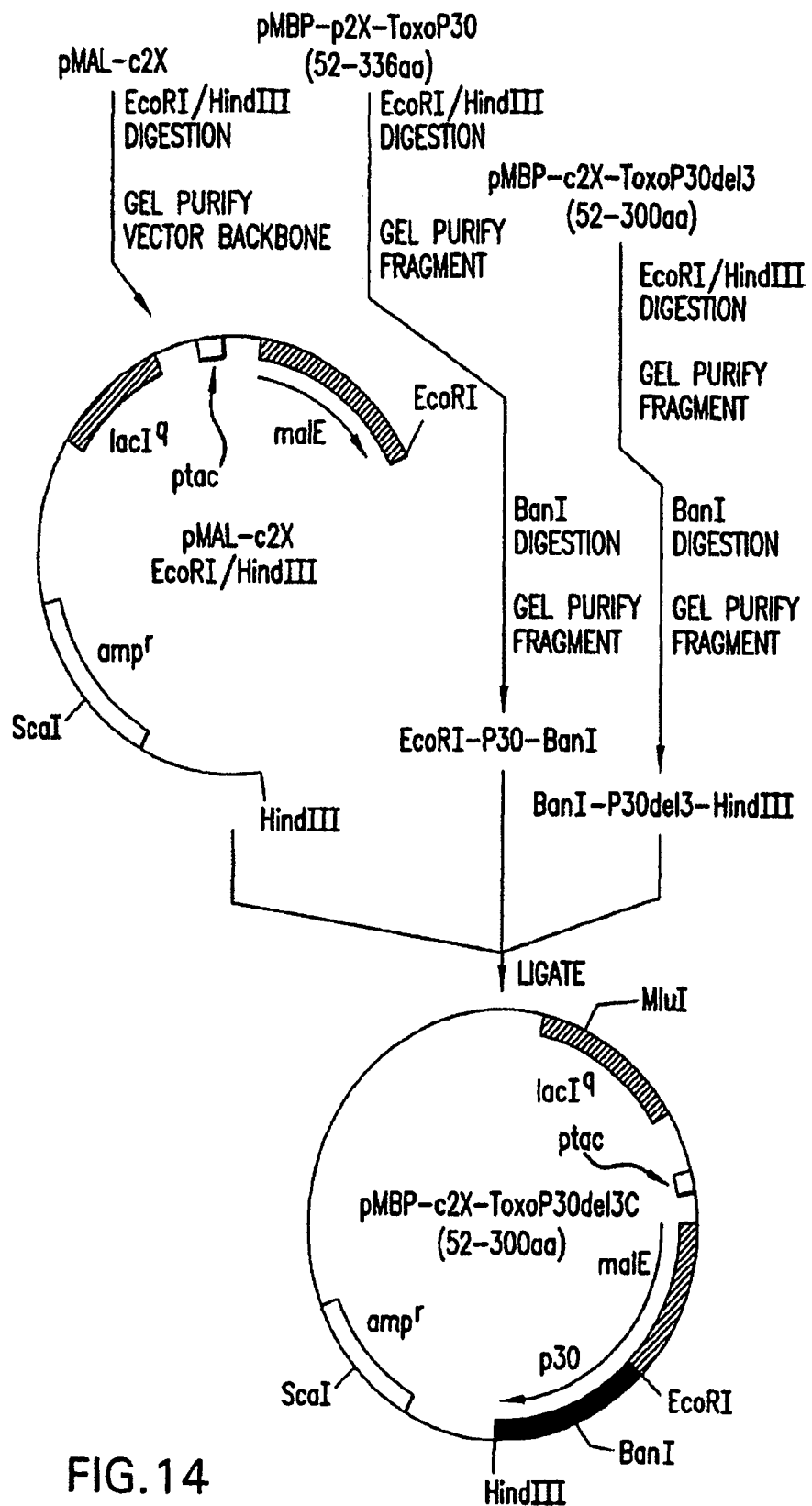
FIG. 14 is a schematic of the construction of plasmid pMBP-c2X-ToxoP30del3C(52-300aa).
Figure 17:
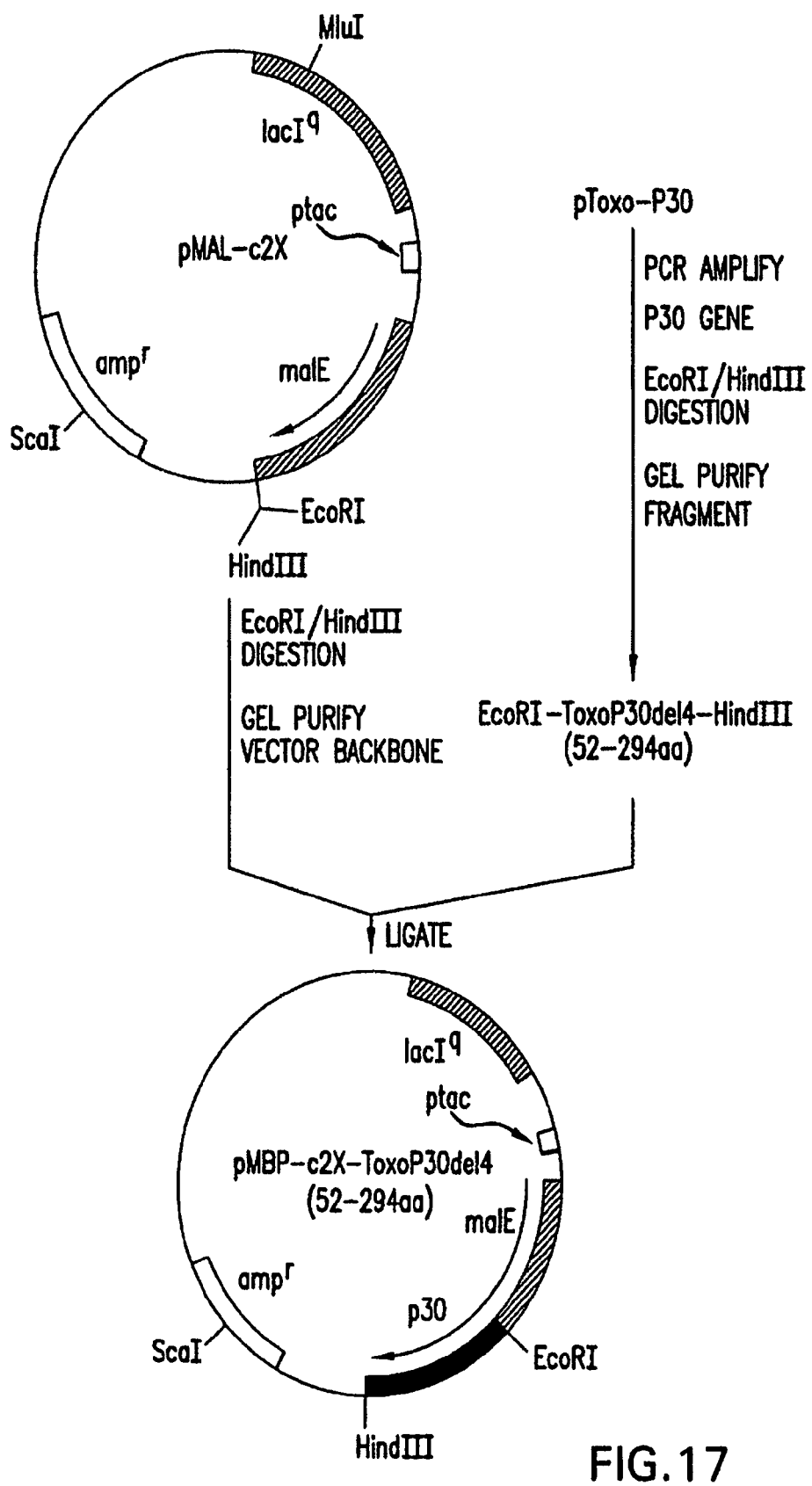
FIG. 17 is a schematic of the construction of plasmid pMBP-c2X-ToxoP30del4(52-294aa).

The plasmid pMBP-c2X-ToxoP30del2(52-311aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 10). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 1243 of the P30 gene (Burg et al. (1988) J. Immunol. 141:3584-3591) were synthesized as shown below:

```
Sense Primer
                                   [SEQ ID NO: 1]
5'-GGCGAATTCCTTGTTGCCAATCAAGTTGTCACC-3'

(EcoRI site is underlined)

Antisense Primer
                                  [SEQ ID NO: 14]
5'-CAGGTCAAGCTTTCAAGCCGATTTTGCTGACCCTGCAGCCC-3'

(HindIII site is underlined.)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 780 base pair DNA fragment containing Toxo P30del2 was purified on an agarose gel. The purified 780 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del2(52-311aa) contained the Toxo P30del2 gene cloned at the EcoRI/HindIII sites of PMAL-c2X. The complete DNA sequence [SEQ ID NO:15] of plasmid pMBP-c2X-ToxoP30del2(52-311aa) is shown in FIG. 11, and the corresponding amino acid sequence [SEQ ID NO:16] of the MBP-ToxoP30del2(52-311aa) fusion protein is also shown in FIG. 11, wherein amino acid residues 392-651 of SEQ ID NO:16 correspond to amino acids 52-311 of the P30 antigen of *Toxoplasma gondii*. The DNA sequence [SEQ ID NO:17] of ToxoP30del2(52-311aa) is shown in FIG. 12 and the corresponding amino acid sequence [SEQ ID NO:18] of the ToxoP30del2(52-311aa) protein is also shown in FIG. 12, wherein amino acid residues 1-260 of SEQ ID NO:18 correspond to amino acids 52-311 of the P30 antigen of *Toxoplasma gondii.*

Step E: Construction of pMBP-c2X-ToxoP30del3C(52-300aa)

The plasmid pMBP-c2X-ToxoP30del3(52-300aa), an intermediate in the construction of plasmid pMBP-c2X-ToxoP30del3C(52-300aa), was constructed by cloning a DNA fragment containing Toxo P30, obtained by PCR amplification of Toxo P30 DNA contained in plasmid pToxo-P30, into the EcoRI/HindIII sites of pMAL-c2X (FIG. 13). Plasmid pMAL-c2X was digested with EcoRI/HindIII, and the vector backbone was purified on an agarose gel. A sense primer, starting at nucleotide 464 of the P30 gene containing an EcoRI site, and an antisense primer containing a HindIII site, starting at nucleotide 1210 of the P30 gene (Burg et al. (1988) J. Immunol. 141:3584-3591) were synthesized as shown below:

```
Sense Primer
                                        [SEQ ID NO: 1]
5'-GGCGAATTCCTTGTTGCCAATCAAGTTGTCACC-3'

(EcoRI site is underlined)

Antisense Primer
                                        [SEQ ID NO: 19]
5'-CAGGTCAAGCTTTCACTCCAGTTTCACGGTACAGTG-3'

(HindIII site is underlined.)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 747 base pair DNA fragment containing Toxo P30del3 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del3(52-300aa) contained the Toxo P30del3 gene cloned at the EcoRI/HindIII sites of pMAL-c2X.

Analysis of the DNA sequence of plasmid pMBP-c2X-ToxoP30del3(52-300aa) and analysis of the corresponding amino acid sequence revealed a single base change in the P30 gene that resulted in the substitution of an amino acid for a stop codon, leading to premature chain termination of the P30 protein. This mutation was located downstream of the synthetic EcoRI site (nucleotide 464) and upstream of a BanI site (nucleotide 1100) following the numbering convention of Burg et al. The mutation in plasmid pMBP-c2X-ToxoP30del3(52-300aa) was corrected as follows:

Plasmid pMBP-c2X-ToxoP30del3C(52-300aa) was constructed by cloning an EcoRI/BanI fragment from plasmid pMBP-p2X-ToxoP30(52-336aa), containing the 5' corrected portion of the Toxo P30 gene, and a BanI/HindIII fragment from plasmid pMBP-c2X-ToxoP30del3(52-300aa), containing the 3' portion of the Toxo P30del3 gene, into the EcoRI/HindIII sites of pMAL-c2X (FIG. 14). Plasmid pMBP-c2X-ToxoP30del3C(52-300aa) was deposited with the ATCC 10801 University Boulevard, Manassas, Va. 20110-2209, under terms of the Budapest Treaty on Sep. 26, 2002, and was accorded Accession No. ATCC 4722.

Plasmid pMAL-c2X was digested with EcoRI/HindIII and the vector backbone was purified on an agarose gel. Plasmid DNAs pMBP-p2X-ToxoP30(52-336aa) and pMBP-c2X-ToxoP30del3(52-300aa) were prepared by general methods. Plasmids pMBP-p2X-ToxoP30(52-336aa) and pMBP-c2X-ToxoP30del3(52-300aa) were digested with EcoRI/HindIII and the 855 and 747 base pair fragments, containing the Toxo P30 gene, were purified on an agarose gel. The 855 base pair EcoRI/HindIII fragment was digested with BanI and the 637 base pair EcoRI/BanI fragment, containing the 5' corrected portion of the Toxo P30 gene, was purified on an agarose gel. The 747 base pair EcoRI/HindIII fragment was digested with BanI and the 110 base pair BanI/HindIII fragment, containing the 3' portion of the Toxo P30del3 gene, was purified on an agarose gel. The purified 637 and 110 base pair fragments were ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del3C (52-300aa) contained the ToxoP30del3C gene cloned at the EcoRI/HindIII sites of pMAL-c2X. The complete DNA sequence [SEQ ID NO:20] of plasmid pMBP-c2X-ToxoP30del3C(52-300aa) is shown in FIG. 15 and the corresponding amino acid sequence [SEQ ID NO:21] of the MBP-ToxoP30del3C(52-300aa) fusion protein is also shown in FIG. 15, wherein amino acid residues 392-640 of SEQ ID NO:21 correspond to amino acids 52-300 of the P30 antigen of *Toxoplasma gondii*. The DNA sequence [SEQ ID NO:22] of ToxoP30del3C(52-300aa) is shown in FIG. 16 and the corresponding amino acid sequence [SEQ ID NO:23] of the ToxoP30del3C(52-300aa) protein is also shown in FIG. 16, wherein amino acid residues 1-249 of SEQ ID NO:23 correspond to amino acids 52-300 of the P30 antigen of *Toxoplasma gondii.*

Step F: Construction of pMBP-c2X-ToxoP30del4C(52-294aa)

The plasmid pMBP-c2X-ToxoP30del4(52-294aa), an intermediate in the construction of plasmid pMBP-c2X-ToxoP30del4C(52-294aa), was constructed by cloning a DNA fragment containing Toxo P30, obtained by PCR amplification of Toxo P30 DNA contained in plasmid pToxo-P30, into the EcoRI/HindIII sites of pMAL-c2X (FIG. 17). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 1192 of the P30 gene (Burg et al. (1988) J. Immunol. 141:3584-3591) were synthesized as shown below:

```
Sense Primer
                                        [SEQ ID NO: 1]
5'-GGCGAATTCCTTGTTGCCAATCAAGTTGTCACC-3'

(EcoRI site is underlined)

Antisense Primer
                                       [SEQ ID NO: 24]
5'-CAGGTCAAGCTTTCAGTGATGCTTCTCAGGCGATCCCC-3'

(HindIII site is underlined)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 729 base pair DNA fragment containing Toxo P30del4 was purified on an agarose gel. The purified 729 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del4(52-294aa) contained the Toxo P30del4 gene cloned at the EcoRI/HindIII sites of pMAL-c2X.

Figure 18:
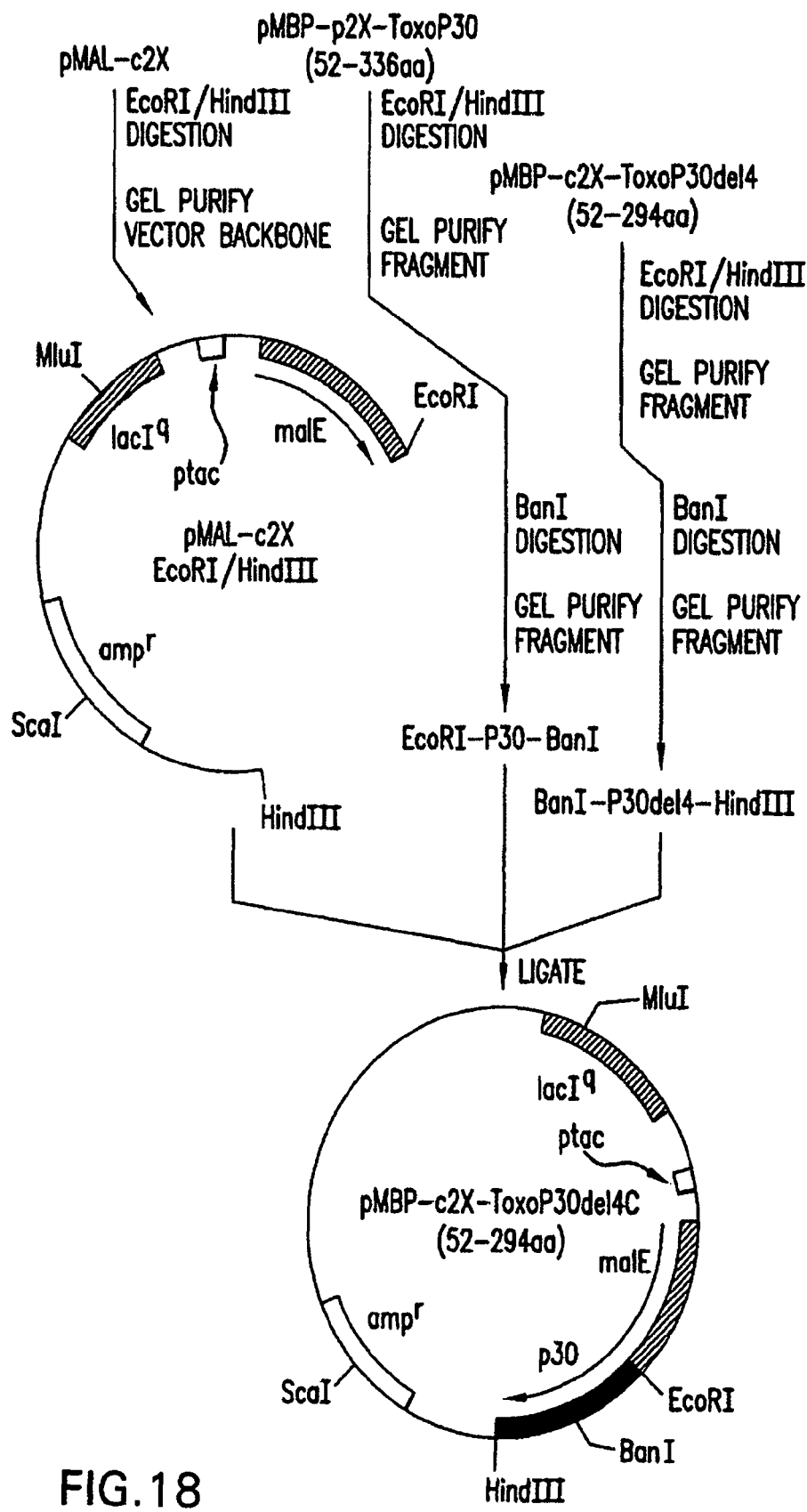
FIG. 18 is a schematic of the construction of plasmid pMBP-c2X-ToxoP30del4C(52-294aa).

Analysis of the DNA sequence of plasmid pMBP-c2X-ToxoP30del4(52-294aa) and analysis of the corresponding amino acid sequence revealed base changes in the P30 gene resulting in two amino acid changes from the published sequence (Burg et al. (1988) J. Immunol. 141:3584-3591). These mutations were located downstream of the synthetic EcoRI site (nucleotide 464) and upstream of a BanI site (nucleotide 1100) following the numbering convention of Burg et al. The mutations in plasmid pMBP-c2X-ToxoP30del4(52-294aa) were corrected as follows:

Plasmid pMBP-c2X-ToxoP30del4C(52-294aa) was constructed by cloning an EcoRI/BanI fragment from plasmid pMBP-p2X-ToxoP30(52-336aa), containing the 5' corrected portion of the Toxo P30 gene, and a BanI/HindIII fragment from plasmid pMBP-c2X-ToxoP30del4(52-294aa), containing the 3' portion of the ToxoP30del4 gene, into the EcoRI/HindIII sites of pMAL-c2X (FIG. 18). Plasmid pMBP-c2X-ToxoP30del4C(52-294aa) was deposited with the ATCC 10801 University Boulevard, Manassas, Va. 20110-2209, under terms of the Budapest Treaty on Sep. 26, 2002, and was accorded Accession No. ATCC 4723.

Plasmid pMAL-c2X was digested with EcoRI/HindIII and the vector backbone was purified on an agarose gel. Plasmid DNAs pMBP-p2X-ToxoP30(52-336aa) and pMBP-c2X-ToxoP30del4(52-294aa) were prepared by general methods. Plasmids pMBP-p2X-ToxoP30(52-336aa) and pMBP-c2X-ToxoP30del4(52-294aa) were digested with EcoRI/HindIII and the 855 and 729 base pair fragments, containing the Toxo P30 gene, were purified on an agarose gel. The 855 base pair EcoRI/HindIII fragment was digested with BanI and the 637 base pair EcoRI/BanI fragment, containing the 5' corrected portion of the Toxo P30 gene, was purified on an agarose gel. The 729 base pair EcoRI/HindIII fragment was digested with BanI and the 92 base pair BanI/HindIII fragment, containing the 3' portion of the Toxo P30del4 gene and purified on an agarose gel. The purified 637 and 92 base pair fragments were ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del4C (52-294aa) contained the Toxo P30del4C gene cloned at the EcoRI/HindIII sites of pMAL-c2X. The complete DNA sequence [SEQ ID NO:25] of plasmid pMBP-c2X-ToxoP30del4C(52-294aa) is shown in FIG. 19 and the corresponding amino acid sequence [SEQ ID NO:26] of the MBP-ToxoP30del4C(52-294aa) fusion protein is also shown in FIG. 19, wherein amino acid residues 392-634 of SEQ ID NO:26 correspond to amino acids 52-294 of the P30 antigen of *Toxoplasma gondii*. The DNA sequence [SEQ ID NO:27] of ToxoP30del4C(52-294aa) is shown in FIG. 20 and the corresponding amino acid sequence [SEQ ID NO:28] of the ToxoP30del4C(52-294aa) protein is also shown in FIG. 20, wherein amino acid residues 1-243 of SEQ ID NO:28 correspond to amino acids 52-294 of the P30 antigen of *Toxoplasma gondii*.

Step G: Construction of pMBP-c2X-ToxoP30del4del8(83-294aa)

Figure 21:
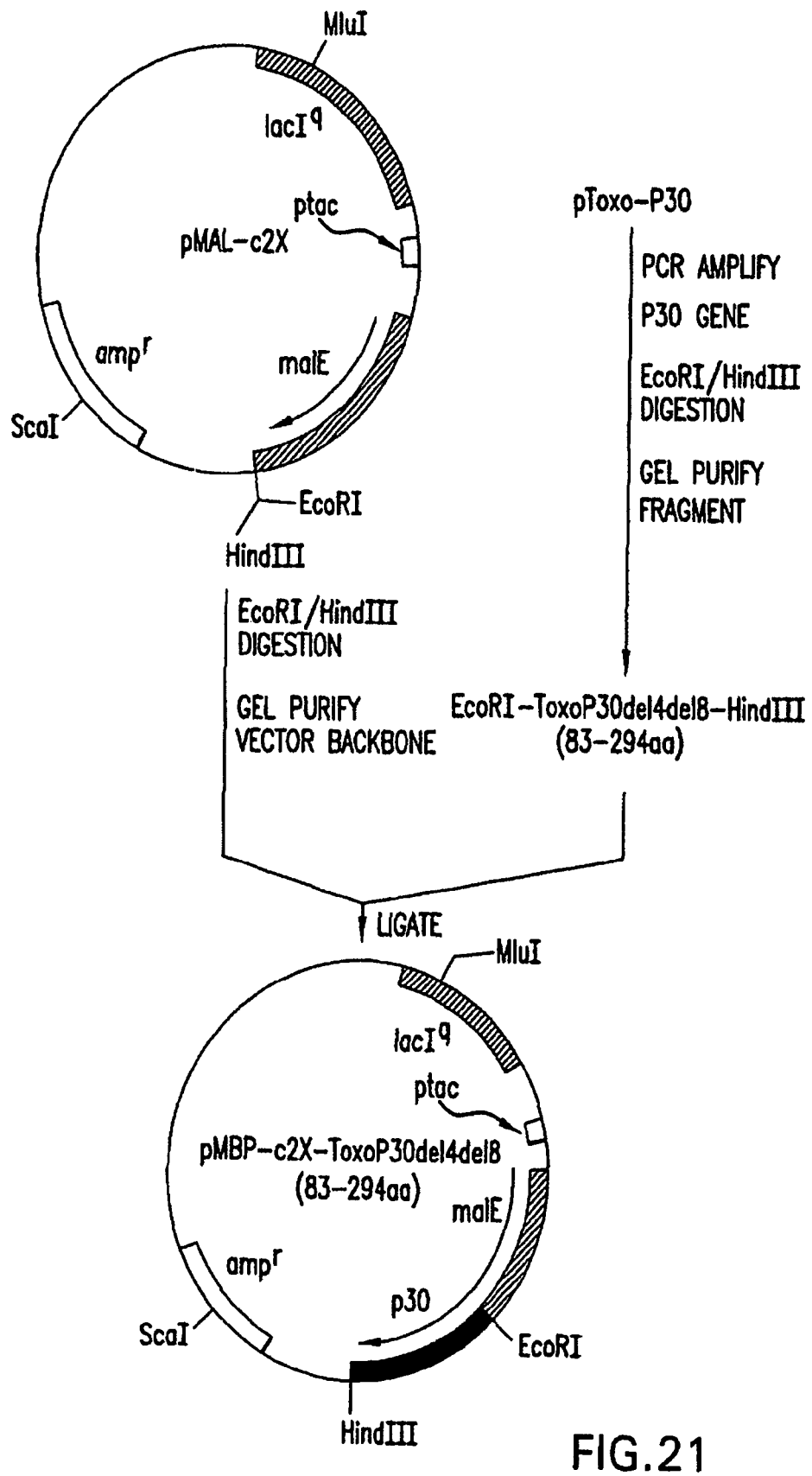
FIG. 21 is a schematic of the construction of plasmid pMBP-c2X-ToxoP30del4del8(83-294aa).
Figure 24:
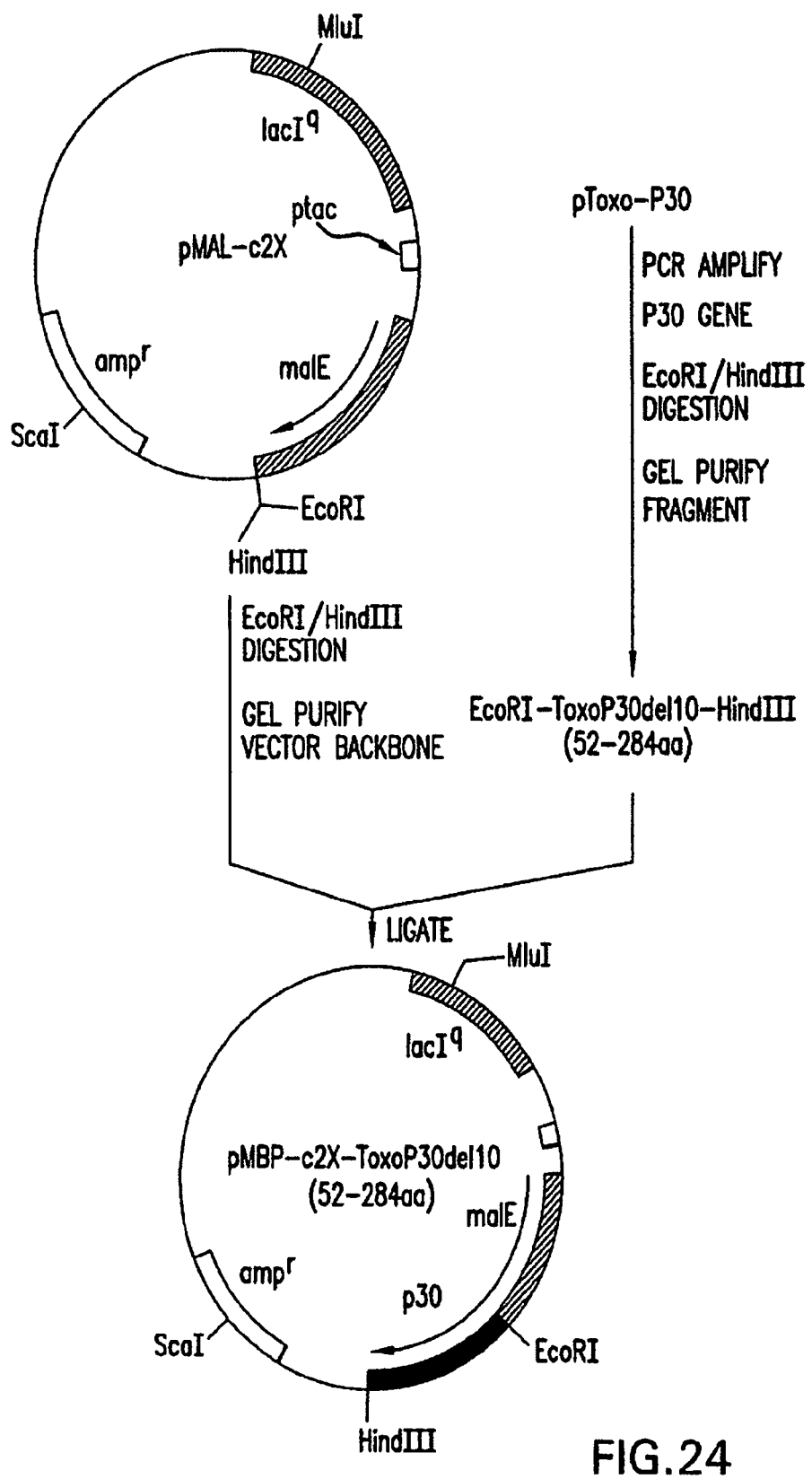
FIG. 24 is a schematic of the construction of plasmid pMBP-c2X-ToxoP30del10(52-284aa).
Figure 27:
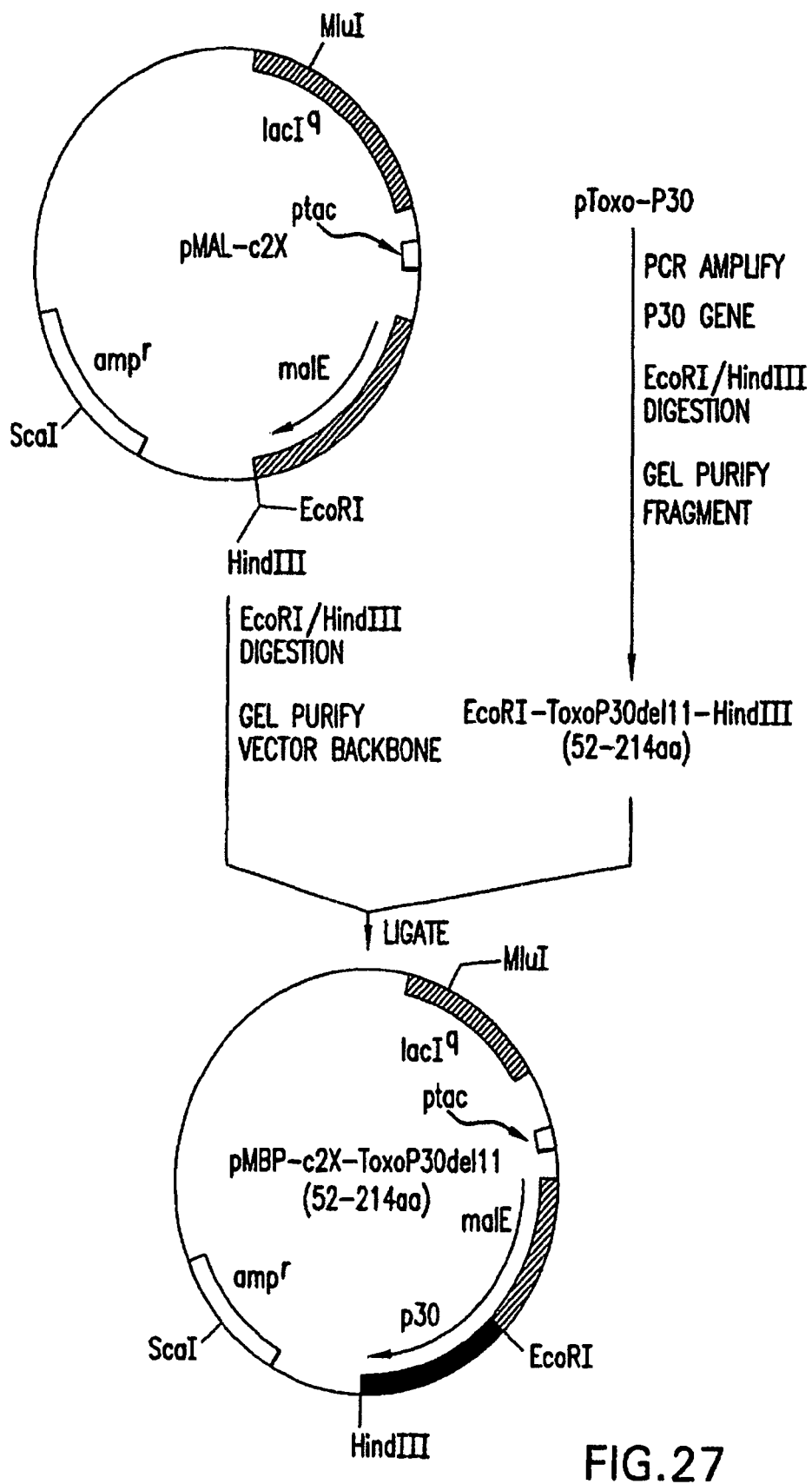
FIG. 27 is a schematic of the construction of plasmid pMBP-c2X-ToxoP30del11(52-214aa).

The plasmid pMBP-c2X-ToxoP30del4del8(83-294aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 21). Plasmid pMAL-c2X was digested with EcoRI/HindIII and the vector backbone was purified on an agarose gel. A sense primer, starting at nucleotide 557 of the P30 gene containing an EcoRI site, and an antisense primer containing a HindIII site, starting at nucleotide 1192 of the P30 gene (Burg et al. (1988) J. Immunol. 141:3584-3591) were synthesized as shown below:

```
Sense Primer
                                       [SEQ ID NO: 29]
5'-GGCGAATTCCCTAAAACAGCGCTCACAGAG-3'

(EcoRI site is underlined.)

Antisense Primer
                                       [SEQ ID NO: 24]
5'-CAGGTCAAGCTTTCAGTGATGCTTCTCAGGCGATCCCC-3'

(HindIII site is underlined.)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 636 base pair DNA fragment containing Toxo P30del4del8 was purified on an agarose gel. The purified 636 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del4del8(83-294aa) contained the ToxoP30del4del8 gene cloned at the EcoRI/HindIII sites of pMAL-c2X. The complete DNA sequence [SEQ ID NO:30] of plasmid pMBP-c2X-ToxoP30del4del8(83-294aa) is shown in FIG. 22 and the corresponding amino acid sequence [SEQ ID NO:31] of the MBP-ToxoP30del4del8(83-294aa) fusion protein is also shown in FIG. 22, wherein amino acid residues 392-603 of SEQ ID NO:31 correspond to amino acids 83-294 of the P30 antigen of *Toxoplasma gondii*. The DNA sequence [SEQ ID NO:32] of ToxoP30del4del8(83-294aa) is shown in FIG. 23 and the corresponding amino acid sequence [SEQ ID NO:33] of the ToxoP30del4del8(83-294aa) protein is also shown in FIG. 23, wherein amino acid residues 1-212 of SEQ ID NO:33 correspond to amino acids 83-294 of the P30 antigen of *Toxoplasma gondii*.

Step H: Construction of pMBP-c2X-ToxoP30del10(52-284aa)

The plasmid pMBP-c2X-ToxoP30del10(52-284aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 24). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 1162 of the P30 gene (Burg et al. (1988) J. Immunol. 141:3584-3591) were synthesized as shown below:

```
Sense Primer
                                        [SEQ ID NO: 1]
5'-GGCGAATTCCTTGTTGCCAATCAAGTTGTCACC-3'

(EcoRI site is underlined)

Antisense Primer
                                       [SEQ ID NO: 34]
5'-CAGGTCAAGCTTTCATCCAATAATGACGCTTTTTGACTC-3'

(HindIII site is underlined.)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 699 base pair DNA fragment containing Toxo P30del10 was purified on an agarose gel. The purified 699 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del10(52-284aa) contained the Toxo P30del10 gene cloned at the EcoRI/HindIII sites of pMAL-c2X. The complete DNA sequence [SEQ ID NO:35] of plasmid pMBP-c2X-ToxoP30del10(52-284aa) is shown in FIG. 25 and the corresponding amino acid sequence [SEQ ID NO:36] of the MBP-ToxoP30del10(52-284aa) fusion protein is also shown in FIG. 25, wherein amino acid residues 392-624 of SEQ ID NO:36 correspond to amino acids 52-284 of the P30 antigen of *Toxoplasma gondii*, with the exception that amino acid residue 546 of SEQ ID NO:36 is glycine instead of glutamic acid. The DNA sequence [SEQ ID NO:37] of ToxoP30del10 (52-284aa) is shown in FIG. 26 and the corresponding amino acid sequence [SEQ ID NO:38] of the ToxoP30del10(52-284aa) protein is also shown in FIG. 26, wherein amino acid residues 1-233 of SEQ ID NO:38 correspond to amino acids 52-284 of the P30 antigen of *Toxoplasma gondii*, with the exception that amino acid residue 155 of SEQ ID NO:38 is glycine instead of glutamic acid.

Step I: Construction of pMBP-c2X-ToxoP30del11(52-214aa)

The plasmid pMBP-c2X-ToxoP30del11(52-214aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 27). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 952 of the P30 gene (Burg et al. (1988) J. Immunol. 141:3584-3591) were synthesized as shown below:

```
Sense Primer
                                        [SEQ ID NO: 1]
5'-GGCGAATTCCTTGTTGCCAATCAAGTTGTCACC-3'

(EcoRI site is underlined.)

Antisense Primer
                                       [SEQ ID NO: 39]
5'-CAGGTCAAGCTTTCACACGAGGGTCATTGTAGTGGG-3'

(HindIII site is underlined.)
```

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 489 base pair DNA fragment containing Toxo P30del11 was purified on an agarose gel. The purified 489 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del11(52-214aa) contained the Toxo P30del11 gene cloned at the EcoRI/HindIII sites of pMAL-c2X. The complete DNA sequence [SEQ ID NO:40] of plasmid pMBP-c2X-ToxoP30del11(52-214aa) is shown in FIG. 28 and the corresponding amino acid sequence [SEQ ID NO:41] of the MBP-ToxoP30del11(52-214aa) fusion protein is also shown in FIG. 28, wherein amino acid residues 392-554 of SEQ ID NO:41 correspond to amino acids 52-214 of the P30 antigen of *Toxoplasma gondii*. The DNA sequence [SEQ ID NO:42] of ToxoP30del11(52-214aa) is shown in FIG. 29 and the corresponding amino acid sequence [SEQ ID NO:43] of the ToxoP30del11(52-214aa) protein is also shown in FIG. 29, wherein amino acid residues 1-163 of SEQ ID NO:43 correspond to amino acids 52-214 of the P30 antigen of *Toxoplasma gondii.*

EXAMPLE 3

Expression of rpMBP-c2X-ToxoP30 Antigens in *E. coli*

Step A: Expression of Cloned Genes in *E. coli* Bacterial clones pMBP-c2X-ToxoP30(52-336aa), pMBP-c2X-ToxoP30del1C(52-324aa), pMBP-c2X-ToxoP30del2(52-311aa), pMBP-c2X-ToxoP30del3C(52-300aa), pMBP-c2X-ToxoP30del4C(52-294aa), pMBP-c2X-ToxoP30del4del8 (83-294aa), pMBP-c2X-ToxoP30del10(52-284aa) and pMBP-c2X-ToxoP30del11(52-214aa) expressing the MBP fusion proteins rpMBP-c2X-ToxoP30(52-336aa), rpMBP-c2X-ToxoP30del1C(52-324aa), rpMBP-c2X-ToxoP30del2 (52-311aa), rpMBP-c2X-ToxoP30del3C(52-300aa), rpMBP-c2X-ToxoP30del4C(52-294aa), rpMBP-c2X-ToxoP30del4del8(83-294aa), rpMBP-c2X-ToxoP30del10 (52-284aa) and rpMBP-c2X-ToxoP30del11(52-214aa) of Example 2 were grown in "SUPERBROTH II" media containing 100 µg/ml ampicillin to log phase, and the synthesis of the MBP-ToxoP30 fusion proteins was induced by the addition of IPTG as previously described (Robinson et al. (1993) J. Clin. Microbiol. 31:629-635). After 4 hours post-induction, the cells were harvested, and the cell pellets were stored at −80° C. until protein purification occurred.

Step B: Purification of MBP-ToxoP30 Fusion Proteins

Soluble fusion proteins rpMBP-c2X-ToxoP30(52-336aa), rpMBP-c2X-ToxoP30del1C(52-324aa), rpMBP-c2X-ToxoP30del2(52-311aa), rpMBP-c2X-ToxoP30del3C(52-300aa), rpMBP-c2X-ToxoP30del4C(52-294aa), rpMBP-c2X-ToxoP30del4del8(83-294aa), rpMBP-c2X-ToxoP30del10(52-284aa) and rpMBP-c2X-ToxoP30del11 (52-214aa) were purified after lysis from cell paste following the New England Biolabs pMAL Protein Fusion and Purification instruction manual. Following lysis and centrifugation, the crude supernatants containing the fusion proteins were loaded onto an amylose affinity column. Following washing of the column, the fusion proteins were eluted from the column with maltose, appropriate column fractions were pooled and filtered through a 0.2µ filter, and then stored at 2-8° C. until coating onto microparticles.

EXAMPLE 4

Evaluation of rpMBP-c2X-ToxoP30 Antigens in an Automated Toxo IgG and IgM Immunoassay Step A: Coating of rpMBP-c2X-ToxoP30 Antigens onto Microparticles Prior to coating microparticles, the rpMBP-c2X-ToxoP30 (52-336aa), rpMBP-c2X-ToxoP30del1C(52-324aa), rpMBP-c2X-ToxoP30del2(52-311aa), rpMBP-c2X-ToxoP30del3C(52-300aa), rpMBP-c2X-ToxoP30del4C(52-294aa), rpMBP-c2X-ToxoP30del4del8(83-294aa), rpMBP-c2X-ToxoP30del10(52-284aa) and rpMBP-c2X-ToxoP30del11(52-214aa) antigens were diluted to a concentration of 1 mg/ml and incubated at 37° C. for 24 hours. Following the heat treatment step, the rpMBP-c2X-ToxoP30 antigens were coated separately onto sulfate-derivatized polystyrene microparticles (1-5% solids) in a vessel containing MES pH 6.2 buffer with EDAC for 30 minutes at room temperature, on an end over end rotator. The coated microparticles were then collected by centrifugation at 14,000×g for 10 minutes, and the supernatant was discarded. The microparticles were resuspended in a microparticle storage buffer containing Tris buffer, pH 7.5, EDTA, sodium chloride, Tween 20, fetal calf serum (Toxo antibody free), sodium azide, and sucrose using a syringe and needle. The microparticles were then diluted with microparticle storage buffer to a final concentration of 0.1-0.3% solids and filled into plastic bottles.

Step B: Description of the AxSYM® Toxo IgG v2 Reagent Pack, Calibrators, Controls, Panel 6, and Assay Diskette The reagent pack for the automated AxSYM Toxo IgG v2 assay is designed for the detection of human anti-Toxo IgG and consists of the following components. Bottle number one contains microparticles coated with purified recombinant Toxo antigens (Example 4A) in a microparticle storage buffer. In order to prevent human anti-MBP or anti-CKS antibodies causing a false positive reaction in the assay, purified MBP or CKS can be added to the microparticle storage buffer. Bottle number two contains the preferred conjugate, a goat anti-human IgG alkaline phosphatase conjugate. This conjugate is titered to determine a working concentration of 0.1-5 µg/ml. The conjugate is diluted into a conjugate diluent containing Tris buffer, pH 7.4, sodium, calcium, magnesium, and zinc chloride, Nipasept, A56620, non-fat dry milk, Brij-35, mouse serum, and mannitol. Bottle number three contains the preferred assay diluent to minimize non-specific binding to the microparticles and assay matrix. This assay diluent consists of a Tris buffer, pH 7.5 containing sodium chloride, sodium EDTA, non-fat dry milk, Nipasept, A56620, and Tween 20. Bottle number four contains a phosphate buffer line diluent.

Six Assay Calibrators labeled A-F are derived from Toxo IgG positive plasma pools or human anti-Toxo IgG monoclonal antibodies and are required to calibrate the AxSYM® Toxo IgG v2 assay. These calibrators are matched to calibrators previously matched to the TOX-S WHO International Standard. The concentration range of these calibrators is 0-300 IU/ml. Positive and Negative controls are required to evaluate the assay calibration and establish assay validity. The Positive Control is prepared from Toxo IgG positive plasma pools or human anti-Toxo IgG monoclonal antibodies. The Negative Control is prepared from Toxo IgG negative plasma pools. Panel 6 is a pool of Toxo IgG and IgM positive plasma units derived from blood donors with an acute toxoplasmosis.

The assay diskette for the AxSYM® Toxo IgG v2 assay contains the assay protocol software necessary to run the automated immunoassay on the Abbott "AxSYM®" instrument (Abbott Laboratories, Abbott Park, Ill.). In addition to the AxSYM® Toxo IgG v2 Reagent Pack, assay Calibrators, and Controls described above, the following assay components located on the instrument are required to run the assay: Sample Cups, AxSYM® Line Diluent, MEIA buffer, Reaction Vessels, MUP, and Matrix Cells. The sequence of events for the automated assay are as follows: The pipetting probe in the kitting center delivers the patient sample and line diluent to the reaction vessel sample well; the pipetting probe then kits the appropriate volumes of assay diluent, line diluent, and conjugate required for the assay from the reagent pack into the designated reaction vessel wells; this probe then delivers the recombinant Toxo antigen coated microparticles from the reagent pack and an aliquot of the diluted sample to the designated reaction vessel well; the reaction vessel is then transferred to the process carousel; Toxo-specific antibodies bind to the Toxo recombinant antigen coated microparticles forming an antigen-antibody complex; assay diluent is added to the reaction mixture and matrix cell and then an aliquot of the reaction mixture is transferred to the glass fiber matrix in the auxiliary carousel; the microparticles bind irreversibly to the matrix; the matrix is washed with MEIA buffer and line diluent to remove unbound antibodies; goat anti-human IgG alkaline phosphate conjugate is added to the matrix and binds to the Toxo-specific IgG captured by the Toxo recombinant antigens; the matrix is then washed with MEIA buffer to remove any unbound enzyme-antibody conjugate; the enzyme substrate MUP is added to the matrix; the alkaline phosphatase enzyme present on the matrix attached to the goat anti-human IgG catalyzes the hydrolysis of the phosphoryl moiety from MUP, producing a highly fluorescent product which is measured by the AxSYM MEIA optical system; the signal intensity (rate counts) is proportional to the amount of Toxo-specific IgG antibodies present in the sample.

Step C: Description of the AxSYM Toxo® IgM v2 Reagent Pack, Index Calibrator, Controls, and Assay Diskette The reagent pack for the automated AxSYM Toxo IgM v2 assay is designed for the detection of human anti-Toxo IgM and consists of the following components. Bottle number one contains microparticles coated with purified recombinant Toxo antigens (Example 4A) in a microparticle storage buffer. In order to prevent human anti-MBP or anti-CKS antibodies causing a false positive reaction in the assay, purified MBP or CKS can be added to the microparticle storage buffer. Bottle number two contains the preferred conjugate, a goat anti-human IgM alkaline phosphatase conjugate. This conjugate is titered to determine a working concentration of 0.1-5 µg/ml. The conjugate is diluted into a conjugate diluent containing Tris buffer, pH 7.4, sodium, calcium, magnesium, and zinc chloride, Nipasept, A56620, non-fat dry milk, Brij-35, mouse serum, and mannitol. Bottle number three contains the preferred assay diluent to minimize non-specific binding to the microparticles and assay matrix. This assay diluent consists of a Tris buffer, pH 7.5 containing sodium chloride, sodium EDTA, non-fat dry milk, Nipasept, A56620, and Tween 20. Bottle number four contains either phosphate buffer line diluent or RF Neutralization Buffer.

The Index Calibrator is derived from Toxo IgM positive plasma pools or human anti-Toxo IgM monoclonal antibodies and is required to calibrate the AxSYM® Toxo IgM v2 assay. Positive and Negative controls are required to evaluate the assay calibration and establish assay validity. The Positive Control is prepared from Toxo IgM positive plasma pools or human anti-Toxo IgM monoclonal antibodies. The Negative Control is prepared from Toxo IgM negative plasma pools.

The assay diskette for the AxSYM® Toxo IgM v2 assay contains the assay protocol software necessary to run the automated immunoassay on the Abbott "AxSYM" instrument (Abbott Laboratories, Abbott Park, Ill.). In addition to the AxSYM® Toxo IgM v2 Reagent Pack, Index Calibrator, and Controls described above, the following assay components located on the instrument are required to run the assay: Sample Cups, AxSYM® Line Diluent, MEIA buffer, Reaction Vessels, MUP, and Matrix Cells. The sequence of events for the automated assay are as follows: The pipetting probe in the kitting center delivers the patient sample and line diluent to the reaction vessel sample well; the pipetting probe then kits the appropriate volumes of assay diluent, line diluent or RF Neutralization Buffer, and conjugate required for the assay from the reagent pack into the designated reaction vessel wells; this probe then delivers the recombinant Toxo antigen coated microparticles from the reagent pack and an aliquot of the diluted sample to the designated reaction vessel well; the reaction vessel is then transferred to the process carousel; Toxo-specific antibodies bind to the Toxo recombinant antigen coated microparticles forming an antigen-antibody complex; assay diluent is added to the reaction mixture and matrix cell and then an aliquot of the reaction mixture is transferred to the glass fiber matrix in the auxiliary carousel; the microparticles bind irreversibly to the matrix; the matrix is washed with MEIA buffer and line diluent or RF Neutralization Buffer to remove unbound antibodies; goat anti-human IgM alkaline phosphate conjugate is added to the matrix and binds to the Toxo-specific IgM captured by the Toxo recombinant antigens; the matrix is then washed with MEIA buffer to remove any unbound enzyme-antibody conjugate; the enzyme substrate MUP is added to the matrix; the alkaline phosphatase enzyme present on the matrix attached to the goat anti-human IgM catalyzes the hydrolysis of the phosphoryl moiety from MUP, producing a highly fluorescent product which is measured by the AxSYM® MEIA optical system; the signal intensity (rate counts) is proportional to the amount of Toxo-specific IgM antibodies present in the sample.

Step D: Evaluation of MBP fusion proteins rpMBP-c2X-ToxoP30(52-336aa), rpMBP-c2X-ToxoP30del1C(52-324aa), rpMBP-c2X-ToxoP30del2(52-311aa), rpMBP-c2X-ToxoP30del3C(52-300aa), rpMBP-c2X-ToxoP30del4C(52-294aa), rpMBP-c2X-ToxoP30del4del8(83-294aa), rpMBP-c2X-ToxoP30del10(52-284aa) and rpMBP-c2X-ToxoP30del11(52-214aa) in the AxSYM® Toxo IgG v2 and Toxo IgM v2 Immunoassays The AxSYM® Toxo IgG and IgM reagent packs were assembled as described in Examples 4B and 4C using the microparticles coated with the Toxo antigens described in Example 4A. The Toxo IgG A and F calibrators (Acal and Fcal) and Panel 6 (PNL6) were tested with the AxSYM Toxo IgG v2 reagent packs and the Toxo IgM Negative Control (NC), Index Calibrator (IC), and Panel 6 (PNL6) were tested with the AxSYM® Toxo IgM v2 reagent packs. The results are shown below in Tables 1 and 2.

TABLE 1

Evaluation of the rpMBP-c2X-ToxoP30 Antigens in the AxSYM ® Toxo IgG v2 Assay

| Antigen Coated | Rate Counts | | | | |
|---|---|---|---|---|---|
| | Acal | Fcal | Fcal/Acal | PNL6 | PNL6/Acal |
| rpMBP-c2X-ToxoP30 (52-336aa) | 40 | 3495 | 87 | 643 | 16 |
| rpMBP-c2X-ToxoP30 del1C(52-324aa) | 29 | 2599 | 90 | 544 | 19 |
| rpMBP-c2X-ToxoP30 del2(52-311aa) | 28 | 3191 | 114 | 1129 | 40 |
| rpMBP-c2X-ToxoP30 del3C(52-300aa) | 29 | 3199 | 110 | 1112 | 38 |
| rpMBP-c2X-ToxoP30 del4C(52-294aa) | 29 | 3352 | 116 | 1302 | 45 |
| rpMBP-c2X-ToxoP30 del10(52-284aa) | 40 | 4277 | 107 | 1285 | 32 |
| rpMBP-c2X-ToxoP30 del11(52-214aa) | 48 | 4076 | 85 | 1118 | 23 |
| rpMBP-c2X-ToxoP30 del4del8(83-294aa) | 34 | 59 | 1.7 | 37 | 1.1 |

TABLE 2

Evaluation of the rpMBP-c2X-ToxoP30 Antigens in the AxSYM ® Toxo IgM v2 Assay

| Antigen Coated | Rate Counts | | | |
|---|---|---|---|---|
| | NC | IC | PNL6 | PNL6/NC |
| rpMBP-c2X-ToxoP30 (52-336aa) | 33 | 175 | 210 | 6.4 |
| rpMBP-c2X-ToxoP30del1C (52-324aa) | 48 | 189 | 250 | 5.2 |
| rpMBP-c2X-ToxoP30del2 (52-311aa) | 43 | 315 | 440 | 10.2 |
| rpMBP-c2X-ToxoP30del3C (52-300aa) | 49 | 187 | 459 | 9.4 |
| rpMBP-c2X-ToxoP30del4C (52-294aa) | 51 | 203 | 527 | 10.3 |
| rpMBP-c2X-ToxoP30del10 (52-284aa) | 39 | 158 | 370 | 9.5 |
| rpMBP-c2X-ToxoP30del11 (52-214aa) | 36 | 130 | 312 | 8.7 |
| rpMBP-c2X-ToxoP30del4 del8(83-294aa) | 38 | 75 | 38 | 1.0 |

As can be seen in both Tables 1 and 2, a surprising result was obtained. In particular, deletion of amino acids from the C-terminus of the ToxoP30 antigen resulted in improved Toxo-specific IgG and IgM immunoreactiv by increased rate counts for Panel 6 and improved rate count ratios for Fcal/Acal, Panel 6/Acal, and Panel 6/NC, up to a deletion of 42 amino acids (compare protein rpMBP-c2X-ToxoP30del4C(52-294aa) with protein rpMBP-c2X-ToxoP30(52-336aa) in Tables 1 and 2). The genetically engineered rpMBP-c2X-ToxoP30del4C(52-294aa) protein yielded maximal rate counts for Panel 6 and maximal rate count ratios in both assays. These results suggest that small deletions of the C-terminus of ToxoP30 reveal or make available new epitopes for binding of Toxo-specific IgG and IgM that are occluded in the full-length protein. Deletion of additional C-terminal amino acids (compare protein rpMBP-c2X-ToxoP30del10(52-284aa) and rpMBP-c2X-ToxoP30del11(52-214aa) with protein rpMBP-c2X-ToxoP30del4C(52-294aa) in Tables 1 and 2) resulted in reduced immunoreactivity, suggesting the loss of IgG and IgM epitopes with larger C-terminal deletions. In contrast, the introduction of a small 30 amino acid deletion in the N-terminus of the optimal protein rpMBP-c2X-ToxoP30del4C, which generated the protein rpMBP-c2X-ToxoP30del4del8 (83-294aa), completely abolished Toxo-specific IgG and IgM immunoreactivity. These results also suggest that some of the cysteine residues present in the C-terminal portion of the ToxoP30 protein are dispensable for optimal Toxo IgG and IgM immunoreactivity. For example, the optimal protein rpMBP-c2X-ToxoP30del4C(52-294aa) contains 11 cysteine residues and the protein rpMBP-c2X-ToxoP30del11(52-214aa), which demonstrated good but not optimal immunoreactivity, contains 7 cysteine residues.

EXAMPLE 5

Construction of Toxo P30 Synthetic Genes Containing Mutations Which Change Cysteine Residues to Alanine Based on the results obtained from deletion analysis of the Toxo P30 gene in Example 4D, a new series of MBP-ToxoP30 fusion proteins was constructed. Since there are 12 cysteine residues present in the mature Toxo P30 protein (Burg et al. (1988) J. Immunol. 141:3584-3591; Velge-Roussel et al. (1994) Molec. Biochem. Parasitol. 66:31-38), there are mathematically $2^{12}$ or 4,096 different Toxo P30 proteins that can be constructed which contain various combinations of changing one or more of the twelve cysteine residues to alanine. It would certainly be impossible to try all 4,096 different cysteine to alanine combinations to further optimize the immunoreactivity of the Toxo P30 antigen. Hence, the results in Example 4D were used to narrow the number of different mutant Toxo P30 genes to build that have the potential for improved Toxo IgG and IgM immunoreactivity in an automated immunoassay. Mutant oligonucleotides were designed for the in vitro synthesis of three Toxo P30 genes that contain mutations which change various cysteine residues to alanine, and also introduce the same 3' deletion in the Toxo P30 gene present in ToxoP30del3C(52-300aa) (SEQ ID NO:22 and FIG. 16).

The synthesis of each Toxo P30 gene required the synthesis and assembly of 16 overlapping oligonucleotides. These oligonucleotides ranged from 67-72 bases in length with neighboring oligonucleotides overlapping by 20-23 residues. The P30 genes were assembled by recursive PCR followed by PCR amplification of the assembled genes (Withers-Martinez et al. (1999) Protein Engr. 12:1113-1120; Prytulla et al. (1996) FEBS Lett. 399:283-289; Kataoka et al. (1998) Biochem. Biophys. Res. Comm. 250:409-413) using a P30 sense primer containing an EcoRI site and an antisense primer containing a HindIII site. After PCR amplification, the P30 gene was digested with EcoRI and HindIII, purified on an agarose gel, and ligated to the pMAL-c2X vector backbone which had been digested by EcoRI and HindIII as shown schematically in FIG. 30.

Step A: Construction of pMBP-c2X-ToxoP30MIX1

Figure 30:
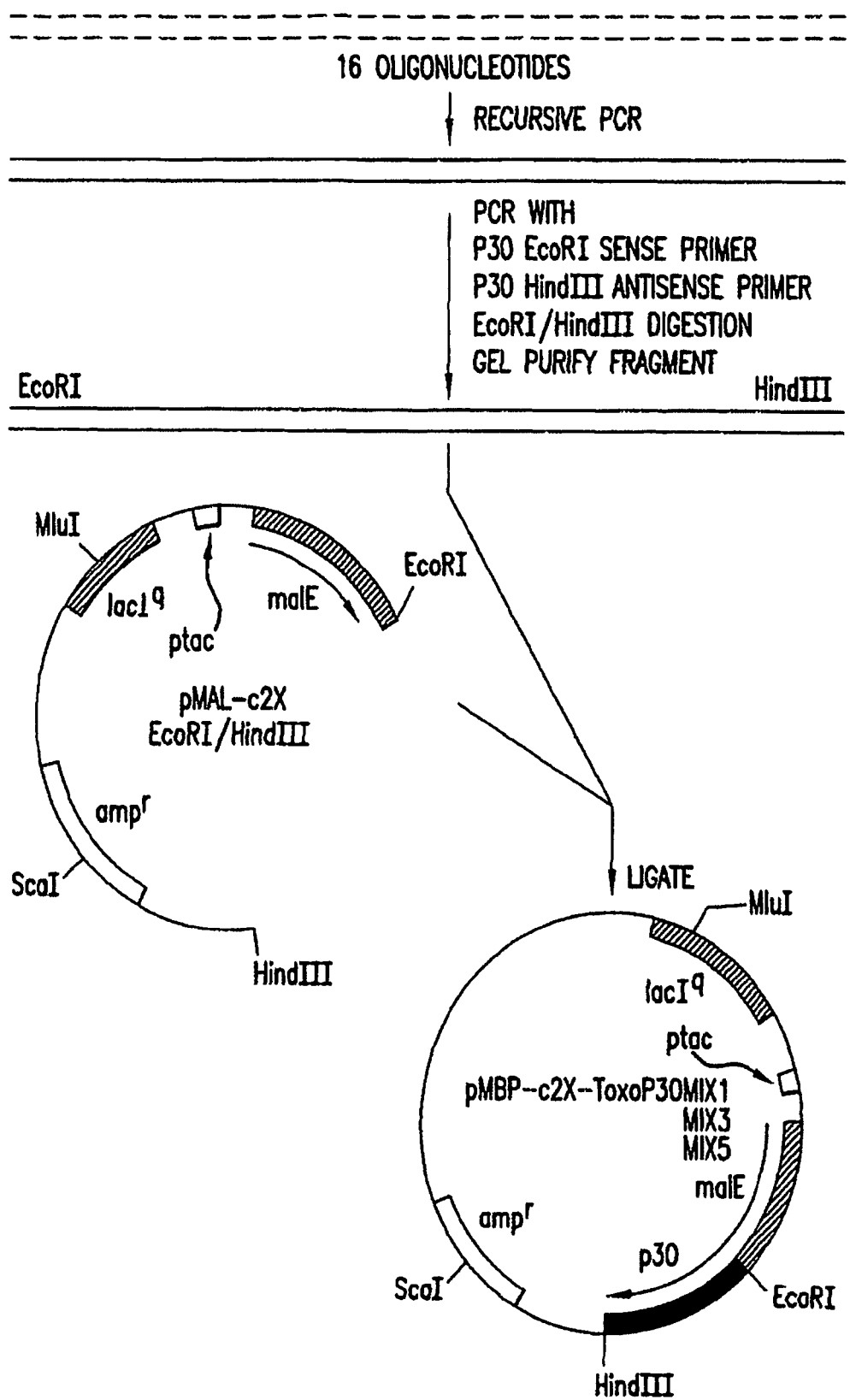
FIG. 30 is a schematic of the construction of plasmids pMBP-c2X-ToxoP30MIX1, pMBP-c2X-ToxoP30MIX3, and pMBP-c2X-ToxoP30MIX5.

The plasmid pMBP-c2X-ToxoP30MIX1 was constructed by cloning a synthetic DNA fragment containing Toxo P30, obtained by the synthesis and assembly of 16 oligonucleotides, into the EcoRI/HindIII sites of pMAL-c2X (FIG. 30). This plasmid differs from plasmid pMBP-c2X-ToxoP30del3C(52-300aa) of EXAMPLE 2E in that the Toxo P30 DNA sequence in plasmid pMBP-c2X-ToxoP30MIX1 has been changed so that five of the twelve cysteine residues of Toxo P30 (cysteine nos. 8-12) have been changed to alanine. Plasmid pMAL-c2X was digested with EcoRI/HindIII and the vector backbone was purified on an agarose gel. The following oligonucleotides were synthesized for construction of the ToxoP30MIX1 gene:

P30.001

[SEQ ID NO: 44]
5'-CTTGTTGCCAATCAAGTTGTCACCTGCCCAGATAAAAAATCGACAGC

CGCGGTCATTCTCACACCGACGG-3'

P30.002

[SEQ ID NO: 45]
5'-GAGGCTCTGTGAGCGCTGTTTTAGGGCACTTGAGAGTGAAGTGGTTC

TCCGTCGGTGTGAGAATGACCG-3'

P30.003

[SEQ ID NO: 46]
5'-CCTAAAACAGCGCTCACAGAGCCTCCCACTCTTGCGTACTCACCCAA

CAGGCAAATCTGCCCAGCGG-3'

P30.004

[SEQ ID NO: 47]
5'-GGAATCAAGGAGCTCAATGTTACAGCCTTTGATGTACAGCTACTTGT

AGTACCCGCTGGGCAGATTTGCCTG-3'

P30.005

[SEQ ID NO: 48]
5'-GTAACATTGAGCTCCTTGATTCCTGAAGCAGAAGATAGCTGGTGGAC

GGGGGATTCTGCTAGTCTCGACACGG-3'

P30.006

[SEQ ID NO: 49]
5'-CTGCGTTGTCACGGGGAACTTCTCGATTGGAACTGTGAGTTTGATGC

CTGCCGTGTCGAGACTAGCAGAATC-3'

P30.007

[SEQ ID NO: 50]
5'-GAAGTTCCCCGTGACAACGCAGACGTTTGTGGTCGGTTGCATCAAGG

GAGACGACGCACAGAGTTGTATG-3'

P30.008

[SEQ ID NO: 51]
5'-GCGACATTATTGACGACCGATGAGGCTCTGGCTTGTACTGTCACCGT

GACCATACAACTCTGTGCGTCGTC-3'

P30.009

[SEQ ID NO: 52]
5'-CATCGGTCGTCAATAATGTCGCAAGGTGCTCCTACGGTGCAGACAGC

ACTCTTGGTCCTGTCAAGTTGTC-3'

-continued

P30.010Ala8
[SEQ ID NO: 53]
5'-GACTCCATCTTTCCCAGCCACGAGGGTCATTGTAGTGGGTCCTTCCG

CAGACAACTTGACAGGACCAAGAG-3'

P30.011Ala8Ala9
[SEQ ID NO: 54]
5'-GTGGCTGGGAAAGATGGAGTCAAAGTTCCTCAAGACAACAATCAGTA

CGCTTCCGGGACGACGCTGACTGG-3'

P30.012Ala9Ala10
[SEQ ID NO: 55]
5'-GTTCTCAGTTAATTTTGGCAAAATATCTTTGAACGATTTCTCGTTAG

CACCAGTCAGCGTCGTCCCGGAAG-3'

P30.013
[SEQ ID NO: 56]
5'-GATATTTTGCCAAAATTAACTGAGAACCCGTGGCAGGGTAACGCTTC

GAGTGATAAGGGTGCCACGCTAAC-3'

P30.014
[SEQ ID NO: 57]
5'-CCAATAATGACGCTTTTTGACTCGGCTGGAAATGCTTCCTTCTTGAT

CGTTAGCGTGGCACCCTTATCAC-3'

P30.015Ala11Ala12
[SEQ ID NO: 58]
5'-GTCAAAAAGCGTCATTATTGGAGCTACAGGGGGATCGCCTGAGAAGC

ATCACGCTACCGTGAAACTGGAG-3'

P30.016Ala12
[SEQ ID NO: 59]
5'-GACTGGCTGTTCCCGCAGCCGATTTTGCTGACCCTGCAGCCCCGGCA

AACTCCAGTTTCACGGTAGCGTG-3'

In the first step of gene synthesis, 4 picomoles of each oligonucleotide were mixed together and assembled using recursive PCR as follows: 1 cycle at 95° C. for 5 minutes followed by 35 cycles at 95° C. for 1 minute, 55° C. for 2 minutes, 72° C. for 2 minutes; 1 cycle at 72° C. for 10 minutes followed by a soak cycle at 4° C. In the second step of gene synthesis, a sense primer, starting at nucleotide 464 of the P30 gene containing an EcoRI site, and an antisense primer containing a HindIII site, starting at nucleotide 1210 of the P30 gene (Burg et al. (1988) J. Immunol. 141:3584-3591) were synthesized as shown below:

Sense Primer
[SEQ ID NO: 1]
5'-GGC<u>GAATTC</u>CTTGTTGCCAATCAAGTTGTCACC-3'

(EcoRI site is underlined)

Antisense Primer
[SEQ ID NO: 60]
5'-CAGGTC<u>AAGCTTT</u>CACTCCAGTTTCACGGTAGCGTG-3'

(HindIII site is underlined.)

The sense and antisense primers were added to a PCR reaction mixture containing the assembled oligonucleotides from the first step of gene synthesis. After PCR amplification and purification of the reaction mixture with a Qiaquick PCR purification kit, the reaction mixture was digested with EcoRI and HindIII, and the 747 base pair DNA fragment containing Toxo P30MIX1 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 synthetic DNA sequence by restriction enzyme analysis. Plasmid pMBP-c2X-ToxoP30MIX1 contained the Toxo P30MIX1 gene cloned at the EcoRI/HindIII sites of pMAL-c2X. The complete DNA sequence [SEQ ID NO:61] of plasmid pMBP-c2X-ToxoP30MIX1 is shown in FIG. 31, and the corresponding amino acid sequence [SEQ ID NO:62] of the MBP-ToxoP30MIX1 fusion protein is also shown in FIG. 31, wherein cysteine amino acid residues located at 555, 570, 578, 625, 635 of SEQ ID NO:21 are now alanine amino acids located at 555, 570, 578, 625, 635 of SEQ ID NO:62. Plasmid pMBP-c2X-ToxoP30MIX1 was deposited with the ATCC 10801 University Boulevard, Manassas, Va. 20110-2209, under terms of the Budapest Treaty on Sep. 26, 2002, and was accorded Accession No. ATCC 4721. The DNA sequence [SEQ ID NO:63] of ToxoP30MIX1 is shown in FIG. 32, and the corresponding amino acid sequence [SEQ ID NO:64] of the ToxoP30MIX1 protein is also shown in FIG. 32, wherein cysteine amino acid residues located at 164, 179, 187, 234, 244 of SEQ ID NO:23 are now alanine amino acids located at 164, 179, 187, 234, 244 of SEQ ID NO:64.

Step B: Construction of pMBP-c2X-ToxoP30MIX3

The plasmid pMBP-c2X-ToxoP30MIX3 was constructed by cloning a synthetic DNA fragment containing Toxo P30, obtained by the synthesis and assembly of 16 oligonucleotides, into the EcoRI/HindIII sites of pMAL-c2X (FIG. 30). This plasmid differs from plasmid pMBP-c2X-ToxoP30del3C(52-300aa) of EXAMPLE 2E in that the Toxo P30 DNA sequence in plasmid pMBP-c2X-ToxoP30MIX3 has been changed so that six of the twelve cysteine residues of Toxo P30 (cysteine nos. 7-12) have been changed to alanine. Plasmid pMAL-c2X was digested with EcoRI/HindIII, and the vector backbone was purified on an agarose gel. The following oligonucleotides were synthesized for construction of the ToxoP30MIX3 gene:

P30.001
[SEQ ID NO: 44]
5'-CTTGTTGCCAATCAAGTTGTCACCTGCCCAGATAAAAAATCGACAGC

CGCGGTCATTCTCACACCGACGG-3'

P30.002
[SEQ ID NO: 45]
5'-GAGGCTCTGTGAGCGCTGTTTTAGGGCACTTGAGAGTGAAGTGGTTC

TCCGTCGGTGTGAGAATGACCG-3'

P30.003
[SEQ ID NO: 46]
5'-CCTAAAACAGCGCTCACAGAGCCTCCCACTCTTGCGTACTCACCCAA

CAGGCAAATCTGCCCAGCGG-3'

P30.004
[SEQ ID NO: 47]
5'-GGAATCAAGGAGCTCAATGTTACAGCCTTTGATGTACAGCTACTTGT

AGTACCCGCTGGGCAGATTTGCCTG-3'

P30.005
[SEQ ID NO: 48]
5'-GTAACATTGAGCTCCTTGATTCCTGAAGCAGAAGATAGCTGGTGGAC

GGGGGATTCTGCTAGTCTCGACACGG-3'

P30.006
[SEQ ID NO: 49]
5'-CTGCGTTGTCACGGGGAACTTCTCGATTGGAACTGTGAGTTTGATGC

CTGCCGTGTCGAGACTAGCAGAATC-3'

-continued

P30.007
[SEQ ID NO: 50]
5'-GAAGTTCCCCGTGACAACGCAGACGTTTGTGGTCGGTTGCATCAAGG
GAGACGACGCACAGAGTTGTATG-3'

P30.008
[SEQ ID NO: 51]
5'-GCGACATTATTGACGACCGATGAGGCTCTGGCTTGTACTGTCACCGT
GACCATACAACTCTGTGCGTCGTC-3'

P30.009Ala7
[SEQ ID NO: 65]
5'-CATCGGTCGTCAATAATGTCGCAAGGGCTTCCTACGGTGCAGACAGC
ACTCTTGGTCCTGTCAAGTTGTC-3'

P30.010Ala8
[SEQ ID NO: 53]
5'-GACTCCATCTTTCCCAGCCACGAGGGTCATTGTAGTGGGTCCTTCCG
CAGACAACTTGACAGGACCAAGAG-3'

P30.011Ala8Ala9
[SEQ ID NO: 54]
5'-GTGGCTGGGAAAGATGGAGTCAAAGTTCCTCAAGACAACAATCAGTA
CGCTTCCGGGACGACGCTGACTGG-3'

P30.012Ala9Ala10
[SEQ ID NO: 55]
5'-GTTCTCAGTTAATTTTGGCAAAATATCTTTGAACGATTTCTCGTTAG
CACCAGTCAGCGTCGTCCCGGAAG-3'

P30.013
[SEQ ID NO: 56]
5'-GATATTTTGCCAAAATTAACTGAGAACCCGTGGCAGGGTAACGCTTC
GAGTGATAAGGGTGCCACGCTAAC-3'

P30.014
[SEQ ID NO: 57]
5'-CCAATAATGACGCTTTTTGACTCGGCTGGAAATGCTTCCTTCTTGAT
CGTTAGCGTGGCACCCTTATCAC-3'

P30.015Ala11Ala12
[SEQ ID NO: 58]
5'-GTCAAAAAGCGTCATTATTGGAGCTACAGGGGGATCGCCTGAGAAGC
ATCACGCTACCGTGAAACTGGAG-3'

P30.016Ala12
[SEQ ID NO: 59]
5'-GACTGGCTGTTCCCGCAGCCGATTTTGCTGACCCTGCAGCCCCGGCA
AACTCCAGTTTCACGGTAGCGTG-3'

In the first step of gene synthesis, 4 picomoles of each oligonucleotide were mixed together and assembled using recursive PCR as follows: 1 cycle at 95° C. for 5 minutes followed by 35 cycles at 95° C. for 1 minute, 55° C. for 2 minutes, 72° C. for 2 minutes; 1 cycle at 72° C. for 10 minutes followed by a soak cycle at 4° C. In the second step of gene synthesis, a sense primer, starting at nucleotide 464 of the P30 gene containing an EcoRI site, and an antisense primer containing a HindIII site, starting at nucleotide 1210 of the P30 gene (Burg et al. (1988) J. Immunol. 141:3584-3591) were synthesized as shown below:

Sense Primer
[SEQ ID NO: 1]
5'-GGCGAATTCCTTGTTGCCAATCAAGTTGTCACC-3'

(EcoRI site is underlined)

Antisense Primer
[SEQ ID NO: 60]
5'-CAGGTCAAGCTTTCACTCCAGTTTCACGGTAGCGTG-3'

(HindIII site is underlined.)

The sense and antisense primers were added to a PCR reaction mixture containing the assembled oligonucleotides from the first step of gene synthesis. After PCR amplification and purification of the reaction mixture with a Qiaquick PCR purification kit, the reaction mixture was digested with EcoRI and HindIII, and the 747 base pair DNA fragment containing Toxo P30MIX3 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 synthetic DNA sequence by restriction enzyme analysis. Plasmid pMBP-c2X-ToxoP30MIX3 contained the Toxo P30MIX3 gene cloned at the EcoRI/HindIII sites of pMAL-c2X. The complete DNA sequence [SEQ ID NO:66] of plasmid pMBP-c2X-ToxoP30MIX3 is shown in FIG. 33, and the corresponding amino acid sequence [SEQ ID NO:67] of the MBP-ToxoP30MIX3 fusion protein is also shown in FIG. 33, wherein cysteine amino acid residues located at 530, 555, 570, 578, 625, 635 of SEQ ID NO:21 are now alanine amino acids located at 530, 555, 570, 578, 625, 635 of SEQ ID NO:67. The DNA sequence [SEQ ID NO:68] of ToxoP30MIX3 is shown in FIG. 34, and the corresponding amino acid sequence [SEQ ID NO:69] of the ToxoP30MIX3 protein is also shown in FIG. 34, wherein cysteine amino acid residues located at 139, 164, 179, 187, 234, 244 of SEQ ID NO:23 are now alanine amino acids located at 139, 164, 179, 187, 234, 244 of SEQ ID NO:69.

Step C: Construction of pMBP-c2X-ToxoP30MIX5

The plasmid pMBP-c2X-ToxoP30MIX5 was constructed by cloning a synthetic DNA fragment containing Toxo P30, obtained by the synthesis and assembly of 16 oligonucleotides, into the EcoRI/HindIII sites of pMAL-c2X (FIG. 30). This plasmid differs from plasmid pMBP-c2X-ToxoP30del3C(52-300aa) of EXAMPLE 2E in that the Toxo P30 DNA sequence in plasmid pMBP-c2X-ToxoP30MIX5 has been changed so that six of the twelve cysteine residues of Toxo P30 (cysteine nos. 2 and 8-12) have been changed to alanine. Plasmid pMAL-c2X was digested with EcoRI/HindIII and the vector backbone was purified on an agarose gel. The following oligonucleotides were synthesized for construction of the ToxoP30MIX5 gene:

P30.001
[SEQ ID NO: 44]
5'-CTTGTTGCCAATCAAGTTGTCACCTGCCCAGATAAAAAATCGACAGC
CGCGGTCATTCTCACACCGACGG-3'

P30.002Ala2
[SEQ ID NO: 70]
5'-GAGGCTCTGTGAGCGCTGTTTTAGGAGCCTTGAGAGTGAAGTGGTTC
TCCGTCGGTGTGAGAATGACCG-3'

-continued

P30.003
[SEQ ID NO: 46]
5'-CCTAAAACAGCGCTCACAGAGCCTCCCACTCTTGCGTACTCACCCAA

CAGGCAAATCTGCCCAGCGG-3'

P30.004
[SEQ ID NO: 47]
5'-GGAATCAAGGAGCTCAATGTTACAGCCTTTGATGTACAGCTACTTGT

AGTACCCGCTGGGCAGATTTGCCTG-3'

P30.005
[SEQ ID NO: 48]
5'-GTAACATTGAGCTCCTTGATTCCTGAAGCAGAAGATAGCTGGTGGAC

GGGGGATTCTGCTAGTCTCGACACGG-3'

P30.006
[SEQ ID NO: 49]
5'-CTGCGTTGTCACGGGGAACTTCTCGATTGGAACTGTGAGTTTGATGC

CTGCCGTGTCGAGACTAGCAGAATC-3'

P30.007
[SEQ ID NO: 50]
5'-GAAGTTCCCCGTGACAACGCAGACGTTTGTGGTCGGTTGCATCAAGG

GAGACGACGCACAGAGTTGTATG-3'

P30.008
[SEQ ID NO: 51]
5'-GCGACATTATTGACGACCGATGAGGCTCTGGCTTGTACTGTCACCGT

GACCATACAACTCTGTGCGTCGTC-3'

P30.009
[SEQ ID NO: 52]
5'-CATCGGTCGTCAATAATGTCGCAAGGTGCTCCTACGGTGCAGACAGC

ACTCTTGGTCCTGTCAAGTTGTC-3'

P30.010Ala8
[SEQ ID NO: 53]
5'-GACTCCATCTTTCCCAGCCACGAGGGTCATTGTAGTGGGTCCTTCCG

CAGACAACTTGACAGGACCAAGAG-3'

P30.011Ala8Ala9
[SEQ ID NO: 54]
5'-GTGGCTGGGAAAGATGGAGTCAAAGTTCCTCAAGACAACAATCAGTA

CGCTTCCGGACGACGCTGACTGG-3'

P30.012Ala9Ala10
[SEQ ID NO: 55]
5'-GTTCTCAGTTAATTTTGGCAAAATATCTTTGAACGATTTCTCGTTAG

CACCAGTCAGCGTCGTCCCGGAAG-3'

P30.013
[SEQ ID NO: 56]
5'-GATATTTTGCCAAAATTAACTGAGAACCCGTGGCAGGGTAACGCTTC

GAGTGATAAGGGTGCCACGCTAAC-3'

P30.014
[SEQ ID NO: 57]
5'-CCAATAATGACGCTTTTTGACTCGGCTGGAAATGCTTCCTTCTTGAT

CGTTAGCGTGGCACCCTTATCAC-3'

P30.015Ala11Ala12
[SEQ ID NO: 58]
5'-GTCAAAAAGCGTCATTATTGGAGCTACAGGGGGATCGCCTGAGAAGC

ATCACGCTACCGTGAAACTGGAG-3'

-continued

P30.016Ala12
[SEQ ID NO: 59]
5'-GACTGGCTGTTCCCGCAGCCGATTTTGCTGACCCTGCAGCCCCGGCA

AACTCCAGTTTCACGGTAGCGTG-3'

In the first step of gene synthesis, 4 picomoles of each oligonucleotide were mixed together and assembled using recursive PCR as follows: 1 cycle at 95° C. for 5 minutes followed by 35 cycles at 95° C. for 1 minute, 55° C. for 2 minutes, 72° C. for 2 minutes; 1 cycle at 72° C. for 10 minutes followed by a soak cycle at 4° C. In the second step of gene synthesis, a sense primer, starting at nucleotide 464 of the P30 gene containing an EcoRI site, and an antisense primer containing a HindIII site, starting at nucleotide 1210 of the P30 gene (Burg et al. (1988) J. Immunol. 141:3584-3591) were synthesized as shown below:

Sense Primer
[SEQ ID NO: 1]
5'-GGCGAATTCCTTGTTGCCAATCAAGTTGTCACC-3'

(EcoRI site is underlined)

Antisense Primer
[SEQ ID NO: 60]
5'-CAGGTCAAGCTTTCACTCCAGTTTCACGGTAGCGTG-3'

(HindIII site is underlined.)

The sense and antisense primers were added to a PCR reaction mixture containing the assembled oligonucleotides from the first step of gene synthesis. After PCR amplification and purification of the reaction mixture with a Qiaquick PCR purification kit, the reaction mixture was digested with EcoRI and HindIII, and the 747 base pair DNA fragment containing Toxo P30MIX5 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 synthetic DNA sequence by restriction enzyme analysis. Plasmid pMBP-c2X-ToxoP30MIX5 contained the Toxo P30MIX5 gene cloned at the EcoRI/HindIII sites of pMAL-c2X. The complete DNA sequence [SEQ ID NO:71] of plasmid pMBP-c2X-ToxoP30MIX5 is shown in FIG. 35, and the corresponding amino acid sequence [SEQ ID NO:72] of the MBP-ToxoP30MIX5 fusion protein is also shown in FIG. 35, wherein cysteine amino acid residues located at 422, 555, 570, 578, 625, 635 of SEQ ID NO:21 are now alanine amino acids located at 422, 555, 570, 578, 625, 635 of SEQ ID NO:72. The DNA sequence [SEQ ID NO:73] of ToxoP30MIX5 is shown in FIG. 36, and the corresponding amino acid sequence [SEQ ID NO:74] of the ToxoP30MIX5 protein is also shown in FIG. 36, wherein cysteine amino acid residues located at 31, 164, 179, 187, 234, 244 of SEQ ID NO:23 are now alanine amino acids located at 31, 164, 179, 187, 234, 244 of SEQ ID NO:74.

EXAMPLE 6

Expression of rpMBP-c2X-ToxoP30MIX Antigens in *E. coli*

Step A: Expression of Cloned Genes in *E. coli*

Bacterial clones pMBP-c2X-ToxoP30MIX1, pMBP-c2X-ToxoP30MIX3, and pMBP-c2X-ToxoP30MIX5 expressing the MBP fusion proteins rpMBP-c2X-ToxoP30MIX1, rpMBP-c2X-ToxoP30MIX3, and rpMBP-c2X-ToxoP30MIX5 of Example 5 were grown in "SUPERBROTH II" media containing 100 µg/ml ampicillin to log phase, and the synthesis of the MBP-ToxoP30MIX fusion proteins was induced by the addition of IPTG as previously described (Robinson et al. (1993) J. Clin. Microbiol. 31:629-635). After 4 hours post-induction, the cells were harvested, and the cell pellets were stored at −80 C until protein purification occurred.

Step B: Purification of MBP-ToxoP30MIX Fusion Proteins

Soluble fusion proteins rpMBP-c2X-ToxoP30MIX1, rpMBP-c2X-ToxoP30MIX3, and rpMBP-c2X-ToxoP30MIX5 were purified after lysis from cell paste following the New England Biolabs pMAL Protein Fusion and Purification instruction manual. Following lysis and centrifugation, the crude supernatants containing the fusion proteins were loaded onto an amylose affinity column. Following washing of the column, the fusion proteins were eluted from the column with maltose, appropriate column fractions were pooled and filtered through a 0.2µ filter, and then stored at 2-8° C. until coating onto microparticles.

EXAMPLE 7

Evaluation of rpMBP-c2X-ToxoP30MIX Antigens in an Automated Toxo IgG and IgM Immunoassay Step A: Coating of rpMBP-c2X-ToxoP30MIX Antigens onto Microparticles Prior to coating microparticles, the rpMBP-c2X-ToxoP30MIX1, rpMBP-c2X-ToxoP30MIX3 and rpMBP-c2X-ToxoP30MIX5 antigens were diluted to a concentration of 1 mg/ml and incubated at 37° C. for 24 hours. Following the heat treatment step, the rpMBP-c2X-ToxoP30MIX antigens were coated separately onto sulfate-derivatized polystyrene microparticles (1-5% solids) in a vessel containing MES pH 6.2 buffer with EDAC for 30 minutes at room temperature, on an end over end rotator. The coated microparticles were then collected by centrifugation at 14,000×g for 10 minutes and the supernatant was discarded. The microparticles were resuspended in a microparticle storage buffer containing Tris buffer, pH 7.5, EDTA, sodium chloride, Tween 20, fetal calf serum (Toxo antibody free), sodium azide, and sucrose using a syringe and needle. The microparticles were then diluted with microparticle storage buffer to a final concentration of 0.1-0.3% solids and filled into plastic bottles.

Step B: Evaluation of MBP fusion proteins rpMBP-c2X-ToxoP30MIX1, rpMBP-c2X-ToxoP30MIX3 and rpMBP-c2X-ToxoP30MIX5 in the AxSYM Toxo IgG v2 and Toxo IgM v2 Immunoassays The AxSYM® Toxo IgG and IgM reagent packs were assembled as described in Examples 4B and 4C using the microparticles coated with the Toxo antigens described in Example 7A. The Toxo IgG A and F calibrators (Acal and Fcal) and Panel 6 (PNL6) were tested with the AxSYM Toxo IgG v2 reagent packs and the Toxo IgM Negative Control (NC), Index Calibrator (IC), and Panel 6 (PNL6) were tested with the AxSYM Toxo IgM v2 reagent packs. The results are shown below in Tables 3 and 4.

TABLE 3

Evaluation of the rpMBP-c2X-ToxoP30MIX Antigens in the AxSYM Toxo IgG v2 Assay

| Antigen Coated | Rate Counts | | | | |
| --- | --- | --- | --- | --- | --- |
| | Acal | Fcal | Fcal/Acal | PNL6 | PNL6/Acal |
| rpMBP-c2X-ToxoP30 MIX1 (Ala8-12) | 34 | 3847 | 113 | 1445 | 43 |
| rpMBP-c2X-ToxoP30 MIX3 (Ala7-12) | 35 | 3704 | 106 | 1043 | 30 |
| rpMBP-c2X-ToxoP30 MIX5 (Ala2, Ala8-12) | 35 | 57 | 1.6 | 23 | 0.7 |

TABLE 4

Evaluation of the rpMBP-c2X-ToxoP30MIX Antigens in the AxSYM Toxo IgM v2 Assay

| Antigen Coated | Rate Counts | | | |
| --- | --- | --- | --- | --- |
| | NC | IC | PNL6 | PNL6/NC |
| rpMBP-c2X-ToxoP30 MIX1 (Ala8-12) | 37 | 149 | 459 | 12.4 |
| rpMBP-c2X-ToxoP30 MIX3 (Ala7-12) | 44 | 111 | 368 | 8.4 |
| rpMBP-c2X-ToxoP30 MIX5 (Ala2, Ala8-12) | 31 | 49 | 27 | 0.9 |

As can be seen in Tables 3 and 4, the genetically engineered rpMBP-c2X-ToxoP30MIX1 antigen, which contained five C-terminal cysteine residues substituted with alanine, yielded the best Toxo IgG and IgM immunoreactivity as measured by the highest rate counts for Panel 6 and highest rate count ratios for Fcal/Acal, Panel 6/Acal, and Panel 6/NC. In addition, the rpMBP-c2X-ToxoP30MIX1 antigen yielded the highest rate counts for Panel6 and the highest Panel6/NC rate count ratio in the Toxo IgM v2 assay for any rpMBP-c2X-ToxoP30 antigen tested (see Tables 1 and 2). The rpMBP-c2X-ToxoP30MIX5 antigen, which contained five C-terminal cysteine residues substituted with alanine residues plus the substitution of cysteine no. 2 with alanine, was not immunoreactive in either assay. This result was consistent with the results obtained with the rpMBP-c2X-ToxoP30del4del8(83-294aa) antigen (see Tables 1 and 2), in which deletion of the first two cysteine residues of Toxo P30 resulted in complete loss of immunoreactivity. Thus, the surprising result was obtained that substitution of several cysteine residues in the C-terminal half of Toxo P30 with alanine results in superior Toxo IgG and IgM immunoreactivity of the antigen whereas substitution of a single cysteine with alanine in the N-terminal half of Toxo P30 completely abolishes immunoreactivity.

EXAMPLE 8

Purification and Coating of the rpToxoP35S Antigen

The rpToxoP35S antigen described in U.S. Pat. No. 6,329,157 B1 was expressed in *E. coli*, and cell paste was harvested as described in Example 6A. This antigen was then purified from cell paste and coated onto microparticles as described below.

Step A: Purification of the rpToxoP35S Antigen

The rpToxoP35S antigen was expressed in *E. coli* as an insoluble fusion protein. Following lysis of the cell paste, the inclusion bodies containing the rpToxoP35S antigen were washed with water, phosphate buffer, Triton X-100, and urea. The rpToxoP35S antigen was then solubilized in a SDS/DTT buffer and applied to a Sephacryl S-300 column. The appropriate column fractions were pooled, diluted to a concentration of 1 mg/ml and filtered through a 0.2μ filter, and then stored at −80° C. until coating.

Step B: Coating of the rpToxoP35S Antigen onto Microparticles

The rpToxoP35S antigen was thawed and brought into solution by mild warming followed by centrifugation to remove particulate matter. This antigen was then dialyzed against three changes of MES buffer, pH 6.2 at room temperature overnight and then coated onto sulfate-derivatized polystyrene microparticles (1-5% solids) in a vessel containing MES pH 6.2 buffer with EDAC for 30 minutes at room temperature, on an end over end rotator. The coated microparticles were then collected by centrifugation at 14,000×g for 10 minutes and the supernatant was discarded. The microparticles were resuspended in a microparticle storage buffer containing Tris buffer, pH 7.5, EDTA, sodium chloride, Tween 20, fetal calf serum (Toxo antibody free), sodium azide, and sucrose using a syringe and needle. The microparticles were then diluted with microparticle storage buffer to a final concentration of 0.1-0.3% solids and filled into plastic bottles.

EXAMPLE 9

Development of Antigen Cocktails Employing the Genetically Engineered P30 Antigens After achieving a significant improvement in the Toxo IgG and IgM immunoreactivity of the P30 antigen through genetic engineering (Examples 4 and 7), a preliminary re-evaluation of microparticles coated with the Toxo antigens described in U.S. Pat. No. 6,329,157 B1 in the AxSYM® Toxo IgG v2 and IgM v2 assays was performed. Evaluation of these antigen coated microparticles in conjunction with microparticles coated with the P30 antigens rpMBP-c2X-ToxoP30del3C (52-300aa), rpMBP-c2X-ToxoP30del4C(52-294aa), and rpMBP-c2X-ToxoP30MIX1 suggested that a new combination of either the rpMBP-c2X-ToxoP30del3C(52-300aa), rpMBP-c2X-ToxoP30del4C(52-294aa), or rpMBP-c2X-ToxoP30MIX1 antigen with the rpToxoP35S antigen could improve the performance of the AxSYM® Toxo IgG v2 assay. In addition, the rpMBP-c2X-ToxoP30del3C(52-300aa), rpMBP-c2X-ToxoP30del4C(52-294aa), or rpMBP-c2X-ToxoP30MIX1 antigens alone could improve the performance of the AxSYM® Toxo IgM v2 assay. In order to demonstrate the diagnostic utility of the genetically engineered P30 antigens and the new genetically engineered P30/P35 antigen cocktail, human sera negative for Toxo antibodies and sera sourced from patients with an acute or chronic toxoplasmosis were tested in the AxSYM® Toxo IgG v2 and IgM v2 assays as described below.

Step A: Assembly of AxSYM® Toxo IgG v2 Reagent Packs

Purified Toxo antigens rpMBP-c2X-ToxoP30del3C(52-300aa), rpMBP-c2X-ToxoP30del4C(52-294aa), rpMBP-c2X-ToxoP30MIX1, and rpToxoP35S were coated unto microparticles as previously described in Examples 4A and 7A. The microparticles were then diluted to a final concentration 0.2% solids and the following three microparticle blends were made: 2:1 v/v blend of rpMBP-c2X-ToxoP30del3C(52-300aa):rpToxoP35S coated microparticles (labeled as P30del3/P35); 2:1 v/v blend of rpMBP-c2X-ToxoP30del4C(52-294aa):rpToxoP35S coated microparticles (labeled as P30del4/P35); and a 2:1 v/v blend of rpMBP-c2X-ToxoP30MIX1:rpToxoP35S coated microparticles (labeled as P30MIX1/P35). These three microparticle blends were filled into plastic bottles, assembled into individual AxSYM® Toxo IgG v2 reagent kits as described in Example 4B, and labeled as P30del3C/35, P30del4C/P35, and P30MIX1/P35.

Step B: Assembly of AxSYM® Toxo IgM v2 Reagent Packs

Purified Toxo antigens rpMBP-c2X-ToxoP30del3C(52-300aa), rpMBP-c2X-ToxoP30del4C(52-294aa), rpMBP-c2X-ToxoP30MIX1, and rpToxoP35S were coated onto microparticles as previously described in Examples 4A and 7A. The microparticles were then diluted to a final concentration of 0.2% solids and filled into plastic bottles. AxSYM® Toxo IgM v2 kits were assembled with each coated microparticle as described in Example 4C and labeled as P30del3C, P30del4C, and P30MIX1.

Step C: Human Sera for Testing

Three groups of human sera from a French population were tested in this evaluation: Group 1 (n=100) human sera negative for Toxo IgG and IgM antibodies by the Abbott IMx® Toxo IgG and IgM assays, respectively (Abbott Laboratories, Abbott Park, Ill.); Group 2 (n=56) human sera positive for Toxo IgG and negative for Toxo IgM antibodies by the Abbott IMx® Toxo IgG and IgM assays, respectively; Group 3 (n=52) human sera positive for Toxo IgG antibodies by a high sensitivity direct agglutination assay (HSDA) (Desmonts, G. and Remington, J. S. (1980) J. Clin. Microbiol. 11:562-568) and positive for Toxo IgM antibodies by an IgM immunocapture assay (IC-M) (Pouletty et al. (1985) J. Immunol. Methods 76:289-298). The assay calibrators and controls for the AxSYM® Toxo IgG v2 and Toxo IgM v2 assays were run as previously described in Examples 4B-D. The Abbott AxSYM® Toxo IgG and IgM assays (Abbott Laboratories Abbott Park, Ill.), which use the tachyzoite antigen for detection of Toxo-specific IgG and IgM, were included as reference assays during specimen testing.

Step D: Evaluation of the AxSYM® Toxo IgG v2 assays

All specimens in Groups 1-3 were tested by the AxSYM® Toxo IgG v2 assays (P30del3C/35, P30del4C/P35, and P30MIX1/P35) and by the AxSYM® Toxo IgG assay. The same assay cutoff of 3 IU/ml for the AxSYM Toxo IgG assay was employed for AxSYM® Toxo IgG v2 assays, with an equivocal zone from 2-3 IU/ml. The performance of the recombinant antigen based AxSYM® Toxo IgG v2 assays was compared to the tachyzoite antigen based AxSYM® Toxo IgG assay and is shown in Tables 5-7.

TABLE 5

Evaluation of the AxSYM ® Toxo IgG v2 P30del3C/P35 assay

| | | AxSYM ® Toxo IgG | | | |
|---|---|---|---|---|---|
| | | POS | EQV | NEG | TOTAL |
| AxSYM ® Toxo IgG v2 P30del3C/P35 | POS | 108 | 0 | 0 | 108 |
| | EQV | 0 | 0 | 1 | 1 |
| | NEG | 0 | 0 | 99 | 99 |
| | TOTAL | 108 | 0 | 100 | 208 |

Sensitivity: 108/108 = 100%
Specificity: 99/99 = 100%
Agreement: 207/207 = 100%
Correlation Coefficient: r = 0.9751

TABLE 6

Evaluation of the AxSYM ® Toxo IgG v2 P30del4C/P35 assay

|  |  | AxSYM ® Toxo IgG | | | |
|---|---|---|---|---|---|
|  |  | POS | EQV | NEG | TOTAL |
| AxSYM ® Toxo | POS | 108 | 0 | 0 | 108 |
| IgG v2 | EQV | 0 | 0 | 1 | 1 |
| P30del4C/P35 | NEG | 0 | 0 | 99 | 99 |
|  | TOTAL | 108 | 0 | 100 | 208 |

Sensitivity: 108/108 = 100%
Specificity: 99/99 = 100%
Agreement: 207/207 = 100%
Correlation Coefficient: r = 0.9778

TABLE 7

Evaluation of the AxSYM ® Toxo IgG v2 P30MIX1/P35 assay

|  |  | AxSYM ® Toxo IgG | | | |
|---|---|---|---|---|---|
|  |  | POS | EQV | NEG | TOTAL |
| AxSYM ® Toxo | POS | 108 | 0 | 0 | 108 |
| IgG v2 | EQV | 0 | 0 | 1 | 1 |
| P30MIX1/P35 | NEG | 0 | 0 | 99 | 99 |
|  | TOTAL | 108 | 0 | 100 | 208 |

Sensitivity: 108/108 = 100%
Specificity: 99/99 = 100%
Agreement: 207/207 = 100%
Correlation Coefficient: r = 0.9563

As can be seen from Tables 5-7, the AxSYM® Toxo IgG v2 assay using the combination of a genetically engineered antigen P30 antigen (P30del3C, P30del4C, or P30MIX1) with the P35 antigen is both a sensitive and specific assay for the detection of *Toxoplasma*-specific IgG as demonstrated by the overall high relative diagnostic sensitivity (100%), specificity (100%), and agreement (100%). All three AxSYM® Toxo IgG v2 assays were in excellent agreement quantitatively with the AxSYM® Toxo IgG assay, as measured by the correlation coefficients, all of which were 0.95 or greater. The Toxo recombinant antigen cocktail comprised of the genetically engineered Toxo P30 antigen (P30del3C, P30del4C, or P30MIX1) and the P35 antigen, in combination with the AxSYM® Toxo IgG v2 assay, is both necessary and sufficient to replace the tachyzoite for the detection of *Toxoplasma*-specific IgG antibody.

Furthermore, there are several advantages of the recombinant antigen cocktail over the tachyzoite antigen for use in detection of IgG antibodies. First, the antigens are purified, and the amount of each antigen loaded into the immunoassay can be accurately determined and standardized, e.g., protein concentration. This minimizes between lot differences commonly observed in kits manufactured with different tachyzoite antigen lots. Hence, different lots of kits manufactured with different antigen cocktail lots will be very consistent from lot to lot. Secondly, mouse or human monoclonal antibodies to the individual recombinant Toxo antigens are used to monitor coating of the proteins to the solid phase. This further ensures that each lot produced is consistent. Third, the true clinical sensitivity of the assay using the purified antigens will be higher by virtue of the fact of the higher specific activity of the purified antigens. Finally, kits manufactured with the antigen cocktail are more stable during storage over time, and the performance of the assay using these antigens remains consistent over the shelf life of the assay. Kits manufactured with the tachyzoite antigen are not as stable and their performance may vary over time.

Additionally, there are many advantages of using a cocktail over using a single antigen alone. For example, an immune response to infection varies by individual. Some individuals produce antibodies to P35 and not to P30 early in infection (acute toxoplasmosis), whereas some individuals produce antibodies to P30 and not to P35 later in infection (chronic toxoplasmosis). Thus, the antigen cocktail of the present invention will detect both groups of individuals.

Moreover, immune responses vary with time. For example, one individual may produce antibodies against P35 first and then later produce antibodies to only P30. Thus, the present cocktail will detect both types of "positive" individuals.

Furthermore, individuals may be infected with different Toxo serotypes, strains or isolates. Thus, the immune response may be such that multiple antigens are needed to detect the presence of all antibodies being produced. Again, the present cocktail allows for such detection.

Also, it is known from previous Western Blot experiments with tachyzoite proteins that the immune response to *Toxoplasma* is directed against several antigens. Once again, the present antigen cocktail will allow for the detection of all antibodies produced in response to these antigens.

Step E: Evaluation of the AxSYM® Toxo IgM v2 Assays

All specimens in Groups 1-3 were tested by the AxSYM® Toxo IgM v2 assays (P30del3C, P30del4C, and P30MIX1) and by the AxSYM® Toxo IgM assay. A receiver operator characteristic (ROC) was used to assist the determination of the preliminary cutoff for the AxSYM® Toxo IgM v2 assays (Index value≧0.6) (Zweig, H M (1993) Clin. Chem. 39:561-577). In addition, an equivocal zone of Index value 0.500-0.599 was introduced to account for assay imprecision. The performance of the recombinant antigen based AxSYM® Toxo IgM v2 assays was compared to the tachyzoite antigen based AxSYM® Toxo IgM assay and is shown in Tables 8-10.

TABLE 8

Evaluation of the AxSYM ® Toxo IgM v2 P30del3C assay

|  |  | AxSYM ® Toxo IgM | | | |
|---|---|---|---|---|---|
|  |  | POS | EQV | NEG | TOTAL |
| AxSYM ® TOXO | POS | 33 | 2 | 7 | 42 |
| IgM v2 | EQV | 5 | 1 | 3 | 9 |
| P30del3C | NEG | 0 | 2 | 155 | 157 |
|  | TOTAL | 38 | 5 | 165 | 208 |

Sensitivity: 33/33 = 100%
Specificity: 155/162 = 95.7%
Agreement: 188/195 = 96.4%

TABLE 9

Evaluation of the AxSYM ® Toxo IgM v2 P30del4C assay

|  |  | AxSYM ® Toxo IgM | | | |
|---|---|---|---|---|---|
|  |  | POS | EQV | NEG | TOTAL |
| AxSYM ® Toxo | POS | 34 | 2 | 9 | 45 |
| IgM v2 | EQV | 4 | 2 | 2 | 8 |
| P30del4C | NEG | 0 | 1 | 154 | 155 |
|  | TOTAL | 38 | 5 | 165 | 208 |

Sensitivity: 34/34 = 100%
Specificity: 154/163 = 94.5%
Agreement: 188/197 = 95.4%

TABLE 10

Evaluation of the AxSYM ® Toxo IgM v2 P30MIX1 assay

| | | AxSYM ® Toxo IgM | | | |
|---|---|---|---|---|---|
| | | POS | EQV | NEG | TOTAL |
| AxSYM ® Toxo | POS | 35 | 2 | 8 | 45 |
| IgM v2 | EQV | 2 | 0 | 3 | 5 |
| P30MIX1 | NEG | 1 | 3 | 154 | 158 |
| | TOTAL | 38 | 5 | 165 | 208 |

Sensitivity: 35/36 = 97.2%
Specificity: 154/162 = 95.1%
Agreement: 189/198 = 95.5%

As can be seen from Tables 8-10, the AxSYM® Toxo IgM v2 assay using the genetically engineered antigen P30 antigen (P30del3C, P30del4C, or P30MIX1) is both a sensitive and specific assay for the detection of *Toxoplasma*-specific IgG as demonstrated by the overall high relative diagnostic sensitivity (range=97.2%-100%), specificity (range 94.5%-95.7%), and agreement (range=95.4%-96.4%). The genetically engineered Toxo recombinant P30 antigen (P30del3C, P30del4C, or P30MIX1), in combination with the AxSYM® Toxo IgM v2 assay, is both necessary and sufficient to replace the tachyzoite for the detection of *Toxoplasma*-specific IgM antibody.

Furthermore, there are several advantages of the genetically engineered recombinant Toxo P30 antigen over the tachyzoite antigen for use in detection of IgM antibodies. First, the antigen is purified, and the amount of antigen loaded into the immunoassay can be accurately determined and standardized, e.g., protein concentration. This minimizes lot-to-lot differences commonly observed in kits manufactured with different tachyzoite antigen lots. Hence, different lots of kits manufactured with different recombinant antigen lots will be very consistent from lot to lot. Secondly, mouse or human monoclonal antibodies to the recombinant Toxo antigen are used to monitor coating of the proteins to the solid phase. This further ensures that each lot produced is consistent. Third, the true clinical sensitivity of the assay using the purified antigens will be higher by virtue of the fact of the higher specific activity of the purified antigen. Finally, kits manufactured with the recombinant antigen are more stable during storage over time, and the performance of the assay using this antigen remains consistent over the shelf life of the assay. Kits manufactured with the tachyzoite antigen are not as stable and their performance may vary over time.

---

SEQUENCE LISTING

```
<160> NUMBER OF SEQ ID NOS: 74

<210> SEQ ID NO 1
<211> LENGTH: 33
<212> TYPE: DNA
<213> ORGANISM: Artificial Sequence
<220> FEATURE:
<223> OTHER INFORMATION: Sense Primer

<400> SEQUENCE: 1
ggcgaattcc ttgttgccaa tcaagttgtc acc                              33

<210> SEQ ID NO 2
<211> LENGTH: 31
<212> TYPE: DNA
<213> ORGANISM: Artificial Sequence
<220> FEATURE:
<223> OTHER INFORMATION: Antisense Primer

<400> SEQUENCE: 2
cgctgaagct ttcacgcgac acaagctgcg a                                31

<210> SEQ ID NO 3
<211> LENGTH: 7478
<212> TYPE: DNA
<213> ORGANISM: Toxoplasma gondii
<220> FEATURE:
<221> NAME/KEY: CDS
<222> LOCATION: (1528)...(3555)
<223> OTHER INFORMATION: pMBP-c2X-ToxoP30 (52-336aa)

<400> SEQUENCE: 3
ccgacaccat cgaatggtgc aaaacctttc gcggtatggc atgatagcgc ccggaagaga    60
gtcaattcag ggtggtgaat gtgaaaccag taacgttata cgatgtcgca gagtatgccg   120
gtgtctctta tcagaccgtt tcccgcgtgg tgaaccaggc cagccacgtt tctgcgaaaa   180
cgcgggaaaa agtggaagcg gcgatggcgg agctgaatta cattcccaac cgcgtggcac   240
```

-continued

```
aacaactggc gggcaaacag tcgttgctga ttggcgttgc cacctccagt ctggccctgc      300
acgcgccgtc gcaaattgtc gcggcgatta atctcgcgc cgatcaactg ggtgccagcg       360
tggtggtgtc gatggtagaa cgaagcggcg tcgaagcctg taaagcggcg gtgcacaatc      420
ttctcgcgca acgcgtcagt gggctgatca ttaactatcc gctggatgac caggatgcca      480
tgctgtggda agctgcctgc actaatgttc cggcgttatt tcttgatgtc tctgaccaga      540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatggcg ctgggcgcaa     840
tgcgcgccat taccgagtcc gggctgcgcg ttggtgcgga tatctcggta gtgggatacg     900
acgataccga agacagctca tgttatatcc gccgttaac caccatcaaa caggattttc      960
gcctgctggg gcaaaccagc gtggaccgct tgctgcaact ctctcagggc caggcggtga    1020
agggcaatca gctgttgccc gtctcactgg tgaaaagaaa accaccctg gcgcccaata     1080 cgcaaaccgc ctctcccgc gcgttggccg attcattaat gcagctggca cgacaggttt     1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt ccgtttaggt gttttcacga    1500
gcacttcacc aacaaggacc atagcat atg aaa atc gaa gaa ggt aaa ctg gta    1554
                                Met Lys Ile Glu Glu Gly Lys Leu Val
                                 1               5 atc tgg att aac ggc gat aaa ggc tat aac ggt ctc gct gaa gtc ggt      1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg      1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
             45                  50                  55 cct gac att atc ttc tgg gca cac gac cgc ttt ggt ggc tac gct caa      1746
Pro Asp Ile Ile Phe Trp Ala His Asp Arg Phe Gly Gly Tyr Ala Gln
             60                  65                  70 tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
            125                 130                 135
```

```
                                          -continued aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
155                 160                 165 ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
            190                 195                 200 aac aaa cac atg aat gca gac acc gat tac tcc atc gca gaa gct gcc      2178
Asn Lys His Met Asn Ala Asp Thr Asp Tyr Ser Ile Ala Glu Ala Ala
        205                 210                 215 ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
220                 225                 230 tcc aac atc gac acc agc aaa gtg aat tat ggt gta acg gta ctg ccg      2274
Ser Asn Ile Asp Thr Ser Lys Val Asn Tyr Gly Val Thr Val Leu Pro
        235                 240                 245 acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
            270                 275                 280 gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
        285                 290                 295 aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
300                 305                 310 aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
        315                 320                 325 atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
            350                 355                 360 ctg aaa gac gcg cag act aat tcg agc tcg aac aac aac aat aac           2658
Leu Lys Asp Ala Gln Thr Asn Ser Ser Ser Asn Asn Asn Asn Asn
        365                 370                 375 aat aac aac aac ctc ggg atc gag gga agg att tca gaa ttc ctt gtt      2706
Asn Asn Asn Asn Leu Gly Ile Glu Gly Arg Ile Ser Glu Phe Leu Val
            380                 385                 390 gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
        395                 400                 405 att ctc aca ccg acg gag aac cac ttc act ctc aag tgc cct aaa aca      2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
            430                 435                 440 tgc cca gcg ggt act aca agt agc tgt aca tca aag gct gta aca ttg      2898
Cys Pro Ala Gly Thr Thr Ser Ser Cys Thr Ser Lys Ala Val Thr Leu
        445                 450                 455
```

-continued

| | |
|---|---|
| agc tcc ttg att cct gaa gca gaa gat agc tgg tgg acg ggg gat tct<br>Ser Ser Leu Ile Pro Glu Ala Glu Asp Ser Trp Trp Thr Gly Asp Ser<br>460                                465                          470 | 2946 |
| gct agt ctc gac acg gca ggc atc aaa ctc acg gtt cca atc gag aag<br>Ala Ser Leu Asp Thr Ala Gly Ile Lys Leu Thr Val Pro Ile Glu Lys<br>        475                          480                          485 | 2994 |
| ttc ccc gtg aca acg cag acg ttt gtg gtc ggt tgc atc aag gga gac<br>Phe Pro Val Thr Thr Gln Thr Phe Val Val Gly Cys Ile Lys Gly Asp<br>490                                495                          500                505 | 3042 |
| gac gca cag agt tgt atg gtc aca gtg aca gta caa gcc aga gcc tca<br>Asp Ala Gln Ser Cys Met Val Thr Val Thr Val Gln Ala Arg Ala Ser<br>                          510                          515                        520 | 3090 |
| tcg gtc gtc aat aat gtc gca agg tgc tcc tac ggt gca gac agc act<br>Ser Val Val Asn Asn Val Ala Arg Cys Ser Tyr Gly Ala Asp Ser Thr<br>        525                          530                          535 | 3138 |
| ctt ggt cct gtc aag ttg tct gcg gaa gga ccc act aca atg acc ctc<br>Leu Gly Pro Val Lys Leu Ser Ala Glu Gly Pro Thr Thr Met Thr Leu<br>540                                545                          550 | 3186 |
| gtg tgc ggg aaa gat gga gtc aaa gtt cct caa gac aac aat cag tac<br>Val Cys Gly Lys Asp Gly Val Lys Val Pro Gln Asp Asn Asn Gln Tyr<br>        555                          560                          565 | 3234 |
| tgt tcc ggg acg acg ctg act ggt tgc aac gag aaa tcg ttc aaa gat<br>Cys Ser Gly Thr Thr Leu Thr Gly Cys Asn Glu Lys Ser Phe Lys Asp<br>570                                575                          580                585 | 3282 |
| att ttg cca aaa tta act gag aac ccg tgg cag ggt aac gct tcg agt<br>Ile Leu Pro Lys Leu Thr Glu Asn Pro Trp Gln Gly Asn Ala Ser Ser<br>                          590                          595                        600 | 3330 |
| gat aag ggt gcc acg cta acg atc aag aag gaa gca ttt cca gcc gag<br>Asp Lys Gly Ala Thr Leu Thr Ile Lys Lys Glu Ala Phe Pro Ala Glu<br>                    605                          610                        615 | 3378 |
| tca aaa agc gtc att att gga tgc aca ggg gga tcg cct gag aag cat<br>Ser Lys Ser Val Ile Ile Gly Cys Thr Gly Gly Ser Pro Glu Lys His<br>        620                          625                          630 | 3426 |
| cac tgt acc gtg aaa ctg gag ttt gcc ggg gct gca ggg tca gca aaa<br>His Cys Thr Val Lys Leu Glu Phe Ala Gly Ala Ala Gly Ser Ala Lys<br>                635                          640                        645 | 3474 |
| tcg gct gcg gga aca gcc agt cac gtt tcc att ttt gcc atg gtg atc<br>Ser Ala Ala Gly Thr Ala Ser His Val Ser Ile Phe Ala Met Val Ile<br>650                                655                          660                665 | 3522 |
| gga ctt att ggc tct atc gca gct tgt gtc gcg tgaaagcttg gcactggccg<br>Gly Leu Ile Gly Ser Ile Ala Ala Cys Val Ala<br>                    670                          675 | 3575 |
| tcgttttaca acgtcgtgac tgggaaaacc ctggcgttac ccaacttaat cgccttgcag | 3635 |
| cacatccccc tttcgccagc tggcgtaata gcgaagaggc ccgcaccgat cgccttccc | 3695 |
| aacagttgcg cagcctgaat ggcgaatggc agcttggctg ttttggcgga tgagataaga | 3755 |
| ttttcagcct gatacagatt aaatcagaac gcagaagcgg tctgataaaa cagaatttgc | 3815 |
| ctggcggcag tagcgcggtg gtcccacctg accccatgcc gaactcagaa gtgaaacgcc | 3875 |
| gtagcgccga tggtagtgtg gggtctcccc atgcgagagt agggaactgc caggcatcaa | 3935 |
| ataaaacgaa aggctcagtc gaaagactgg gcctttcgtt ttatctgttg tttgtcggtg | 3995 |
| aacgctctcc tgagtaggac aaatccgccg ggagcggatt tgaacgttgc gaagcaacgg | 4055 |
| cccggagggt ggcgggcagg acgcccgcca taaactgcca ggcatcaaat taagcagaag | 4115 |
| gccatcctga cggatggcct ttttgcgttt ctacaaactc ttttttgttta ttttttctaaa | 4175 |
| tacattcaaa tatgtatccg ctcatgagac aataaccctg ataaatgctt caataatatt | 4235 |

```
gaaaaaggaa gagtatgagt attcaacatt tccgtgtcgc ccttattccc ttttttgcgg   4295
cattttgcct tcctgttttt gctcacccag aaacgctggt gaaagtaaaa gatgctgaag   4355
atcagttggg tgcacgagtg ggttacatcg aactggatct caacagcggt aagatccttg   4415
agagttttcg ccccgaagaa cgttctccaa tgatgagcac ttttaaagtt ctgctatgtg   4475
gcgcggtatt atcccgtgtt gacgccgggc aagagcaact cggtcgccgc atacactatt   4535
ctcagaatga cttggttgag tactcaccag tcacagaaaa gcatcttacg gatggcatga   4595
cagtaagaga attatgcagt gctgccataa ccatgagtga taacactgcg gccaacttac   4655
ttctgacaac gatcggagga ccgaaggagc taaccgcttt tttgcacaac atgggggatc   4715
atgtaactcg ccttgatcgt tgggaaccgg agctgaatga agccatacca aacgacgagc   4775
gtgacaccac gatgcctgta gcaatggcaa caacgttgcg caaactatta actggcgaac   4835
tacttactct agcttcccgg caacaattaa tagactggat ggaggcggat aaagttgcag   4895
gaccacttct gcgctcggcc cttccggctg gctggtttat tgctgataaa tctggagccg   4955
gtgagcgtgg gtctcgcggt atcattgcag cactggggcc agatggtaag ccctcccgta   5015
tcgtagttat ctacacgacg gggagtcagg caactatgga tgaacgaaat agacagatcg   5075
ctgagatagg tgcctcactg attaagcatt ggtaactgtc agaccaagtt tactcatata   5135
tactttagat tgatttaccc cggttgataa tcagaaaagc cccaaaaaca ggaagattgt   5195
ataagcaaat atttaaattg taaacgttaa tattttgtta aaattcgcgt taaattttg    5255 ttaaatcagc tcattttttta accaataggc cgaaatcggc aaaatccctt ataaatcaaa   5315
agaatagacc gagatagggt tgagtgttgt tccagtttgg aacaagagtc cactattaaa   5375
gaacgtggac tccaacgtca aagggcgaaa aaccgtctat cagggcgatg gcccactacg   5435
tgaaccatca cccaaatcaa gttttttggg gtcgaggtgc cgtaaagcac taaatcggaa   5495
ccctaaaggg agccccgat ttagagcttg acggggaaag ccggcgaacg tggcgagaaa    5555
ggaagggaag aaagcgaaag gagcgggcgc tagggcgctg gcaagtgtag cggtcacgct   5615
gcgcgtaacc accacacccg ccgcgcttaa tgcgccgcta cagggcgcgt aaaaggatct   5675
aggtgaagat cctttttgat aatctcatga ccaaaatccc ttaacgtgag ttttcgttcc   5735
actgagcgtc agaccccgta gaaaagatca aaggatcttc ttgagatcct ttttttctgc   5795
gcgtaatctg ctgcttgcaa acaaaaaaac caccgctacc agcggtggtt tgtttgccgg   5855
atcaagagct accaactctt tttccgaagg taactggctt cagcagagcg cagataccaa   5915
atactgtcct tctagtgtag ccgtagttag gccaccactt caagaactct gtagcaccgc   5975
ctacatacct cgctctgcta atcctgttac cagtggctgc tgccagtggc gataagtcgt   6035
gtcttaccgg gttggactca agacgatagt taccggataa ggcgcagcgg tcgggctgaa   6095
cggggggttc gtgcacacag cccagcttgg agcgaacgac ctacaccgaa ctgagatacc   6155
tacagcgtga gctatgagaa agcgccacgc ttcccgaagg gagaaaggcg gacaggtatc   6215
cggtaagcgg cagggtcgga acaggagagc gcacgaggga gcttccaggg ggaaacgcct   6275
ggtatcttta tagtcctgtc gggtttcgcc acctctgact tgagcgtcga ttttgtgat    6335 gctcgtcagg ggggcggagc ctatggaaaa acgccagcaa cgcggccttt ttacggttcc   6395
tggccttttg ctggcctttt gctcacatgt tctttcctgc gttatcccct gattctgtgg   6455
ataaccgtat taccgccttt gagtgagctg ataccgctcg ccgcagccga acgaccgagc   6515
gcagcgagtc agtgagcgag gaagcggaag agcgcctgat gcggtatttt ctccttacgc   6575
atctgtgcgg tatttcacac cgcatatatg gtgcactctc agtacaatct gctctgatgc   6635
```

```
cgcatagtta agccagtata cactccgcta tcgctacgtg actgggtcat ggctgcgccc    6695
cgacacccgc caacacccgc tgacgcgccc tgacgggctt gtctgctccc ggcatccgct    6755
tacagacaag ctgtgaccgt ctccgggagc tgcatgtgtc agaggttttc accgtcatca    6815
ccgaaacgcg cgaggcagct gcggtaaagc tcatcagcgt ggtcgtgcag cgattcacag    6875
atgtctgcct gttcatccgc gtccagctcg ttgagtttct ccagaagcgt taatgtctgg    6935
cttctgataa agcgggccat gttaagggcg ttttttcct gtttggtcac tgatgcctcc    6995
gtgtaagggg gatttctgtt catggggta atgataccga tgaaacgaga gggatgctc     7055 acgatacggg ttactgatga tgaacatgcc cggttactgg aacgttgtga gggtaaacaa    7115
ctggcggtat ggatgcggcg ggaccagaga aaaatcactc agggtcaatg ccagcgcttc    7175
gttaatacag atgtaggtgt tccacagggt agccagcagc atcctgcgat gcagatccgg    7235
aacataatgg tgcagggcgc tgacttccgc gtttccagac tttacgaaac acggaaaccg    7295
aagaccattc atgttgttgc tcaggtcgca gacgttttgc agcagcagtc gcttcacgtt    7355
cgctcgcgta tcggtgattc attctgctaa ccagtaaggc aaccccgcca gcctagccgg    7415
gtcctcaacg acaggagcac gatcatgcgc acccgtggcc aggacccaac gctgcccgaa    7475
att                                                                 7478

<210> SEQ ID NO 4
<211> LENGTH: 676
<212> TYPE: PRT
<213> ORGANISM: Toxoplasma gondii
<220> FEATURE:
<223> OTHER INFORMATION: pMBP-c2X-ToxoP30 (52-336aa)

<400> SEQUENCE: 4

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
     50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205
```

-continued

```
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
                260                 265                 270
Asn Lys Glu Leu Ala Lys Glu Phe Leu Glu Asn Tyr Leu Leu Thr Asp
            275                 280                 285
Glu Gly Leu Glu Ala Val Asn Lys Asp Lys Pro Leu Gly Ala Val Ala
        290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
                340                 345                 350
Ser Gly Arg Gln Thr Val Asp Glu Ala Leu Lys Asp Ala Gln Thr Asn
            355                 360                 365
Ser Ser Ser Asn Asn Asn Asn Asn Asn Asn Asn Asn Leu Gly Ile
        370                 375                 380
Glu Gly Arg Ile Ser Glu Phe Leu Val Ala Asn Gln Val Val Thr Cys
385                 390                 395                 400
Pro Asp Lys Lys Ser Thr Ala Ala Val Ile Leu Thr Pro Thr Glu Asn
                405                 410                 415
His Phe Thr Leu Lys Cys Pro Lys Thr Ala Leu Thr Glu Pro Pro Thr
                420                 425                 430
Leu Ala Tyr Ser Pro Asn Arg Gln Ile Cys Pro Ala Gly Thr Thr Ser
            435                 440                 445
Ser Cys Thr Ser Lys Ala Val Thr Leu Ser Ser Leu Ile Pro Glu Ala
        450                 455                 460
Glu Asp Ser Trp Trp Thr Gly Asp Ser Ala Ser Leu Asp Thr Ala Gly
465                 470                 475                 480
Ile Lys Leu Thr Val Pro Ile Glu Lys Phe Pro Val Thr Thr Gln Thr
                485                 490                 495
Phe Val Val Gly Cys Ile Lys Gly Asp Asp Ala Gln Ser Cys Met Val
                500                 505                 510
Thr Val Thr Val Gln Ala Arg Ala Ser Ser Val Val Asn Asn Val Ala
            515                 520                 525
Arg Cys Ser Tyr Gly Ala Asp Ser Thr Leu Gly Pro Val Lys Leu Ser
        530                 535                 540
Ala Glu Gly Pro Thr Thr Met Thr Leu Val Cys Gly Lys Asp Gly Val
545                 550                 555                 560
Lys Val Pro Gln Asp Asn Asn Gln Tyr Cys Ser Gly Thr Thr Leu Thr
                565                 570                 575
Gly Cys Asn Glu Lys Ser Phe Lys Asp Ile Leu Pro Lys Leu Thr Glu
            580                 585                 590
Asn Pro Trp Gln Gly Asn Ala Ser Ser Asp Lys Gly Thr Leu Thr
        595                 600                 605
Ile Lys Lys Glu Ala Phe Pro Ala Glu Ser Lys Ser Val Ile Ile Gly
610                 615                 620
```

```
Cys Thr Gly Gly Ser Pro Glu Lys His His Cys Thr Val Lys Leu Glu
625                 630                 635                 640

Phe Ala Gly Ala Ala Gly Ser Ala Lys Ser Ala Ala Gly Thr Ala Ser
                645                 650                 655

His Val Ser Ile Phe Ala Met Val Ile Gly Leu Ile Gly Ser Ile Ala
                660                 665                 670

Ala Cys Val Ala
        675

<210> SEQ ID NO 5
<211> LENGTH: 855
<212> TYPE: DNA
<213> ORGANISM: Toxoplasma gondii
<220> FEATURE:
<221> NAME/KEY: CDS
<222> LOCATION: (1)...(855)
<223> OTHER INFORMATION: ToxoP30 (52-336aa)

<400> SEQUENCE: 5 ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
1               5                   10                  15 gcg gtc att ctc aca ccg acg gag aac cac ttc act ctc aag tgc cct      96
Ala Val Ile Leu Thr Pro Thr Glu Asn His Phe Thr Leu Lys Cys Pro
                20                  25                  30 aaa aca gcg ctc aca gag cct ccc act ctt gcg tac tca ccc aac agg     144
Lys Thr Ala Leu Thr Glu Pro Pro Thr Leu Ala Tyr Ser Pro Asn Arg
            35                  40                  45 caa atc tgc cca gcg ggt act aca agt agc tgt aca tca aag gct gta     192
Gln Ile Cys Pro Ala Gly Thr Thr Ser Ser Cys Thr Ser Lys Ala Val
        50                  55                  60 aca ttg agc tcc ttg att cct gaa gca gaa gat agc tgg tgg acg ggg     240
Thr Leu Ser Ser Leu Ile Pro Glu Ala Glu Asp Ser Trp Trp Thr Gly
65                  70                  75                  80 gat tct gct agt ctc gac acg gca ggc atc aaa ctc acg gtt cca atc     288
Asp Ser Ala Ser Leu Asp Thr Ala Gly Ile Lys Leu Thr Val Pro Ile
                85                  90                  95 gag aag ttc ccc gtg aca acg cag acg ttt gtg gtc ggt tgc atc aag     336
Glu Lys Phe Pro Val Thr Thr Gln Thr Phe Val Val Gly Cys Ile Lys
                100                 105                 110 gga gac gac gca cag agt tgt atg gtc aca gtg aca gta caa gcc aga     384
Gly Asp Asp Ala Gln Ser Cys Met Val Thr Val Thr Val Gln Ala Arg
            115                 120                 125 gcc tca tcg gtc gtc aat aat gtc gca agg tgc tcc tac ggt gca gac     432
Ala Ser Ser Val Val Asn Asn Val Ala Arg Cys Ser Tyr Gly Ala Asp
        130                 135                 140 agc act ctt ggt cct gtc aag ttg tct gcg gaa gga ccc act aca atg     480
Ser Thr Leu Gly Pro Val Lys Leu Ser Ala Glu Gly Pro Thr Thr Met
145                 150                 155                 160 acc ctc gtg tgc ggg aaa gat gga gtc aaa gtt cct caa gac aac aat     528
Thr Leu Val Cys Gly Lys Asp Gly Val Lys Val Pro Gln Asp Asn Asn
                165                 170                 175 cag tac tgt tcc ggg acg acg ctg act ggt tgc aac gag aaa tcg ttc     576
Gln Tyr Cys Ser Gly Thr Thr Leu Thr Gly Cys Asn Glu Lys Ser Phe
                180                 185                 190 aaa gat att ttg cca aaa tta act gag aac ccg tgg cag ggt aac gct     624
Lys Asp Ile Leu Pro Lys Leu Thr Glu Asn Pro Trp Gln Gly Asn Ala
            195                 200                 205 tcg agt gat aag ggt gcc acg cta acg atc aag aag gaa gca ttt cca     672
Ser Ser Asp Lys Gly Ala Thr Leu Thr Ile Lys Lys Glu Ala Phe Pro
        210                 215                 220
```

-continued

```
gcc gag tca aaa agc gtc att att gga tgc aca ggg gga tcg cct gag    720
Ala Glu Ser Lys Ser Val Ile Ile Gly Cys Thr Gly Gly Ser Pro Glu
225                 230                 235                 240 aag cat cac tgt acc gtg aaa ctg gag ttt gcc ggg gct gca ggg tca    768
Lys His His Cys Thr Val Lys Leu Glu Phe Ala Gly Ala Ala Gly Ser
            245                 250                 255 gca aaa tcg gct gcg gga aca gcc agt cac gtt tcc att ttt gcc atg    816
Ala Lys Ser Ala Ala Gly Thr Ala Ser His Val Ser Ile Phe Ala Met
        260                 265                 270 gtg atc gga ctt att ggc tct atc gca gct tgt gtc gcg                855
Val Ile Gly Leu Ile Gly Ser Ile Ala Ala Cys Val Ala
    275                 280                 285
```

<210> SEQ ID NO 6
<211> LENGTH: 285
<212> TYPE: PRT
<213> ORGANISM: Toxoplasma gondii
<220> FEATURE:
<223> OTHER INFORMATION: ToxoP30 (52-336aa)

<400> SEQUENCE: 6

```
Leu Val Ala Asn Gln Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Cys Thr Gly Gly Ser Pro Glu
225                 230                 235                 240

Lys His His Cys Thr Val Lys Leu Glu Phe Ala Gly Ala Ala Gly Ser
                245                 250                 255

Ala Lys Ser Ala Ala Gly Thr Ala Ser His Val Ser Ile Phe Ala Met
            260                 265                 270

Val Ile Gly Leu Ile Gly Ser Ile Ala Ala Cys Val Ala
```

-continued

```
        275                 280                 285

<210> SEQ ID NO 7
<211> LENGTH: 7553
<212> TYPE: DNA
<213> ORGANISM: Toxoplasma gondii
<220> FEATURE:
<221> NAME/KEY: CDS
<222> LOCATION: (1528)...(3630)
<223> OTHER INFORMATION: pMBP-p2X-ToxoP30 (52-336aa)

<400> SEQUENCE: 7
ccgacaccat cgaatggtgc aaaacctttc gcggtatggc atgatagcgc ccggaagaga     60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta aatctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa aaccaccctg gcgcccaata   1080
cgcaaaccgc ctctccccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgtttttt gcgccgacat cataacggtt   1380
ctggcaaata ttctgaaatg agctgttgac aattaatcat cggctcgtat aatgtgtgga   1440
attgtgagcg gataacaatt tcacacagga aacagccagt ccgtttaggt gttttcacga   1500
gcacttcacc aacaaggacc atagcat atg aaa ata aaa aca ggt gca cgc atc   1554
                              Met Lys Ile Lys Thr Gly Ala Arg Ile
                               1               5 ctc gca tta tcc gca tta acg acg atg atg ttt tcc gcc tcg gct ctc     1602
Leu Ala Leu Ser Ala Leu Thr Thr Met Met Phe Ser Ala Ser Ala Leu
 10                  15                  20                  25 gcc aaa atc gaa gaa ggt aaa ctg gta atc tgg att aac ggc gat aaa     1650
Ala Lys Ile Glu Glu Gly Lys Leu Val Ile Trp Ile Asn Gly Asp Lys
                 30                  35                  40 ggc tat aac ggt ctc gct gaa gtc ggt aag aaa ttc gag aaa gat acc     1698
Gly Tyr Asn Gly Leu Ala Glu Val Gly Lys Lys Phe Glu Lys Asp Thr
             45                  50                  55
```

-continued

| | |
|---|---|
| gga att aaa gtc acc gtt gag cat ccg gat aaa ctg gaa gag aaa ttc<br>Gly Ile Lys Val Thr Val Glu His Pro Asp Lys Leu Glu Glu Lys Phe<br>        60                        65                        70 | 1746 |
| cca cag gtt gcg gca act ggc gat ggc cct gac att atc ttc tgg gca<br>Pro Gln Val Ala Ala Thr Gly Asp Gly Pro Asp Ile Ile Phe Trp Ala<br>        75                        80                        85 | 1794 |
| cac gac cgc ttt ggt ggc tac gct caa tct ggc ctg ttg gct gaa atc<br>His Asp Arg Phe Gly Gly Tyr Ala Gln Ser Gly Leu Leu Ala Glu Ile<br>        90                        95                     100            105 | 1842 |
| acc ccg gac aaa gcg ttc cag gac aag ctg tat ccg ttt acc tgg gat<br>Thr Pro Asp Lys Ala Phe Gln Asp Lys Leu Tyr Pro Phe Thr Trp Asp<br>                  110                        115                     120 | 1890 |
| gcc gta cgt tac aac ggc aag ctg att gct tac ccg atc gct gtt gaa<br>Ala Val Arg Tyr Asn Gly Lys Leu Ile Ala Tyr Pro Ile Ala Val Glu<br>                  125                        130                     135 | 1938 |
| gcg tta tcg ctg att tat aac aaa gat ctg ctg ccg aac ccg cca aaa<br>Ala Leu Ser Leu Ile Tyr Asn Lys Asp Leu Leu Pro Asn Pro Pro Lys<br>              140                        145                     150 | 1986 |
| acc tgg gaa gag atc ccg gcg ctg gat aaa gaa ctg aaa gcg aaa ggt<br>Thr Trp Glu Glu Ile Pro Ala Leu Asp Lys Glu Leu Lys Ala Lys Gly<br>    155                        160                     165 | 2034 |
| aag agc gcg ctg atg ttc aac ctg caa gaa ccg tac ttc acc tgg ccg<br>Lys Ser Ala Leu Met Phe Asn Leu Gln Glu Pro Tyr Phe Thr Trp Pro<br>170                     175                        180                     185 | 2082 |
| ctg att gct gct gac ggg ggt tat gcg ttc aag tat gaa aac ggc aag<br>Leu Ile Ala Ala Asp Gly Gly Tyr Ala Phe Lys Tyr Glu Asn Gly Lys<br>                  190                        195                     200 | 2130 |
| tac gac att aaa gac gtg ggc gtg gat aac gct ggc gcg aaa gcg ggt<br>Tyr Asp Ile Lys Asp Val Gly Val Asp Asn Ala Gly Ala Lys Ala Gly<br>                  205                        210                     215 | 2178 |
| ctg acc ttc ctg gtt gac ctg att aaa aac aaa cac atg aat gca gac<br>Leu Thr Phe Leu Val Asp Leu Ile Lys Asn Lys His Met Asn Ala Asp<br>              220                        225                     230 | 2226 |
| acc gat tac tcc atc gca gaa gct gcc ttt aat aaa ggc gaa aca gcg<br>Thr Asp Tyr Ser Ile Ala Glu Ala Ala Phe Asn Lys Gly Glu Thr Ala<br>              235                        240                     245 | 2274 |
| atg acc atc aac ggc ccg tgg gca tgg tcc aac atc gac acc agc aaa<br>Met Thr Ile Asn Gly Pro Trp Ala Trp Ser Asn Ile Asp Thr Ser Lys<br>250                     255                        260                     265 | 2322 |
| gtg aat tat ggt gta acg gta ctg ccg acc ttc aag ggt caa cca tcc<br>Val Asn Tyr Gly Val Thr Val Leu Pro Thr Phe Lys Gly Gln Pro Ser<br>                  270                        275                     280 | 2370 |
| aaa ccg ttc gtt ggc gtg ctg agc gca ggt att aac gcc gcc agt ccg<br>Lys Pro Phe Val Gly Val Leu Ser Ala Gly Ile Asn Ala Ala Ser Pro<br>              285                        290                     295 | 2418 |
| aac aaa gag ctg gca aaa gag ttc ctc gaa aac tat ctg ctg act gat<br>Asn Lys Glu Leu Ala Lys Glu Phe Leu Glu Asn Tyr Leu Leu Thr Asp<br>              300                        305                     310 | 2466 |
| gaa ggt ctg gaa gcg gtt aat aaa gac aaa ccg ctg ggt gcc gta gcg<br>Glu Gly Leu Glu Ala Val Asn Lys Asp Lys Pro Leu Gly Ala Val Ala<br>    315                        320                     325 | 2514 |
| ctg aag tct tac gag gaa gag ttg gcg aaa gat cca cgt att gcc gcc<br>Leu Lys Ser Tyr Glu Glu Glu Leu Ala Lys Asp Pro Arg Ile Ala Ala<br>330                     335                        340                     345 | 2562 |
| act atg gaa aac gcc cag aaa ggt gaa atc atg ccg aac atc ccg cag<br>Thr Met Glu Asn Ala Gln Lys Gly Glu Ile Met Pro Asn Ile Pro Gln<br>              350                        355                     360 | 2610 |
| atg tcc gct ttc tgg tat gcc gtg cgt act gcg gtg atc aac gcc gcc<br>Met Ser Ala Phe Trp Tyr Ala Val Arg Thr Ala Val Ile Asn Ala Ala | 2658 |

|       |       |       |       |       |       | 365   |       |       |       |       |       | 370   |       |       |       |       |       | 375   |       |       |      |
|-------|-------|-------|-------|-------|-------|-------|-------|-------|-------|-------|-------|-------|-------|-------|-------|-------|-------|-------|-------|-------|------|

```
agc ggt cgt cag act gtc gat gaa gcc ctg aaa gac gcg cag act aat        2706
Ser Gly Arg Gln Thr Val Asp Glu Ala Leu Lys Asp Ala Gln Thr Asn
        380                 385                 390 tcg agc tcg aac aac aac aat aac aat aac aac ctc ggg atc                2754
Ser Ser Ser Asn Asn Asn Asn Asn Asn Asn Asn Leu Gly Ile
    395                 400                 405 gag gga agg att tca gaa ttc ctt gtt gcc aat caa gtt gtc acc tgc        2802
Glu Gly Arg Ile Ser Glu Phe Leu Val Ala Asn Gln Val Val Thr Cys
410                 415                 420                 425 cca gat aaa aaa tcg aca gcc gcg gtc att ctc aca ccg acg gag aac        2850
Pro Asp Lys Lys Ser Thr Ala Ala Val Ile Leu Thr Pro Thr Glu Asn
                430                 435                 440 cac ttc act ctc aag tgc cct aaa aca gcg ctc aca gag cct ccc act        2898
His Phe Thr Leu Lys Cys Pro Lys Thr Ala Leu Thr Glu Pro Pro Thr
            445                 450                 455 ctt gcg tac tca ccc aac agg caa atc tgc cca gcg ggt act aca agt        2946
Leu Ala Tyr Ser Pro Asn Arg Gln Ile Cys Pro Ala Gly Thr Thr Ser
        460                 465                 470 agc tgt aca tca aag gct gta aca ttg agc tcc ttg att cct gaa gca        2994
Ser Cys Thr Ser Lys Ala Val Thr Leu Ser Ser Leu Ile Pro Glu Ala
    475                 480                 485 gaa gat agc tgg tgg acg ggg gat tct gct agt ctc gac acg gca ggc        3042
Glu Asp Ser Trp Trp Thr Gly Asp Ser Ala Ser Leu Asp Thr Ala Gly
490                 495                 500                 505 atc aaa ctc aca gtt cca atc gag aag ttc ccc gtg aca acg cag acg        3090
Ile Lys Leu Thr Val Pro Ile Glu Lys Phe Pro Val Thr Thr Gln Thr
                510                 515                 520 ttt gtg gtc ggt tgc atc aag gga gac gac gca cag agt tgt atg gtc        3138
Phe Val Val Gly Cys Ile Lys Gly Asp Asp Ala Gln Ser Cys Met Val
            525                 530                 535 aca gtg aca gta caa gcc aga gcc tca tcg gtc gtc aat aat gtc gca        3186
Thr Val Thr Val Gln Ala Arg Ala Ser Ser Val Val Asn Asn Val Ala
        540                 545                 550 agg tgc tcc tac ggt gca gac agc act ctt ggt cct gtc aag ttg tct        3234
Arg Cys Ser Tyr Gly Ala Asp Ser Thr Leu Gly Pro Val Lys Leu Ser
    555                 560                 565 gcg gaa gga ccc act aca atg acc ctc gtg tgc ggg aaa gat gga gtc        3282
Ala Glu Gly Pro Thr Thr Met Thr Leu Val Cys Gly Lys Asp Gly Val
570                 575                 580                 585 aaa gtt cct caa gac aac aat cag tac tgt tcc ggg acg acg ctg act        3330
Lys Val Pro Gln Asp Asn Asn Gln Tyr Cys Ser Gly Thr Thr Leu Thr
                590                 595                 600 ggt tgc aac gag aaa tcg ttc aaa gat att ttg cca aaa tta act gag        3378
Gly Cys Asn Glu Lys Ser Phe Lys Asp Ile Leu Pro Lys Leu Thr Glu
            605                 610                 615 aac ccg tgg cag ggt aac gct tcg agt gat aag ggt gcc acg cta acg        3426
Asn Pro Trp Gln Gly Asn Ala Ser Ser Asp Lys Gly Ala Thr Leu Thr
        620                 625                 630 atc aag aag gaa gca ttt cca gcc gag tca aaa agc gtc att att gga        3474
Ile Lys Lys Glu Ala Phe Pro Ala Glu Ser Lys Ser Val Ile Ile Gly
    635                 640                 645 tgc aca ggg gga tcg cct gag aag cat cac tgt acc gtg aaa ctg gag        3522
Cys Thr Gly Gly Ser Pro Glu Lys His His Cys Thr Val Lys Leu Glu
650                 655                 660                 665 ttt gcc ggg gct gca ggg tca gca aaa tcg gct gcg gga aca gcc agt        3570
Phe Ala Gly Ala Ala Gly Ser Ala Lys Ser Ala Ala Gly Thr Ala Ser
                670                 675                 680 cac gtt tcc att ttt gcc atg gtg atc gga ctt att ggc tct atc gca        3618
His Val Ser Ile Phe Ala Met Val Ile Gly Leu Ile Gly Ser Ile Ala
```

```
His Val Ser Ile Phe Ala Met Val Ile Gly Leu Ile Gly Ser Ile Ala
            685                 690                 695 gct tgt gtc gcg tgaaagcttg gcactggccg tcgttttaca acgtcgtgac           3670
Ala Cys Val Ala
        700 tgggaaaacc ctggcgttac ccaacttaat cgccttgcag cacatccccc tttcgccagc    3730 tggcgtaata gcgaagaggc ccgcaccgat cgcccttccc aacagttgcg cagcctgaat    3790 ggcgaatggc agcttggctg ttttggcgga tgagataaga ttttcagcct gatacagatt    3850 aaatcagaac gcagaagcgg tctgataaaa cagaatttgc ctggcggcag tagcgcggtg    3910 gtcccacctg accccatgcc gaactcagaa gtgaaacgcc gtagcgccga tggtagtgtg    3970 gggtctcccc atgcgagagt agggaactgc caggcatcaa ataaaacgaa aggctcagtc    4030 gaaagactgg gcctttcgtt ttatctgttg tttgtcggtg aacgctctcc tgagtaggac    4090 aaatccgccg ggagcggatt tgaacgttgc gaagcaacgg cccggagggt ggcgggcagg    4150 acgcccgcca taaactgcca ggcatcaaat taagcagaag gccatcctga cggatggcct    4210 ttttgcgttt ctacaaactc ttttttgttta tttttctaaa tacattcaaa tatgtatccg    4270 ctcatgagac aataaccctg ataaatgctt caataatatt gaaaaggaa gagtatgagt     4330 attcaacatt ccgtgtcgc ccttattccc tttttttgcgg cattttgcct tcctgttttt    4390 gctcacccag aaacgctggt gaaagtaaaa gatgctgaag atcagttggg tgcacgagtg    4450 ggttacatcg aactggatct caacagcggt aagatccttg agagttttcg ccccgaagaa    4510 cgttctccaa tgatgagcac ttttaaagtt ctgctatgtg gcgcggtatt atcccgtgtt    4570 gacgccgggc aagagcaact cggtcgccgc atacactatt ctcagaatga cttggttgag    4630 tactcaccag tcacagaaaa gcatcttacg gatggcatga cagtaagaga attatgcagt    4690 gctgccataa ccatgagtga taacactgcg ccaacttac ttctgacaac gatcggagga    4750 ccgaaggagc taaccgcttt tttgcacaac atggggatc atgtaactcg ccttgatcgt     4810 tgggaaccgg agctgaatga agccatacca aacgacgagc gtgacaccac gatgcctgta    4870 gcaatggcaa caacgttgcg caaactatta actggcgaac tacttactct agcttcccgg    4930 caacaattaa tagactggat ggaggcggat aaagttgcag gaccacttct gcgctcggcc    4990 cttccggctg gctggtttat tgctgataaa tctggagccg gtgagcgtgg gtctcgcggt    5050 atcattgcag cactggggcc agatggtaag ccctcccgta tcgtagttat ctacacgacg    5110 gggagtcagg caactatgga tgaacgaaat agacagatcg ctgagatagg tgcctcactg    5170 attaagcatt ggtaactgtc agaccaagtt tactcatata ctttagat tgatttaccc      5230 cggttgataa tcagaaaagc cccaaaaaca ggaagattgt ataagcaaat atttaaattg    5290 taaacgttaa tattttgtta aaattcgcgt taaattttg ttaaatcagc tcattttta      5350 accaataggc cgaaatcggc aaaatcccct taaatcaaa agaatagacc gagatagggt     5410 tgagtgttgt tccagtttgg aacaagagtc cactattaaa gaacgtggac tccaacgtca    5470 aagggcgaaa aaccgtctat cagggcgatg gcccactacg tgaaccatca cccaaatcaa    5530 gttttttggg gtcgaggtgc cgtaaagcac taaatcggaa ccctaaaggg agcccccgat    5590 ttagagcttg acggggaaag ccggcgaacg tggcgagaaa ggaagggaag aaagcgaaag    5650 gagcgggcgc tagggcgctg gcaagtgtag cggtcacgct gcgcgtaacc accacacccg    5710 ccgcgcttaa tgcgccgcta cagggcgcgt aaaaggatct aggtgaagat ccttttgat    5770 aatctcatga ccaaaatccc ttaacgtgag ttttcgttcc actgagcgtc agaccccgta    5830
```

-continued

```
gaaaagatca aaggatcttc ttgagatcct tttttctgc gcgtaatctg ctgcttgcaa    5890
acaaaaaaac caccgctacc agcggtggtt tgtttgccgg atcaagagct accaactctt    5950
tttccgaagg taactggctt cagcagagcg cagataccaa atactgtcct tctagtgtag    6010
ccgtagttag gccaccactt caagaactct gtagcaccgc ctacatacct cgctctgcta    6070
atcctgttac cagtggctgc tgccagtggc gataagtcgt gtcttaccgg gttggactca    6130
agacgatagt taccggataa ggcgcagcgg tcgggctgaa cggggggttc gtgcacacag    6190
cccagcttgg agcgaacgac ctacaccgaa ctgagatacc tacagcgtga gctatgagaa    6250
agcgccacgc ttcccgaagg gagaaaggcg gacaggtatc cggtaagcgg cagggtcgga    6310
acaggagagc gcacgaggga gcttccaggg ggaaacgcct ggtatcttta tagtcctgtc    6370
gggtttcgcc acctctgact tgagcgtcga ttttgtgat gctcgtcagg ggggcggagc    6430
ctatggaaaa acgccagcaa cgcggccttt ttacggttcc tggccttttg ctggcctttt    6490
gctcacatgt tctttcctgc gttatcccct gattctgtgg ataaccgtat taccgccttt    6550
gagtgagctg ataccgctcg ccgcagccga acgaccgagc gcagcgagtc agtgagcgag    6610
gaagcggaag agcgcctgat gcggtatttt ctccttacgc atctgtgcgg tatttcacac    6670
cgcatatatg gtgcactctc agtacaatct gctctgatgc cgcatagtta agccagtata    6730
cactccgcta tcgctacgtg actgggtcat ggctgcgccc cgacacccgc caacacccgc    6790
tgacgcgccc tgacgggctt gtctgctccc ggcatccgct tacagacaag ctgtgaccgt    6850
ctccgggagc tgcatgtgtc agaggttttc accgtcatca ccgaaacgcg cgaggcagct    6910
gcggtaaagc tcatcagcgt ggtcgtgcag cgattcacag atgtctgcct gttcatccgc    6970
gtccagctcg ttgagtttct ccagaagcgt taatgtctgg cttctgataa agcgggccat    7030
gttaagggcg ttttttcct gtttggtcac tgatgcctcc gtgtaagggg gatttctgtt    7090
catgggggta atgataccga tgaaacgaga gaggatgctc acgatacggg ttactgatga    7150
tgaacatgcc cggttactgg aacgttgtga gggtaaacaa ctggcggtat ggatgcggcg    7210
ggaccagaga aaaatcactc agggtcaatg ccagcgcttc gttaatacag atgtaggtgt    7270
tccacagggt agccagcagc atcctgcgat gcagatccgg aacataatgg tgcagggcgc    7330
tgacttccgc gtttccagac tttacgaaac acggaaaccg aagaccattc atgttgttgc    7390
tcaggtcgca gacgttttgc agcagcagtc gcttcacgtt cgctcgcgta tcggtgattc    7450
attctgctaa ccagtaaggc aaccccgcca gcctagccgg gtcctcaacg acaggagcac    7510
gatcatgcgc acccgtggcc aggacccaac gctgcccgaa att    7553
```

<210> SEQ ID NO 8
<211> LENGTH: 701
<212> TYPE: PRT
<213> ORGANISM: Toxoplasma gondii
<220> FEATURE:
<223> OTHER INFORMATION: pMBP-p2X-ToxoP30 (52-336aa)

<400> SEQUENCE: 8

```
Met Lys Ile Lys Thr Gly Ala Arg Ile Leu Ala Leu Ser Ala Leu Thr
 1               5                  10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60
```

```
His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Ile Glu Gly Arg Ile Ser Glu Phe
                405                 410                 415

Leu Val Ala Asn Gln Val Val Thr Cys Pro Asp Lys Ser Thr Ala
            420                 425                 430

Ala Val Ile Leu Thr Pro Thr Glu Asn His Phe Thr Leu Lys Cys Pro
        435                 440                 445

Lys Thr Ala Leu Thr Glu Pro Pro Thr Leu Ala Tyr Ser Pro Asn Arg
    450                 455                 460

Gln Ile Cys Pro Ala Gly Thr Thr Ser Ser Cys Thr Ser Lys Ala Val
465                 470                 475                 480
```

```
Thr Leu Ser Ser Leu Ile Pro Glu Ala Glu Asp Ser Trp Trp Thr Gly
            485                 490                 495
Asp Ser Ala Ser Leu Asp Thr Ala Gly Ile Lys Leu Thr Val Pro Ile
        500                 505                 510
Glu Lys Phe Pro Val Thr Thr Gln Thr Phe Val Val Gly Cys Ile Lys
    515                 520                 525
Gly Asp Asp Ala Gln Ser Cys Met Val Thr Val Thr Val Gln Ala Arg
530                 535                 540
Ala Ser Ser Val Val Asn Asn Val Ala Arg Cys Ser Tyr Gly Ala Asp
545                 550                 555                 560
Ser Thr Leu Gly Pro Val Lys Leu Ser Ala Glu Gly Pro Thr Thr Met
                565                 570                 575
Thr Leu Val Cys Gly Lys Asp Gly Val Lys Val Pro Gln Asp Asn Asn
            580                 585                 590
Gln Tyr Cys Ser Gly Thr Thr Leu Thr Gly Cys Asn Glu Lys Ser Phe
        595                 600                 605
Lys Asp Ile Leu Pro Lys Leu Thr Glu Asn Pro Trp Gln Gly Asn Ala
    610                 615                 620
Ser Ser Asp Lys Gly Ala Thr Leu Thr Ile Lys Lys Glu Ala Phe Pro
625                 630                 635                 640
Ala Glu Ser Lys Ser Val Ile Ile Gly Cys Thr Gly Ser Pro Glu
                645                 650                 655
Lys His His Cys Thr Val Lys Leu Glu Phe Ala Gly Ala Ala Gly Ser
            660                 665                 670
Ala Lys Ser Ala Ala Gly Thr Ala Ser His Val Ser Ile Phe Ala Met
        675                 680                 685
Val Ile Gly Leu Ile Gly Ser Ile Ala Ala Cys Val Ala
    690                 695                 700

<210> SEQ ID NO 9
<211> LENGTH: 39
<212> TYPE: DNA
<213> ORGANISM: Artificial Sequence
<220> FEATURE:
<223> OTHER INFORMATION: Antisense Primer

<400> SEQUENCE: 9
caggtcaagc tttcacacca tggcaaaaat ggaaacgtg                      39

<210> SEQ ID NO 10
<211> LENGTH: 7442
<212> TYPE: DNA
<213> ORGANISM: Toxoplasma gondii
<220> FEATURE:
<221> NAME/KEY: CDS
<222> LOCATION: (1528)...(3519)
<223> OTHER INFORMATION: pMBP-c2X-ToxoP30del1C (52-324aa)

<400> SEQUENCE: 10
ccgacaccat cgaatggtgc aaaacctttc gcggtatggc atgatagcgc ccggaagaga    60
gtcaattcag ggtggtgaat gtgaaaccag taacgttata cgatgtcgca gagtatgccg   120
gtgtctctta tcagaccgtt tcccgcgtgg tgaaccaggc cagccacgtt tctgcgaaaa   180
cgcgggaaaa agtggaagcg gcgatggcgg agctgaatta cattcccaac cgcgtggcac   240
aacaactggc gggcaaacag tcgttgctga ttggcgttgc cacctccagt ctggccctgc   300
acgcgccgtc gcaaattgtc gcggcgatta atctcgcgc cgatcaactg ggtgccagcg   360
tggtggtgtc gatggtagaa cgaagcggcg tcgaagcctg taaagcggcg gtgcacaatc   420
```

```
ttctcgcgca acgcgtcagt gggctgatca ttaactatcc gctggatgac caggatgcca      480
ttgctgtgga agctgcctgc actaatgttc cggcgttatt tcttgatgtc tctgaccaga      540
cacccatcaa cagtattatt ttctcccatg aagacggtac gcgactgggc gtggagcatc      600
tggtcgcatt gggtcaccag caaatcgcgc tgttagcggg cccattaagt tctgtctcgg      660
cgcgtctgcg tctggctggc tggcataaat atctcactcg caatcaaatt cagccgatag      720
cggaacggga aggcgactgg agtgccatgt ccggttttca acaaaccatg caaatgctga      780
atgagggcat cgttcccact gcgatgctgg ttgccaacga tcagatgcg  ctgggcgcaa      840 tgcgcgccat taccgagtcc gggctgcgcg ttggtgcgga tatctcggta gtgggatacg      900
acgataccga agacagctca tgttatatcc gccgttaac  caccatcaaa caggattttc      960
gcctgctggg gcaaaccagc gtggaccgct tgctgcaact ctctcagggc caggcggtga     1020
agggcaatca gctgttgccc gtctcactgg tgaaaagaaa aaccaccctg cgcccaata      1080 cgcaaaccgc ctctccccgc gcgttggccg attcattaat gcagctggca cgacaggttt     1140
cccgactgga aagcgggcag tgagcgcaac gcaattaatg taagttagct cactcattag     1200
gcacaattct catgtttgac agcttatcat cgactgcacg gtgcaccaat gcttctggcg     1260
tcaggcagcc atcggaagct gtggtatggc tgtgcaggtc gtaaatcact gcataattcg     1320
tgtcgctcaa ggcgcactcc cgttctggat aatgtttttt gcgccgacat cataacggtt     1380
ctggcaaata ttctgaaatg agctgttgac aattaatcat cggctcgtat aatgtgtgga     1440
attgtgagcg gataacaatt tcacacagga aacagccagt ccgtttaggt gttttcacga     1500
gcacttcacc aacaaggacc atagcat atg aaa atc gaa gaa ggt aaa ctg gta     1554
                                Met Lys Ile Glu Glu Gly Lys Leu Val
                                 1               5 atc tgg att aac ggc gat aaa ggc tat aac ggt ctc gct gaa gtc ggt        1602
Ile Trp Ile Asn Gly Asp Lys Gly Tyr Asn Gly Leu Ala Glu Val Gly
 10                  15                  20                  25 aag aaa ttc gag aaa gat acc gga att aaa gtc acc gtt gag cat ccg        1650
Lys Lys Phe Glu Lys Asp Thr Gly Ile Lys Val Thr Val Glu His Pro
                 30                  35                  40 gat aaa ctg gaa gag aaa ttc cca cag gtt gcg gca act ggc gat ggc        1698
Asp Lys Leu Glu Glu Lys Phe Pro Gln Val Ala Ala Thr Gly Asp Gly
             45                  50                  55 cct gac att atc ttc tgg gca cac gac cgc ttt ggt ggc tac gct caa        1746
Pro Asp Ile Ile Phe Trp Ala His Asp Arg Phe Gly Gly Tyr Ala Gln
         60                  65                  70 tct ggc ctg ttg gct gaa atc acc ccg gac aaa gcg ttc cag gac aag        1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att        1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat        1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat        1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa        1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg        2034
Glu Pro Tyr Phe Thr Trp Pro Leu Ile Ala Ala Asp Gly Gly Tyr Ala
```

-continued

```
            155                 160                 165
ttc aag tat gaa aac ggc aag tac gac att aaa gac gtg ggc gtg gat         2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa         2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc         2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg         2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg         2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca         2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc         2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac         2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg         2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa         2514
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt         2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc         2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac         2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc ctt gtt         2706
Asn Asn Asn Asn Leu Gly Ile Glu Gly Arg Ile Ser Glu Phe Leu Val
        380                 385                 390 gcc aat caa gtt gtc acc tgc cca gat aaa aaa tcg aca gcc gcg gtc         2754
Ala Asn Gln Val Val Thr Cys Pro Asp Lys Lys Ser Thr Ala Ala Val
    395                 400                 405 att ctc aca ccg acg gag aac cac ttc act ctc aag tgc cct aaa aca         2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc         2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg         2898
Cys Pro Ala Gly Thr Thr Ser Ser Cys Thr Ser Lys Ala Val Thr Leu
            445                 450                 455 agc tcc ttg att cct gaa gca gaa gat agc tgg tgg acg ggg gat tct         2946
Ser Ser Leu Ile Pro Glu Ala Glu Asp Ser Trp Trp Thr Gly Asp Ser
        460                 465                 470 gct agt ctc gac acg gca ggc atc aaa ctc aca gtt cca atc gag aag         2994
```

```
        Ala Ser Leu Asp Thr Ala Gly Ile Lys Leu Thr Val Pro Ile Glu Lys
                475                 480                 485 ttc ccc gtg aca acg cag acg ttt gtg gtc ggt tgc atc aag gga gac        3042
Phe Pro Val Thr Thr Gln Thr Phe Val Val Gly Cys Ile Lys Gly Asp
490                 495                 500                 505 gac gca cag agt tgt atg gtc aca gtg aca gta caa gcc aga gcc tca        3090
Asp Ala Gln Ser Cys Met Val Thr Val Thr Val Gln Ala Arg Ala Ser
                510                 515                 520 tcg gtc gtc aat aat gtc gca agg tgc tcc tac ggt gca gac agc act        3138
Ser Val Val Asn Asn Val Ala Arg Cys Ser Tyr Gly Ala Asp Ser Thr
                525                 530                 535 ctt ggt cct gtc aag ttg tct gcg gaa gga ccc act aca atg acc ctc        3186
Leu Gly Pro Val Lys Leu Ser Ala Glu Gly Pro Thr Thr Met Thr Leu
            540                 545                 550 gtg tgc ggg aaa gat gga gtc aaa gtt cct caa gac aac aat cag tac        3234
Val Cys Gly Lys Asp Gly Val Lys Val Pro Gln Asp Asn Asn Gln Tyr
            555                 560                 565 tgt tcc ggg acg acg ctg act ggt tgc aac gag aaa tcg ttc aaa gat        3282
Cys Ser Gly Thr Thr Leu Thr Gly Cys Asn Glu Lys Ser Phe Lys Asp
570                 575                 580                 585 att ttg cca aaa tta act gag aac ccg tgg cag ggt aac gct tcg agt        3330
Ile Leu Pro Lys Leu Thr Glu Asn Pro Trp Gln Gly Asn Ala Ser Ser
                590                 595                 600 gat aag ggt gcc acg cta acg atc aag aag gaa gca ttt cca gcc gag        3378
Asp Lys Gly Ala Thr Leu Thr Ile Lys Lys Glu Ala Phe Pro Ala Glu
                605                 610                 615 tca aaa agc gtc att att gga tgc aca ggg gga tcg cct gag aag cat        3426
Ser Lys Ser Val Ile Ile Gly Cys Thr Gly Gly Ser Pro Glu Lys His
            620                 625                 630 cac tgt acc gtg aaa ctg gag ttt gcc ggg gct gca ggg tca gca aaa        3474
His Cys Thr Val Lys Leu Glu Phe Ala Gly Ala Ala Gly Ser Ala Lys
            635                 640                 645 tcg gct gcg gga aca gcc agt cac gtt tcc att ttt gcc atg gtg            3519
Ser Ala Ala Gly Thr Ala Ser His Val Ser Ile Phe Ala Met Val
650                 655                 660 tgaaagcttg gcactggccg tcgttttaca acgtcgtgac tgggaaaacc ctggcgttac      3579
ccaacttaat cgccttgcag cacatccccc tttcgccagc tggcgtaata gcgaagaggc      3639
ccgcaccgat cgcccttccc aacagttgcg cagcctgaat ggcgaatggc agcttggctg     3699
ttttggcgga tgagataaga ttttcagcct gatacagatt aaatcagaac gcagaagcgg      3759
tctgataaaa cagaatttgc ctggcggcag tagcgcggtg gtcccacctg accccatgcc     3819
gaactcagaa gtgaaacgcc gtagcgccga tggtagtgtg gggtctcccc atgcgagagt     3879
agggaactgc caggcatcaa ataaaacgaa aggctcagtc gaaagactgg gcctttcgtt     3939
ttatctgttg tttgtcggtg aacgctctcc tgagtaggac aaatccgccg ggagcggatt     3999
tgaacgttgc gaagcaacgg cccggagggt ggcgggcagg acgcccgcca taaactgcca     4059
ggcatcaaat taagcagaag gccatcctga cggatggcct ttttgcgttt ctacaaactc     4119
tttttgttta ttttttctaaa tacattcaaa tatgtatccg ctcatgagac aataaccctg     4179
ataaatgctt caataatatt gaaaaaggaa gagtatgagt attcaacatt tccgtgtcgc     4239
ccttattccc ttttttgcgg cattttgcct tcctgttttt gctcacccag aaacgctggt     4299
gaaagtaaaa gatgctgaag atcagttggg tgcacgagtg ggttacatcg aactggatct     4359
caacagcggt aagatccttg agagttttcg ccccgaagaa cgttctccaa tgatgagcac     4419
ttttaaagtt ctgctatgtg gcgcggtatt atcccgtgtt gacgccgggc aagagcaact     4479
```

-continued

```
cggtcgccgc atacactatt ctcagaatga cttggttgag tactcaccag tcacagaaaa    4539
gcatcttacg gatggcatga cagtaagaga attatgcagt gctgccataa ccatgagtga    4599
taacactgcg gccaacttac ttctgacaac gatcggagga ccgaaggagc taaccgcttt    4659
tttgcacaac atgggggatc atgtaactcg ccttgatcgt tgggaaccgg agctgaatga    4719
agccatacca aacgacgagc gtgacaccac gatgcctgta gcaatggcaa caacgttgcg    4779
caaactatta actggcgaac tacttactct agcttcccgg caacaattaa tagactggat    4839
ggaggcggat aaagttgcag gaccacttct gcgctcggcc cttccggctg gctggtttat    4899
tgctgataaa tctggagccg gtgagcgtgg gtctcgcggt atcattgcag cactggggcc    4959
agatggtaag ccctcccgta tcgtagttat ctacacgacg gggagtcagg caactatgga    5019
tgaacgaaat agacagatcg ctgagatagg tgcctcactg attaagcatt ggtaactgtc    5079
agaccaagtt tactcatata ctttagat tgatttaccc cggttgataa tcagaaaagc    5139
cccaaaaaca ggaagattgt ataagcaaat atttaaattg taaacgttaa tattttgtta    5199
aaattcgcgt taaattttg ttaaatcagc tcattttta accaataggc cgaaatcggc    5259
aaaatccctt ataaatcaaa agaatagacc gagatagggt tgagtgttgt tccagtttgg    5319
aacaagagtc cactattaaa gaacgtggac tccaacgtca aagggcgaaa aaccgtctat    5379
cagggcgatg gcccactacg tgaaccatca cccaaatcaa gttttttggg gtcgaggtgc    5439
cgtaaagcac taaatcggaa ccctaaaggg agcccccgat ttagagcttg acggggaaag    5499
ccggcgaacg tggcgagaaa ggaagggaag aaagcgaaag gagcgggcgc tagggcgctg    5559
gcaagtgtag cggtcacgct gcgcgtaacc accacacccg ccgcgcttaa tgcgccgcta    5619
cagggcgcgt aaaaggatct aggtgaagat ccttttttgat aatctcatga ccaaaatccc    5679
ttaacgtgag ttttcgttcc actgagcgtc agacccgtaa gaaagatca aaggatcttc    5739 ttgagatcct ttttttctgc gcgtaatctg ctgcttgcaa acaaaaaaac caccgctacc    5799
agcggtggtt tgtttgccgg atcaagagct accaactctt tttccgaagg taactggctt    5859
cagcagagcg cagataccaa atactgtcct tctagtgtag ccgtagttag gccaccactt    5919
caagaactct gtagcaccgc ctacatacct cgctctgcta atcctgttac cagtggctgc    5979
tgccagtggc gataagtcgt gtcttaccgg gttggactca agacgatagt taccggataa    6039
ggcgcagcgg tcgggctgaa cggggggttc gtgcacacag cccagcttgg agcgaacgac    6099
ctacaccgaa ctgagatacc tacagcgtga gctatgagaa agcgccacgc ttcccgaagg    6159
gagaaaggcg gacaggtatc cggtaagcgg cagggtcgga acaggagagc gcacgaggga    6219
gcttccaggg ggaaacgcct ggtatcttta tagtcctgtc gggtttcgcc acctctgact    6279
tgagcgtcga ttttttgtgat gctcgtcagg ggggcggagc ctatggaaaa acgccagcaa    6339
cgcggccttt ttacggttcc tggccttttg ctggccttttt gctcacatgt tctttcctgc    6399
gttatcccct gattctgtgg ataaccgtat taccgccttt gagtgagctg ataccgctcg    6459
ccgcagccga acgaccgagc gcagcgagtc agtgagcgag gaagcggaag agcgcctgat    6519
gcggtatttt ctccttacgc atctgtgcgg tatttcacac cgcatatatg gtgcactctc    6579
agtacaatct gctctgatgc cgcatagtta agccagtata cactccgcta tcgctacgtg    6639
actgggtcat ggctgcgccc cgacacccgc caacacccgc tgacgcgccc tgacgggctt    6699
gtctgctccc ggcatccgct tacagacaag ctgtgaccgt ctccgggagc tgcatgtgtc    6759
agaggttttc accgtcatca ccgaaacgcg cgaggcagct gcggtaaagc tcatcagcgt    6819
ggtcgtgcag cgattcacag atgtctgcct gttcatccgc gtccagctcg ttgagtttct    6879
```

-continued

```
ccagaagcgt taatgtctgg cttctgataa agcgggccat gttaagggcg gttttttcct     6939
gtttggtcac tgatgcctcc gtgtaagggg gatttctgtt catggggggta atgataccga    6999
tgaaacgaga gaggatgctc acgatacggg ttactgatga tgaacatgcc cggttactgg     7059
aacgttgtga gggtaaacaa ctggcggtat ggatgcggcg ggaccagaga aaaatcactc     7119
agggtcaatg ccagcgcttc gttaatacag atgtaggtgt tccacagggt agccagcagc     7179
atcctgcgat gcagatccgg aacataatgg tgcagggcgc tgacttccgc gtttccagac     7239
tttacgaaac acggaaaccg aagaccattc atgttgttgc tcaggtcgca gacgttttgc     7299
agcagcagtc gcttcacgtt cgctcgcgta tcggtgattc attctgctaa ccagtaaggc     7359
aaccccgcca gcctagccgg gtcctcaacg acaggagcac gatcatgcgc acccgtggcc     7419
aggacccaac gctgcccgaa att                                             7442
```

<210> SEQ ID NO 11
<211> LENGTH: 664
<212> TYPE: PRT
<213> ORGANISM: Toxoplasma gondii
<220> FEATURE:
<223> OTHER INFORMATION: pMBP-c2X-ToxoP30del1C (52-324aa)

<400> SEQUENCE: 11

```
Met Lys Ile Glu Glu Gly Lys Leu Val Ile Trp Ile Asn Gly Asp Lys
 1               5                  10                  15
Gly Tyr Asn Gly Leu Ala Glu Val Gly Lys Lys Phe Glu Lys Asp Thr
            20                  25                  30
Gly Ile Lys Val Thr Val Glu His Pro Asp Lys Leu Glu Glu Lys Phe
        35                  40                  45
Pro Gln Val Ala Ala Thr Gly Asp Gly Pro Asp Ile Ile Phe Trp Ala
    50                  55                  60
His Asp Arg Phe Gly Gly Tyr Ala Gln Ser Gly Leu Leu Ala Glu Ile
65                  70                  75                  80
Thr Pro Asp Lys Ala Phe Gln Asp Lys Leu Tyr Pro Phe Thr Trp Asp
                85                  90                  95
Ala Val Arg Tyr Asn Gly Lys Leu Ile Ala Tyr Pro Ile Ala Val Glu
            100                 105                 110
Ala Leu Ser Leu Ile Tyr Asn Lys Asp Leu Leu Pro Asn Pro Pro Lys
        115                 120                 125
Thr Trp Glu Glu Ile Pro Ala Leu Asp Lys Glu Leu Lys Ala Lys Gly
    130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
            180                 185                 190
Leu Thr Phe Leu Val Asp Leu Ile Lys Asn Lys His Met Asn Ala Asp
        195                 200                 205
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
```

```
Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
    610                 615                 620

Cys Thr Gly Gly Ser Pro Glu Lys His His Cys Thr Val Lys Leu Glu
625                 630                 635                 640

Phe Ala Gly Ala Ala Gly Ser Ala Lys Ser Ala Gly Thr Ala Ser
                645                 650                 655

His Val Ser Ile Phe Ala Met Val
            660
```

```
<210> SEQ ID NO 12
<211> LENGTH: 819
<212> TYPE: DNA
<213> ORGANISM: Toxoplasma gondii
<220> FEATURE:
<221> NAME/KEY: CDS
<222> LOCATION: (1)...(819)
<223> OTHER INFORMATION: ToxoP30del1C (52-324aa)

<400> SEQUENCE: 12 ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag tgc cct      96
Ala Val Ile Leu Thr Pro Thr Glu Asn His Phe Thr Leu Lys Cys Pro
                20                  25                  30 aaa aca gcg ctc aca gag cct ccc act ctt gcg tac tca ccc aac agg     144
Lys Thr Ala Leu Thr Glu Pro Pro Thr Leu Ala Tyr Ser Pro Asn Arg
            35                  40                  45 caa atc tgc cca gcg ggt act aca agt agc tgt aca tca aag gct gta     192
Gln Ile Cys Pro Ala Gly Thr Thr Ser Ser Cys Thr Ser Lys Ala Val
     50                  55                  60 aca ttg agc tcc ttg att cct gaa gca gaa gat agc tgg tgg acg ggg     240
Thr Leu Ser Ser Leu Ile Pro Glu Ala Glu Asp Ser Trp Trp Thr Gly
 65                  70                  75                  80 gat tct gct agt ctc gac acg gca ggc atc aaa ctc aca gtt cca atc     288
Asp Ser Ala Ser Leu Asp Thr Ala Gly Ile Lys Leu Thr Val Pro Ile
                 85                  90                  95 gag aag ttc ccc gtg aca acg cag acg ttt gtg gtc ggt tgc atc aag     336
Glu Lys Phe Pro Val Thr Thr Gln Thr Phe Val Val Gly Cys Ile Lys
                100                 105                 110 gga gac gac gca cag agt tgt atg gtc aca gtg aca gta caa gcc aga     384
Gly Asp Asp Ala Gln Ser Cys Met Val Thr Val Thr Val Gln Ala Arg
            115                 120                 125 gcc tca tcg gtc gtc aat aat gtc gca agg tgc tcc tac ggt gca gac     432
Ala Ser Ser Val Val Asn Asn Val Ala Arg Cys Ser Tyr Gly Ala Asp
    130                 135                 140 agc act ctt ggt cct gtc aag ttg tct gcg gaa gga ccc act aca atg     480
Ser Thr Leu Gly Pro Val Lys Leu Ser Ala Glu Gly Pro Thr Thr Met
145                 150                 155                 160 acc ctc gtg tgc ggg aaa gat gga gtc aaa gtt cct caa gac aac aat     528
Thr Leu Val Cys Gly Lys Asp Gly Val Lys Val Pro Gln Asp Asn Asn
                165                 170                 175 cag tac tgt tcc ggg acg acg ctg act ggt tgc aac gag aaa tcg ttc     576
Gln Tyr Cys Ser Gly Thr Thr Leu Thr Gly Cys Asn Glu Lys Ser Phe
            180                 185                 190 aaa gat att ttg cca aaa tta act gag aac ccg tgg cag ggt aac gct     624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca     672
Ser Ser Asp Lys Gly Ala Thr Leu Thr Ile Lys Lys Glu Ala Phe Pro
    210                 215                 220 gcc gag tca aaa agc gtc att att gga tgc aca ggg gga tcg cct gag     720
Ala Glu Ser Lys Ser Val Ile Ile Gly Cys Thr Gly Gly Ser Pro Glu
225                 230                 235                 240 aag cat cac tgt acc gtg aaa ctg gag ttt gcc ggg gct gca ggg tca     768
Lys His His Cys Thr Val Lys Leu Glu Phe Ala Gly Ala Ala Gly Ser
                245                 250                 255 gca aaa tcg gct gcg gga aca gcc agt cac gtt tcc att ttt gcc atg     816
Ala Lys Ser Ala Ala Gly Thr Ala Ser His Val Ser Ile Phe Ala Met
            260                 265                 270
```

```
gtg                                                                          819
Val <210> SEQ ID NO 13
<211> LENGTH: 273
<212> TYPE: PRT
<213> ORGANISM: Toxoplasma gondii
<220> FEATURE:
<223> OTHER INFORMATION: ToxoP30del1C (52-324aa)

<400> SEQUENCE: 13

Leu Val Ala Asn Gln Val Val Thr Cys Pro Asp Lys Lys Ser Thr Ala
  1               5                  10                  15

Ala Val Ile Leu Thr Pro Thr Glu Asn His Phe Thr Leu Lys Cys Pro
             20                  25                  30

Lys Thr Ala Leu Thr Glu Pro Pro Thr Leu Ala Tyr Ser Pro Asn Arg
         35                  40                  45

Gln Ile Cys Pro Ala Gly Thr Thr Ser Ser Cys Thr Ser Lys Ala Val
     50                  55                  60

Thr Leu Ser Ser Leu Ile Pro Glu Ala Glu Asp Ser Trp Trp Thr Gly
 65                  70                  75                  80

Asp Ser Ala Ser Leu Asp Thr Ala Gly Ile Lys Leu Thr Val Pro Ile
                 85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Cys Thr Gly Gly Ser Pro Glu
225                 230                 235                 240

Lys His His Cys Thr Val Lys Leu Glu Phe Ala Gly Ala Ala Gly Ser
                245                 250                 255

Ala Lys Ser Ala Ala Gly Thr Ala Ser His Val Ser Ile Phe Ala Met
            260                 265                 270

Val

<210> SEQ ID NO 14
<211> LENGTH: 41
<212> TYPE: DNA
<213> ORGANISM: Artificial Sequence
<220> FEATURE:
<223> OTHER INFORMATION: Antisense Primer

<400> SEQUENCE: 14
caggtcaagc tttcaagccg attttgctga ccctgcagcc c                          41
```

-continued

```
<210> SEQ ID NO 15
<211> LENGTH: 7403
<212> TYPE: DNA
<213> ORGANISM: Toxoplasma gondii
<220> FEATURE:
<221> NAME/KEY: CDS
<222> LOCATION: (1528)...(3480)
<223> OTHER INFORMATION: pMBP-c2X-ToxoP30del2 (52-311aa)

<400> SEQUENCE: 15
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta aatctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc cggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatggcg ctgggcgcaa     840
tgcgcgccat taccgagtcc gggctgcgcg ttggtgcgga tatctcggta gtgggatacg     900
acgataccga agacagctca tgttatatcc cgccgttaac caccatcaaa caggattttc     960
gcctgctggg gcaaaccagc gtggaccgct tgctgcaact ctctcagggc caggcggtga    1020
agggcaatca gctgttgccc gtctcactgg tgaaaagaaa aaccaccctg gcgcccaata    1080
cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga aacagccagt ccgtttaggt gttttcacga    1500
gcacttcacc aacaaggacc atagcat atg aaa atc gaa gaa ggt aaa ctg gta    1554
                              Met Lys Ile Glu Glu Gly Lys Leu Val
                               1               5 atc tgg att aac ggc gat aaa ggc tat aac ggt ctc gct gaa gtc ggt      1602
Ile Trp Ile Asn Gly Asp Lys Gly Tyr Asn Gly Leu Ala Glu Val Gly
 10                  15                  20                  25 aag aaa ttc gag aaa gat acc gga att aaa gtc acc gtt gag cat ccg      1650
Lys Lys Phe Glu Lys Asp Thr Gly Ile Lys Val Thr Val Glu His Pro
                 30                  35                  40 gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
             45                  50                  55 cct gac att atc ttc tgg gca cac gac cgc ttt ggt ggc tac gct caa      1746
Pro Asp Ile Ile Phe Trp Ala His Asp Arg Phe Gly Gly Tyr Ala Gln
```

-continued

```
                    60                  65                  70
tct ggc ctg ttg gct gaa atc acc ccg gac aaa gcg ttc cag gac aag    1794
Ser Gly Leu Leu Ala Glu Ile Thr Pro Asp Lys Ala Phe Gln Asp Lys
    75                  80                  85 ctg tat ccg ttt acc tgg gat gcc gta cgt tac aac ggc aag ctg att    1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat    1890
Ala Tyr Pro Ile Ala Val Glu Ala Leu Ser Leu Ile Tyr Asn Lys Asp
                    110                 115                 120 ctg ctg ccg aac ccg cca aaa acc tgg gaa gag atc ccg gcg ctg gat    1938
Leu Leu Pro Asn Pro Pro Lys Thr Trp Glu Glu Ile Pro Ala Leu Asp
                125                 130                 135 aaa gaa ctg aaa gcg aaa ggt aag agc gcg ctg atg ttc aac ctg caa    1986
Lys Glu Leu Lys Ala Lys Gly Lys Ser Ala Leu Met Phe Asn Leu Gln
            140                 145                 150 gaa ccg tac ttc acc tgg ccg ctg att gct gct gac ggg ggt tat gcg    2034
Glu Pro Tyr Phe Thr Trp Pro Leu Ile Ala Ala Asp Gly Gly Tyr Ala
        155                 160                 165 ttc aag tat gaa aac ggc aag tac gac att aaa gac gtg ggc gtg gat    2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa    2130
Asn Ala Gly Ala Lys Ala Gly Leu Thr Phe Leu Val Asp Leu Ile Lys
                    190                 195                 200 aac aaa cac atg aat gca gac acc gat tac tcc atc gca gaa gct gcc    2178
Asn Lys His Met Asn Ala Asp Thr Asp Tyr Ser Ile Ala Glu Ala Ala
                205                 210                 215 ttt aat aaa ggc gaa aca gcg atg acc atc aac ggc ccg tgg gca tgg    2226
Phe Asn Lys Gly Glu Thr Ala Met Thr Ile Asn Gly Pro Trp Ala Trp
            220                 225                 230 tcc aac atc gac acc agc aaa gtg aat tat ggt gta acg gta ctg ccg    2274
Ser Asn Ile Asp Thr Ser Lys Val Asn Tyr Gly Val Thr Val Leu Pro
        235                 240                 245 acc ttc aag ggt caa cca tcc aaa ccg ttc gtt ggc gtg ctg agc gca    2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc    2370
Gly Ile Asn Ala Ala Ser Pro Asn Lys Glu Leu Ala Lys Glu Phe Leu
                    270                 275                 280 gaa aac tat ctg ctg act gat gaa ggt ctg gaa gcg gtt aat aaa gac    2418
Glu Asn Tyr Leu Leu Thr Asp Glu Gly Leu Glu Ala Val Asn Lys Asp
                285                 290                 295 aaa ccg ctg ggt gcc gta gcg ctg aag tct tac gag gaa gag ttg gcg    2466
Lys Pro Leu Gly Ala Val Ala Leu Lys Ser Tyr Glu Glu Glu Leu Ala
            300                 305                 310 aaa gat cca cgt att gcc gcc act atg gaa aac gcc cag aaa ggt gaa    2514
Lys Asp Pro Arg Ile Ala Ala Thr Met Glu Asn Ala Gln Lys Gly Glu
        315                 320                 325 atc atg ccg aac atc ccg cag atg tcc gct ttc tgg tat gcc gtg cgt    2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc    2610
Thr Ala Val Ile Asn Ala Ala Ser Gly Arg Gln Thr Val Asp Glu Ala
                    350                 355                 360 ctg aaa gac gcg cag act aat tcg agc tcg aac aac aac aac aat aac    2658
Leu Lys Asp Ala Gln Thr Asn Ser Ser Ser Asn Asn Asn Asn Asn Asn
                365                 370                 375 aat aac aac aac ctc ggg atc gag gga agg att tca gaa ttc ctt gtt    2706
```

```
                Asn Asn Asn Leu Gly Ile Glu Gly Arg Ile Ser Glu Phe Leu Val
                        380                 385                 390 gcc aat caa gtt gtc acc tgc cca gat aaa aaa tcg aca gcc gcg gtc          2754
Ala Asn Gln Val Val Thr Cys Pro Asp Lys Lys Ser Thr Ala Ala Val
395                 400                 405 att ctc aca ccg acg gag aac cac ttc act ctc aag tgc cct aaa aca          2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc          2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg          2898
Cys Pro Ala Gly Thr Thr Ser Ser Cys Thr Ser Lys Ala Val Thr Leu
            445                 450                 455 agc tcc ttg att cct gaa gca gaa gat agc tgg tgg acg ggg gat tct          2946
Ser Ser Leu Ile Pro Glu Ala Glu Asp Ser Trp Trp Thr Gly Asp Ser
        460                 465                 470 gct agt ctc gac acg gca ggc atc aaa ctc aca gtt cca atc gag aag          2994
Ala Ser Leu Asp Thr Ala Gly Ile Lys Leu Thr Val Pro Ile Glu Lys
    475                 480                 485 ttc ccc gtg aca acg cag acg ttt gtg gtc ggt tgc atc aag gga gac          3042
Phe Pro Val Thr Thr Gln Thr Phe Val Val Gly Cys Ile Lys Gly Asp
490                 495                 500                 505 gac gca cag agt tgt atg gtc aca gtg aca gta caa gcc aga gcc tca          3090
Asp Ala Gln Ser Cys Met Val Thr Val Thr Val Gln Ala Arg Ala Ser
                510                 515                 520 tcg gtc gtc aat aat gtc gca agg tgc tcc tac ggt gca gac agc act          3138
Ser Val Val Asn Asn Val Ala Arg Cys Ser Tyr Gly Ala Asp Ser Thr
            525                 530                 535 ctt ggt cct gtc aag ttg tct gcg gaa gga ccc act aca atg acc ctc          3186
Leu Gly Pro Val Lys Leu Ser Ala Glu Gly Pro Thr Thr Met Thr Leu
        540                 545                 550 gtg tgc ggg aaa gat gga gtc aaa gtt cct caa gac aac aat cag tac          3234
Val Cys Gly Lys Asp Gly Val Lys Val Pro Gln Asp Asn Asn Gln Tyr
555                 560                 565 tgt tcc ggg acg acg ctg act ggt tgc aac gag aaa tcg ttc aaa gat          3282
Cys Ser Gly Thr Thr Leu Thr Gly Cys Asn Glu Lys Ser Phe Lys Asp
570                 575                 580                 585 att ttg cca aaa tta act gag aac ccg tgg cag ggt aac gct tcg agt          3330
Ile Leu Pro Lys Leu Thr Glu Asn Pro Trp Gln Gly Asn Ala Ser Ser
                590                 595                 600 gat aag ggt gcc acg cta acg atc aag aag gaa gca ttt cca gcc gag          3378
Asp Lys Gly Ala Thr Leu Thr Ile Lys Lys Glu Ala Phe Pro Ala Glu
            605                 610                 615 tca aaa agc gtc att att gga tgc aca ggg gga tcg cct gag aag cat          3426
Ser Lys Ser Val Ile Ile Gly Cys Thr Gly Gly Ser Pro Glu Lys His
        620                 625                 630 cac tgt acc gtg aaa ctg gag ttt gcc ggg gct gca ggg tca gca aaa          3474
His Cys Thr Val Lys Leu Glu Phe Ala Gly Ala Ala Gly Ser Ala Lys
    635                 640                 645 tcg gct tgaaagcttg gcactggccg tcgttttaca acgtcgtgac tgggaaaacc          3530
Ser Ala
650 ctggcgttac ccaacttaat cgccttgcag cacatccccc tttcgccagc tggcgtaata      3590 gcgaagaggc ccgcaccgat cgcccttccc aacagttgcg cagcctgaat ggcgaatggc      3650 agcttggctg ttttggcgga tgagataaga ttttcagcct gatacagatt aaatcagaac      3710 gcagaagcgg tctgataaaa cagaatttgc ctggcggcag tagcgcggtg gtcccacctg      3770
```

-continued

```
accccatgcc gaactcagaa gtgaaacgcc gtagcgccga tggtagtgtg gggtctcccc   3830
atgcgagagt agggaactgc caggcatcaa ataaaacgaa aggctcagtc gaaagactgg   3890
gcctttcgtt ttatctgttg tttgtcggtg aacgctctcc tgagtaggac aaatccgccg   3950
ggagcggatt tgaacgttgc gaagcaacgg cccggagggt ggcgggcagg acgcccgcca   4010
taaactgcca ggcatcaaat taagcagaag gccatcctga cggatggcct ttttgcgttt   4070
ctacaaactc tttttgttta tttttctaaa tacattcaaa tatgtatccg ctcatgagac   4130
aataaccctg ataaatgctt caataatatt gaaaaaggaa gagtatgagt attcaacatt   4190
tccgtgtcgc ccttattccc ttttttgcgg cattttgcct tcctgttttt gctcacccag   4250
aaacgctggt gaaagtaaaa gatgctgaag atcagttggg tgcacgagtg ggttacatcg   4310
aactggatct caacagcggt aagatccttg agagttttcg ccccgaagaa cgttctccaa   4370
tgatgagcac ttttaaagtt ctgctatgtg gcgcggtatt atcccgtgtt gacgccgggc   4430
aagagcaact cggtcgccgc atacactatt ctcagaatga cttggttgag tactcaccag   4490
tcacagaaaa gcatcttacg gatggcatga cagtaagaga attatgcagt gctgccataa   4550
ccatgagtga taacactgcg gccaacttac ttctgacaac gatcggagga ccgaaggagc   4610
taaccgcttt tttgcacaac atgggggatc atgtaactcg ccttgatcgt tgggaaccgg   4670
agctgaatga agccatacca aacgacgagc gtgacaccac gatgcctgta gcaatggcaa   4730
caacgttgcg caaactatta actggcgaac tacttactct agcttcccgg caacaattaa   4790
tagactggat ggaggcggat aaagttgcag gaccacttct gcgctcggcc cttccggctg   4850
gctggtttat tgctgataaa tctggagccg gtgagcgtgg gtctcgcggt atcattgcag   4910
cactggggcc agatggtaag ccctcccgta tcgtagttat ctacacgacg gggagtcagg   4970
caactatgga tgaacgaaat agacagatcg ctgagatagg tgcctcactg attaagcatt   5030
ggtaactgtc agaccaagtt tactcatata tactttagat tgatttaccc cggttgataa   5090
tcagaaaagc cccaaaaaca ggaagattgt ataagcaaat atttaaattg taaacgttaa   5150
tattttgtta aaattcgcgt taaatttttg ttaaatcagc tcatttttta accaataggc   5210
cgaaatcggc aaaatccctt ataaatcaaa agaatagacc gagatagggt tgagtgttgt   5270
tccagtttgg aacaagagtc cactattaaa gaacgtggac tccaacgtca aagggcgaaa   5330
aaccgtctat cagggcgatg gcccactacg tgaaccatca cccaaatcaa gttttttggg   5390
gtcgaggtgc cgtaaagcac taaatcggaa ccctaaaggg agcccccgat ttagagcttg   5450
acggggaaag ccggcgaacg tggcgagaaa ggaagggaag aaagcgaaag gagcgggcgc   5510
tagggcgctg gcaagtgtag cggtcacgct gcgcgtaacc accacacccg ccgcgcttaa   5570
tgcgccgcta cagggcgcgt aaaaggatct aggtgaagat cctttttgat aatctcatga   5630
ccaaaatccc ttaacgtgag ttttcgttcc actgagcgtc agaccccgta gaaaagatca   5690
aaggatcttc ttgagatcct ttttttctgc gcgtaatctg ctgcttgcaa acaaaaaaac   5750
caccgctacc agcggtggtt tgtttgccgg atcaagagct accaactctt tttccgaagg   5810
taactggctt cagcagagcg cagataccaa atactgtcct tctagtgtag ccgtagttag   5870
gccaccactt caagaactct gtagcaccgc ctacatacct cgctctgcta atcctgttac   5930
cagtggctgc tgccagtggc gataagtcgt gtcttaccgg gttggactca agacgatagt   5990
taccggataa ggcgcagcgg tcgggctgaa cggggggttc gtgcacacag cccagcttgg   6050
agcgaacgac ctacaccgaa ctgagatacc tacagcgtga gctatgagaa agcgccacgc   6110
ttcccgaagg gagaaaggcg gacaggtatc cggtaagcgg cagggtcgga acaggagagc   6170
```

-continued

```
gcacgaggga gcttccaggg ggaaacgcct ggtatcttta tagtcctgtc gggtttcgcc   6230
acctctgact tgagcgtcga tttttgtgat gctcgtcagg ggggcggagc ctatggaaaa   6290
acgccagcaa cgcggccttt ttacggttcc tggccttttg ctggcctttt gctcacatgt   6350
tctttcctgc gttatcccct gattctgtgg ataaccgtat taccgccttt gagtgagctg   6410
ataccgctcg ccgcagccga acgaccgagc gcagcgagtc agtgagcgag gaagcggaag   6470
agcgcctgat gcggtatttt ctccttacgc atctgtgcgg tatttcacac cgcatatatg   6530
gtgcactctc agtacaatct gctctgatgc cgcatagtta agccagtata cactccgcta   6590
tcgctacgtg actgggtcat ggctgcgccc cgacacccgc caacacccgc tgacgcgccc   6650
tgacgggctt gtctgctccc ggcatccgct tacagacaag ctgtgaccgt ctccgggagc   6710
tgcatgtgtc agaggttttc accgtcatca ccgaaacgcg cgaggcagct gcggtaaagc   6770
tcatcagcgt ggtcgtgcag cgattcacag atgtctgcct gttcatccgc gtccagctcg   6830
ttgagtttct ccagaagcgt taatgtctgg cttctgataa agcgggccat gttaagggcg   6890 gtttttttcct gtttggtcac tgatgcctcc gtgtaagggg gatttctgtt catgggggta   6950
atgataccga tgaaacgaga gaggatgctc acgatacggg ttactgatga tgaacatgcc   7010
cggttactgg aacgttgtga gggtaaacaa ctggcggtat ggatgcggcg ggaccagaga   7070
aaaatcactc agggtcaatg ccagcgcttc gttaatacag atgtaggtgt tccacagggt   7130
agccagcagc atcctgcgat gcagatccgg aacataatgg tgcagggcgc tgacttccgc   7190
gtttccagac tttacgaaac acggaaaccg aagaccattc atgttgttgc tcaggtcgca   7250
gacgttttgc agcagcagtc gcttcacgtt cgctcgcgta tcggtgattc attctgctaa   7310
ccagtaaggc aaccccgcca gcctagccgg gtcctcaacg acaggagcac gatcatgcgc   7370
acccgtggcc aggacccaac gctgcccgaa att                                7403
```

<210> SEQ ID NO 16
<211> LENGTH: 651
<212> TYPE: PRT
<213> ORGANISM: Toxoplasma gondii
<220> FEATURE:
<223> OTHER INFORMATION: pMBP-c2X-ToxoP30del2 (52-311aa)

<400> SEQUENCE: 16

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140
```

-continued

```
Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
                195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
                275                 280                 285

Glu Gly Leu Glu Ala Val Asn Lys Asp Lys Pro Leu Gly Ala Val Ala
290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Asn Leu Gly Ile
                370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
                420                 425                 430

Leu Ala Tyr Ser Pro Asn Arg Gln Ile Cys Pro Ala Gly Thr Thr Ser
                435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
                500                 505                 510

Thr Val Thr Val Gln Ala Arg Ala Ser Ser Val Val Asn Asn Val Ala
                515                 520                 525

Arg Cys Ser Tyr Gly Ala Asp Ser Thr Leu Gly Pro Val Lys Leu Ser
                530                 535                 540

Ala Glu Gly Pro Thr Thr Met Thr Leu Val Cys Gly Lys Asp Gly Val
545                 550                 555                 560
```

```
Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
                580                 585                 590

Asn Pro Trp Gln Gly Asn Ala Ser Ser Asp Lys Gly Ala Thr Leu Thr
                595                 600                 605

Ile Lys Lys Glu Ala Phe Pro Ala Glu Ser Lys Ser Val Ile Ile Gly
                610                 615                 620

Cys Thr Gly Gly Ser Pro Glu Lys His His Cys Thr Val Lys Leu Glu
625                 630                 635                 640

Phe Ala Gly Ala Ala Gly Ser Ala Lys Ser Ala
                645                 650

<210> SEQ ID NO 17
<211> LENGTH: 780
<212> TYPE: DNA
<213> ORGANISM: Toxoplasma gondii
<220> FEATURE:
<221> NAME/KEY: CDS
<222> LOCATION: (1)...(780)
<223> OTHER INFORMATION: ToxoP30del2 (52-311aa)

<400> SEQUENCE: 17 ctt gtt gcc aat caa gtt gtc acc tgc cca gat aaa aaa tcg aca gcc        48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag tgc cct        96
Ala Val Ile Leu Thr Pro Thr Glu Asn His Phe Thr Leu Lys Cys Pro
                 20                  25                  30 aaa aca gcg ctc aca gag cct ccc act ctt gcg tac tca ccc aac agg       144
Lys Thr Ala Leu Thr Glu Pro Pro Thr Leu Ala Tyr Ser Pro Asn Arg
             35                  40                  45 caa atc tgc cca gcg ggt act aca agt agc tgt aca tca aag gct gta       192
Gln Ile Cys Pro Ala Gly Thr Thr Ser Ser Cys Thr Ser Lys Ala Val
         50                  55                  60 aca ttg agc tcc ttg att cct gaa gca gaa gat agc tgg tgg acg ggg       240
Thr Leu Ser Ser Leu Ile Pro Glu Ala Glu Asp Ser Trp Trp Thr Gly
 65                  70                  75                  80 gat tct gct agt ctc gac acg gca ggc atc aaa ctc aca gtt cca atc       288
Asp Ser Ala Ser Leu Asp Thr Ala Gly Ile Lys Leu Thr Val Pro Ile
                 85                  90                  95 gag aag ttc ccc gtg aca acg cag acg ttt gtg gtc ggt tgc atc aag       336
Glu Lys Phe Pro Val Thr Thr Gln Thr Phe Val Val Gly Cys Ile Lys
                100                 105                 110 gga gac gac gca cag agt tgt atg gtc aca gtg aca gta caa gcc aga       384
Gly Asp Asp Ala Gln Ser Cys Met Val Thr Val Thr Val Gln Ala Arg
            115                 120                 125 gcc tca tcg gtc gtc aat aat gtc gca agg tgc tcc tac ggt gca gac       432
Ala Ser Ser Val Val Asn Asn Val Ala Arg Cys Ser Tyr Gly Ala Asp
        130                 135                 140 agc act ctt ggt cct gtc aag ttg tct gcg gaa gga ccc act aca atg       480
Ser Thr Leu Gly Pro Val Lys Leu Ser Ala Glu Gly Pro Thr Thr Met
145                 150                 155                 160 acc ctc gtg tgc ggg aaa gat gga gtc aaa gtt cct caa gac aac aat       528
Thr Leu Val Cys Gly Lys Asp Gly Val Lys Val Pro Gln Asp Asn Asn
                165                 170                 175 cag tac tgt tcc ggg acg acg ctg act ggt tgc aac gag aaa tcg ttc       576
Gln Tyr Cys Ser Gly Thr Thr Leu Thr Gly Cys Asn Glu Lys Ser Phe
                180                 185                 190 aaa gat att ttg cca aaa tta act gag aac ccg tgg cag ggt aac gct       624
Lys Asp Ile Leu Pro Lys Leu Thr Glu Asn Pro Trp Gln Gly Asn Ala
```

```
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca      672
Ser Ser Asp Lys Gly Ala Thr Leu Thr Ile Lys Lys Glu Ala Phe Pro
210                 215                 220 gcc gag tca aaa agc gtc att att gga tgc aca ggg gga tcg cct gag      720
Ala Glu Ser Lys Ser Val Ile Ile Gly Cys Thr Gly Gly Ser Pro Glu
225                 230                 235                 240 aag cat cac tgt acc gtg aaa ctg gag ttt gcc ggg gct gca ggg tca      768
Lys His His Cys Thr Val Lys Leu Glu Phe Ala Gly Ala Ala Gly Ser
        245                 250                 255 gca aaa tcg gct                                                       780
Ala Lys Ser Ala
        260

<210> SEQ ID NO 18
<211> LENGTH: 260
<212> TYPE: PRT
<213> ORGANISM: Toxoplasma gondii
<220> FEATURE:
<223> OTHER INFORMATION: ToxoP30del2 (52-311aa)

<400> SEQUENCE: 18

Leu Val Ala Asn Gln Val Val Thr Cys Pro Asp Lys Lys Ser Thr Ala
1               5                   10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Cys Thr Gly Gly Ser Pro Glu
225                 230                 235                 240

Lys His His Cys Thr Val Lys Leu Glu Phe Ala Gly Ala Ala Gly Ser
                245                 250                 255

Ala Lys Ser Ala
        260
```

-continued

<210> SEQ ID NO 19
<211> LENGTH: 36
<212> TYPE: DNA
<213> ORGANISM: Artificial Sequence
<220> FEATURE:
<223> OTHER INFORMATION: Antisense Primer

<400> SEQUENCE: 19
caggtcaagc tttcactcca gtttcacggt acagtg 36

<210> SEQ ID NO 20
<211> LENGTH: 7370
<212> TYPE: DNA
<213> ORGANISM: Toxoplasma gondii
<220> FEATURE:
<221> NAME/KEY: CDS
<222> LOCATION: (1528)...(3447)
<223> OTHER INFORMATION: pMBP-c2X-Toxo30del3C (52-300aa)

<400> SEQUENCE: 20
ccgacaccat cgaatggtgc aaaacctttc gcggtatggc atgatagcgc ccggaagaga 60
gtcaattcag ggtggtgaat gtgaaaccag taacgttata cgatgtcgca gagtatgccg 120
gtgtctctta tcagaccgtt tcccgcgtgg tgaaccaggc cagccacgtt tctgcgaaaa 180
cgcgggaaaa agtggaagcg gcgatggcgg agctgaatta cattcccaac cgcgtggcac 240
aacaactggc gggcaaacag tcgttgctga ttggcgttgc cacctccagt ctggccctgc 300
acgcgccgtc gcaaattgtc gcggcgatta aatctcgcgc cgatcaactg ggtgccagcg 360
tggtggtgtc gatggtagaa cgaagcggcg tcgaagcctg taaagcggcg gtgcacaatc 420
ttctcgcgca acgcgtcagt gggctgatca ttaactatcc gctggatgac caggatgcca 480
ttgctgtgga agctgcctgc actaatgttc cggcgttatt tcttgatgtc tctgaccaga 540
cacccatcaa cagtattatt ttctcccatg aagacggtac gcgactgggc gtggagcatc 600
tggtcgcatt gggtcaccag caaatcgcgc tgttagcggg cccattaagt tctgtctcgg 660
cgcgtctgcg tctggctggc tggcataaat atctcactcg caatcaaatt cagccgatag 720
cggaacggga aggcgactgg agtgccatgt ccggttttca acaaaccatg caaatgctga 780
atgagggcat cgttcccact gcgatgctgg ttgccaacga tcagatggcg ctgggcgcaa 840
tgcgcgccat taccgagtcc gggctgcgcg ttggtgcgga tatctcggta gtgggatacg 900
acgataccga agacagctca tgttatatcc cgccgttaac caccatcaaa caggattttc 960
gcctgctggg gcaaaccagc gtggaccgct tgctgcaact ctctcagggc caggcggtga 1020
agggcaatca gctgttgccc gtctcactgg tgaaaagaaa aaccaccctg gcgcccaata 1080
cgcaaaccgc ctctccccgc gcgttggccg attcattaat gcagctggca cgacaggttt 1140
cccgactgga aagcgggcag tgagcgcaac gcaattaatg taagttagct cactcattag 1200
gcacaattct catgtttgac agcttatcat cgactgcacg gtgcaccaat gcttctggcg 1260
tcaggcagcc atcggaagct gtggtatggc tgtgcaggtc gtaaatcact gcataattcg 1320
tgtcgctcaa ggcgcactcc cgttctggat aatgtttttt gcgccgacat cataacggtt 1380
ctggcaaata ttctgaaatg agctgttgac aattaatcat cggctcgtat aatgtgtgga 1440
attgtgagcg gataacaatt tcacacagga aacagccagt ccgtttaggt gttttcacga 1500
gcacttcacc aacaaggacc atagcat atg aaa atc gaa gaa ggt aaa ctg gta 1554
Met Lys Ile Glu Glu Gly Lys Leu Val
1 5

-continued

```
atc tgg att aac ggc gat aaa ggc tat aac ggt ctc gct gaa gtc ggt      1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg      1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
         45                  50                  55 cct gac att atc ttc tgg gca cac gac cgc ttt ggt ggc tac gct caa      1746
Pro Asp Ile Ile Phe Trp Ala His Asp Arg Phe Gly Gly Tyr Ala Gln
     60                  65                  70 tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
             90                  95                 100                 105 gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
    155                 160                 165 ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc      2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg      2274
Ser Asn Ile Asp Thr Ser Lys Val Asn Tyr Gly Val Thr Val Leu Pro
235                 240                 245 acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
    315                 320                 325
```

```
atc atg ccg aac atc ccg cag atg tcc gct ttc tgg tat gcc gtg cgt       2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc       2610
Thr Ala Val Ile Asn Ala Ala Ser Gly Arg Gln Thr Val Asp Glu Ala
            350                 355                 360 ctg aaa gac gcg cag act aat tcg agc tcg aac aac aac aac aat aac       2658
Leu Lys Asp Ala Gln Thr Asn Ser Ser Ser Asn Asn Asn Asn Asn Asn
        365                 370                 375 aat aac aac aac ctc ggg atc gag gga agg att tca gaa ttc ctt gtt       2706
Asn Asn Asn Asn Leu Gly Ile Glu Gly Arg Ile Ser Glu Phe Leu Val
    380                 385                 390 gcc aat caa gtt gtc acc tgc cca gat aaa aaa tcg aca gcc gcg gtc       2754
Ala Asn Gln Val Val Thr Cys Pro Asp Lys Lys Ser Thr Ala Ala Val
395                 400                 405 att ctc aca ccg acg gag aac cac ttc act ctc aag tgc cct aaa aca       2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc       2850
Ala Leu Thr Glu Pro Pro Thr Leu Ala Tyr Ser Pro Asn Arg Gln Ile
            430                 435                 440 tgc cca gcg ggt act aca agt agc tgt aca tca aag gct gta aca ttg       2898
Cys Pro Ala Gly Thr Thr Ser Ser Cys Thr Ser Lys Ala Val Thr Leu
        445                 450                 455 agc tcc ttg att cct gaa gca gaa gat agc tgg tgg acg ggg gat tct       2946
Ser Ser Leu Ile Pro Glu Ala Glu Asp Ser Trp Trp Thr Gly Asp Ser
    460                 465                 470 gct agt ctc gac acg gca ggc atc aaa ctc aca gtt cca atc gag aag       2994
Ala Ser Leu Asp Thr Ala Gly Ile Lys Leu Thr Val Pro Ile Glu Lys
475                 480                 485 ttc ccc gtg aca acg cag acg ttt gtg gtc ggt tgc atc aag gga gac       3042
Phe Pro Val Thr Thr Gln Thr Phe Val Val Gly Cys Ile Lys Gly Asp
490                 495                 500                 505 gac gca cag agt tgt atg gtc aca gtg aca gta caa gcc aga gcc tca       3090
Asp Ala Gln Ser Cys Met Val Thr Val Thr Val Gln Ala Arg Ala Ser
            510                 515                 520 tcg gtc gtc aat aat gtc gca agg tgc tcc tac ggt gca gac agc act       3138
Ser Val Val Asn Asn Val Ala Arg Cys Ser Tyr Gly Ala Asp Ser Thr
        525                 530                 535 ctt ggt cct gtc aag ttg tct gcg gaa gga ccc act aca atg acc ctc       3186
Leu Gly Pro Val Lys Leu Ser Ala Glu Gly Pro Thr Thr Met Thr Leu
    540                 545                 550 gtg tgc ggg aaa gat gga gtc aaa gtt cct caa gac aac aat cag tac       3234
Val Cys Gly Lys Asp Gly Val Lys Val Pro Gln Asp Asn Asn Gln Tyr
555                 560                 565 tgt tcc ggg acg acg ctg act ggt tgc aac gag aaa tcg ttc aaa gat       3282
Cys Ser Gly Thr Thr Leu Thr Gly Cys Asn Glu Lys Ser Phe Lys Asp
570                 575                 580                 585 att ttg cca aaa tta act gag aac ccg tgg cag ggt aac gct tcg agt       3330
Ile Leu Pro Lys Leu Thr Glu Asn Pro Trp Gln Gly Asn Ala Ser Ser
            590                 595                 600 gat aag ggt gcc acg cta acg atc aag aag gaa gca ttt cca gcc gag       3378
Asp Lys Gly Ala Thr Leu Thr Ile Lys Lys Glu Ala Phe Pro Ala Glu
        605                 610                 615 tca aaa agc gtc att att gga tgc aca ggg gga tcg cct gag aag cat       3426
Ser Lys Ser Val Ile Ile Gly Cys Thr Gly Gly Ser Pro Glu Lys His
    620                 625                 630 cac tgt acc gtg aaa ctg gag tgaaagcttg gcactggccg tcgttttaca          3477
His Cys Thr Val Lys Leu Glu
```

-continued

```
                635         640
acgtcgtgac tgggaaaacc ctggcgttac ccaacttaat cgccttgcag cacatccccc    3537
tttcgccagc tggcgtaata gcgaagaggc ccgcaccgat cgcccttccc aacagttgcg    3597
cagcctgaat ggcgaatggc agcttggctg ttttggcgga tgagataaga ttttcagcct    3657
gatacagatt aaatcagaac gcagaagcgg tctgataaaa cagaatttgc ctggcggcag    3717
tagcgcggtg gtcccacctg accccatgcc gaactcagaa gtgaaacgcc gtagcgccga    3777
tggtagtgtg gggtctcccc atgcgagagt agggaactgc caggcatcaa ataaaacgaa    3837
aggctcagtc gaaagactgg gcctttcgtt ttatctgttg tttgtcggtg aacgctctcc    3897
tgagtaggac aaatccgccg ggagcggatt tgaacgttgc gaagcaacgg cccggagggt    3957
ggcgggcagg acgcccgcca taaactgcca ggcatcaaat taagcagaag gccatcctga    4017
cggatggcct ttttgcgttt ctacaaactc ttttgttta tttttctaaa tacattcaaa    4077
tatgtatccg ctcatgagac aataaccctg ataaatgctt caataatatt gaaaaggaa    4137
gagtatgagt attcaacatt tccgtgtcgc ccttattccc ttttttgcgg cattttgcct    4197
tcctgttttt gctcacccag aaacgctggt gaaagtaaaa gatgctgaag atcagttggg    4257
tgcacgagtg ggttacatcg aactggatct caacagcggt aagatccttg agagttttcg    4317
ccccgaagaa cgttctccaa tgatgagcac ttttaaagtt ctgctatgtg gcgcggtatt    4377
atcccgtgtt gacgccgggc aagagcaact cggtcgccgc atacactatt ctcagaatga    4437
cttggttgag tactcaccag tcacagaaaa gcatcttacg gatggcatga cagtaagaga    4497
attatgcagt gctgccataa ccatgagtga taacactgcg gccaacttac ttctgacaac    4557
gatcggagga ccgaaggagc taaccgcttt tttgcacaac atgggggatc atgtaactcg    4617
ccttgatcgt tgggaaccgg agctgaatga agccatacca aacgacgagc gtgacaccac    4677
gatgcctgta gcaatggcaa caacgttgcg caaactatta actggcgaac tacttactct    4737
agcttcccgg caacaattaa tagactggat ggaggcggat aaagttgcag gaccacttct    4797
gcgctcggcc cttccggctg gctggtttat tgctgataaa tctggagccg gtgagcgtgg    4857
gtctcgcggt atcattgcag cactggggcc agatggtaag ccctcccgta tcgtagttat    4917
ctacacgacg gggagtcagg caactatgga tgaacgaaat agacagatcg ctgagatagg    4977
tgcctcactg attaagcatt ggtaactgtc agaccaagtt tactcatata ctttagat     5037
tgatttaccc cggttgataa tcagaaaagc cccaaaaaca ggaagattgt ataagcaaat    5097
atttaaattg taaacgttaa tattttgtta aaattcgcgt taaattttg ttaaatcagc    5157
tcattttta accaataggc cgaaatcggc aaaatccctt ataaatcaaa agaatagacc    5217
gagatagggt tgagtgttgt tccagtttgg aacaagagtc cactattaaa gaacgtggac    5277
tccaacgtca aagggcgaaa aaccgtctat cagggcgatg gcccactacg tgaaccatca    5337
cccaaatcaa gttttttggg gtcgaggtgc cgtaaagcac taaatcggaa ccctaaaggg    5397
agcccccgat ttagagcttg acggggaaag ccggcgaacg tggcgagaaa ggaagggaag    5457
aaagcgaaag gagcgggcgc tagggcgctg gcaagtgtag cggtcacgct gcgcgtaacc    5517
accacacccg ccgcgcttaa tgcgccgcta caggcgcgt aaaaggatct aggtgaagat    5577
cctttttgat aatctcatga ccaaaatccc ttaacgtgag ttttcgttcc actgagcgtc    5637
agaccccgta gaaaagatca aaggatcttc ttgagatcct ttttttctgc gcgtaatctg    5697
ctgcttgcaa acaaaaaaac caccgctacc agcggtggtt tgtttgccgg atcaagagct    5757
accaactctt tttccgaagg taactggctt cagcagagcg cagataccaa atactgtcct    5817
```

-continued

```
tctagtgtag ccgtagttag gccaccactt caagaactct gtagcaccgc ctacatacct   5877
cgctctgcta atcctgttac cagtggctgc tgccagtggc gataagtcgt gtcttaccgg   5937
gttggactca agacgatagt taccggataa ggcgcagcgg tcgggctgaa cggggggttc   5997
gtgcacacag cccagcttgg agcgaacgac ctacaccgaa ctgagatacc tacagcgtga   6057
gctatgagaa agcgccacgc ttcccgaagg gagaaaggcg gacaggtatc cggtaagcgg   6117
cagggtcgga acaggagagc gcacgaggga gcttccaggg ggaaacgcct ggtatcttta   6177
tagtcctgtc gggtttcgcc acctctgact tgagcgtcga tttttgtgat gctcgtcagg   6237
ggggcggagc ctatggaaaa acgccagcaa cgcggccttt ttacggttcc tggccttttg   6297
ctggcctttt gctcacatgt tctttcctgc gttatcccct gattctgtgg ataaccgtat   6357
taccgccttt gagtgagctg ataccgctcg ccgcagccga acgaccgagc gcagcgagtc   6417
agtgagcgag gaagcggaag agcgcctgat gcggtatttt ctccttacgc atctgtgcgg   6477
tatttcacac cgcatatatg gtgcactctc agtacaatct gctctgatgc cgcatagtta   6537
agccagtata cactccgcta tcgctacgtg actgggtcat ggctgcgccc cgacacccgc   6597
caacacccgc tgacgcgccc tgacgggctt gtctgctccc ggcatccgct tacagacaag   6657
ctgtgaccgt ctccgggagc tgcatgtgtc agaggttttc accgtcatca ccgaaacgcg   6717
cgaggcagct gcggtaaagc tcatcagcgt ggtcgtgcag cgattcacag atgtctgcct   6777
gttcatccgc gtccagctcg ttgagtttct ccagaagcgt taatgtctgg cttctgataa   6837
agcgggccat gttaagggcg gtttttttcct gtttggtcac tgatgcctcc gtgtaagggg   6897
gatttctgtt catgggggta atgataccga tgaaacgaga gaggatgctc acgatacggg   6957
ttactgatga tgaacatgcc cggttactgg aacgttgtga gggtaaacaa ctggcggtat   7017
ggatgcggcg ggaccagaga aaaatcactc agggtcaatg ccagcgcttc gttaatacag   7077
atgtaggtgt tccacagggt agccagcagc atcctgcgat gcagatccgg aacataatgg   7137
tgcagggcgc tgacttccgc gtttccagac tttacgaaac acggaaaccg aagaccattc   7197
atgttgttgc tcaggtcgca gacgttttgc agcagcagtc gcttcacgtt cgctcgcgta   7257
tcggtgattc attctgctaa ccagtaaggc aaccccgcca gcctagccgg gtcctcaacg   7317
acaggagcac gatcatgcgc acccgtggcc aggacccaac gctgcccgaa att          7370
```

```

<210> SEQ ID NO 21
<211> LENGTH: 640
<212> TYPE: PRT
<213> ORGANISM: Toxoplasma gondii
<220> FEATURE:
<223> OTHER INFORMATION: pMBP-c2X-Toxo30del3C (52-300aa)

<400> SEQUENCE: 21

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
```

```
                85                  90                  95
Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
                115                 120                 125

Thr Trp Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
                275                 280                 285

Glu Gly Leu Glu Ala Val Asn Lys Asp Lys Pro Leu Gly Ala Val Ala
                290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Asn Leu Gly Ile
        370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
                420                 425                 430

Leu Ala Tyr Ser Pro Asn Arg Gln Ile Cys Pro Ala Gly Thr Thr Ser
                435                 440                 445

Ser Cys Thr Ser Lys Ala Val Thr Leu Ser Ser Leu Ile Pro Glu Ala
        450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
                500                 505                 510
```

```
Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
        530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
        610                 615                 620

Cys Thr Gly Gly Ser Pro Glu Lys His His Cys Thr Val Lys Leu Glu
625                 630                 635                 640

<210> SEQ ID NO 22
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: Toxo30del3C (52-300aa)

<400> SEQUENCE: 22 ctt gtt gcc aat caa gtt gtc acc tgc cca gat aaa aaa tcg aca gcc    48
Leu Val Ala Asn Gln Val Val Thr Cys Pro Asp Lys Lys Ser Thr Ala
1               5                   10                  15 gcg gtc att ctc aca ccg acg gag aac cac ttc act ctc aag tgc cct    96
Ala Val Ile Leu Thr Pro Thr Glu Asn His Phe Thr Leu Lys Cys Pro
            20                  25                  30 aaa aca gcg ctc aca gag cct ccc act ctt gcg tac tca ccc aac agg   144
Lys Thr Ala Leu Thr Glu Pro Pro Thr Leu Ala Tyr Ser Pro Asn Arg
        35                  40                  45 caa atc tgc cca gcg ggt act aca agt agc tgt aca tca aag gct gta   192
Gln Ile Cys Pro Ala Gly Thr Thr Ser Ser Cys Thr Ser Lys Ala Val
    50                  55                  60 aca ttg agc tcc ttg att cct gaa gca gaa gat agc tgg tgg acg ggg   240
Thr Leu Ser Ser Leu Ile Pro Glu Ala Glu Asp Ser Trp Trp Thr Gly
65                  70                  75                  80 gat tct gct agt ctc gac acg gca ggc atc aaa ctc aca gtt cca atc   288
Asp Ser Ala Ser Leu Asp Thr Ala Gly Ile Lys Leu Thr Val Pro Ile
                85                  90                  95 gag aag ttc ccc gtg aca acg cag acg ttt gtg gtc ggt tgc atc aag   336
Glu Lys Phe Pro Val Thr Thr Gln Thr Phe Val Val Gly Cys Ile Lys
            100                 105                 110 gga gac gac gca cag agt tgt atg gtc aca gtg aca gta caa gcc aga   384
Gly Asp Asp Ala Gln Ser Cys Met Val Thr Val Thr Val Gln Ala Arg
        115                 120                 125 gcc tca tcg gtc gtc aat aat gtc gca agg tgc tcc tac ggt gca gac   432
Ala Ser Ser Val Val Asn Asn Val Ala Arg Cys Ser Tyr Gly Ala Asp
    130                 135                 140 agc act ctt ggt cct gtc aag ttg tct gcg gaa gga ccc act aca atg   480
Ser Thr Leu Gly Pro Val Lys Leu Ser Ala Glu Gly Pro Thr Thr Met
145                 150                 155                 160 acc ctc gtg tgc ggg aaa gat gga gtc aaa gtt cct caa gac aac aat   528
Thr Leu Val Cys Gly Lys Asp Gly Val Lys Val Pro Gln Asp Asn Asn
```

```
                165                 170                 175
cag tac tgt tcc ggg acg acg ctg act ggt tgc aac gag aaa tcg ttc       576
Gln Tyr Cys Ser Gly Thr Thr Leu Thr Gly Cys Asn Glu Lys Ser Phe
            180                 185                 190 aaa gat att ttg cca aaa tta act gag aac ccg tgg cag ggt aac gct       624
Lys Asp Ile Leu Pro Lys Leu Thr Glu Asn Pro Trp Gln Gly Asn Ala
            195                 200                 205 tcg agt gat aag ggt gcc acg cta acg atc aag aag gaa gca ttt cca       672
Ser Ser Asp Lys Gly Ala Thr Leu Thr Ile Lys Lys Glu Ala Phe Pro
        210                 215                 220 gcc gag tca aaa agc gtc att att gga tgc aca ggg gga tcg cct gag       720
Ala Glu Ser Lys Ser Val Ile Ile Gly Cys Thr Gly Gly Ser Pro Glu
225                 230                 235                 240 aag cat cac tgt acc gtg aaa ctg gag                                   747
Lys His His Cys Thr Val Lys Leu Glu
                245
```

<210> SEQ ID NO 23
<211> LENGTH: 249
<212> TYPE: PRT
<213> ORGANISM: Toxoplasma gondii
<220> FEATURE:
<223> OTHER INFORMATION: Toxo30del3C (52-300aa)

<400> SEQUENCE: 23

```
Leu Val Ala Asn Gln Val Val Thr Cys Pro Asp Lys Lys Ser Thr Ala
1               5                   10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Cys Thr Gly Gly Ser Pro Glu
225                 230                 235                 240

Lys His His Cys Thr Val Lys Leu Glu
                245
```

-continued

<210> SEQ ID NO 24
<211> LENGTH: 38
<212> TYPE: DNA
<213> ORGANISM: Artificial Sequence
<220> FEATURE:
<223> OTHER INFORMATION: Antisense Primer

<400> SEQUENCE: 24
caggtcaagc tttcagtgat gcttctcagg cgatcccc 38

<210> SEQ ID NO 25
<211> LENGTH: 7352
<212> TYPE: DNA
<213> ORGANISM: Toxoplasma gondii
<220> FEATURE:
<221> NAME/KEY: CDS
<222> LOCATION: (1528)...(3429)
<223> OTHER INFORMATION: pMBP-c2X-ToxoP30del4C (52-294aa)

<400> SEQUENCE: 25
ccgacaccat cgaatggtgc aaaacctttc gcggtatggc atgatagcgc ccggaagaga 60
gtcaattcag ggtggtgaat gtgaaaccag taacgttata cgatgtcgca gagtatgccg 120
gtgtctctta tcagaccgtt tcccgcgtgg tgaaccaggc cagccacgtt tctgcgaaaa 180
cgcgggaaaa agtggaagcg gcgatggcgg agctgaatta cattcccaac cgcgtggcac 240
aacaactggc gggcaaacag tcgttgctga ttggcgttgc cacctccagt ctggccctgc 300
acgcgccgtc gcaaattgtc gcggcgatta aatctcgcgc cgatcaactg ggtgccagcg 360
tggtggtgtc gatggtagaa cgaagcggcg tcgaagcctg taaagcggcg gtgcacaatc 420
ttctcgcgca acgcgtcagt gggctgatca ttaactatcc gctggatgac caggatgcca 480
ttgctgtgga agctgcctgc actaatgttc cggcgttatt tcttgatgtc tctgaccaga 540
cacccatcaa cagtattatt ttctcccatg aagacggtac gcgactgggc gtggagcatc 600
tggtcgcatt gggtcaccag caaatcgcgc tgttagcggg cccattaagt tctgtctcgg 660
cgcgtctgcg tctggctggc tggcataaat atctcactcg caatcaaatt cagccgatag 720
cggaacggga aggcgactgg agtgccatgt ccggttttca acaaaccatg caaatgctga 780
atgagggcat cgttcccact gcgatgctgg ttgccaacga tcagatggcg ctgggcgcaa 840
tgcgcgccat taccgagtcc gggctgcgcg ttggtgcgga tatctcggta gtgggatacg 900
acgataccga agacagctca tgttatatcc cgccgttaac caccatcaaa caggattttc 960
gcctgctggg gcaaaccagc gtggaccgct tgctgcaact ctctcagggc caggcggtga 1020
agggcaatca gctgttgccc gtctcactgg tgaaaagaaa aaccaccctg gcgcccaata 1080
cgcaaaccgc ctctccccgc gcgttggccg attcattaat gcagctggca cgacaggttt 1140
cccgactgga aagcgggcag tgagcgcaac gcaattaatg taagttagct cactcattag 1200
gcacaattct catgtttgac agcttatcat cgactgcacg gtgcaccaat gcttctggcg 1260
tcaggcagcc atcggaagct gtggtatggc tgtgcaggtc gtaaatcact gcataattcg 1320
tgtcgctcaa ggcgcactcc cgttctggat aatgtttttt gcgccgacat cataacggtt 1380
ctggcaaata ttctgaaatg agctgttgac aattaatcat cggctcgtat aatgtgtgga 1440
attgtgagcg gataacaatt tcacacagga aacagccagt ccgtttaggt gttttcacga 1500
gcacttcacc aacaaggacc atagcat atg aaa atc gaa gaa ggt aaa ctg gta 1554
Met Lys Ile Glu Glu Gly Lys Leu Val
1 5

-continued

```
atc tgg att aac ggc gat aaa ggc tat aac ggt ctc gct gaa gtc ggt    1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg    1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc    1698
Asp Lys Leu Glu Glu Lys Phe Pro Gln Val Ala Ala Thr Gly Asp Gly
         45                  50                  55 cct gac att atc ttc tgg gca cac gac cgc ttt ggt ggc tac gct caa    1746
Pro Asp Ile Ile Phe Trp Ala His Asp Arg Phe Gly Gly Tyr Ala Gln
     60                  65                  70 tct ggc ctg ttg gct gaa atc acc ccg gac aaa gcg ttc cag gac aag    1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att    1842
Leu Tyr Pro Phe Thr Trp Asp Ala Val Arg Tyr Asn Gly Lys Leu Ile
 90                  95                  100                 105 gct tac ccg atc gct gtt gaa gcg tta tcg ctg att tat aac aaa gat    1890
Ala Tyr Pro Ile Ala Val Glu Ala Leu Ser Leu Ile Tyr Asn Lys Asp
             110                 115                 120 ctg ctg ccg aac ccg cca aaa acc tgg gaa gag atc ccg gcg ctg gat    1938
Leu Leu Pro Asn Pro Pro Lys Thr Trp Glu Glu Ile Pro Ala Leu Asp
         125                 130                 135 aaa gaa ctg aaa gcg aaa ggt aag agc gcg ctg atg ttc aac ctg caa    1986
Lys Glu Leu Lys Ala Lys Gly Lys Ser Ala Leu Met Phe Asn Leu Gln
     140                 145                 150 gaa ccg tac ttc acc tgg ccg ctg att gct gct gac ggg ggt tat gcg    2034
Glu Pro Tyr Phe Thr Trp Pro Leu Ile Ala Ala Asp Gly Gly Tyr Ala
 155                 160                 165 ttc aag tat gaa aac ggc aag tac gac att aaa gac gtg ggc gtg gat    2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa    2130
Asn Ala Gly Ala Lys Ala Gly Leu Thr Phe Leu Val Asp Leu Ile Lys
             190                 195                 200 aac aaa cac atg aat gca gac acc gat tac tcc atc gca gaa gct gcc    2178
Asn Lys His Met Asn Ala Asp Thr Asp Tyr Ser Ile Ala Glu Ala Ala
         205                 210                 215 ttt aat aaa ggc gaa aca gcg atg acc atc aac ggc ccg tgg gca tgg    2226
Phe Asn Lys Gly Glu Thr Ala Met Thr Ile Asn Gly Pro Trp Ala Trp
     220                 225                 230 tcc aac atc gac acc agc aaa gtg aat tat ggt gta acg gta ctg ccg    2274
Ser Asn Ile Asp Thr Ser Lys Val Asn Tyr Gly Val Thr Val Leu Pro
 235                 240                 245 acc ttc aag ggt caa cca tcc aaa ccg ttc gtt ggc gtg ctg agc gca    2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc    2370
Gly Ile Asn Ala Ala Ser Pro Asn Lys Glu Leu Ala Lys Glu Phe Leu
             270                 275                 280 gaa aac tat ctg ctg act gat gaa ggt ctg gaa gcg gtt aat aaa gac    2418
Glu Asn Tyr Leu Leu Thr Asp Glu Gly Leu Glu Ala Val Asn Lys Asp
         285                 290                 295 aaa ccg ctg ggt gcc gta gcg ctg aag tct tac gag gaa gag ttg gcg    2466
Lys Pro Leu Gly Ala Val Ala Leu Lys Ser Tyr Glu Glu Glu Leu Ala
     300                 305                 310 aaa gat cca cgt att gcc gcc act atg gaa aac gcc cag aaa ggt gaa    2514
Lys Asp Pro Arg Ile Ala Ala Thr Met Glu Asn Ala Gln Lys Gly Glu
 315                 320                 325
```

```
atc atg ccg aac atc ccg cag atg tcc gct ttc tgg tat gcc gtg cgt   2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc   2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac   2658
Leu Lys Asp Ala Gln Thr Asn Ser Ser Ser Asn Asn Asn Asn Asn Asn
        365                 370                 375 aat aac aac aac ctc ggg atc gag gga agg att tca gaa ttc ctt gtt   2706
Asn Asn Asn Asn Leu Gly Ile Glu Gly Arg Ile Ser Glu Phe Leu Val
        380                 385                 390 gcc aat caa gtt gtc acc tgc cca gat aaa aaa tcg aca gcc gcg gtc   2754
Ala Asn Gln Val Val Thr Cys Pro Asp Lys Lys Ser Thr Ala Ala Val
        395                 400                 405 att ctc aca ccg acg gag aac cac ttc act ctc aag tgc cct aaa aca   2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc   2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg   2898
Cys Pro Ala Gly Thr Thr Ser Ser Cys Thr Ser Lys Ala Val Thr Leu
                445                 450                 455 agc tcc ttg att cct gaa gca gaa gat agc tgg tgg acg ggg gat tct   2946
Ser Ser Leu Ile Pro Glu Ala Glu Asp Ser Trp Trp Thr Gly Asp Ser
        460                 465                 470 gct agt ctc gac acg gca ggc atc aaa ctc aca gtt cca atc gag aag   2994
Ala Ser Leu Asp Thr Ala Gly Ile Lys Leu Thr Val Pro Ile Glu Lys
475                 480                 485 ttc ccc gtg aca acg cag acg ttt gtg gtc ggt tgc atc aag gga gac   3042
Phe Pro Val Thr Thr Gln Thr Phe Val Val Gly Cys Ile Lys Gly Asp
490                 495                 500                 505 gac gca cag agt tgt atg gtc aca gtg aca gta caa gcc aga gcc tca   3090
Asp Ala Gln Ser Cys Met Val Thr Val Thr Val Gln Ala Arg Ala Ser
                510                 515                 520 tcg gtc gtc aat aat gtc gca agg tgc tcc tac ggt gca gac agc act   3138
Ser Val Val Asn Asn Val Ala Arg Cys Ser Tyr Gly Ala Asp Ser Thr
                525                 530                 535 ctt ggt cct gtc aag ttg tct gcg gaa gga ccc act aca atg acc ctc   3186
Leu Gly Pro Val Lys Leu Ser Ala Glu Gly Pro Thr Thr Met Thr Leu
        540                 545                 550 gtg tgc ggg aaa gat gga gtc aaa gtt cct caa gac aac aat cag tac   3234
Val Cys Gly Lys Asp Gly Val Lys Val Pro Gln Asp Asn Asn Gln Tyr
555                 560                 565 tgt tcc ggg acg acg ctg act ggt tgc aac gag aaa tcg ttc aaa gat   3282
Cys Ser Gly Thr Thr Leu Thr Gly Cys Asn Glu Lys Ser Phe Lys Asp
570                 575                 580                 585 att ttg cca aaa tta act gag aac ccg tgg cag ggt aac gct tcg agt   3330
Ile Leu Pro Lys Leu Thr Glu Asn Pro Trp Gln Gly Asn Ala Ser Ser
                590                 595                 600 gat aag ggt gcc acg cta acg atc aag aag gaa gca ttt cca gcc gag   3378
Asp Lys Gly Ala Thr Leu Thr Ile Lys Lys Glu Ala Phe Pro Ala Glu
                605                 610                 615 tca aaa agc gtc att att gga tgc aca ggg gga tcg cct gag aag cat   3426
Ser Lys Ser Val Ile Ile Gly Cys Thr Gly Gly Ser Pro Glu Lys His
        620                 625                 630 cac tgaaagcttg gcactggccg tcgttttaca acgtcgtgac tgggaaaacc        3479
His
```

```
ctggcgttac ccaacttaat cgccttgcag cacatccccc tttcgccagc tggcgtaata    3539
gcgaagaggc ccgcaccgat cgcccttccc aacagttgcg cagcctgaat ggcgaatggc    3599
agcttggctg ttttggcgga tgagataaga ttttcagcct gatacagatt aaatcagaac    3659
gcagaagcgg tctgataaaa cagaatttgc ctggcggcag tagcgcggtg gtcccacctg    3719
accccatgcc gaactcagaa gtgaaacgcc gtagcgccga tggtagtgtg gggtctcccc    3779
atgcgagagt agggaactgc caggcatcaa ataaaacgaa aggctcagtc gaaagactgg    3839
gcctttcgtt ttatctgttg tttgtcggtg aacgctctcc tgagtaggac aaatccgccg    3899
ggagcggatt tgaacgttgc gaagcaacgg cccggagggt ggcgggcagg acgcccgcca    3959
taaactgcca ggcatcaaat taagcagaag gccatcctga cggatggcct ttttgcgttt    4019
ctacaaactc ttttttgttta tttttctaaa tacattcaaa tatgtatccg ctcatgagac    4079
aataaccctg ataaatgctt caataatatt gaaaaaggaa gagtatgagt attcaacatt    4139
tccgtgtcgc ccttattccc ttttttgcgg cattttgcct tcctgttttt gctcacccag    4199
aaacgctggt gaaagtaaaa gatgctgaag atcagttggg tgcacgagtg gttacatcg    4259 aactggatct caacagcggt aagatccttg agagttttcg ccccgaagaa cgttctccaa    4319
tgatgagcac ttttaaagtt ctgctatgtg gcgcggtatt atcccgtgtt gacgccgggc    4379
aagagcaact cggtcgccgc atacactatt ctcagaatga cttggttgag tactcaccag    4439
tcacagaaaa gcatcttacg gatggcatga cagtaagaga attatgcagt gctgccataa    4499
ccatgagtga taacactgcg gccaacttac ttctgacaac gatcggagga ccgaaggagc    4559
taaccgcttt tttgcacaac atgggggatc atgtaactcg ccttgatcgt tgggaaccgg    4619
agctgaatga agccatacca aacgacgagc gtgacaccac gatgcctgta gcaatggcaa    4679
caacgttgcg caaactatta actggcgaac tacttactct agcttcccgg caacaattaa    4739
tagactggat ggaggcggat aaagttgcag gaccacttct gcgctcggcc cttccggctg    4799
gctggtttat tgctgataaa tctggagccg gtgagcgtgg gtctcgcggt atcattgcag    4859
cactggggcc agatggtaag ccctcccgta tcgtagttat ctacacgacg gggagtcagg    4919
caactatgga tgaacgaaat agacagatcg ctgagatagg tgcctcactg attaagcatt    4979
ggtaactgtc agaccaagtt tactcatata ctttagat tgatttaccc cggttgataa    5039
tcagaaaagc cccaaaaaca ggaagattgt ataagcaaat atttaaattg taaacgttaa    5099
tattttgtta aaattcgcgt taaattttg ttaaatcagc tcatttttta accaataggc    5159
cgaaatcggc aaaatccctt ataaatcaaa agaatagacc gagatagggt tgagtgttgt    5219
tccagtttgg aacaagagtc cactattaaa gaacgtggac tccaacgtca aagggcgaaa    5279
aaccgtctat cagggcgatg gcccactacg tgaaccatca cccaaatcaa gttttttggg    5339
gtcgaggtgc cgtaaagcac taaatcggaa ccctaaaggg agcccccgat ttagagcttg    5399
acggggaaag ccggcgaacg tggcgagaaa ggaagggaag aaagcgaaag gagcgggcgc    5459
tagggcgctg gcaagtgtag cggtcacgct gcgcgtaacc accacacccg ccgcgcttaa    5519
tgcgccgcta cagggcgcgt aaaaggatct aggtgaagat ccttttgat aatctcatga    5579 ccaaaatccc ttaacgtgag ttttcgttcc actgagcgtc agaccccgta gaaaagatca    5639
aaggatcttc ttgagatcct ttttttctgc gcgtaatctg ctgcttgcaa acaaaaaaac    5699
caccgctacc agcggtggtt tgtttgccgg atcaagagct accaactctt tttccgaagg    5759
taactggctt cagcagagcg cagataccaa atactgtcct tctagtgtag ccgtagttag    5819
```

-continued

```
gccaccactt caagaactct gtagcaccgc ctacatacct cgctctgcta atcctgttac   5879
cagtggctgc tgccagtggc gataagtcgt gtcttaccgg gttggactca agacgatagt   5939
taccggataa ggcgcagcgg tcgggctgaa cggggggttc gtgcacacag cccagcttgg   5999
agcgaacgac ctacaccgaa ctgagatacc tacagcgtga gctatgagaa agcgccacgc   6059
ttcccgaagg gagaaaggcg gacaggtatc cggtaagcgg cagggtcgga acaggagagc   6119
gcacgaggga gcttccaggg ggaaacgcct ggtatcttta tagtcctgtc gggtttcgcc   6179
acctctgact tgagcgtcga tttttgtgat gctcgtcagg ggggcggagc ctatggaaaa   6239
acgccagcaa cgcggccttt ttacggttcc tggccttttg ctggcctttt gctcacatgt   6299
tctttcctgc gttatcccct gattctgtgg ataaccgtat taccgccttt gagtgagctg   6359
ataccgctcg ccgcagccga acgaccgagc gcagcgagtc agtgagcgag gaagcggaag   6419
agcgcctgat gcggtatttt ctccttacgc atctgtgcgg tatttcacac cgcatatatg   6479
gtgcactctc agtacaatct gctctgatgc cgcatagtta agccagtata cactccgcta   6539
tcgctacgtg actgggtcat ggctgcgccc cgacacccgc caacacccgc tgacgcgccc   6599
tgacgggctt gtctgctccc ggcatccgct tacagacaag ctgtgaccgt ctccgggagc   6659
tgcatgtgtc agaggttttc accgtcatca ccgaaacgcg cgaggcagct gcggtaaagc   6719
tcatcagcgt ggtcgtgcag cgattcacag atgtctgcct gttcatccgc gtccagctcg   6779
ttgagtttct ccagaagcgt taatgtctgg cttctgataa agcgggccat gttaagggcg   6839 gtttttttcct gtttggtcac tgatgcctcc gtgtaagggg gatttctgtt catgggggta   6899
atgataccga tgaaacgaga gaggatgctc acgatacggg ttactgatga tgaacatgcc   6959
cggttactgg aacgttgtga gggtaaacaa ctggcggtat ggatgcggcg ggaccagaga   7019
aaaatcactc agggtcaatg ccagcgcttc gttaatacag atgtaggtgt tccacagggt   7079
agccagcagc atcctgcgat gcagatccgg aacataatgg tgcagggcgc tgacttccgc   7139
gtttccagac tttacgaaac acggaaaccg aagaccattc atgttgttgc tcaggtcgca   7199
gacgttttgc agcagcagtc gcttcacgtt cgctcgcgta tcggtgattc attctgctaa   7259
ccagtaaggc aaccccgcca gcctagccgg gtcctcaacg acaggagcac gatcatgcgc   7319
acccgtggcc aggacccaac gctgcccgaa att                                 7352

<210> SEQ ID NO 26
<211> LENGTH: 634
<212> TYPE: PRT
<213> ORGANISM: Toxoplasma gondii
<220> FEATURE:
<223> OTHER INFORMATION: pMBP-c2X-ToxoP30del4C (52-294aa)

<400> SEQUENCE: 26

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95
```

-continued

```
Ala Val Arg Tyr Asn Gly Lys Leu Ile Ala Tyr Pro Ile Ala Val Glu
            100                 105                 110
Ala Leu Ser Leu Ile Tyr Asn Lys Asp Leu Leu Pro Asn Pro Pro Lys
            115                 120                 125
Thr Trp Glu Glu Ile Pro Ala Leu Asp Lys Glu Leu Lys Ala Lys Gly
            130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
            180                 185                 190
Leu Thr Phe Leu Val Asp Leu Ile Lys Asn Lys His Met Asn Ala Asp
            195                 200                 205
Thr Asp Tyr Ser Ile Ala Glu Ala Ala Phe Asn Lys Gly Glu Thr Ala
            210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
            260                 265                 270
Asn Lys Glu Leu Ala Lys Glu Phe Leu Glu Asn Tyr Leu Leu Thr Asp
            275                 280                 285
Glu Gly Leu Glu Ala Val Asn Lys Asp Lys Pro Leu Gly Ala Val Ala
            290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Asn
            355                 360                 365
Ser Ser Ser Asn Asn Asn Asn Asn Asn Asn Asn Asn Leu Gly Ile
            370                 375                 380
Glu Gly Arg Ile Ser Glu Phe Leu Val Ala Asn Gln Val Val Thr Cys
385                 390                 395                 400
Pro Asp Lys Lys Ser Thr Ala Ala Val Ile Leu Thr Pro Thr Glu Asn
                405                 410                 415
His Phe Thr Leu Lys Cys Pro Lys Thr Ala Leu Thr Glu Pro Pro Thr
            420                 425                 430
Leu Ala Tyr Ser Pro Asn Arg Gln Ile Cys Pro Ala Gly Thr Thr Ser
            435                 440                 445
Ser Cys Thr Ser Lys Ala Val Thr Leu Ser Ser Leu Ile Pro Glu Ala
            450                 455                 460
Glu Asp Ser Trp Trp Thr Gly Asp Ser Ala Ser Leu Asp Thr Ala Gly
465                 470                 475                 480
Ile Lys Leu Thr Val Pro Ile Glu Lys Phe Pro Val Thr Thr Gln Thr
                485                 490                 495
Phe Val Val Gly Cys Ile Lys Gly Asp Asp Ala Gln Ser Cys Met Val
            500                 505                 510
```

```
Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
        530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
                580                 585                 590

Asn Pro Trp Gln Gly Asn Ala Ser Ser Asp Lys Gly Ala Thr Leu Thr
                595                 600                 605

Ile Lys Lys Glu Ala Phe Pro Ala Glu Ser Lys Ser Val Ile Ile Gly
        610                 615                 620

Cys Thr Gly Gly Ser Pro Glu Lys His His
625                 630

<210> SEQ ID NO 27
<211> LENGTH: 729
<212> TYPE: DNA
<213> ORGANISM: Toxoplasma gondii
<220> FEATURE:
<221> NAME/KEY: CDS
<222> LOCATION: (1)...(729)
<223> OTHER INFORMATION: ToxoP30del4C (52-294aa)

<400> SEQUENCE: 27 ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
1               5                   10                  15 gcg gtc att ctc aca ccg acg gag aac cac ttc act ctc aag tgc cct      96
Ala Val Ile Leu Thr Pro Thr Glu Asn His Phe Thr Leu Lys Cys Pro
                20                  25                  30 aaa aca gcg ctc aca gag cct ccc act ctt gcg tac tca ccc aac agg     144
Lys Thr Ala Leu Thr Glu Pro Pro Thr Leu Ala Tyr Ser Pro Asn Arg
            35                  40                  45 caa atc tgc cca gcg ggt act aca agt agc tgt aca tca aag gct gta     192
Gln Ile Cys Pro Ala Gly Thr Thr Ser Ser Cys Thr Ser Lys Ala Val
        50                  55                  60 aca ttg agc tcc ttg att cct gaa gca gaa gat agc tgg tgg acg ggg     240
Thr Leu Ser Ser Leu Ile Pro Glu Ala Glu Asp Ser Trp Trp Thr Gly
65                  70                  75                  80 gat tct gct agt ctc gac acg gca ggc atc aaa ctc aca gtt cca atc     288
Asp Ser Ala Ser Leu Asp Thr Ala Gly Ile Lys Leu Thr Val Pro Ile
                85                  90                  95 gag aag ttc ccc gtg aca acg cag acg ttt gtg gtc ggt tgc atc aag     336
Glu Lys Phe Pro Val Thr Thr Gln Thr Phe Val Val Gly Cys Ile Lys
                100                 105                 110 gga gac gac gca cag agt tgt atg gtc aca gtg aca gta caa gcc aga     384
Gly Asp Asp Ala Gln Ser Cys Met Val Thr Val Thr Val Gln Ala Arg
            115                 120                 125 gcc tca tcg gtc gtc aat aat gtc gca agg tgc tcc tac ggt gca gac     432
Ala Ser Ser Val Val Asn Asn Val Ala Arg Cys Ser Tyr Gly Ala Asp
        130                 135                 140 agc act ctt ggt cct gtc aag ttg tct gcg gaa gga ccc act aca atg     480
Ser Thr Leu Gly Pro Val Lys Leu Ser Ala Glu Gly Pro Thr Thr Met
145                 150                 155                 160 acc ctc gtg tgc ggg aaa gat gga gtc aaa gtt cct caa gac aac aat     528
Thr Leu Val Cys Gly Lys Asp Gly Val Lys Val Pro Gln Asp Asn Asn
                165                 170                 175
```

-continued

```
cag tac tgt tcc ggg acg acg ctg act ggt tgc aac gag aaa tcg ttc    576
Gln Tyr Cys Ser Gly Thr Thr Leu Thr Gly Cys Asn Glu Lys Ser Phe
        180                 185                 190 aaa gat att ttg cca aaa tta act gag aac ccg tgg cag ggt aac gct    624
Lys Asp Ile Leu Pro Lys Leu Thr Glu Asn Pro Trp Gln Gly Asn Ala
            195                 200                 205 tcg agt gat aag ggt gcc acg cta acg atc aag aag gaa gca ttt cca    672
Ser Ser Asp Lys Gly Ala Thr Leu Thr Ile Lys Lys Glu Ala Phe Pro
    210                 215                 220 gcc gag tca aaa agc gtc att att gga tgc aca ggg gga tcg cct gag    720
Ala Glu Ser Lys Ser Val Ile Ile Gly Cys Thr Gly Gly Ser Pro Glu
225                 230                 235                 240 aag cat cac                                                        729
Lys His His
```

<210> SEQ ID NO 28
<211> LENGTH: 243
<212> TYPE: PRT
<213> ORGANISM: Toxoplasma gondii
<220> FEATURE:
<223> OTHER INFORMATION: ToxoP30del4C (52-294aa)

<400> SEQUENCE: 28

```
Leu Val Ala Asn Gln Val Val Thr Cys Pro Asp Lys Lys Ser Thr Ala
  1               5                  10                  15

Ala Val Ile Leu Thr Pro Thr Glu Asn His Phe Thr Leu Lys Cys Pro
             20                  25                  30

Lys Thr Ala Leu Thr Glu Pro Pro Thr Leu Ala Tyr Ser Pro Asn Arg
         35                  40                  45

Gln Ile Cys Pro Ala Gly Thr Thr Ser Ser Cys Thr Ser Lys Ala Val
     50                  55                  60

Thr Leu Ser Ser Leu Ile Pro Glu Ala Glu Asp Ser Trp Trp Thr Gly
 65                  70                  75                  80

Asp Ser Ala Ser Leu Asp Thr Ala Gly Ile Lys Leu Thr Val Pro Ile
                 85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Cys Thr Gly Gly Ser Pro Glu
225                 230                 235                 240

Lys His His
```

<210> SEQ ID NO 29

-continued

```
<211> LENGTH: 30
<212> TYPE: DNA
<213> ORGANISM: Artificial Sequence
<220> FEATURE:
<223> OTHER INFORMATION: Sense Primer

<400> SEQUENCE: 29
ggcgaattcc ctaaaacagc gctcacagag                                      30

<210> SEQ ID NO 30
<211> LENGTH: 7259
<212> TYPE: DNA
<213> ORGANISM: Toxoplasma gondii
<220> FEATURE:
<221> NAME/KEY: CDS
<222> LOCATION: (1528)...(3336)
<223> OTHER INFORMATION: pMBP-c2X-ToxoP30del4del8 (83-294aa)
<400> SEQUENCE: 30
ccgacaccat cgaatggtgc aaaacctttc gcggtatggc atgatagcgc ccggaagaga     60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta aatctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa aaccaccctg gcgcccaata   1080
cgcaaaccgc ctctccccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgtttttt gcgccgacat cataacggtt   1380
ctggcaaata ttctgaaatg agctgttgac aattaatcat cggctcgtat aatgtgtgga   1440
attgtgagcg gataacaatt tcacacagga aacagccagt ccgtttaggt gttttcacga   1500
gcacttcacc aacaaggacc atagcat atg aaa atc gaa gaa ggt aaa ctg gta   1554
                              Met Lys Ile Glu Glu Gly Lys Leu Val
                               1               5 atc tgg att aac ggc gat aaa ggc tat aac ggt ctc gct gaa gtc ggt     1602
Ile Trp Ile Asn Gly Asp Lys Gly Tyr Asn Gly Leu Ala Glu Val Gly
 10                  15                  20                  25
```

-continued

```
aag aaa ttc gag aaa gat acc gga att aaa gtc acc gtt gag cat ccg      1650
Lys Lys Phe Glu Lys Asp Thr Gly Ile Lys Val Thr Val Glu His Pro
                30                  35                  40 gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
            45                  50                  55 cct gac att atc ttc tgg gca cac gac cgc ttt ggt ggc tac gct caa      1746
Pro Asp Ile Ile Phe Trp Ala His Asp Arg Phe Gly Gly Tyr Ala Gln
        60                  65                  70 tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
    75                  80                  85 ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
    155                 160                 165 ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc      2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg      2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
```

```
                   330             335             340             345
act gcg gtg atc aac gcc gcc agc ggt cgt cag act gtc gat gaa gcc    2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac    2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc cct aaa    2706
Asn Asn Asn Asn Leu Gly Ile Glu Gly Arg Ile Ser Glu Phe Pro Lys
        380                 385                 390 aca gcg ctc aca gag cct ccc act ctt gcg tac tca ccc aac agg caa    2754
Thr Ala Leu Thr Glu Pro Pro Thr Leu Ala Tyr Ser Pro Asn Arg Gln
    395                 400                 405 atc tgc cca gcg ggt act aca agt agc tgt aca tca aag gct gta aca    2802
Ile Cys Pro Ala Gly Thr Thr Ser Ser Cys Thr Ser Lys Ala Val Thr
410                 415                 420                 425 ttg agc tcc ttg att cct gaa gca gaa gat agc tgg tgg acg ggg gat    2850
Leu Ser Ser Leu Ile Pro Glu Ala Glu Asp Ser Trp Trp Thr Gly Asp
                430                 435                 440 tct gct agt ctc gac acg gca ggc atc aaa ctc aca gtt cca atc gag    2898
Ser Ala Ser Leu Asp Thr Ala Gly Ile Lys Leu Thr Val Pro Ile Glu
            445                 450                 455 aag ttc ccc gtg aca acg cag acg ttt gtg gtc ggt tgc atc aag gga    2946
Lys Phe Pro Val Thr Thr Gln Thr Phe Val Val Gly Cys Ile Lys Gly
        460                 465                 470 gac gac gca cag agt tgt atg gtc aca gtg aca gta caa gcc aga gcc    2994
Asp Asp Ala Gln Ser Cys Met Val Thr Val Thr Val Gln Ala Arg Ala
    475                 480                 485 tca tcg gtc gtc aat aat gtc gca agg tgc tcc tac ggt gca gac agc    3042
Ser Ser Val Val Asn Asn Val Ala Arg Cys Ser Tyr Gly Ala Asp Ser
490                 495                 500                 505 act ctt ggt cct gtc aag ttg tct gcg gaa gga ccc act aca atg acc    3090
Thr Leu Gly Pro Val Lys Leu Ser Ala Glu Gly Pro Thr Thr Met Thr
                510                 515                 520 ctc gtg tgc ggg aaa gat gga gtc aaa gtt cct caa gac aac aat cag    3138
Leu Val Cys Gly Lys Asp Gly Val Lys Val Pro Gln Asp Asn Asn Gln
            525                 530                 535 tac tgt tcc ggg acg acg ctg act ggt tgc aac gag aaa tcg ttc aaa    3186
Tyr Cys Ser Gly Thr Thr Leu Thr Gly Cys Asn Glu Lys Ser Phe Lys
        540                 545                 550 gat att ttg cca aaa tta act gag aac ccg tgg cag ggt aac gct tcg    3234
Asp Ile Leu Pro Lys Leu Thr Glu Asn Pro Trp Gln Gly Asn Ala Ser
    555                 560                 565 agt gat aag ggt gcc acg cta acg atc aag aag gaa gca ttt cca gcc    3282
Ser Asp Lys Gly Ala Thr Leu Thr Ile Lys Lys Glu Ala Phe Pro Ala
570                 575                 580                 585 gag tca aaa agc gtc att att gga tgc aca ggg gga tcg cct gag aag    3330
Glu Ser Lys Ser Val Ile Ile Gly Cys Thr Gly Gly Ser Pro Glu Lys
                590                 595                 600 cat cac tgaaagcttg gcactggccg tcgttttaca acgtcgtgac tgggaaaacc    3386
His His ctggcgttac ccaacttaat cgccttgcag cacatccccc tttcgccagc tggcgtaata    3446
gcgaagaggc ccgcaccgat cgcccttccc aacagttgcg cagcctgaat ggcgaatggc    3506
agcttggctg ttttggcgga tgagataaga ttttcagcct gatacagatt aaatcagaac    3566
gcagaagcgg tctgataaaa cagaatttgc ctggcggcag tagcgcggtg gtcccacctg    3626
accccatgcc gaactcagaa gtgaaacgcc gtagcgccga tggtagtgtg gggtctcccc    3686
```

-continued

```
atgcgagagt agggaactgc caggcatcaa ataaaacgaa aggctcagtc gaaagactgg    3746
gcctttcgtt ttatctgttg tttgtcggtg aacgctctcc tgagtaggac aaatccgccg    3806
ggagcggatt tgaacgttgc gaagcaacgg cccggagggt ggcgggcagg acgcccgcca    3866
taaactgcca ggcatcaaat taagcagaag gccatcctga cggatggcct ttttgcgttt    3926
ctacaaactc ttttttgttta ttttctaaa tacattcaaa tatgtatccg ctcatgagac    3986
aataaccctg ataaatgctt caataatatt gaaaaaggaa gagtatgagt attcaacatt    4046
tccgtgtcgc ccttattccc ttttttgcgg cattttgcct tcctgttttt gctcacccag    4106
aaaacgctggt gaaagtaaaa gatgctgaag atcagttggg tgcacgagtg ggttacatcg    4166
aactggatct caacagcggt aagatccttg agagttttcg ccccgaagaa cgttctccaa    4226
tgatgagcac ttttaaagtt ctgctatgtg gcgcggtatt atcccgtgtt gacgccgggc    4286
aagagcaact cggtcgccgc atacactatt ctcagaatga cttggttgag tactcaccag    4346
tcacagaaaa gcatcttacg gatggcatga cagtaagaga attatgcagt gctgccataa    4406
ccatgagtga taacactgcg gccaacttac ttctgacaac gatcggagga ccgaaggagc    4466
taaccgcttt tttgcacaac atgggggatc atgtaactcg ccttgatcgt tgggaaccgg    4526
agctgaatga agccatacca aacgacgagc gtgacaccac gatgcctgta gcaatggcaa    4586
caacgttgcg caaactatta actggcgaac tacttactct agcttcccgg caacaattaa    4646
tagactggat ggaggcggat aaagttgcag gaccacttct gcgctcggcc cttccggctg    4706
gctggttta t tgctgataaa tctggagccg gtgagcgtgg gtctcgcggt atcattgcag    4766
cactggggcc agatggtaag ccctcccgta tcgtagttat ctacacgacg gggagtcagg    4826
caactatgga tgaacgaaat agacagatcg ctgagatagg tgcctcactg attaagcatt    4886
ggtaactgtc agaccaagtt tactcatata tactttagat tgatttaccc cggttgataa    4946
tcagaaaagc cccaaaaaca ggaagattgt ataagcaaat atttaaattg taaacgttaa    5006
tattttgtta aaattcgcgt taaattttg ttaaatcagc tcatttttta accaataggc    5066
cgaaatcggc aaaatccctt ataaatcaaa agaatagacc gagataggt tgagtgttgt    5126
tccagtttgg aacaagagtc cactattaaa gaacgtggac tccaacgtca aagggcgaaa    5186
aaccgtctat cagggcgatg gcccactacg tgaaccatca cccaaatcaa gttttttggg    5246
gtcgaggtgc cgtaaagcac taaatcggaa ccctaaaggg agcccccgat ttagagcttg    5306
acggggaaag ccggcgaacg tggcgagaaa ggaagggaag aaagcgaaag gagcgggcgc    5366
tagggcgctg gcaagtgtag cggtcacgct gcgcgtaacc accacacccg ccgcgcttaa    5426
tgcgccgcta cagggcgcgt aaaggatct aggtgaagat ccttttttgat aatctcatga    5486
ccaaaatccc ttaacgtgag ttttcgttcc actgagcgtc agacccgta gaaaagatca    5546
aaggatcttc ttgagatcct ttttttctgc gcgtaatctg ctgcttgcaa acaaaaaaac    5606
caccgctacc agcggtggtt tgtttgccgg atcaagagct accaactctt tttccgaagg    5666
taactggctt cagcagagcg cagataccaa atactgtcct tctagtgtag ccgtagttag    5726
gccaccactt caagaactct gtagcaccgc ctacatacct cgctctgcta atcctgttac    5786
cagtggctgc tgccagtggc gataagtcgt gtcttaccgg gttggactca agacgatagt    5846
taccggataa ggcgcagcgg tcgggctgaa cggggggttc gtgcacacag cccagcttgg    5906
agcgaacgac ctacaccgaa ctgagatacc tacagcgtga gctatgagaa agcgccacgc    5966
ttcccgaagg gagaaaggcg gacaggtatc cggtaagcgg cagggtcgga acaggagagc    6026
gcacgaggga gcttccaggg ggaaacgcct ggtatcttta gtcctgtc gggtttcgcc    6086
```

```
acctctgact tgagcgtcga ttttgtgat gctcgtcagg ggggcggagc ctatggaaaa    6146
acgccagcaa cgcggccttt ttacggttcc tggccttttg ctggccttt gctcacatgt    6206 tctttcctgc gttatcccct gattctgtgg ataaccgtat taccgccttt gagtgagctg    6266
ataccgctcg ccgcagccga acgaccgagc gcagcgagtc agtgagcgag gaagcggaag    6326
agcgcctgat gcggtatttt ctccttacgc atctgtgcgg tatttcacac cgcatatatg    6386
gtgcactctc agtacaatct gctctgatgc cgcatagtta agccagtata cactccgcta    6446
tcgctacgtg actgggtcat ggctgcgccc cgacacccgc caacacccgc tgacgcgccc    6506
tgacgggctt gtctgctccc ggcatccgct tacagacaag ctgtgaccgt ctccgggagc    6566
tgcatgtgtc agaggttttc accgtcatca ccgaaacgcg cgaggcagct gcggtaaagc    6626
tcatcagcgt ggtcgtgcag cgattcacag atgtctgcct gttcatccgc gtccagctcg    6686
ttgagtttct ccagaagcgt taatgtctgg cttctgataa agcgggccat gttaagggcg    6746
gttttttcct gtttggtcac tgatgcctcc gtgtaagggg gatttctgtt catgggggta    6806
atgataccga tgaaacgaga gaggatgctc acgatacggg ttactgatga tgaacatgcc    6866
cggttactgg aacgttgtga gggtaaacaa ctggcggtat ggatgcggcg ggaccagaga    6926
aaaatcactc agggtcaatg ccagcgcttc gttaatacag atgtaggtgt tccacagggt    6986
agccagcagc atcctgcgat gcagatccgg aacataatgg tgcagggcgc tgacttccgc    7046
gtttccagac tttacgaaac acggaaaccg aagaccattc atgttgttgc tcaggtcgca    7106
gacgttttgc agcagcagtc gcttcacgtt cgctcgcgta tcggtgattc attctgctaa    7166
ccagtaaggc aaccccgcca gcctagccgg gtcctcaacg acaggagcac gatcatgcgc    7226
acccgtggcc aggacccaac gctgcccgaa att                                 7259
```

<210> SEQ ID NO 31
<211> LENGTH: 603
<212> TYPE: PRT
<213> ORGANISM: Toxoplasma gondii
<220> FEATURE:
<223> OTHER INFORMATION: pMBP-c2X-ToxoP30del4del8 (83-294aa)

<400> SEQUENCE: 31

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
               100                 105                 110

Ala Leu Ser Leu Ile Tyr Asn Lys Asp Leu Leu Pro Asn Pro Pro Lys
           115                 120                 125

Thr Trp Glu Glu Ile Pro Ala Leu Asp Lys Glu Leu Lys Ala Lys Gly
       130                 135                 140

Lys Ser Ala Leu Met Phe Asn Leu Gln Glu Pro Tyr Phe Thr Trp Pro
```

-continued

```
         145                 150                 155                 160
Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
                195                 200                 205

Thr Asp Tyr Ser Ile Ala Glu Ala Ala Phe Asn Lys Gly Glu Thr Ala
                210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
                275                 280                 285

Glu Gly Leu Glu Ala Val Asn Lys Asp Lys Pro Leu Gly Ala Val Ala
                290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Asn Leu Gly Ile
                370                 375                 380

Glu Gly Arg Ile Ser Glu Phe Pro Lys Thr Ala Leu Thr Glu Pro Pro
385                 390                 395                 400

Thr Leu Ala Tyr Ser Pro Asn Arg Gln Ile Cys Pro Ala Gly Thr Thr
                405                 410                 415

Ser Ser Cys Thr Ser Lys Ala Val Thr Leu Ser Ser Leu Ile Pro Glu
                420                 425                 430

Ala Glu Asp Ser Trp Trp Thr Gly Asp Ser Ala Ser Leu Asp Thr Ala
                435                 440                 445

Gly Ile Lys Leu Thr Val Pro Ile Glu Lys Phe Pro Val Thr Thr Gln
                450                 455                 460

Thr Phe Val Val Gly Cys Ile Lys Gly Asp Asp Ala Gln Ser Cys Met
465                 470                 475                 480

Val Thr Val Thr Val Gln Ala Arg Ala Ser Ser Val Val Asn Asn Val
                485                 490                 495

Ala Arg Cys Ser Tyr Gly Ala Asp Ser Thr Leu Gly Pro Val Lys Leu
                500                 505                 510

Ser Ala Glu Gly Pro Thr Thr Met Thr Leu Val Cys Gly Lys Asp Gly
                515                 520                 525

Val Lys Val Pro Gln Asp Asn Asn Gln Tyr Cys Ser Gly Thr Thr Leu
                530                 535                 540

Thr Gly Cys Asn Glu Lys Ser Phe Lys Asp Ile Leu Pro Lys Leu Thr
545                 550                 555                 560

Glu Asn Pro Trp Gln Gly Asn Ala Ser Ser Asp Lys Gly Ala Thr Leu
                565                 570                 575
```

```
Thr Ile Lys Lys Glu Ala Phe Pro Ala Glu Ser Lys Ser Val Ile Ile
            580                 585                 590

Gly Cys Thr Gly Gly Ser Pro Glu Lys His His
        595                 600

<210> SEQ ID NO 32
<211> LENGTH: 636
<212> TYPE: DNA
<213> ORGANISM: Toxoplasma gondii
<220> FEATURE:
<221> NAME/KEY: CDS
<222> LOCATION: (1)...(636)
<223> OTHER INFORMATION: ToxoP30del4del8 (83-294aa)

<400> SEQUENCE: 32 cct aaa aca gcg ctc aca gag cct ccc act ctt gcg tac tca ccc aac        48
Pro Lys Thr Ala Leu Thr Glu Pro Pro Thr Leu Ala Tyr Ser Pro Asn
 1               5                  10                  15 agg caa atc tgc cca gcg ggt act aca agt agc tgt aca tca aag gct        96
Arg Gln Ile Cys Pro Ala Gly Thr Thr Ser Ser Cys Thr Ser Lys Ala
             20                  25                  30 gta aca ttg agc tcc ttg att cct gaa gca gaa gat agc tgg tgg acg       144
Val Thr Leu Ser Ser Leu Ile Pro Glu Ala Glu Asp Ser Trp Trp Thr
         35                  40                  45 ggg gat tct gct agt ctc gac acg gca ggc atc aaa ctc aca gtt cca       192
Gly Asp Ser Ala Ser Leu Asp Thr Ala Gly Ile Lys Leu Thr Val Pro
     50                  55                  60 atc gag aag ttc ccc gtg aca acg cag acg ttt gtg gtc ggt tgc atc       240
Ile Glu Lys Phe Pro Val Thr Thr Gln Thr Phe Val Val Gly Cys Ile
 65                  70                  75                  80 aag gga gac gac gca cag agt tgt atg gtc aca gtg aca gta caa gcc       288
Lys Gly Asp Asp Ala Gln Ser Cys Met Val Thr Val Thr Val Gln Ala
                 85                  90                  95 aga gcc tca tcg gtc gtc aat aat gtc gca agg tgc tcc tac ggt gca       336
Arg Ala Ser Ser Val Val Asn Asn Val Ala Arg Cys Ser Tyr Gly Ala
            100                 105                 110 gac agc act ctt ggt cct gtc aag ttg tct gcg gaa gga ccc act aca       384
Asp Ser Thr Leu Gly Pro Val Lys Leu Ser Ala Glu Gly Pro Thr Thr
        115                 120                 125 atg acc ctc gtg tgc ggg aaa gat gga gtc aaa gtt cct caa gac aac       432
Met Thr Leu Val Cys Gly Lys Asp Gly Val Lys Val Pro Gln Asp Asn
    130                 135                 140 aat cag tac tgt tcc ggg acg acg ctg act ggt tgc aac gag aaa tcg       480
Asn Gln Tyr Cys Ser Gly Thr Thr Leu Thr Gly Cys Asn Glu Lys Ser
145                 150                 155                 160 ttc aaa gat att ttg cca aaa tta act gag aac ccg tgg cag ggt aac       528
Phe Lys Asp Ile Leu Pro Lys Leu Thr Glu Asn Pro Trp Gln Gly Asn
                165                 170                 175 gct tcg agt gat aag ggt gcc acg cta acg atc aag aag gaa gca ttt       576
Ala Ser Ser Asp Lys Gly Ala Thr Leu Thr Ile Lys Lys Glu Ala Phe
            180                 185                 190 cca gcc gag tca aaa agc gtc att att gga tgc aca ggg gga tcg cct       624
Pro Ala Glu Ser Lys Ser Val Ile Ile Gly Cys Thr Gly Gly Ser Pro
        195                 200                 205 gag aag cat cac                                                       636
Glu Lys His His
    210

<210> SEQ ID NO 33
<211> LENGTH: 212
<212> TYPE: PRT
```

<213> ORGANISM: Toxoplasma gondii
<220> FEATURE:
<223> OTHER INFORMATION: ToxoP30del4del8 (83-294aa)

<400> SEQUENCE: 33

```
Pro Lys Thr Ala Leu Thr Glu Pro Pro Thr Leu Ala Tyr Ser Pro Asn
 1               5                  10                  15

Arg Gln Ile Cys Pro Ala Gly Thr Thr Ser Ser Cys Thr Ser Lys Ala
            20                  25                  30

Val Thr Leu Ser Ser Leu Ile Pro Glu Ala Glu Asp Ser Trp Trp Thr
        35                  40                  45

Gly Asp Ser Ala Ser Leu Asp Thr Ala Gly Ile Lys Leu Thr Val Pro
    50                  55                  60

Ile Glu Lys Phe Pro Val Thr Thr Gln Thr Phe Val Val Gly Cys Ile
65                  70                  75                  80

Lys Gly Asp Asp Ala Gln Ser Cys Met Val Thr Val Thr Val Gln Ala
                85                  90                  95

Arg Ala Ser Ser Val Val Asn Asn Val Ala Arg Cys Ser Tyr Gly Ala
            100                 105                 110

Asp Ser Thr Leu Gly Pro Val Lys Leu Ser Ala Glu Gly Pro Thr Thr
        115                 120                 125

Met Thr Leu Val Cys Gly Lys Asp Gly Val Lys Val Pro Gln Asp Asn
    130                 135                 140

Asn Gln Tyr Cys Ser Gly Thr Thr Leu Thr Gly Cys Asn Glu Lys Ser
145                 150                 155                 160

Phe Lys Asp Ile Leu Pro Lys Leu Thr Glu Asn Pro Trp Gln Gly Asn
                165                 170                 175

Ala Ser Ser Asp Lys Gly Ala Thr Leu Thr Ile Lys Lys Glu Ala Phe
            180                 185                 190

Pro Ala Glu Ser Lys Ser Val Ile Ile Gly Cys Thr Gly Gly Ser Pro
        195                 200                 205

Glu Lys His His
    210
```

<210> SEQ ID NO 34
<211> LENGTH: 39
<212> TYPE: DNA
<213> ORGANISM: Artificial Sequence
<220> FEATURE:
<223> OTHER INFORMATION: Antisense Primer

<400> SEQUENCE: 34
caggtcaagc tttcatccaa taatgacgct ttttgactc                     39

<210> SEQ ID NO 35
<211> LENGTH: 7322
<212> TYPE: DNA
<213> ORGANISM: Toxoplasma gondii
<220> FEATURE:
<221> NAME/KEY: CDS
<222> LOCATION: (1528)...(3399)
<223> OTHER INFORMATION: pMBP-c2X-ToxoP30del10 (52-284aa)

<400> SEQUENCE: 35
ccgacaccat cgaatggtgc aaaacctttc gcggtatggc atgatagcgc ccggaagaga    60
gtcaattcag ggtggtgaat gtgaaaccag taacgttata cgatgtcgca gagtatgccg   120
gtgtctctta tcagaccgtt tcccgcgtgg tgaaccaggc cagccacgtt tctgcgaaaa   180
cgcgggaaaa agtggaagcg gcgatggcgg agctgaatta cattcccaac cgcgtggcac   240

```
aacaactggc gggcaaacag tcgttgctga ttggcgttgc cacctccagt ctggccctgc    300
acgcgccgtc gcaaattgtc gcggcgatta aatctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480 tgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga    1020
agggcaatca gctgttgccc gtctcactgg tgaaaagaaa accaccctg gcgcccaata     1080 cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt ccgtttaggt gttttcacga     1500
gcacttcacc aacaaggacc atagcat atg aaa atc gaa gaa ggt aaa ctg gta    1554
                                Met Lys Ile Glu Glu Gly Lys Leu Val
                                 1               5 atc tgg att aac ggc gat aaa ggc tat aac ggt ctc gct gaa gtc ggt      1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg      1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
         45                  50                  55 cct gac att atc ttc tgg gca cac gac cgc ttt ggt ggc tac gct caa      1746
Pro Asp Ile Ile Phe Trp Ala His Asp Arg Phe Gly Gly Tyr Ala Gln
     60                  65                  70 tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90                  95                  100                 105 gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                 110                 115                 120 ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
             125                 130                 135
```

```
                                                          -continued aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
155                 160                 165 ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc      2178
Asn Lys His Met Asn Ala Asp Thr Asp Tyr Ser Ile Ala Glu Ala Ala
        205                 210                 215 ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
    220                 225                 230 tcc aac atc gac acc agc aaa gtg aat tat ggt gta acg gta ctg ccg      2274
Ser Asn Ile Asp Thr Ser Lys Val Asn Tyr Gly Val Thr Val Leu Pro
235                 240                 245 acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
        285                 290                 295 aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
    300                 305                 310 aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
315                 320                 325 atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aat aac            2658
Leu Lys Asp Ala Gln Thr Asn Ser Ser Ser Asn Asn Asn Asn Asn
        365                 370                 375 aat aac aac aac ctc ggg atc gag gga agg att tca gaa ttc ctt gtt      2706
Asn Asn Asn Asn Leu Gly Ile Glu Gly Arg Ile Ser Glu Phe Leu Val
    380                 385                 390 gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
395                 400                 405 att ctc aca ccg acg gag aac cac ttc act ctc aag tgc cct aaa aca      2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg      2898
Cys Pro Ala Gly Thr Thr Ser Ser Cys Thr Ser Lys Ala Val Thr Leu
        445                 450                 455
```

| | |
|---|---|
| agc tcc ttg att cct gaa gca gaa gat agc tgg tgg acg ggg gat tct<br>Ser Ser Leu Ile Pro Glu Ala Glu Asp Ser Trp Trp Thr Gly Asp Ser<br>460 465 470 | 2946 |
| gct agt ctc gac acg gca ggc atc aaa ctc aca gtt cca atc gag aag<br>Ala Ser Leu Asp Thr Ala Gly Ile Lys Leu Thr Val Pro Ile Glu Lys<br>475 480 485 | 2994 |
| ttc ccc gtg aca acg cag acg ttt gtg gtc ggt tgc atc aag gga gac<br>Phe Pro Val Thr Thr Gln Thr Phe Val Val Gly Cys Ile Lys Gly Asp<br>490 495 500 505 | 3042 |
| gac gca cag agt tgt atg gtc aca gtg aca gta caa gcc aga gcc tca<br>Asp Ala Gln Ser Cys Met Val Thr Val Thr Val Gln Ala Arg Ala Ser<br>510 515 520 | 3090 |
| tcg gtc gtc aat aat gtc gca agg tgc tcc tac ggt gca gac agc act<br>Ser Val Val Asn Asn Val Ala Arg Cys Ser Tyr Gly Ala Asp Ser Thr<br>525 530 535 | 3138 |
| ctt ggt cct gtc aag ttg tct gcg gga gga ccc act aca atg acc ctc<br>Leu Gly Pro Val Lys Leu Ser Ala Gly Gly Pro Thr Thr Met Thr Leu<br>540 545 550 | 3186 |
| gtg tgc ggg aaa gat gga gtc aaa gtt cct caa gac aac aat cag tac<br>Val Cys Gly Lys Asp Gly Val Lys Val Pro Gln Asp Asn Asn Gln Tyr<br>555 560 565 | 3234 |
| tgt tcc ggg acg acg ctg act ggt tgc aac gag aaa tcg ttc aaa gat<br>Cys Ser Gly Thr Thr Leu Thr Gly Cys Asn Glu Lys Ser Phe Lys Asp<br>570 575 580 585 | 3282 |
| att ttg cca aaa tta act gag aac ccg tgg cag ggt aac gct tcg agt<br>Ile Leu Pro Lys Leu Thr Glu Asn Pro Trp Gln Gly Asn Ala Ser Ser<br>590 595 600 | 3330 |
| gat aag ggt gcc acg cta acg atc aag aag gaa gca ttt cca gcc gag<br>Asp Lys Gly Ala Thr Leu Thr Ile Lys Lys Glu Ala Phe Pro Ala Glu<br>605 610 615 | 3378 |
| tca aaa agc gtc att att gga tgaaagcttg cactggccg tcgttttaca<br>Ser Lys Ser Val Ile Ile Gly<br>620 | 3429 |
| acgtcgtgac tgggaaaacc ctggcgttac ccaacttaat cgccttgcag cacatccccc | 3489 |
| tttcgccagc tggcgtaata gcgaagaggc ccgcaccgat cgcccttccc aacagttgcg | 3549 |
| cagcctgaat ggcgaatggc agcttggctg ttttggcgga tgagataaga ttttcagcct | 3609 |
| gatacagatt aaatcagaac gcagaagcgg tctgataaaa cagaatttgc ctggcggcag | 3669 |
| tagcgcggtg gtcccacctg accccatgcc gaactcagaa gtgaaacgcc gtagcgccga | 3729 |
| tggtagtgtg gggtctcccc atgcgagagt agggaactgc caggcatcaa ataaaacgaa | 3789 |
| aggctcagtc gaaagactgg gcctttcgtt ttatctgttg tttgtcggtg aacgctctcc | 3849 |
| tgagtaggac aaatccgccg ggagcggatt tgaacgttgc gaagcaacgg cccggagggt | 3909 |
| ggcgggcagg acgcccgcca taaactgcca ggcatcaaat taagcagaag gccatcctga | 3969 |
| cggatggcct ttttgcgttt ctacaaactc ttttgttta tttttctaaa tacattcaaa | 4029 |
| tatgtatccg ctcatgagac aataaccctg ataaatgctt caataatatt gaaaaggaa | 4089 |
| gagtatgagt attcaacatt tccgtgtcgc ccttattccc ttttttgcgg cattttgcct | 4149 |
| tcctgttttt gctcacccag aaacgctggt gaaagtaaaa gatgctgaag atcagttggg | 4209 |
| tgcacgagtg ggttacatcg aactggatct caacagcggt aagatccttg agagttttcg | 4269 |
| ccccgaagaa cgttctccaa tgatgagcac ttttaaagtt ctgctatgtg gcgcggtatt | 4329 |
| atcccgtgtt gacgccggc aagagcaact cggtcgccgc atacactatt ctcagaatga | 4389 |
| cttggttgag tactcaccag tcacagaaaa gcatcttacg gatggcatga cagtaagaga | 4449 |

-continued

```
attatgcagt gctgccataa ccatgagtga taacactgcg gccaacttac ttctgacaac   4509
gatcggagga ccgaaggagc taaccgcttt tttgcacaac atgggggatc atgtaactcg   4569
ccttgatcgt tgggaaccgg agctgaatga agccatacca aacgacgagc gtgacaccac   4629
gatgcctgta gcaatggcaa caacgttgcg caaactatta actggcgaac tacttactct   4689
agcttcccgg caacaattaa tagactggat ggaggcggat aaagttgcag gaccacttct   4749
gcgctcggcc cttccggctg gctggtttat tgctgataaa tctggagccg gtgagcgtgg   4809
gtctcgcggt atcattgcag cactggggcc agatggtaag ccctcccgta tcgtagttat   4869
ctacacgacg gggagtcagg caactatgga tgaacgaaat agacagatcg ctgagatagg   4929
tgcctcactg attaagcatt ggtaactgtc agaccaagtt tactcatata tactttagat   4989
tgatttaccc cggttgataa tcagaaaagc cccaaaaaca ggaagattgt ataagcaaat   5049
atttaaattg taaacgttaa tattttgtta aaattcgcgt taaatttttg ttaaatcagc   5109
tcatttttta accaataggc cgaaatcggc aaaatccctt ataaatcaaa agaatagacc   5169
gagatagggt tgagtgttgt tccagtttgg aacaagagtc cactattaaa gaacgtggac   5229
tccaacgtca aagggcgaaa aaccgtctat cagggcgatg gcccactacg tgaaccatca   5289
cccaaatcaa gttttttggg gtcgaggtgc cgtaaagcac taaatcggaa ccctaaaggg   5349
agcccccgat ttagagcttg acggggaaag ccggcgaacg tggcgagaaa ggaagggaag   5409
aaagcgaaag gagcgggcgc tagggcgctg gcaagtgtag cggtcacgct gcgcgtaacc   5469
accacacccg ccgcgcttaa tgcgccgcta cagggcgcgt aaaaggatct aggtgaagat   5529
cctttttgat aatctcatga ccaaaatccc ttaacgtgag ttttcgttcc actgagcgtc   5589
agaccccgta gaaaagatca aaggatcttc ttgagatcct ttttttctgc gcgtaatctg   5649
ctgcttgcaa acaaaaaaac caccgctacc agcggtggtt tgtttgccgg atcaagagct   5709
accaactctt tttccgaagg taactggctt cagcagagcg cagataccaa atactgtcct   5769
tctagtgtag ccgtagttag gccaccactt caagaactct gtagcaccgc ctacatacct   5829
cgctctgcta atcctgttac cagtggctgc tgccagtggc gataagtcgt gtcttaccgg   5889
gttggactca agacgatagt taccggataa ggcgcagcgg tcgggctgaa cggggggttc   5949
gtgcacacag cccagcttgg agcgaacgac ctacaccgaa ctgagatacc tacagcgtga   6009
gctatgagaa agcgccacgc ttcccgaagg gagaaaggcg gacaggtatc cggtaagcgg   6069
cagggtcgga acaggagagc gcacgaggga gcttccaggg ggaaacgcct ggtatcttta   6129
tagtcctgtc gggtttcgcc acctctgact tgagcgtcga tttttgtgat gctcgtcagg   6189
ggggcggagc ctatggaaaa acgccagcaa cgcggccttt ttacggttcc tggccttttg   6249
ctggcctttt gctcacatgt tctttcctgc gttatcccct gattctgtgg ataaccgtat   6309
taccgccttt gagtgagctg ataccgctcg ccgcagccga acgaccgagc gcagcgagtc   6369
agtgagcgag gaagcggaag agcgcctgat gcggtatttt ctccttacgc atctgtgcgg   6429
tatttcacac cgcatatatg gtgcactctc agtacaatct gctctgatgc cgcatagtta   6489
agccagtata cactccgcta tcgctacgtg actgggtcat ggctgcgccc cgacacccgc   6549
caacacccgc tgacgcgccc tgacgggctt gtctgctccc ggcatccgct tacagacaag   6609
ctgtgaccgt ctccgggagc tgcatgtgtc agaggttttc accgtcatca ccgaaacgcg   6669
cgaggcagct gcggtaaagc tcatcagcgt ggtcgtgcag cgattcacag atgtctgcct   6729
gttcatccgc gtccagctcg ttgagtttct ccagaagcgt taatgtctgg cttctgataa   6789
agcgggccat gttaagggcg gtttttcct gtttggtcac tgatgcctcc gtgtaagggg   6849
```

```
gatttctgtt catggggta atgataccga tgaaacgaga gaggatgctc acgatacggg    6909
ttactgatga tgaacatgcc cggttactgg aacgttgtga gggtaaacaa ctggcggtat    6969
ggatgcggcg ggaccagaga aaaatcactc agggtcaatg ccagcgcttc gttaatacag    7029
atgtaggtgt tccacagggt agccagcagc atcctgcgat gcagatccgg aacataatgg    7089
tgcagggcgc tgacttccgc gtttccagac tttacgaaac acggaaaccg aagaccattc    7149
atgttgttgc tcaggtcgca gacgttttgc agcagcagtc gcttcacgtt cgctcgcgta    7209
tcggtgattc attctgctaa ccagtaaggc aaccccgcca gcctagccgg gtcctcaacg    7269
acaggagcac gatcatgcgc accgtggcc aggacccaac gctgcccgaa att           7322
```

<210> SEQ ID NO 36
<211> LENGTH: 624
<212> TYPE: PRT
<213> ORGANISM: Toxoplasma gondii
<220> FEATURE:
<223> OTHER INFORMATION: pMBP-c2X-ToxoP30del10 (52-284aa)

<400> SEQUENCE: 36

```
Met Lys Ile Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
 50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
             85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
            165                 170                 175

Tyr Asp Ile Lys Asp Val Gly Val Asp Asn Ala Gly Ala Lys Ala Gly
        180                 185                 190

Leu Thr Phe Leu Val Asp Leu Ile Lys Asn Lys His Met Asn Ala Asp
    195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255

Lys Pro Phe Val Gly Val Leu Ser Ala Gly Ile Asn Ala Ala Ser Pro
        260                 265                 270

Asn Lys Glu Leu Ala Lys Glu Phe Leu Glu Asn Tyr Leu Leu Thr Asp
```

```
                275                 280                 285
Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Asn Leu Gly Ile
370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
                420                 425                 430

Leu Ala Tyr Ser Pro Asn Arg Gln Ile Cys Pro Ala Gly Thr Thr Ser
                435                 440                 445

Ser Cys Thr Ser Lys Ala Val Thr Leu Ser Ser Leu Ile Pro Glu Ala
450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
                500                 505                 510

Thr Val Thr Val Gln Ala Arg Ala Ser Ser Val Val Asn Asn Val Ala
                515                 520                 525

Arg Cys Ser Tyr Gly Ala Asp Ser Thr Leu Gly Pro Val Lys Leu Ser
530                 535                 540

Ala Gly Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
                580                 585                 590

Asn Pro Trp Gln Gly Asn Ala Ser Ser Asp Lys Gly Ala Thr Leu Thr
                595                 600                 605

Ile Lys Lys Glu Ala Phe Pro Ala Glu Ser Lys Ser Val Ile Ile Gly
                610                 615                 620

<210> SEQ ID NO 37
<211> LENGTH: 699
<212> TYPE: DNA
<213> ORGANISM: Toxoplasma gondii
<220> FEATURE:
<221> NAME/KEY: CDS
<222> LOCATION: (1)...(699)
<223> OTHER INFORMATION: ToxoP30del10 (52-284aa)

<400> SEQUENCE: 37 ctt gtt gcc aat caa gtt gtc acc tgc cca gat aaa aaa tcg aca gcc    48
Leu Val Ala Asn Gln Val Val Thr Cys Pro Asp Lys Lys Ser Thr Ala
```

```
                    1               5                  10                 15 gcg gtc att ctc aca ccg acg gag aac cac ttc act ctc aag tgc cct          96
Ala Val Ile Leu Thr Pro Thr Glu Asn His Phe Thr Leu Lys Cys Pro
                    20                 25                 30 aaa aca gcg ctc aca gag cct ccc act ctt gcg tac tca ccc aac agg         144
Lys Thr Ala Leu Thr Glu Pro Pro Thr Leu Ala Tyr Ser Pro Asn Arg
                35                 40                 45 caa atc tgc cca gcg ggt act aca agt agc tgt aca tca aag gct gta         192
Gln Ile Cys Pro Ala Gly Thr Thr Ser Ser Cys Thr Ser Lys Ala Val
            50                 55                 60 aca ttg agc tcc ttg att cct gaa gca gaa gat agc tgg tgg acg ggg         240
Thr Leu Ser Ser Leu Ile Pro Glu Ala Glu Asp Ser Trp Trp Thr Gly
65                 70                 75                 80 gat tct gct agt ctc gac acg gca ggc atc aaa ctc aca gtt cca atc         288
Asp Ser Ala Ser Leu Asp Thr Ala Gly Ile Lys Leu Thr Val Pro Ile
                    85                 90                 95 gag aag ttc ccc gtg aca acg cag acg ttt gtg gtc ggt tgc atc aag         336
Glu Lys Phe Pro Val Thr Thr Gln Thr Phe Val Val Gly Cys Ile Lys
                100                105                110 gga gac gac gca cag agt tgt atg gtc aca gtg aca gta caa gcc aga         384
Gly Asp Asp Ala Gln Ser Cys Met Val Thr Val Thr Val Gln Ala Arg
            115                120                125 gcc tca tcg gtc gtc aat aat gtc gca agg tgc tcc tac ggt gca gac         432
Ala Ser Ser Val Val Asn Asn Val Ala Arg Cys Ser Tyr Gly Ala Asp
130                135                140 agc act ctt ggt cct gtc aag ttg tct gcg gga gga ccc act aca atg         480
Ser Thr Leu Gly Pro Val Lys Leu Ser Ala Gly Gly Pro Thr Thr Met
145                150                155                160 acc ctc gtg tgc ggg aaa gat gga gtc aaa gtt cct caa gac aac aat         528
Thr Leu Val Cys Gly Lys Asp Gly Val Lys Val Pro Gln Asp Asn Asn
                    165                170                175 cag tac tgt tcc ggg acg acg ctg act ggt tgc aac gag aaa tcg ttc         576
Gln Tyr Cys Ser Gly Thr Thr Leu Thr Gly Cys Asn Glu Lys Ser Phe
                180                185                190 aaa gat att ttg cca aaa tta act gag aac ccg tgg cag ggt aac gct         624
Lys Asp Ile Leu Pro Lys Leu Thr Glu Asn Pro Trp Gln Gly Asn Ala
            195                200                205 tcg agt gat aag ggt gcc acg cta acg atc aag aag gaa gca ttt cca         672
Ser Ser Asp Lys Gly Ala Thr Leu Thr Ile Lys Lys Glu Ala Phe Pro
210                215                220 gcc gag tca aaa agc gtc att att gga                                     699
Ala Glu Ser Lys Ser Val Ile Ile Gly
225                230

<210> SEQ ID NO 38
<211> LENGTH: 233
<212> TYPE: PRT
<213> ORGANISM: Toxoplasma gondii
<220> FEATURE:
<223> OTHER INFORMATION: ToxoP30del10 (52-284aa)

<400> SEQUENCE: 38

Leu Val Ala Asn Gln Val Val Thr Cys Pro Asp Lys Lys Ser Thr Ala
1               5                  10                 15

Ala Val Ile Leu Thr Pro Thr Glu Asn His Phe Thr Leu Lys Cys Pro
                20                 25                 30

Lys Thr Ala Leu Thr Glu Pro Pro Thr Leu Ala Tyr Ser Pro Asn Arg
            35                 40                 45

Gln Ile Cys Pro Ala Gly Thr Thr Ser Ser Cys Thr Ser Lys Ala Val
        50                 55                 60
```

```
Thr Leu Ser Ser Leu Ile Pro Glu Ala Glu Asp Ser Trp Trp Thr Gly
 65                  70                  75                  80

Asp Ser Ala Ser Leu Asp Thr Ala Gly Ile Lys Leu Thr Val Pro Ile
                 85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Gly Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly
225                 230
```

```
<210> SEQ ID NO 39
<211> LENGTH: 36
<212> TYPE: DNA
<213> ORGANISM: Artificial Sequence
<220> FEATURE:
<223> OTHER INFORMATION: Antisense Primer

<400> SEQUENCE: 39
caggtcaagc tttcacacga gggtcattgt agtggg                             36

<210> SEQ ID NO 40
<211> LENGTH: 7112
<212> TYPE: DNA
<213> ORGANISM: Toxoplasma gondii
<220> FEATURE:
<221> NAME/KEY: CDS
<222> LOCATION: (1528)...(3189)
<223> OTHER INFORMATION: pMBP-c2X-ToxoP30del11 (52-214aa)

<400> SEQUENCE: 40
ccgacaccat cgaatggtgc aaaacctttc gcggtatggc atgatagcgc ccggaagaga     60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta atctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt cttgatgtc tctgaccaga    540 cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
```

-continued

```
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa aaccaccctg cgcccaata    1080 cgcaaaccgc ctctccccgc gcgttggccg attcattaat gcagctggca cgacaggttt   1140
cccgactgga agcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgttttt gcgccgacat cataacggtt   1380
ctggcaaata ttctgaaatg agctgttgac aattaatcat cggctcgtat aatgtgtgga   1440
attgtgagcg gataacaatt tcacacagga acagccagt ccgtttaggt gttttcacga   1500
gcacttcacc aacaaggacc atagcat atg aaa atc gaa gaa ggt aaa ctg gta   1554
                                Met Lys Ile Glu Glu Gly Lys Leu Val
                                 1               5 atc tgg att aac ggc gat aaa ggc tat aac ggt ctc gct gaa gtc ggt    1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg    1650
Lys Lys Phe Glu Lys Asp Thr Gly Ile Lys Val Thr Val Glu His Pro
         30                  35                  40 gat aaa ctg gaa gag aaa ttc cca cag gtt gcg gca act ggc gat ggc    1698
Asp Lys Leu Glu Glu Lys Phe Pro Gln Val Ala Ala Thr Gly Asp Gly
                 45                  50                  55 cct gac att atc ttc tgg gca cac gac cgc ttt ggt ggc tac gct caa    1746
Pro Asp Ile Ile Phe Trp Ala His Asp Arg Phe Gly Gly Tyr Ala Gln
             60                  65                  70 tct ggc ctg ttg gct gaa atc acc ccg gac aaa gcg ttc cag gac aag    1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att    1842
Leu Tyr Pro Phe Thr Trp Asp Ala Val Arg Tyr Asn Gly Lys Leu Ile
         90                  95                 100                 105 gct tac ccg atc gct gtt gaa gcg tta tcg ctg att tat aac aaa gat    1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat    1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa    1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg    2034
Glu Pro Tyr Phe Thr Trp Pro Leu Ile Ala Ala Asp Gly Gly Tyr Ala
155                 160                 165 ttc aag tat gaa aac ggc aag tac gac att aaa gac gtg ggc gtg gat    2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa    2130
Asn Ala Gly Ala Lys Ala Gly Leu Thr Phe Leu Val Asp Leu Ile Lys
```

```
                     190                 195                 200
aac aaa cac atg aat gca gac acc gat tac tcc atc gca gaa gct gcc        2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg        2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg        2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca        2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc        2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac        2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg        2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa        2514
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt        2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc        2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac        2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc ctt gtt        2706
Asn Asn Asn Asn Leu Gly Ile Glu Gly Arg Ile Ser Glu Phe Leu Val
        380                 385                 390 gcc aat caa gtt gtc acc tgc cca gat aaa aaa tcg aca gcc gcg gtc        2754
Ala Asn Gln Val Val Thr Cys Pro Asp Lys Lys Ser Thr Ala Ala Val
    395                 400                 405 att ctc aca ccg acg gag aac cac ttc act ctc aag tgc cct aaa aca        2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc        2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg        2898
Cys Pro Ala Gly Thr Thr Ser Ser Cys Thr Ser Lys Ala Val Thr Leu
            445                 450                 455 agc tcc ttg att cct gaa gca gaa gat agc tgg tgg acg ggg gat tct        2946
Ser Ser Leu Ile Pro Glu Ala Glu Asp Ser Trp Trp Thr Gly Asp Ser
        460                 465                 470 gct agt ctc gac acg gca ggc atc aaa ctc aca gtt cca atc gag aag        2994
Ala Ser Leu Asp Thr Ala Gly Ile Lys Leu Thr Val Pro Ile Glu Lys
    475                 480                 485 ttc ccc gtg aca acg cag acg ttt gtg gtc ggt tgc atc aag gga gac        3042
Phe Pro Val Thr Thr Gln Thr Phe Val Val Gly Cys Ile Lys Gly Asp
490                 495                 500                 505 gac gca cag agt tgt atg gtc aca gtg aca gta caa gcc aga gcc tca        3090
```

-continued

```
Asp Ala Gln Ser Cys Met Val Thr Val Thr Val Gln Ala Arg Ala Ser
                510                 515                 520 tcg gtc gtc aat aat gtc gca agg tgc tcc tac ggt gca gac agc act     3138
Ser Val Val Asn Asn Val Ala Arg Cys Ser Tyr Gly Ala Asp Ser Thr
            525                 530                 535 ctt ggt cct gtc aag ttg tct gcg gaa gga ccc act aca atg acc ctc     3186
Leu Gly Pro Val Lys Leu Ser Ala Glu Gly Pro Thr Thr Met Thr Leu
        540                 545                 550 gtg tgaaagcttg gcactggccg tcgttttaca acgtcgtgac tgggaaaacc         3239
Val ctggcgttac ccaacttaat cgccttgcag cacatccccc tttcgccagc tggcgtaata   3299
gcgaagaggc ccgcaccgat cgcccttccc aacagttgcg cagcctgaat ggcgaatggc   3359
agcttggctg ttttggcgga tgagataaga ttttcagcct gatacagatt aaatcagaac   3419
gcagaagcgg tctgataaaa cagaatttgc ctggcggcag tagcgcggtg gtcccacctg   3479
accccatgcc gaactcagaa gtgaaacgcc gtagcgccga tggtagtgtg gggtctcccc   3539
atgcgagagt agggaactgc caggcatcaa ataaaacgaa aggctcagtc gaaagactgg   3599
gcctttcgtt ttatctgttg tttgtcggtg aacgctctcc tgagtaggac aaatccgccg   3659
ggagcggatt tgaacgttgc gaagcaacgg cccggagggt ggcgggcagg acgcccgcca   3719
taaactgcca ggcatcaaat taagcagaag gccatcctga cggatggcct ttttgcgttt   3779
ctacaaactc tttttgttta tttttctaaa tacattcaaa tatgtatccg ctcatgagac   3839
aataaccctg ataaatgctt caataatatt gaaaaaggaa gagtatgagt attcaacatt   3899
tccgtgtcgc ccttattccc ttttttgcgg cattttgcct tcctgttttt gctcacccag   3959
aaacgctggt gaaagtaaaa gatgctgaag atcagttggg tgcacgagtg ggttacatcg   4019
aactggatct caacagcggt aagatccttg agagttttcg ccccgaagaa cgttctccaa   4079
tgatgagcac ttttaaagtt ctgctatgtg gcgcggtatt atcccgtgtt gacgccgggc   4139
aagagcaact cggtcgccgc atacactatt ctcagaatga cttggttgag tactcaccag   4199
tcacagaaaa gcatcttacg gatggcatga cagtaagaga attatgcagt gctgccataa   4259
ccatgagtga taacactgcg gccaacttac ttctgacaac gatcggagga ccgaaggagc   4319
taaccgcttt tttgcacaac atgggggatc atgtaactcg ccttgatcgt tgggaaccgg   4379
agctgaatga agccatacca aacgacgagc gtgacaccac gatgcctgta gcaatggcaa   4439
caacgttgcg caaactatta actggcgaac tacttactct agcttcccgg caacaattaa   4499
tagactggat ggaggcggat aaagttgcag gaccacttct gcgctcggcc cttccggctg   4559
gctggtttat tgctgataaa tctggagccg gtgagcgtgg gtctcgcggt atcattgcag   4619
cactggggcc agatggtaag ccctcccgta tcgtagttat ctacacgacg gggagtcagg   4679
caactatgga tgaacgaaat agacagatcg ctgagatagg tgcctcactg attaagcatt   4739
ggtaactgtc agaccaagtt tactcatata tactttagat tgatttaccc cggttgataa   4799
tcagaaaagc cccaaaaaca ggaagattgt ataagcaaat atttaaattg taaacgttaa   4859
tattttgtta aaattcgcgt taaatttttg ttaaatcagc tcatttttta accaataggc   4919
cgaaatcggc aaaatccctt ataaatcaaa agaatagacc gagatagggt tgagtgttgt   4979
tccagtttgg aacaagagtc cactattaaa gaacgtggac tccaacgtca aagggcgaaa   5039
aaccgtctat cagggcgatg gcccactacg tgaaccatca cccaaatcaa gtttttggg    5099 gtcgaggtgc cgtaaagcac taaatcggaa ccctaaaggg agcccccgat ttagagcttg   5159
acggggaaag ccggcgaacg tggcgagaaa ggaagggaag aaagcgaaag gagcgggcgc   5219
```

-continued

```
tagggcgctg gcaagtgtag cggtcacgct gcgcgtaacc accacacccg ccgcgcttaa   5279
tgcgccgcta cagggcgcgt aaaaggatct aggtgaagat cctttttgat aatctcatga   5339
ccaaaatccc ttaacgtgag ttttcgttcc actgagcgtc agaccccgta gaaaagatca   5399
aaggatcttc ttgagatcct ttttttctgc gcgtaatctg ctgcttgcaa acaaaaaaac   5459
caccgctacc agcggtggtt tgtttgccgg atcaagagct accaactctt tttccgaagg   5519
taactggctt cagcagagcg cagataccaa atactgtcct tctagtgtag ccgtagttag   5579
gccaccactt caagaactct gtagcaccgc ctacatacct cgctctgcta atcctgttac   5639
cagtggctgc tgccagtggc gataagtcgt gtcttaccgg gttggactca agacgatagt   5699
taccggataa ggcgcagcgg tcgggctgaa cggggggttc gtgcacacag cccagcttgg   5759
agcgaacgac ctacaccgaa ctgagatacc tacagcgtga gctatgagaa agcgccacgc   5819
ttcccgaagg gagaaaggcg gacaggtatc cggtaagcgg cagggtcgga acaggagagc   5879
gcacgaggga gcttccaggg ggaaacgcct ggtatcttta tagtcctgtc gggtttcgcc   5939
acctctgact tgagcgtcga tttttgtgat gctcgtcagg ggggcggagc ctatggaaaa   5999
acgccagcaa cgcggccttt ttacggttcc tggccttttg ctggcctttt gctcacatgt   6059
tctttcctgc gttatcccct gattctgtgg ataaccgtat taccgccttt gagtgagctg   6119
ataccgctcg ccgcagccga acgaccgagc gcagcgagtc agtgagcgag gaagcggaag   6179
agcgcctgat gcggtatttt ctccttacgc atctgtgcgg tatttcacac cgcatatatg   6239
gtgcactctc agtacaatct gctctgatgc cgcatagtta agccagtata cactccgcta   6299
tcgctacgtg actgggtcat ggctgcgccc cgacacccgc caacacccgc tgacgcgccc   6359
tgacgggctt gtctgctccc ggcatccgct tacagacaag ctgtgaccgt ctccgggagc   6419
tgcatgtgtc agaggttttc accgtcatca ccgaaacgcg cgaggcagct gcggtaaagc   6479
tcatcagcgt ggtcgtgcag cgattcacag atgtctgcct gttcatccgc gtccagctcg   6539
ttgagtttct ccagaagcgt taatgtctgg cttctgataa agcgggccat gttaagggcg   6599 gtttttcct gtttggtcac tgatgcctcc gtgtaagggg gatttctgtt catgggggta   6659
atgataccga tgaaacgaga gaggatgctc acgatacggg ttactgatga tgaacatgcc   6719
cggttactgg aacgttgtga gggtaaacaa ctggcggtat ggatgcggcg ggaccagaga   6779
aaaatcactc agggtcaatg ccagcgcttc gttaatacag atgtaggtgt tccacagggt   6839
agccagcagc atcctgcgat gcagatccgg aacataatgg tgcagggcgc tgacttccgc   6899
gtttccagac tttacgaaac acggaaaccg aagaccattc atgttgttgc tcaggtcgca   6959
gacgttttgc agcagcagtc gcttcacgtt cgctcgcgta tcggtgattc attctgctaa   7019
ccagtaaggc aaccccgcca gcctagccgg gtcctcaacg acaggagcac gatcatgcgc   7079
acccgtggcc aggacccaac gctgcccgaa att                                 7112
```

<210> SEQ ID NO 41
<211> LENGTH: 554
<212> TYPE: PRT
<213> ORGANISM: Toxoplasma gondii
<220> FEATURE:
<223> OTHER INFORMATION: pMBP-c2X-ToxoP30del11 (52-214aa)

<400> SEQUENCE: 41

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
```

-continued

```
                20                  25                  30
Gly Ile Lys Val Thr Val Glu His Pro Asp Lys Leu Glu Lys Phe
             35                  40                  45
Pro Gln Val Ala Ala Thr Gly Asp Gly Pro Asp Ile Ile Phe Trp Ala
 50                  55                  60
His Asp Arg Phe Gly Gly Tyr Ala Gln Ser Gly Leu Leu Ala Glu Ile
 65                  70                  75                  80
Thr Pro Asp Lys Ala Phe Gln Asp Lys Leu Tyr Pro Phe Thr Trp Asp
             85                  90                  95
Ala Val Arg Tyr Asn Gly Lys Leu Ile Ala Tyr Pro Ile Ala Val Glu
                100                 105                 110
Ala Leu Ser Leu Ile Tyr Asn Lys Asp Leu Leu Pro Asn Pro Pro Lys
                115                 120                 125
Thr Trp Glu Glu Ile Pro Ala Leu Asp Lys Glu Leu Lys Ala Lys Gly
             130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
             180                 185                 190
Leu Thr Phe Leu Val Asp Leu Ile Lys Asn Lys His Met Asn Ala Asp
             195                 200                 205
Thr Asp Tyr Ser Ile Ala Glu Ala Ala Phe Asn Lys Gly Glu Thr Ala
 210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
             260                 265                 270
Asn Lys Glu Leu Ala Lys Glu Phe Leu Glu Asn Tyr Leu Leu Thr Asp
             275                 280                 285
Glu Gly Leu Glu Ala Val Asn Lys Asp Lys Pro Leu Gly Ala Val Ala
 290                 295                 300
Leu Lys Ser Tyr Glu Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
             340                 345                 350
Ser Gly Arg Gln Thr Val Asp Glu Ala Leu Lys Asp Ala Gln Thr Asn
             355                 360                 365
Ser Ser Ser Asn Asn Asn Asn Asn Asn Asn Asn Asn Leu Gly Ile
             370                 375                 380
Glu Gly Arg Ile Ser Glu Phe Leu Val Ala Asn Gln Val Val Thr Cys
385                 390                 395                 400
Pro Asp Lys Lys Ser Thr Ala Ala Val Ile Leu Thr Pro Thr Glu Asn
                405                 410                 415
His Phe Thr Leu Lys Cys Pro Lys Thr Ala Leu Thr Glu Pro Pro Thr
             420                 425                 430
Leu Ala Tyr Ser Pro Asn Arg Gln Ile Cys Pro Ala Gly Thr Thr Ser
             435                 440                 445
```

```
Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
                500                 505                 510

Thr Val Thr Val Gln Ala Arg Ala Ser Ser Val Val Asn Asn Val Ala
            515                 520                 525

Arg Cys Ser Tyr Gly Ala Asp Ser Thr Leu Gly Pro Val Lys Leu Ser
        530                 535                 540

Ala Glu Gly Pro Thr Thr Met Thr Leu Val
545                 550

<210> SEQ ID NO 42
<211> LENGTH: 489
<212> TYPE: DNA
<213> ORGANISM: Toxoplasma gondii
<220> FEATURE:
<221> NAME/KEY: CDS
<222> LOCATION: (1)...(489)
<223> OTHER INFORMATION: ToxoP30del11 (52-214aa)

<400> SEQUENCE: 42 ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag tgc cct      96
Ala Val Ile Leu Thr Pro Thr Glu Asn His Phe Thr Leu Lys Cys Pro
             20                  25                  30 aaa aca gcg ctc aca gag cct ccc act ctt gcg tac tca ccc aac agg     144
Lys Thr Ala Leu Thr Glu Pro Pro Thr Leu Ala Tyr Ser Pro Asn Arg
         35                  40                  45 caa atc tgc cca gcg ggt act aca agt agc tgt aca tca aag gct gta     192
Gln Ile Cys Pro Ala Gly Thr Thr Ser Ser Cys Thr Ser Lys Ala Val
     50                  55                  60 aca ttg agc tcc ttg att cct gaa gca gaa gat agc tgg tgg acg ggg     240
Thr Leu Ser Ser Leu Ile Pro Glu Ala Glu Asp Ser Trp Trp Thr Gly
 65                  70                  75                  80 gat tct gct agt ctc gac acg gca ggc atc aaa ctc aca gtt cca atc     288
Asp Ser Ala Ser Leu Asp Thr Ala Gly Ile Lys Leu Thr Val Pro Ile
                 85                  90                  95 gag aag ttc ccc gtg aca acg cag acg ttt gtg gtc ggt tgc atc aag     336
Glu Lys Phe Pro Val Thr Thr Gln Thr Phe Val Val Gly Cys Ile Lys
            100                 105                 110 gga gac gac gca cag agt tgt atg gtc aca gtg aca gta caa gcc aga     384
Gly Asp Asp Ala Gln Ser Cys Met Val Thr Val Thr Val Gln Ala Arg
        115                 120                 125 gcc tca tcg gtc gtc aat aat gtc gca agg tgc tcc tac ggt gca gac     432
Ala Ser Ser Val Val Asn Asn Val Ala Arg Cys Ser Tyr Gly Ala Asp
    130                 135                 140 agc act ctt ggt cct gtc aag ttg tct gcg gaa gga ccc act aca atg     480
Ser Thr Leu Gly Pro Val Lys Leu Ser Ala Glu Gly Pro Thr Thr Met
145                 150                 155                 160 acc ctc gtg                                                          489
Thr Leu Val

<210> SEQ ID NO 43
```

```
<211> LENGTH: 163
<212> TYPE: PRT
<213> ORGANISM: Toxoplasma gondii
<220> FEATURE:
<223> OTHER INFORMATION: ToxoP30del11 (52-214aa)

<400> SEQUENCE: 43

Leu Val Ala Asn Gln Val Val Thr Cys Pro Asp Lys Lys Ser Thr Ala
 1               5                  10                  15
Ala Val Ile Leu Thr Pro Thr Glu Asn His Phe Thr Leu Lys Cys Pro
            20                  25                  30
Lys Thr Ala Leu Thr Glu Pro Pro Thr Leu Ala Tyr Ser Pro Asn Arg
        35                  40                  45
Gln Ile Cys Pro Ala Gly Thr Thr Ser Ser Cys Thr Ser Lys Ala Val
    50                  55                  60
Thr Leu Ser Ser Leu Ile Pro Glu Ala Glu Asp Ser Trp Trp Thr Gly
65                  70                  75                  80
Asp Ser Ala Ser Leu Asp Thr Ala Gly Ile Lys Leu Thr Val Pro Ile
                85                  90                  95
Glu Lys Phe Pro Val Thr Thr Gln Thr Phe Val Val Gly Cys Ile Lys
            100                 105                 110
Gly Asp Asp Ala Gln Ser Cys Met Val Thr Val Thr Val Gln Ala Arg
        115                 120                 125
Ala Ser Ser Val Val Asn Asn Val Ala Arg Cys Ser Tyr Gly Ala Asp
    130                 135                 140
Ser Thr Leu Gly Pro Val Lys Leu Ser Ala Glu Gly Pro Thr Thr Met
145                 150                 155                 160
Thr Leu Val

<210> SEQ ID NO 44
<211> LENGTH: 70
<212> TYPE: DNA
<213> ORGANISM: Artificial Sequence
<220> FEATURE:
<223> OTHER INFORMATION: P30.001 Primer

<400> SEQUENCE: 44
cttgttgcca atcaagttgt cacctgccca gataaaaaat cgacagccgc ggtcattctc    60
acaccgacgg                                                          70

<210> SEQ ID NO 45
<211> LENGTH: 69
<212> TYPE: DNA
<213> ORGANISM: Artificial Sequence
<220> FEATURE:
<223> OTHER INFORMATION: P30.002 Primer

<400> SEQUENCE: 45
gaggctctgt gagcgctgtt ttagggcact tgagagtgaa gtggttctcc gtcggtgtga    60
gaatgaccg                                                           69

<210> SEQ ID NO 46
<211> LENGTH: 67
<212> TYPE: DNA
<213> ORGANISM: Artificial Sequence
<220> FEATURE:
<223> OTHER INFORMATION: P30.003 Primer

<400> SEQUENCE: 46
cctaaaacag cgctcacaga gcctcccact cttgcgtact cacccaacag gcaaatctgc    60
```

```
ccagcgg                                                                 67

<210> SEQ ID NO 47
<211> LENGTH: 72
<212> TYPE: DNA
<213> ORGANISM: Artificial Sequence
<220> FEATURE:
<223> OTHER INFORMATION: P30.004 Primer

<400> SEQUENCE: 47
ggaatcaagg agctcaatgt tacagccttt gatgtacagc tacttgtagt acccgctggg      60
cagatttgcc tg                                                           72

<210> SEQ ID NO 48
<211> LENGTH: 73
<212> TYPE: DNA
<213> ORGANISM: Artificial Sequence
<220> FEATURE:
<223> OTHER INFORMATION: P30.005 Primer

<400> SEQUENCE: 48
gtaacattga gctccttgat tcctgaagca gaagatagct ggtggacggg ggattctgct      60
agtctcgaca cgg                                                          73

<210> SEQ ID NO 49
<211> LENGTH: 72
<212> TYPE: DNA
<213> ORGANISM: Artificial Sequence
<220> FEATURE:
<223> OTHER INFORMATION: P30.006 Primer

<400> SEQUENCE: 49
ctgcgttgtc acggggaact tctcgattgg aactgtgagt ttgatgcctg ccgtgtcgag      60
actagcagaa tc                                                           72

<210> SEQ ID NO 50
<211> LENGTH: 70
<212> TYPE: DNA
<213> ORGANISM: Artificial Sequence
<220> FEATURE:
<223> OTHER INFORMATION: P30.007 Primer

<400> SEQUENCE: 50
gaagttcccc gtgacaacgc agacgtttgt ggtcggttgc atcaagggag acgacgcaca      60
gagttgtatg                                                              70

<210> SEQ ID NO 51
<211> LENGTH: 71
<212> TYPE: DNA
<213> ORGANISM: Artificial Sequence
<220> FEATURE:
<223> OTHER INFORMATION: P30.008 Primer

<400> SEQUENCE: 51
gcgacattat tgacgaccga tgaggctctg gcttgtactg tcaccgtgac catacaactc      60
tgtgcgtcgt c                                                            71

<210> SEQ ID NO 52
<211> LENGTH: 70
<212> TYPE: DNA
<213> ORGANISM: Artificial Sequence
<220> FEATURE:
```

<223> OTHER INFORMATION: P30.009 Primer

<400> SEQUENCE: 52
catcggtcgt caataatgtc gcaaggtgct cctacggtgc agacagcact cttggtcctg    60
tcaagttgtc                                                          70

<210> SEQ ID NO 53
<211> LENGTH: 71
<212> TYPE: DNA
<213> ORGANISM: Artificial Sequence
<220> FEATURE:
<223> OTHER INFORMATION: P30.010Ala8 Primer

<400> SEQUENCE: 53
gactccatct ttcccagcca cgagggtcat tgtagtgggt ccttccgcag acaacttgac    60
aggaccaaga g                                                        71

<210> SEQ ID NO 54
<211> LENGTH: 71
<212> TYPE: DNA
<213> ORGANISM: Artificial Sequence
<220> FEATURE:
<223> OTHER INFORMATION: P30.011Ala8Ala9 Primer

<400> SEQUENCE: 54
gtggctggga agatggagt caaagttcct caagacaaca atcagtacgc ttccgggacg     60
acgctgactg g                                                        71

<210> SEQ ID NO 55
<211> LENGTH: 71
<212> TYPE: DNA
<213> ORGANISM: Artificial Sequence
<220> FEATURE:
<223> OTHER INFORMATION: P30.012Ala9Ala10 Primer

<400> SEQUENCE: 55
gttctcagtt aattttggca aaatatcttt gaacgatttc tcgttagcac cagtcagcgt    60
cgtcccggaa g                                                        71

<210> SEQ ID NO 56
<211> LENGTH: 71
<212> TYPE: DNA
<213> ORGANISM: Artificial Sequence
<220> FEATURE:
<223> OTHER INFORMATION: P30.013 Primer

<400> SEQUENCE: 56
gatattttgc caaaattaac tgagaacccg tggcaggta acgcttcgag tgataagggt     60
gccacgctaa c                                                        71

<210> SEQ ID NO 57
<211> LENGTH: 70
<212> TYPE: DNA
<213> ORGANISM: Artificial Sequence
<220> FEATURE:
<223> OTHER INFORMATION: P30.014 Primer

<400> SEQUENCE: 57
ccaataatga cgcttttga ctcggctgga aatgcttcct tcttgatcgt tagcgtggca     60
cccttatcac                                                          70

<210> SEQ ID NO 58
<211> LENGTH: 70
<212> TYPE: DNA
<213> ORGANISM: Artificial Sequence
<220> FEATURE:
<223> OTHER INFORMATION: P30.015Ala11Ala12 Primer

<400> SEQUENCE: 58

```
gtcaaaaagc gtcattattg gagctacagg gggatcgcct gagaagcatc acgctaccgt    60
gaaactggag                                                           70
```

<210> SEQ ID NO 59
<211> LENGTH: 70
<212> TYPE: DNA
<213> ORGANISM: Artificial Sequence
<220> FEATURE:
<223> OTHER INFORMATION: P30.016Ala12 Primer

<400> SEQUENCE: 59

```
gactggctgt tcccgcagcc gattttgctg accctgcagc cccggcaaac tccagtttca    60
cggtagcgtg                                                           70
```

<210> SEQ ID NO 60
<211> LENGTH: 36
<212> TYPE: DNA
<213> ORGANISM: Artificial Sequence
<220> FEATURE:
<223> OTHER INFORMATION: Antisense Primer

<400> SEQUENCE: 60

```
caggtcaagc tttcactcca gtttcacggt agcgtg                              36
```

<210> SEQ ID NO 61
<211> LENGTH: 7370
<212> TYPE: DNA
<213> ORGANISM: Toxoplasma gondii
<220> FEATURE:
<221> NAME/KEY: CDS
<222> LOCATION: (1528)...(3447)
<223> OTHER INFORMATION: pMBP-c2X-ToxoP30MIX1

<400> SEQUENCE: 61

```
ccgacaccat cgaatggtgc aaaacctttc gcggtatggc atgatagcgc ccggaagaga    60
gtcaattcag ggtggtgaat gtgaaaccag taacgttata cgatgtcgca gagtatgccg   120
gtgtctctta tcagaccgtt tcccgcgtgg tgaaccaggc cagccacgtt tctgcgaaaa   180
cgcgggaaaa agtggaagcg gcgatggcgg agctgaatta cattcccaac cgcgtggcac   240
aacaactggc gggcaaacag tcgttgctga ttggcgttgc cacctccagt ctggccctgc   300
acgcgccgtc gcaaattgtc gcggcgatta atctcgcgc cgatcaactg ggtgccagcg   360
tggtggtgtc gatggtagaa cgaagcggcg tcgaagcctg taaagcggcg gtgcacaatc   420
ttctcgcgca acgcgtcagt gggctgatca ttaactatcc gctggatgac caggatgcca   480
ttgctgtgga agctgcctgc actaatgttc cggcgttatt tcttgatgtc tctgaccaga   540
cacccatcaa cagtattatt ttctcccatg aagacggtac gcgactgggc gtggagcatc   600
tggtcgcatt gggtcaccag caaatcgcgc tgttagcggg cccattaagt tctgtctcgg   660
cgcgtctgcg tctggctggc tggcataaat atctcactcg caatcaaatt cagccgatag   720
cggaacggga aggcgactgg agtgccatgt ccgttttca acaaaccatg caaatgctga   780
atgagggcat cgttcccact gcgatgctgg ttgccaacga tcagatggcg ctgggcgcaa   840
```

```
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa aaccaccctg gcgcccaata   1080
cgcaaaccgc ctctccccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgttttt gcgccgacat cataacggtt    1380
ctggcaaata ttctgaaatg agctgttgac aattaatcat cggctcgtat aatgtgtgga   1440
attgtgagcg gataacaatt tcacacagga acagccagt ccgtttaggt gttttcacga    1500
gcacttcacc aacaaggacc atagcat atg aaa atc gaa gaa ggt aaa ctg gta   1554
                                Met Lys Ile Glu Glu Gly Lys Leu Val
                                 1               5
```

```
atc tgg att aac ggc gat aaa ggc tat aac ggt ctc gct gaa gtc ggt      1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg      1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
         45                  50                  55 cct gac att atc ttc tgg gca cac gac cgc ttt ggt ggc tac gct caa      1746
Pro Asp Ile Ile Phe Trp Ala His Asp Arg Phe Gly Gly Tyr Ala Gln
     60                  65                  70 tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
    155                 160                 165 ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc      2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
```

|  |  |  |  |  |  |  |  |  |  |  |  |  |  |  |
|---|---|---|---|---|---|---|---|---|---|---|---|---|---|---|
| Phe | Asn | Lys | Gly | Glu | Thr | Ala | Met | Thr | Ile | Asn | Gly | Pro | Trp | Ala | Trp |
|  | 220 |  |  |  | 225 |  |  |  | 230 |  |  |  |  |  |

```
tcc aac atc gac acc agc aaa gtg aat tat ggt gta acg gta ctg ccg    2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca    2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc    2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac    2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg    2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa    2514
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt    2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc    2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac    2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc ctt gtt    2706
Asn Asn Asn Asn Leu Gly Ile Glu Gly Arg Ile Ser Glu Phe Leu Val
        380                 385                 390 gcc aat caa gtt gtc acc tgc cca gat aaa aaa tcg aca gcc gcg gtc    2754
Ala Asn Gln Val Val Thr Cys Pro Asp Lys Lys Ser Thr Ala Ala Val
    395                 400                 405 att ctc aca ccg acg gag aac cac ttc act ctc aag tgc cct aaa aca    2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc    2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg    2898
Cys Pro Ala Gly Thr Thr Ser Ser Cys Thr Ser Lys Ala Val Thr Leu
            445                 450                 455 agc tcc ttg att cct gaa gca gaa gat agc tgg tgg acg ggg gat tct    2946
Ser Ser Leu Ile Pro Glu Ala Glu Asp Ser Trp Trp Thr Gly Asp Ser
        460                 465                 470 gct agt ctc gac acg gca ggc atc aaa ctc aca gtt cca atc gag aag    2994
Ala Ser Leu Asp Thr Ala Gly Ile Lys Leu Thr Val Pro Ile Glu Lys
    475                 480                 485 ttc ccc gtg aca acg cag acg ttt gtg gtc ggt tgc atc aag gga gac    3042
Phe Pro Val Thr Thr Gln Thr Phe Val Val Gly Cys Ile Lys Gly Asp
490                 495                 500                 505 gac gca cag agt tgt atg gtc acg gtg aca gta caa gcc aga gcc tca    3090
Asp Ala Gln Ser Cys Met Val Thr Val Thr Val Gln Ala Arg Ala Ser
                510                 515                 520 tcg gtc gtc aat aat gtc gca agg tgc tcc tac ggt gca gac agc act    3138
Ser Val Val Asn Asn Val Ala Arg Cys Ser Tyr Gly Ala Asp Ser Thr
            525                 530                 535
```

```
ctt ggt cct gtc aag ttg tct gcg gaa gga ccc act aca atg acc ctc    3186
Leu Gly Pro Val Lys Leu Ser Ala Glu Gly Pro Thr Thr Met Thr Leu
        540                 545                 550 gtg gct ggg aaa gat gga gtc aaa gtt cct caa gac aat aat cag tac    3234
Val Ala Gly Lys Asp Gly Val Lys Val Pro Gln Asp Asn Asn Gln Tyr
555                 560                 565 gct tcc ggg acg acg ctg act ggt gct aac gag aaa tcg ttc aaa gat    3282
Ala Ser Gly Thr Thr Leu Thr Gly Ala Asn Glu Lys Ser Phe Lys Asp
570                 575                 580                 585 att ttg cca aaa tta act gag aac ccg tgg cag ggt aac gct tcg agt    3330
Ile Leu Pro Lys Leu Thr Glu Asn Pro Trp Gln Gly Asn Ala Ser Ser
        590                 595                 600 gat aag ggt gcc acg cta acg atc aag aag gaa gca ttt cca gcc gag    3378
Asp Lys Gly Ala Thr Leu Thr Ile Lys Lys Glu Ala Phe Pro Ala Glu
605                 610                 615 tca aaa agc gtc att att gga gct aca ggg gga tcg cct gag aag cat    3426
Ser Lys Ser Val Ile Ile Gly Ala Thr Gly Gly Ser Pro Glu Lys His
620                 625                 630 cac gct acc gtg aaa ctg gag tgaaagcttg cactggccg tcgttttaca        3477
His Ala Thr Val Lys Leu Glu
        635             640 acgtcgtgac tgggaaaacc ctggcgttac ccaacttaat cgccttgcag cacatccccc  3537
tttcgccagc tggcgtaata gcgaagaggc ccgcaccgat cgcccttccc aacagttgcg  3597
cagcctgaat ggcgaatggc agcttggctg ttttggcgga tgagataaga ttttcagcct  3657
gatacagatt aaatcagaac gcagaagcgg tctgataaaa cagaatttgc ctggcggcag  3717
tagcgcggtg gtcccacctg accccatgcc gaactcagaa gtgaaacgcc gtagcgccga  3777
tggtagtgtg gggtctcccc atgcgagagt agggaactgc caggcatcaa ataaaacgaa  3837
aggctcagtc gaaagactgg gcctttcgtt ttatctgttg tttgtcggtg aacgctctcc  3897
tgagtaggac aaatccgccg ggagcggatt tgaacgttgc gaagcaacgg cccggagggt  3957
ggcgggcagg acgcccgcca taaactgcca ggcatcaaat aagcagaag gccatcctga   4017
cggatggcct ttttgcgttt ctacaaactc ttttttgttta tttttctaaa tacattcaaa  4077
tatgtatccg ctcatgagac aataaccctg ataaatgctt caataatatt gaaaaggaa   4137
gagtatgagt attcaacatt tccgtgtcgc ccttattccc ttttttgcgg cattttgcct  4197
tcctgttttt gctcacccag aaacgctggt gaaagtaaaa gatgctgaag atcagttggg  4257
tgcacgagtg ggttacatcg aactggatct caacagcggt aagatccttg agagttttcg  4317
ccccgaagaa cgttctccaa tgatgagcac ttttaaagtt ctgctatgtg gcgcggtatt  4377
atcccgtgtt gacgccgggc aagagcaact cggtcgccgc atacactatt ctcagaatga  4437
cttggttgag tactcaccag tcacagaaaa gcatcttacg gatggcatga cagtaagaga  4497
attatgcagt gctgccataa ccatgagtga taacactgcg ccaacttac ttctgacaac   4557
gatcggagga ccgaaggagc taaccgcttt tttgcacaac atgggggatc atgtaactcg  4617
ccttgatcgt tgggaaccgg agctgaatga agccatacca aacgacgagc gtgacaccac  4677
gatgcctgta gcaatggcaa caacgttgcg caaactatta actggcgaac tacttactct  4737
agcttcccgg caacaattaa tagactggat ggaggcggat aaagttgcag gaccacttct  4797
gcgctcggcc cttccggctg gctggtttat tgctgataaa tctggagccg gtgagcgtgg  4857
gtctcgcggt atcattgcag cactggggcc agatggtaag ccctcccgta tcgtagttat  4917
ctacacgacg gggagtcagg caactatgga tgaacgaaat agacagatcg ctgagatagg  4977
tgcctcactg attaagcatt ggtaactgtc agaccaagtt tactcatata tactttagat  5037
```

-continued

```
tgatttaccc cggttgataa tcagaaaagc cccaaaaaca ggaagattgt ataagcaaat   5097
atttaaattg taaacgttaa tattttgtta aaattcgcgt taaatttttg ttaaatcagc   5157
tcatttttta accaataggc cgaaatcggc aaaatccctt ataaatcaaa agaatagacc   5217
gagatagggt tgagtgttgt tccagtttgg aacaagagtc cactattaaa gaacgtggac   5277
tccaacgtca aagggcgaaa aaccgtctat cagggcgatg gcccactacg tgaaccatca   5337
cccaaatcaa gttttttggg gtcgaggtgc cgtaaagcac taaatcggaa ccctaaaggg   5397
agcccccgat ttagagcttg acggggaaag ccggcgaacg tggcgagaaa ggaagggaag   5457
aaagcgaaag gagcgggcgc tagggcgctg gcaagtgtag cggtcacgct gcgcgtaacc   5517
accacacccg ccgcgcttaa tgcgccgcta cagggcgcgt aaaaggatct aggtgaagat   5577
cctttttgat aatctcatga ccaaaatccc ttaacgtgag ttttcgttcc actgagcgtc   5637
agaccccgta gaaaagatca aaggatcttc ttgagatcct ttttttctgc gcgtaatctg   5697
ctgcttgcaa acaaaaaaac caccgctacc agcggtggtt tgtttgccgg atcaagagct   5757
accaactctt tttccgaagg taactggctt cagcagagcg cagataccaa atactgtcct   5817
tctagtgtag ccgtagttag gccaccactt caagaactct gtagcaccgc ctacatacct   5877
cgctctgcta atcctgttac cagtggctgc tgccagtggc gataagtcgt gtcttaccgg   5937
gttggactca agacgatagt taccggataa ggcgcagcgg tcgggctgaa cggggggttc   5997
gtgcacacag cccagcttgg agcgaacgac ctacaccgaa ctgagatacc tacagcgtga   6057
gctatgagaa agcgccacgc ttcccgaagg gagaaaggcg gacaggtatc cggtaagcgg   6117
cagggtcgga acaggagagc gcacgaggga gcttccaggg ggaaacgcct ggtatcttta   6177
tagtcctgtc gggtttcgcc acctctgact tgagcgtcga tttttgtgat gctcgtcagg   6237
ggggcggagc ctatggaaaa acgccagcaa cgcggccttt ttacggttcc tggccttttg   6297
ctggcctttt gctcacatgt tctttcctgc gttatcccct gattctgtgg ataaccgtat   6357
taccgccttt gagtgagctg ataccgctcg ccgcagccga acgaccgagc gcagcgagtc   6417
agtgagcgag gaagcggaag agcgcctgat gcggtatttt ctccttacgc atctgtgcgg   6477
tatttcacac cgcatatatg gtgcactctc agtacaatct gctctgatgc cgcatagtta   6537
agccagtata cactccgcta tcgctacgtg actgggtcat ggctgcgccc cgacacccgc   6597
caacacccgc tgacgcgccc tgacgggctt gtctgctccc ggcatccgct tacagacaag   6657
ctgtgaccgt ctccgggagc tgcatgtgtc agaggttttc accgtcatca ccgaaacgcg   6717
cgaggcagct gcggtaaagc tcatcagcgt ggtcgtgcag cgattcacag atgtctgcct   6777
gttcatccgc gtccagctcg ttgagtttct ccagaagcgt taatgtctgg cttctgataa   6837
agcgggccat gttaagggcg gtttttttcct gtttggtcac tgatgcctcc gtgtaagggg   6897
gatttctgtt catgggggta atgataccga tgaaacgaga gaggatgctc acgatacggg   6957
ttactgatga tgaacatgcc cggttactgg aacgttgtga gggtaaacaa ctggcggtat   7017
ggatgcggcg ggaccagaga aaaatcactc agggtcaatg ccagcgcttc gttaatacag   7077
atgtaggtgt tccacagggt agccagcagc atcctgcgat gcagatccgg aacataatgg   7137
tgcagggcgc tgacttccgc gtttccagac tttacgaaac acggaaaccg aagaccattc   7197
atgttgttgc tcaggtcgca gacgttttgc agcagcagtc gcttcacgtt cgctcgcgta   7257
tcggtgattc attctgctaa ccagtaaggc aaccccgcca gcctagccgg gtcctcaacg   7317
acaggagcac gatcatgcgc acccgtggcc aggacccaac gctgcccgaa att          7370
```

<210> SEQ ID NO 62
<211> LENGTH: 640
<212> TYPE: PRT
<213> ORGANISM: Toxoplasma gondii
<220> FEATURE:
<223> OTHER INFORMATION: pMBP-c2X-ToxoP30MIX1

<400> SEQUENCE: 62

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365
```

```
Ser Ser Ser Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
                435                 440                 445

Ser Cys Thr Ser Lys Ala Val Thr Leu Ser Ser Leu Ile Pro Glu Ala
        450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
530                 535                 540

Ala Glu Gly Pro Thr Thr Met Thr Leu Val Ala Gly Lys Asp Gly Val
545                 550                 555                 560

Lys Val Pro Gln Asp Asn Asn Gln Tyr Ala Ser Gly Thr Thr Leu Thr
                565                 570                 575

Gly Ala Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
610                 615                 620

Ala Thr Gly Gly Ser Pro Glu Lys His His Ala Thr Val Lys Leu Glu
625                 630                 635                 640

<210> SEQ ID NO 63
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: ToxoP30MIX1

<400> SEQUENCE: 63 ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
  1               5                  10                  15 gcg gtc att ctc aca ccg acg gag aac cac ttc act ctc aag tgc cct      96
Ala Val Ile Leu Thr Pro Thr Glu Asn His Phe Thr Leu Lys Cys Pro
             20                  25                  30 aaa aca gcg ctc aca gag cct ccc act ctt gcg tac tca ccc aac agg     144
Lys Thr Ala Leu Thr Glu Pro Pro Thr Leu Ala Tyr Ser Pro Asn Arg
         35                  40                  45 caa atc tgc cca gcg ggt act aca agt agc tgt aca tca aag gct gta     192
Gln Ile Cys Pro Ala Gly Thr Thr Ser Ser Cys Thr Ser Lys Ala Val
     50                  55                  60
```

```
aca ttg agc tcc ttg att cct gaa gca gaa gat agc tgg tgg acg ggg         240
Thr Leu Ser Ser Leu Ile Pro Glu Ala Glu Asp Ser Trp Trp Thr Gly
 65                  70                  75                  80 gat tct gct agt ctc gac acg gca ggc atc aaa ctc aca gtt cca atc         288
Asp Ser Ala Ser Leu Asp Thr Ala Gly Ile Lys Leu Thr Val Pro Ile
                 85                  90                  95 gag aag ttc ccc gtg aca acg cag acg ttt gtg gtc ggt tgc atc aag         336
Glu Lys Phe Pro Val Thr Thr Gln Thr Phe Val Val Gly Cys Ile Lys
            100                 105                 110 gga gac gac gca cag agt tgt atg gtc acg gtg aca gta caa gcc aga         384
Gly Asp Asp Ala Gln Ser Cys Met Val Thr Val Thr Val Gln Ala Arg
        115                 120                 125 gcc tca tcg gtc gtc aat aat gtc gca agg tgc tcc tac ggt gca gac         432
Ala Ser Ser Val Val Asn Asn Val Ala Arg Cys Ser Tyr Gly Ala Asp
130                 135                 140 agc act ctt ggt cct gtc aag ttg tct gcg gaa gga ccc act aca atg         480
Ser Thr Leu Gly Pro Val Lys Leu Ser Ala Glu Gly Pro Thr Thr Met
145                 150                 155                 160 acc ctc gtg gct ggg aaa gat gga gtc aaa gtt cct caa gac aat aat         528
Thr Leu Val Ala Gly Lys Asp Gly Val Lys Val Pro Gln Asp Asn Asn
                165                 170                 175 cag tac gct tcc ggg acg acg ctg act ggt gct aac gag aaa tcg ttc         576
Gln Tyr Ala Ser Gly Thr Thr Leu Thr Gly Ala Asn Glu Lys Ser Phe
            180                 185                 190 aaa gat att ttg cca aaa tta act gag aac ccg tgg cag ggt aac gct         624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca         672
Ser Ser Asp Lys Gly Ala Thr Leu Thr Ile Lys Lys Glu Ala Phe Pro
210                 215                 220 gcc gag tca aaa agc gtc att att gga gct aca ggg gga tcg cct gag         720
Ala Glu Ser Lys Ser Val Ile Ile Gly Ala Thr Gly Gly Ser Pro Glu
225                 230                 235                 240 aag cat cac gct acc gtg aaa ctg gag                                     747
Lys His His Ala Thr Val Lys Leu Glu
                245

<210> SEQ ID NO 64
<211> LENGTH: 249
<212> TYPE: PRT
<213> ORGANISM: Toxoplasma gondii
<220> FEATURE:
<223> OTHER INFORMATION: ToxoP30MIX1

<400> SEQUENCE: 64

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
                20                  25                  30

Lys Thr Ala Leu Thr Glu Pro Pro Thr Leu Ala Tyr Ser Pro Asn Arg
            35                  40                  45

Gln Ile Cys Pro Ala Gly Thr Thr Ser Cys Thr Ser Lys Ala Val
        50                  55                  60

Thr Leu Ser Ser Leu Ile Pro Glu Ala Glu Asp Ser Trp Trp Thr Gly
 65                  70                  75                  80

Asp Ser Ala Ser Leu Asp Thr Ala Gly Ile Lys Leu Thr Val Pro Ile
                 85                  90                  95

Glu Lys Phe Pro Val Thr Thr Gln Thr Phe Val Val Gly Cys Ile Lys
            100                 105                 110
```

```
Gly Asp Asp Ala Gln Ser Cys Met Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Ala Gly Lys Asp Gly Val Lys Val Pro Gln Asp Asn Asn
                165                 170                 175

Gln Tyr Ala Ser Gly Thr Thr Leu Thr Gly Ala Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Ala Thr Gly Gly Ser Pro Glu
225                 230                 235                 240

Lys His His Ala Thr Val Lys Leu Glu
                245

<210> SEQ ID NO 65
<211> LENGTH: 70
<212> TYPE: DNA
<213> ORGANISM: Artificial Sequence
<220> FEATURE:
<223> OTHER INFORMATION: P30.009Ala7 Primer

<400> SEQUENCE: 65
catcggtcgt caataatgtc gcaagggctt cctacggtgc agacagcact cttggtcctg    60
tcaagttgtc                                                           70

<210> SEQ ID NO 66
<211> LENGTH: 7370
<212> TYPE: DNA
<213> ORGANISM: Toxoplasma gondii
<220> FEATURE:
<221> NAME/KEY: CDS
<222> LOCATION: (1528)...(3447)
<223> OTHER INFORMATION: pMBP-c2X-ToxoP30MIX3

<400> SEQUENCE: 66
ccgacaccat cgaatggtgc aaaacctttc gcggtatggc atgatagcgc ccggaagaga    60
gtcaattcag gtggtgaatg tgaaaccagt aacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta aatctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
```

```
atgagggcat cgttcccact gcgatgctgg ttgccaacga tcagatgcgc ctgggcgcaa        840
tgcgcgccat taccgagtcc gggctgcgcg ttggtgcgga tatctcggta gtgggatacg        900
acgataccga agacagctca tgttatatcc cgccgttaac caccatcaaa caggattttc        960
gcctgctggg gcaaaccagc gtggaccgct tgctgcaact ctctcagggc caggcggtga       1020
agggcaatca gctgttgccc gtctcactgg tgaaagaaa aaccaccctg cgcccaata        1080 cgcaaaccgc ctctccccgc gcgttggcg attcattaat gcagctggca cgacaggttt       1140
cccgactgga agcgggcag tgagcgcaac gcaattaatg taagttagct cactcattag       1200
gcacaattct catgtttgac agcttatcat cgactgcacg gtgcaccaat gcttctggcg       1260
tcaggcagcc atcggaagct gtggtatggc tgtgcaggtc gtaaatcact gcataattcg       1320
tgtcgctcaa ggcgcactcc cgttctggat aatgttttt cgccgacat cataacggtt       1380 ctggcaaata ttctgaaatg agctgttgac aattaatcat cggctcgtat aatgtgtgga       1440
attgtgagcg gataacaatt tcacacagga acagccagt ccgtttaggt gttttcacga       1500
gcacttcacc aacaaggacc atagcat atg aaa atc gaa gaa ggt aaa ctg gta       1554
                                Met Lys Ile Glu Glu Gly Lys Leu Val
                                  1               5 atc tgg att aac ggc gat aaa ggc tat aac ggt ctc gct gaa gtc ggt          1602
Ile Trp Ile Asn Gly Asp Lys Gly Tyr Asn Gly Leu Ala Glu Val Gly
 10                  15                  20                  25 aag aaa ttc gag aaa gat acc gga att aaa gtc acc gtt gag cat ccg          1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc          1698
Asp Lys Leu Glu Glu Lys Phe Pro Gln Val Ala Ala Thr Gly Asp Gly
         45                  50                  55 cct gac att atc ttc tgg gca cac gac cgc ttt ggt ggc tac gct caa          1746
Pro Asp Ile Ile Phe Trp Ala His Asp Arg Phe Gly Gly Tyr Ala Gln
     60                  65                  70 tct ggc ctg ttg gct gaa atc acc ccg gac aaa gcg ttc cag gac aag          1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att          1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat          1890
Ala Tyr Pro Ile Ala Val Glu Ala Leu Ser Leu Ile Tyr Asn Lys Asp
            110                 115                 120 ctg ctg ccg aac ccg cca aaa acc tgg gaa gag atc ccg gcg ctg gat          1938
Leu Leu Pro Asn Pro Pro Lys Thr Trp Glu Glu Ile Pro Ala Leu Asp
        125                 130                 135 aaa gaa ctg aaa gcg aaa ggt aag agc gcg ctg atg ttc aac ctg caa          1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg          2034
Glu Pro Tyr Phe Thr Trp Pro Leu Ile Ala Ala Asp Gly Gly Tyr Ala
155                 160                 165 ttc aag tat gaa aac ggc aag tac gac att aaa gac gtg ggc gtg gat          2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa          2130
Asn Ala Gly Ala Lys Ala Gly Leu Thr Phe Leu Val Asp Leu Ile Lys
            190                 195                 200 aac aaa cac atg aat gca gac acc gat tac tcc atc gca gaa gct gcc          2178
Asn Lys His Met Asn Ala Asp Thr Asp Tyr Ser Ile Ala Glu Ala Ala
        205                 210                 215
```

-continued

| | | |
|---|---|---|
| ttt aat aaa ggc gaa aca gcg atg acc atc aac ggc ccg tgg gca tgg<br>Phe Asn Lys Gly Glu Thr Ala Met Thr Ile Asn Gly Pro Trp Ala Trp<br>220 225 230 | | 2226 |
| tcc aac atc gac acc agc aaa gtg aat tat ggt gta acg gta ctg ccg<br>Ser Asn Ile Asp Thr Ser Lys Val Asn Tyr Gly Val Thr Val Leu Pro<br>235 240 245 | | 2274 |
| acc ttc aag ggt caa cca tcc aaa ccg ttc gtt ggc gtg ctg agc gca<br>Thr Phe Lys Gly Gln Pro Ser Lys Pro Phe Val Gly Val Leu Ser Ala<br>250 255 260 265 | | 2322 |
| ggt att aac gcc gcc agt ccg aac aaa gag ctg gca aaa gag ttc ctc<br>Gly Ile Asn Ala Ala Ser Pro Asn Lys Glu Leu Ala Lys Glu Phe Leu<br>270 275 280 | | 2370 |
| gaa aac tat ctg ctg act gat gaa ggt ctg gaa gcg gtt aat aaa gac<br>Glu Asn Tyr Leu Leu Thr Asp Glu Gly Leu Glu Ala Val Asn Lys Asp<br>285 290 295 | | 2418 |
| aaa ccg ctg ggt gcc gta gcg ctg aag tct tac gag gaa gag ttg gcg<br>Lys Pro Leu Gly Ala Val Ala Leu Lys Ser Tyr Glu Glu Glu Leu Ala<br>300 305 310 | | 2466 |
| aaa gat cca cgt att gcc gcc act atg gaa aac gcc cag aaa ggt gaa<br>Lys Asp Pro Arg Ile Ala Ala Thr Met Glu Asn Ala Gln Lys Gly Glu<br>315 320 325 | | 2514 |
| atc atg ccg aac atc ccg cag atg tcc gct ttc tgg tat gcc gtg cgt<br>Ile Met Pro Asn Ile Pro Gln Met Ser Ala Phe Trp Tyr Ala Val Arg<br>330 335 340 345 | | 2562 |
| act gcg gtg atc aac gcc gcc agc ggt cgt cag act gtc gat gaa gcc<br>Thr Ala Val Ile Asn Ala Ala Ser Gly Arg Gln Thr Val Asp Glu Ala<br>350 355 360 | | 2610 |
| ctg aaa gac gcg cag act aat tcg agc tcg aac aac aac aac aat aac<br>Leu Lys Asp Ala Gln Thr Asn Ser Ser Ser Asn Asn Asn Asn Asn Asn<br>365 370 375 | | 2658 |
| aat aac aac aac ctc ggg atc gag gga agg att tca gaa ttc ctt gtt<br>Asn Asn Asn Asn Leu Gly Ile Glu Gly Arg Ile Ser Glu Phe Leu Val<br>380 385 390 | | 2706 |
| gcc aat caa gtt gtc acc tgc cca gat aaa aaa tcg aca gcc gcg gtc<br>Ala Asn Gln Val Val Thr Cys Pro Asp Lys Lys Ser Thr Ala Ala Val<br>395 400 405 | | 2754 |
| att ctc aca ccg acg gag aac cac ttc act ctc aag tgc cct aaa aca<br>Ile Leu Thr Pro Thr Glu Asn His Phe Thr Leu Lys Cys Pro Lys Thr<br>410 415 420 425 | | 2802 |
| gcg ctc aca gag cct ccc act ctt gcg tac tca ccc aac agg caa atc<br>Ala Leu Thr Glu Pro Pro Thr Leu Ala Tyr Ser Pro Asn Arg Gln Ile<br>430 435 440 | | 2850 |
| tgc cca gcg ggt act aca agt agc tgt aca tca aag gct gta aca ttg<br>Cys Pro Ala Gly Thr Thr Ser Ser Cys Thr Ser Lys Ala Val Thr Leu<br>445 450 455 | | 2898 |
| agc tcc ttg att cct gaa gca gaa gat agc tgg tgg acg ggg gat tct<br>Ser Ser Leu Ile Pro Glu Ala Glu Asp Ser Trp Trp Thr Gly Asp Ser<br>460 465 470 | | 2946 |
| gct agt ctc gac acg gca ggc atc aaa ctc aca gtt cca atc gag aag<br>Ala Ser Leu Asp Thr Ala Gly Ile Lys Leu Thr Val Pro Ile Glu Lys<br>475 480 485 | | 2994 |
| ttc ccc gtg aca acg cag acg ttt gtg gtc ggt tgc atc aag gga gac<br>Phe Pro Val Thr Thr Gln Thr Phe Val Val Gly Cys Ile Lys Gly Asp<br>490 495 500 505 | | 3042 |
| gac gca cag agt tgt atg gtc acg gtg aca gta caa gcc aga gcc tca<br>Asp Ala Gln Ser Cys Met Val Thr Val Thr Val Gln Ala Arg Ala Ser<br>510 515 520 | | 3090 |
| tcg gtc gtc aat aat gtc gca agg gct tcc tac ggt gca gac agc act<br>Ser Val Val Asn Asn Val Ala Arg Ala Ser Tyr Gly Ala Asp Ser Thr | | 3138 |

```
                   525                 530                 535
ctt ggt cct gtc aag ttg tct gcg gaa gga ccc act aca atg acc ctc     3186
Leu Gly Pro Val Lys Leu Ser Ala Glu Gly Pro Thr Thr Met Thr Leu
        540                 545                 550 gtg gct ggg aaa gat gga gtc aaa gtt cct caa gac aac aat cag tac     3234
Val Ala Gly Lys Asp Gly Val Lys Val Pro Gln Asp Asn Asn Gln Tyr
555                 560                 565 gct tcc ggg acg acg ctg act ggt gct aac gag aaa tcg ttc aaa gat     3282
Ala Ser Gly Thr Thr Leu Thr Gly Ala Asn Glu Lys Ser Phe Lys Asp
570                 575                 580                 585 att ttg cca aaa tta act gag aac ccg tgg cag ggt aac gct tcg agt     3330
Ile Leu Pro Lys Leu Thr Glu Asn Pro Trp Gln Gly Asn Ala Ser Ser
                590                 595                 600 gat aag ggt gcc acg cta acg atc aag aag gaa gca ttt cca gcc gag     3378
Asp Lys Gly Ala Thr Leu Thr Ile Lys Lys Glu Ala Phe Pro Ala Glu
            605                 610                 615 tca aaa agc gtc att att gga gct aca ggg gga tcg cct gag aag cat     3426
Ser Lys Ser Val Ile Ile Gly Ala Thr Gly Gly Ser Pro Glu Lys His
        620                 625                 630 cac gct acc gtg aaa ctg gag tgaaagcttg cactggccg tcgttttaca         3477
His Ala Thr Val Lys Leu Glu
        635                 640 acgtcgtgac tgggaaaacc ctggcgttac ccaacttaat cgccttgcag cacatccccc    3537
tttcgccagc tggcgtaata gcgaagaggc ccgcaccgat cgcccttccc aacagttgcg    3597
cagcctgaat ggcgaatggc agcttggctg ttttggcgga tgagataaga ttttcagcct    3657
gatacagatt aaatcagaac gcagaagcgg tctgataaaa cagaatttgc ctggcggcag    3717
tagcgcggtg gtcccacctg acccatgcc gaactcagaa gtgaaacgcc gtagcgccga     3777
tggtagtgtg gggtctcccc atgcgagagt agggaactgc caggcatcaa ataaaacgaa    3837
aggctcagtc gaaagactgg cctttcgtt ttatctgttg tttgtcggtg aacgctctcc     3897
tgagtaggac aaatccgccg ggagcggatt tgaacgttgc gaagcaacgg cccggagggt    3957
ggcgggcagg acgcccgcca taaactgcca ggcatcaaat taagcagaag gccatcctga    4017
cggatggcct ttttgcgttt ctacaaactc tttttgttta ttttctaaa tacattcaaa    4077 tatgtatccg ctcatgagac aataaccctg ataaatgctt caataatatt gaaaaggaa    4137 gagtatgagt attcaacatt tccgtgtcgc ccttattccc ttttttgcgg cattttgcct   4197
tcctgttttt gctcacccag aaacgctggt gaaagtaaaa gatgctgaag atcagttggg   4257
tgcacgagtg ggttacatcg aactggatct caacagcggt aagatccttg agagttttcg   4317
ccccgaagaa cgttctccaa tgatgagcac ttttaaagtt ctgctatgtg gcgcggtatt   4377
atcccgtgtt gacgccgggc aagagcaact cggtcgccgc atacactatt ctcagaatga   4437
cttggttgag tactcaccag tcacagaaaa gcatcttacg gatggcatga cagtaagaga   4497
attatgcagt gctgccataa ccatgagtga taacactgcg ccaacttac ttctgacaac    4557 gatcggagga ccgaaggagc taaccgcttt tttgcacaac atgggggatc atgtaactcg   4617
ccttgatcgt tgggaaccgg agctgaatga agccatacca aacgacgagc gtgacaccac   4677
gatgcctgta gcaatggcaa caacgttgcg caaactatta actggcgaac tacttactct   4737
agcttcccgg caacaattaa tagactggat ggaggcggat aaagttgcag gaccacttct   4797
gcgctcggcc cttccggctg gctggtttat tgctgataaa tctggagccg gtgagcgtgg   4857
gtctcgcggt atcattgcag cactggggcc agatggtaag ccctcccgta tcgtagttat   4917
ctacacgacg gggagtcagg caactatgga tgaacgaaat agacagatcg ctgagatagg   4977
```

-continued

```
tgcctcactg attaagcatt ggtaactgtc agaccaagtt tactcatata tactttagat   5037
tgatttaccc cggttgataa tcagaaaagc cccaaaaaca ggaagattgt ataagcaaat   5097
atttaaattg taaacgttaa tattttgtta aaattcgcgt taaatttttg ttaaatcagc   5157
tcatttttta accaataggc cgaaatcggc aaaatccctt ataaatcaaa agaatagacc   5217
gagatagggt tgagtgttgt tccagtttgg aacaagagtc cactattaaa gaacgtggac   5277
tccaacgtca aagggcgaaa aaccgtctat cagggcgatg gcccactacg tgaaccatca   5337
cccaaatcaa gttttttggg gtcgaggtgc cgtaaagcac taaatcggaa ccctaaaggg   5397
agcccccgat ttagagcttg acggggaaag ccggcgaacg tggcgagaaa ggaagggaag   5457
aaagcgaaag gagcgggcgc tagggcgctg gcaagtgtag cggtcacgct gcgcgtaacc   5517
accacacccg ccgcgcttaa tgcgccgcta cagggcgcgt aaaaggatct aggtgaagat   5577
cctttttgat aatctcatga ccaaaatccc ttaacgtgag ttttcgttcc actgagcgtc   5637
agaccccgta gaaaagatca aaggatcttc ttgagatcct ttttttctgc gcgtaatctg   5697
ctgcttgcaa acaaaaaaac caccgctacc agcggtggtt tgtttgccgg atcaagagct   5757
accaactctt tttccgaagg taactggctt cagcagagcg cagataccaa atactgtcct   5817
tctagtgtag ccgtagttag gccaccactt caagaactct gtagcaccgc ctacatacct   5877
cgctctgcta atcctgttac cagtggctgc tgccagtggc gataagtcgt gtcttaccgg   5937
gttggactca agacgatagt taccggataa ggcgcagcgg tcgggctgaa cggggggttc   5997
gtgcacacag cccagcttgg agcgaacgac ctacaccgaa ctgagatacc tacagcgtga   6057
gctatgagaa agcgccacgc ttcccgaagg gagaaaggcg gacaggtatc cggtaagcgg   6117
cagggtcgga acaggagagc gcacgaggga gcttccaggg ggaaacgcct ggtatcttta   6177
tagtcctgtc gggtttcgcc acctctgact tgagcgtcga tttttgtgat gctcgtcagg   6237
ggggcggagc ctatggaaaa acgccagcaa cgcggccttt ttacggttcc tggccttttg   6297
ctggcctttt gctcacatgt tctttcctgc gttatcccct gattctgtgg ataaccgtat   6357
taccgccttt gagtgagctg ataccgctcg ccgcagccga acgaccgagc gcagcgagtc   6417
agtgagcgag gaagcggaag agcgcctgat gcggtatttt ctccttacgc atctgtgcgg   6477
tatttcacac cgcatatatg gtgcactctc agtacaatct gctctgatgc cgcatagtta   6537
agccagtata cactccgcta tcgctacgtg actgggtcat ggctgcgccc cgacacccgc   6597
caacacccgc tgacgcgccc tgacgggctt gtctgctccc ggcatccgct tacagacaag   6657
ctgtgaccgt ctccgggagc tgcatgtgtc agaggttttc accgtcatca ccgaaacgcg   6717
cgaggcagct gcggtaaagc tcatcagcgt ggtcgtgcag cgattcacag atgtctgcct   6777
gttcatccgc gtccagctcg ttgagtttct ccagaagcgt taatgtctgg cttctgataa   6837
agcgggccat gttaagggcg gttttttcct gtttggtcac tgatgcctcc gtgtaagggg   6897
gatttctgtt catgggggta atgataccga tgaaacgaga gaggatgctc acgatacggg   6957
ttactgatga tgaacatgcc cggttactgg aacgttgtga gggtaaacaa ctggcggtat   7017
ggatgcggcg ggaccagaga aaaatcactc agggtcaatg ccagcgcttc gttaatacag   7077
atgtaggtgt tccacagggt agccagcagc atcctgcgat gcagatccgg aacataatgg   7137
tgcagggcgc tgacttccgc gtttccagac tttacgaaac acggaaaccg aagaccattc   7197
atgttgttgc tcaggtcgca gacgttttgc agcagcagtc gcttcacgtt cgctcgcgta   7257
tcggtgattc attctgctaa ccagtaaggc aaccccgcca gcctagccgg gtcctcaacg   7317
```

```
                                    acaggagcac gatcatgcgc acccgtggcc aggacccaac gctgcccgaa att          7370
```

<210> SEQ ID NO 67
<211> LENGTH: 640
<212> TYPE: PRT
<213> ORGANISM: Toxoplasma gondii
<220> FEATURE:
<223> OTHER INFORMATION: pMBP-c2X-ToxoP30MIX3

<400> SEQUENCE: 67

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
     50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
           100                 105                 110

Ala Leu Ser Leu Ile Tyr Asn Lys Asp Leu Leu Pro Asn Pro Pro Lys
       115                 120                 125

Thr Trp Glu Glu Ile Pro Ala Leu Asp Lys Glu Leu Lys Ala Lys Gly
   130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
               165                 170                 175

Tyr Asp Ile Lys Asp Val Gly Val Asp Asn Ala Gly Ala Lys Ala Gly
           180                 185                 190

Leu Thr Phe Leu Val Asp Leu Ile Lys Asn Lys His Met Asn Ala Asp
       195                 200                 205

Thr Asp Tyr Ser Ile Ala Glu Ala Ala Phe Asn Lys Gly Glu Thr Ala
   210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
               245                 250                 255

Lys Pro Phe Val Gly Val Leu Ser Ala Gly Ile Asn Ala Ala Ser Pro
           260                 265                 270

Asn Lys Glu Leu Ala Lys Glu Phe Leu Glu Asn Tyr Leu Leu Thr Asp
       275                 280                 285

Glu Gly Leu Glu Ala Val Asn Lys Asp Lys Pro Leu Gly Ala Val Ala
   290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
               325                 330                 335

Met Ser Ala Phe Trp Tyr Ala Val Arg Thr Ala Val Ile Asn Ala Ala
           340                 345                 350

Ser Gly Arg Gln Thr Val Asp Glu Ala Leu Lys Asp Ala Gln Thr Asn
```

```
                    355                 360                 365
Ser Ser Ser Asn Asn Asn Asn Asn Asn Asn Asn Leu Gly Ile
        370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
                420                 425                 430

Leu Ala Tyr Ser Pro Asn Arg Gln Ile Cys Pro Ala Gly Thr Thr Ser
            435                 440                 445

Ser Cys Thr Ser Lys Ala Val Thr Leu Ser Ser Leu Ile Pro Glu Ala
        450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Ala Ser Tyr Gly Ala Asp Ser Thr Leu Gly Pro Val Lys Leu Ser
530                 535                 540

Ala Glu Gly Pro Thr Thr Met Thr Leu Val Ala Gly Lys Asp Gly Val
545                 550                 555                 560

Lys Val Pro Gln Asp Asn Asn Gln Tyr Ala Ser Gly Thr Thr Leu Thr
                565                 570                 575

Gly Ala Asn Glu Lys Ser Phe Lys Asp Ile Leu Pro Lys Leu Thr Glu
            580                 585                 590

Asn Pro Trp Gln Gly Asn Ala Ser Asp Lys Gly Ala Thr Leu Thr
                595                 600                 605

Ile Lys Lys Glu Ala Phe Pro Ala Glu Ser Lys Ser Val Ile Ile Gly
        610                 615                 620

Ala Thr Gly Gly Ser Pro Glu Lys His His Ala Thr Val Lys Leu Glu
625                 630                 635                 640

<210> SEQ ID NO 68
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: ToxoP30MIX3

<400> SEQUENCE: 68 ctt gtt gcc aat caa gtt gtc acc tgc cca gat aaa aaa tcg aca gcc        48
Leu Val Ala Asn Gln Val Val Thr Cys Pro Asp Lys Lys Ser Thr Ala
1               5                   10                  15 gcg gtc att ctc aca ccg acg gag aac cac ttc act ctc aag tgc cct        96
Ala Val Ile Leu Thr Pro Thr Glu Asn His Phe Thr Leu Lys Cys Pro
                20                  25                  30 aaa aca gcg ctc aca gag cct ccc act ctt gcg tac tca ccc aac agg       144
Lys Thr Ala Leu Thr Glu Pro Pro Thr Leu Ala Tyr Ser Pro Asn Arg
            35                  40                  45 caa atc tgc cca gcg ggt act aca agt agc tgt aca tca aag gct gta       192
Gln Ile Cys Pro Ala Gly Thr Thr Ser Ser Cys Thr Ser Lys Ala Val
```

```
              50                  55                  60
aca ttg agc tcc ttg att cct gaa gca gaa gat agc tgg tgg acg ggg      240
Thr Leu Ser Ser Leu Ile Pro Glu Ala Glu Asp Ser Trp Trp Thr Gly
 65                  70                  75                  80 gat tct gct agt ctc gac acg gca ggc atc aaa ctc aca gtt cca atc      288
Asp Ser Ala Ser Leu Asp Thr Ala Gly Ile Lys Leu Thr Val Pro Ile
                 85                  90                  95 gag aag ttc ccc gtg aca acg cag acg ttt gtg gtc ggt tgc atc aag      336
Glu Lys Phe Pro Val Thr Thr Gln Thr Phe Val Val Gly Cys Ile Lys
            100                 105                 110 gga gac gac gca cag agt tgt atg gtc acg gtg aca gta caa gcc aga      384
Gly Asp Asp Ala Gln Ser Cys Met Val Thr Val Thr Val Gln Ala Arg
        115                 120                 125 gcc tca tcg gtc gtc aat aat gtc gca agg gct tcc tac ggt gca gac      432
Ala Ser Ser Val Val Asn Asn Val Ala Arg Ala Ser Tyr Gly Ala Asp
    130                 135                 140 agc act ctt ggt cct gtc aag ttg tct gcg gaa gga ccc act aca atg      480
Ser Thr Leu Gly Pro Val Lys Leu Ser Ala Glu Gly Pro Thr Thr Met
145                 150                 155                 160 acc ctc gtg gct ggg aaa gat gga gtc aaa gtt cct caa gac aac aat      528
Thr Leu Val Ala Gly Lys Asp Gly Val Lys Val Pro Gln Asp Asn Asn
                165                 170                 175 cag tac gct tcc ggg acg acg ctg act ggt gct aac gag aaa tcg ttc      576
Gln Tyr Ala Ser Gly Thr Thr Leu Thr Gly Ala Asn Glu Lys Ser Phe
            180                 185                 190 aaa gat att ttg cca aaa tta act gag aac ccg tgg cag ggt aac gct      624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca      672
Ser Ser Asp Lys Gly Ala Thr Leu Thr Ile Lys Lys Glu Ala Phe Pro
    210                 215                 220 gcc gag tca aaa agc gtc att att gga gct aca ggg gga tcg cct gag      720
Ala Glu Ser Lys Ser Val Ile Ile Gly Ala Thr Gly Gly Ser Pro Glu
225                 230                 235                 240 aag cat cac gct acc gtg aaa ctg gag                                  747
Lys His His Ala Thr Val Lys Leu Glu
                245

<210> SEQ ID NO 69
<211> LENGTH: 249
<212> TYPE: PRT
<213> ORGANISM: Toxoplasma gondii
<220> FEATURE:
<223> OTHER INFORMATION: ToxoP30MIX3

<400> SEQUENCE: 69

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
                20                  25                  30

Lys Thr Ala Leu Thr Glu Pro Pro Thr Leu Ala Tyr Ser Pro Asn Arg
            35                  40                  45

Gln Ile Cys Pro Ala Gly Thr Thr Ser Ser Cys Thr Ser Lys Ala Val
        50                  55                  60

Thr Leu Ser Ser Leu Ile Pro Glu Ala Glu Asp Ser Trp Trp Thr Gly
 65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
```

```
                    100                 105                  110
Gly Asp Asp Ala Gln Ser Cys Met Val Thr Val Thr Val Gln Ala Arg
            115                 120                 125
Ala Ser Ser Val Val Asn Asn Val Ala Arg Ala Ser Tyr Gly Ala Asp
            130                 135                 140
Ser Thr Leu Gly Pro Val Lys Leu Ser Ala Glu Gly Pro Thr Thr Met
145                 150                 155                 160
Thr Leu Val Ala Gly Lys Asp Gly Val Lys Val Pro Gln Asp Asn Asn
                165                 170                 175
Gln Tyr Ala Ser Gly Thr Thr Leu Thr Gly Ala Asn Glu Lys Ser Phe
            180                 185                 190
Lys Asp Ile Leu Pro Lys Leu Thr Glu Asn Pro Trp Gln Gly Asn Ala
            195                 200                 205
Ser Ser Asp Lys Gly Ala Thr Leu Thr Ile Lys Lys Glu Ala Phe Pro
        210                 215                 220
Ala Glu Ser Lys Ser Val Ile Ile Gly Ala Thr Gly Gly Ser Pro Glu
225                 230                 235                 240
Lys His His Ala Thr Val Lys Leu Glu
                245

<210> SEQ ID NO 70
<211> LENGTH: 69
<212> TYPE: DNA
<213> ORGANISM: Artificial Sequence
<220> FEATURE:
<223> OTHER INFORMATION: P30.002Ala2 Primer

<400> SEQUENCE: 70
gaggctctgt gagcgctgtt ttaggagcct tgagagtgaa gtggttctcc gtcggtgtga      60
gaatgaccg                                                             69

<210> SEQ ID NO 71
<211> LENGTH: 7370
<212> TYPE: DNA
<213> ORGANISM: Toxoplasma gondii
<220> FEATURE:
<221> NAME/KEY: CDS
<222> LOCATION: (1528)...(3447)
<223> OTHER INFORMATION: pMBP-c2X-ToxoP30MIX5

<400> SEQUENCE: 71
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta atctcgcgc gatcaactg ggtgccagcg      360 tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc cggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
```

```
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggatttc     960 gcctgctggg gcaaaccagc gtggaccgct tgctgcaact ctctcagggc caggcggtga   1020
agggcaatca gctgttgccc gtctcactgg tgaaaagaaa aaccaccctg cgcccaata    1080 cgcaaaccgc ctctccccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgtttttt gcgccgacat cataacggtt   1380
ctggcaaata ttctgaaatg agctgttgac aattaatcat cggctcgtat aatgtgtgga   1440
attgtgagcg gataacaatt tcacacagga acagccagt  ccgtttaggt gttttcacga   1500
```
gcacttcacc aacaaggacc atagcat atg aaa atc gaa gaa ggt aaa ctg gta    1554
           Met Lys Ile Glu Glu Gly Lys Leu Val
            1      5 atc tgg att aac ggc gat aaa ggc tat aac ggt ctc gct gaa gtc ggt      1602
Ile Trp Ile Asn Gly Asp Lys Gly Tyr Asn Gly Leu Ala Glu Val Gly
 10       15       20       25 aag aaa ttc gag aaa gat acc gga att aaa gtc acc gtt gag cat ccg      1650
Lys Lys Phe Glu Lys Asp Thr Gly Ile Lys Val Thr Val Glu His Pro
      30       35       40 gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
     45       50       55 cct gac att atc ttc tgg gca cac gac cgc ttt ggt ggc tac gct caa      1746
Pro Asp Ile Ile Phe Trp Ala His Asp Arg Phe Gly Gly Tyr Ala Gln
    60       65       70 tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
 75       80       85 ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90       95      100      105 gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
       110      115      120 ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
      125      130      135 aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
    140      145      150 gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
 155      160      165 ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170      175      180      185 aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
      190      195      200 aac aaa cac atg aat gca gac acc gat tac tcc atc gca gaa gct gcc      2178

```
                Asn Lys His Met Asn Ala Asp Thr Asp Tyr Ser Ile Ala Glu Ala Ala
                            205                 210                 215 ttt aat aaa ggc gaa aca gcg atg acc atc aac ggc ccg tgg gca tgg       2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg       2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca       2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc       2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac       2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg       2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa       2514
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt       2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc       2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac       2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc ctt gtt       2706
Asn Asn Asn Asn Leu Gly Ile Glu Gly Arg Ile Ser Glu Phe Leu Val
        380                 385                 390 gcc aat caa gtt gtc acc tgc cca gat aaa aaa tcg aca gcc gcg gtc       2754
Ala Asn Gln Val Val Thr Cys Pro Asp Lys Lys Ser Thr Ala Ala Val
    395                 400                 405 att ctc aca ccg acg gag aac cac ttc act ctc aag gct cct aaa aca       2802
Ile Leu Thr Pro Thr Glu Asn His Phe Thr Leu Lys Ala Pro Lys Thr
410                 415                 420                 425 gcg ctc aca gag cct ccc act ctt gcg tac tca ccc aac agg caa atc       2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg       2898
Cys Pro Ala Gly Thr Thr Ser Ser Cys Thr Ser Lys Ala Val Thr Leu
            445                 450                 455 agc tcc ttg att cct gaa gca gaa gat agc tgg tgg acg ggg gat tct       2946
Ser Ser Leu Ile Pro Glu Ala Glu Asp Ser Trp Trp Thr Gly Asp Ser
        460                 465                 470 gct agt ctc gac acg gca ggc atc aaa ctc aca gtt cca atc gag aag       2994
Ala Ser Leu Asp Thr Ala Gly Ile Lys Leu Thr Val Pro Ile Glu Lys
    475                 480                 485 ttc ccc gtg aca acg cag acg ttt gtg gtc ggt tgc atc aag gga gac       3042
Phe Pro Val Thr Thr Gln Thr Phe Val Val Gly Cys Ile Lys Gly Asp
490                 495                 500                 505 gac gca cag agt tgt atg gtc acg gtg aca gta caa gcc aga gcc tca       3090
Asp Ala Gln Ser Cys Met Val Thr Val Thr Val Gln Ala Arg Ala Ser
                510                 515                 520
```

```
tcg gtc gtc aat aat gtc gca agg tgc tcc tac ggt gca gac agc act     3138
Ser Val Val Asn Asn Val Ala Arg Cys Ser Tyr Gly Ala Asp Ser Thr
            525                 530                 535 ctt ggt cct gtc aag ttg tct gcg gaa gga ccc act aca atg acc ctc     3186
Leu Gly Pro Val Lys Leu Ser Ala Glu Gly Pro Thr Thr Met Thr Leu
        540                 545                 550 gtg gct ggg aaa gat gga gtc aaa gtt cct caa gac aac aat cag tac     3234
Val Ala Gly Lys Asp Gly Val Lys Val Pro Gln Asp Asn Asn Gln Tyr
        555                 560                 565 gct tcc ggg acg acg ctg act ggt gct aac gag aaa tcg ttc aaa gat     3282
Ala Ser Gly Thr Thr Leu Thr Gly Ala Asn Glu Lys Ser Phe Lys Asp
570                 575                 580                 585 att ttg cca aaa tta act gag aac ccg tgg cag ggt aac gct tcg agt     3330
Ile Leu Pro Lys Leu Thr Glu Asn Pro Trp Gln Gly Asn Ala Ser Ser
            590                 595                 600 gat aag ggt gcc acg cta acg atc aag aag gaa gca ttt cca gcc gag     3378
Asp Lys Gly Ala Thr Leu Thr Ile Lys Lys Glu Ala Phe Pro Ala Glu
        605                 610                 615 tca aaa agc gtc att att gga gct aca ggg gga tcg cct gag aag cat     3426
Ser Lys Ser Val Ile Ile Gly Ala Thr Gly Gly Ser Pro Glu Lys His
        620                 625                 630 cac gct acc gtg aaa ctg gag tgaaagcttg gcactggccg tcgttttaca       3477
His Ala Thr Val Lys Leu Glu
        635                 640 acgtcgtgac tgggaaaacc ctggcgttac ccaacttaat cgccttgcag cacatccccc  3537
tttcgccagc tggcgtaata gcgaagaggc ccgcaccgat cgcccttccc aacagttgcg  3597
cagcctgaat ggcgaatggc agcttggctg ttttggcgga tgagataaga ttttcagcct  3657
gatacagatt aaatcagaac gcagaagcgg tctgataaaa cagaatttgc ctggcggcag  3717
tagcgcggtg gtcccacctg accccatgcc gaactcagaa gtgaaacgcc gtagcgccga  3777
tggtagtgtg gggtctcccc atgcgagagt agggaactgc caggcatcaa ataaaacgaa  3837
aggctcagtc gaaagactgg gcctttcgtt ttatctgttg tttgtcggtg aacgctctcc  3897
tgagtaggac aaatccgccg ggagcggatt tgaacgttgc gaagcaacgg cccgagggt   3957 ggcgggcagg acgcccgcca taaactgcca ggcatcaaat taagcagaag gccatcctga  4017
cggatggcct ttttgcgttt ctacaaactc ttttgtttta tttttctaaa tacattcaaa  4077
tatgtatccg ctcatgagac aataaccctg ataaatgctt caataatatt gaaaaggaa  4137 gagtatgagt attcaacatt tccgtgtcgc ccttattccc ttttttgcgg cattttgcct  4197
tcctgttttt gctcacccag aaacgctggt gaaagtaaaa gatgctgaag atcagttggg  4257
tgcacgagtg ggttacatcg aactggatct caacagcggt aagatccttg agagttttcg  4317
ccccgaagaa cgttctccaa tgatgagcac ttttaaagtt ctgctatgtg gcgcggtatt  4377
atcccgtgtt gacgccgggc aagagcaact cggtcgccgc atacactatt ctcagaatga  4437
cttggttgag tactcaccag tcacagaaaa gcatcttacg gatggcatga cagtaagaga  4497
attatgcagt gctgccataa ccatgagtga taacactgcg gccaacttac ttctgacaac  4557
gatcggagga ccgaaggagc taaccgcttt tttgcacaac atgggggatc atgtaactcg  4617
ccttgatcgt tgggaaccgg agctgaatga agccatacca aacgacgagc gtgacaccac  4677
gatgcctgta gcaatggcaa caacgttgcg caaactatta actggcgaac tacttactct  4737
agcttcccgg caacaattaa tagactggat ggaggcggat aaagttgcag gaccacttct  4797
gcgctcggcc cttccggctg gctggtttat tgctgataaa tctggagccg gtgagcgtgg  4857
gtctcgcggt atcattgcag cactggggcc agatggtaag ccctcccgta tcgtagttat  4917
```

-continued

```
ctacacgacg gggagtcagg caactatgga tgaacgaaat agacagatcg ctgagatagg   4977
tgcctcactg attaagcatt ggtaactgtc agaccaagtt tactcatata tactttagat   5037
tgatttaccc cggttgataa tcagaaaagc cccaaaaaca ggaagattgt ataagcaaat   5097
atttaaattg taaacgttaa tattttgtta aaattcgcgt taaatttttg ttaaatcagc   5157
tcatttttta accaataggc cgaaatcggc aaaatccctt ataaatcaaa agaatagacc   5217
gagatagggt tgagtgttgt tccagtttgg aacaagagtc cactattaaa gaacgtggac   5277
tccaacgtca aagggcgaaa aaccgtctat cagggcgatg gcccactacg tgaaccatca   5337
cccaaatcaa gtttttttggg gtcgaggtgc cgtaaagcac taaatcggaa ccctaaaggg   5397
agcccccgat ttagagcttg acggggaaag ccggcgaacg tggcgagaaa ggaagggaag   5457
aaagcgaaag gagcgggcgc tagggcgctg gcaagtgtag cggtcacgct gcgcgtaacc   5517
accacacccg ccgcgcttaa tgcgccgcta cagggcgcgt aaaaggatct aggtgaagat   5577
cctttttgat aatctcatga ccaaaatccc ttaacgtgag ttttcgttcc actgagcgtc   5637
agaccccgta gaaaagatca aaggatcttc ttgagatcct ttttttctgc gcgtaatctg   5697
ctgcttgcaa acaaaaaaac caccgctacc agcggtggtt tgtttgccgg atcaagagct   5757
accaactctt tttccgaagg taactggctt cagcagagcg cagataccaa atactgtcct   5817
tctagtgtag ccgtagttag gccaccactt caagaactct gtagcaccgc ctacatacct   5877
cgctctgcta atcctgttac cagtggctgc tgccagtggc gataagtcgt gtcttaccgg   5937
gttggactca agacgatagt taccggataa ggcgcagcgg tcgggctgaa cggggggttc   5997
gtgcacacag cccagcttgg agcgaacgac ctacaccgaa ctgagatacc tacagcgtga   6057
gctatgagaa agcgccacgc ttcccgaagg gagaaaggcg gacaggtatc cggtaagcgg   6117
cagggtcgga acaggagagc gcacgaggga gcttccaggg ggaaacgcct ggtatcttta   6177
tagtcctgtc gggtttcgcc acctctgact tgagcgtcga tttttgtgat gctcgtcagg   6237
ggggcggagc ctatggaaaa acgccagcaa cgcggccttt ttacggttcc tggccttttg   6297
ctggcctttt gctcacatgt tctttcctgc gttatcccct gattctgtgg ataaccgtat   6357
taccgccttt gagtgagctg ataccgctcg ccgcagccga acgaccgagc gcagcgagtc   6417
agtgagcgag gaagcggaag agcgcctgat gcggtatttt ctccttacgc atctgtgcgg   6477
tatttcacac cgcatatatg gtgcactctc agtacaatct gctctgatgc cgcatagtta   6537
agccagtata cactccgcta tcgctacgtg actgggtcat ggctgcgccc cgacacccgc   6597
caacacccgc tgacgcgccc tgacgggctt gtctgctccc ggcatccgct tacagacaag   6657
ctgtgaccgt ctccgggagc tgcatgtgtc agaggttttc accgtcatca ccgaaacgcg   6717
cgaggcagct gcggtaaagc tcatcagcgt ggtcgtgcag cgattcacag atgtctgcct   6777
gttcatccgc gtccagctcg ttgagtttct ccagaagcgt taatgtctgg cttctgataa   6837
agcgggccat gttaagggcg gttttttcct gtttggtcac tgatgcctcc gtgtaagggg   6897
gatttctgtt catgggggta atgataccga tgaaacgaga gaggatgctc acgatacggg   6957
ttactgatga tgaacatgcc cggttactgg aacgttgtga gggtaaacaa ctggcggtat   7017
ggatgcggcg ggaccagaga aaaatcactc agggtcaatg ccagcgcttc gttaatacag   7077
atgtaggtgt tccacagggt agccagcagc atcctgcgat gcagatccgg aacataatgg   7137
tgcagggcgc tgacttccgc gtttccagac tttacgaaac acggaaaccg aagaccattc   7197
atgttgttgc tcaggtcgca gacgttttgc agcagcagtc gcttcacgtt cgctcgcgta   7257
```

```
tcggtgattc attctgctaa ccagtaaggc aaccccgcca gcctagccgg gtcctcaacg   7317
acaggagcac gatcatgcgc acccgtggcc aggacccaac gctgcccgaa att          7370
```

<210> SEQ ID NO 72
<211> LENGTH: 640
<212> TYPE: PRT
<213> ORGANISM: Toxoplasma gondii
<220> FEATURE:
<223> OTHER INFORMATION: pMBP-c2X-ToxoP30MIX5

<400> SEQUENCE: 72

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
     50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350
```

```
Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
        370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Ala Pro Lys Thr Ala Leu Thr Glu Pro Pro Thr
        420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
        450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
        500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
530                 535                 540

Ala Glu Gly Pro Thr Thr Met Thr Leu Val Ala Gly Lys Asp Gly Val
545                 550                 555                 560

Lys Val Pro Gln Asp Asn Asn Gln Tyr Ala Ser Gly Thr Thr Leu Thr
                565                 570                 575

Gly Ala Asn Glu Lys Ser Phe Lys Asp Ile Leu Pro Lys Leu Thr Glu
        580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
        610                 615                 620

Ala Thr Gly Gly Ser Pro Glu Lys His His Ala Thr Val Lys Leu Glu
625                 630                 635                 640

<210> SEQ ID NO 73
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: ToxoP30MIX5

<400> SEQUENCE: 73 ctt gtt gcc aat caa gtt gtc acc tgc cca gat aaa aaa tcg aca gcc    48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag gct cct    96
Ala Val Ile Leu Thr Pro Thr Glu Asn His Phe Thr Leu Lys Ala Pro
             20                  25                  30 aaa aca gcg ctc aca gag cct ccc act ctt gcg tac tca ccc aac agg   144
Lys Thr Ala Leu Thr Glu Pro Pro Thr Leu Ala Tyr Ser Pro Asn Arg
         35                  40                  45
```

```
caa atc tgc cca gcg ggt act aca agt agc tgt aca tca aag gct gta        192
Gln Ile Cys Pro Ala Gly Thr Thr Ser Ser Cys Thr Ser Lys Ala Val
    50                  55                  60 aca ttg agc tcc ttg att cct gaa gca gaa gat agc tgg tgg acg ggg        240
Thr Leu Ser Ser Leu Ile Pro Glu Ala Glu Asp Ser Trp Trp Thr Gly
65                  70                  75                  80 gat tct gct agt ctc gac acg gca ggc atc aaa ctc aca gtt cca atc        288
Asp Ser Ala Ser Leu Asp Thr Ala Gly Ile Lys Leu Thr Val Pro Ile
                85                  90                  95 gag aag ttc ccc gtg aca acg cag acg ttt gtg gtc ggt tgc atc aag        336
Glu Lys Phe Pro Val Thr Thr Gln Thr Phe Val Val Gly Cys Ile Lys
            100                 105                 110 gga gac gac gca cag agt tgt atg gtc acg gtg aca gta caa gcc aga        384
Gly Asp Asp Ala Gln Ser Cys Met Val Thr Val Thr Val Gln Ala Arg
        115                 120                 125 gcc tca tcg gtc gtc aat aat gtc gca agg tgc tcc tac ggt gca gac        432
Ala Ser Ser Val Val Asn Asn Val Ala Arg Cys Ser Tyr Gly Ala Asp
130                 135                 140 agc act ctt ggt cct gtc aag ttg tct gcg gaa gga ccc act aca atg        480
Ser Thr Leu Gly Pro Val Lys Leu Ser Ala Glu Gly Pro Thr Thr Met
145                 150                 155                 160 acc ctc gtg gct ggg aaa gat gga gtc aaa gtt cct caa gac aac aat        528
Thr Leu Val Ala Gly Lys Asp Gly Val Lys Val Pro Gln Asp Asn Asn
                165                 170                 175 cag tac gct tcc ggg acg acg ctg act ggt gct aac gag aaa tcg ttc        576
Gln Tyr Ala Ser Gly Thr Thr Leu Thr Gly Ala Asn Glu Lys Ser Phe
            180                 185                 190 aaa gat att ttg cca aaa tta act gag aac ccg tgg cag ggt aac gct        624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca        672
Ser Ser Asp Lys Gly Ala Thr Leu Thr Ile Lys Lys Glu Ala Phe Pro
210                 215                 220 gcc gag tca aaa agc gtc att att gga gct aca ggg gga tcg cct gag        720
Ala Glu Ser Lys Ser Val Ile Ile Gly Ala Thr Gly Gly Ser Pro Glu
225                 230                 235                 240 aag cat cac gct acc gtg aaa ctg gag                                    747
Lys His His Ala Thr Val Lys Leu Glu
                245

<210> SEQ ID NO 74
<211> LENGTH: 249
<212> TYPE: PRT
<213> ORGANISM: Toxoplasma gondii
<220> FEATURE:
<223> OTHER INFORMATION: ToxoP30MIX5

<400> SEQUENCE: 74

Leu Val Ala Asn Gln Val Val Thr Cys Pro Asp Lys Lys Ser Thr Ala
1               5                   10                  15

Ala Val Ile Leu Thr Pro Thr Glu Asn His Phe Thr Leu Lys Ala Pro
                20                  25                  30

Lys Thr Ala Leu Thr Glu Pro Pro Thr Leu Ala Tyr Ser Pro Asn Arg
            35                  40                  45

Gln Ile Cys Pro Ala Gly Thr Thr Ser Ser Cys Thr Ser Lys Ala Val
        50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95
```

-continued

```
Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
            115                 120                 125

Ala Ser Ser Val Val Asn Asn Val Ala Arg Cys Ser Tyr Gly Ala Asp
            130                 135                 140

Ser Thr Leu Gly Pro Val Lys Leu Ser Ala Glu Gly Pro Thr Thr Met
145                 150                 155                 160

Thr Leu Val Ala Gly Lys Asp Gly Val Lys Val Pro Gln Asp Asn Asn
            165                 170                 175

Gln Tyr Ala Ser Gly Thr Thr Leu Thr Gly Ala Asn Glu Lys Ser Phe
            180                 185                 190

Lys Asp Ile Leu Pro Lys Leu Thr Glu Asn Pro Trp Gln Gly Asn Ala
            195                 200                 205

Ser Ser Asp Lys Gly Ala Thr Leu Thr Ile Lys Lys Glu Ala Phe Pro
            210                 215                 220

Ala Glu Ser Lys Ser Val Ile Ile Gly Ala Thr Gly Gly Ser Pro Glu
225                 230                 235                 240

Lys His His Ala Thr Val Lys Leu Glu
            245
```

What is claimed is:

1. Plasmid pMBP-c2X-ToxoP30 MIX1 having American Type Culture Collection Accession No. ATCC 4721.

2. An isolated nucleic acid molecule comprising the nucleotide sequence of SEQ ID NO:61.

3. An isolated nucleic acid molecule encoding a polypeptide, wherein said polypeptide comprises the amino acid sequence of SEQ ID NO:62.

* * * * *